US009765399B2

(12) United States Patent
Montagut Viladot et al.

(10) Patent No.: US 9,765,399 B2
(45) Date of Patent: Sep. 19, 2017

(54) MUTATIONS IN THE EPIDERMAL GROWTH FACTOR RECEPTOR GENE

(75) Inventors: Clara Montagut Viladot, Barcelona (ES); Joan Albanell Mestres, Barcelona (ES); Ana Rovira Guerin, Barcelona (ES); Beatriz Bellosillo Paricio, Barcelona (ES); Alba Dalmases Massegú, Barcelona (ES)

(73) Assignee: FUNDACIO INSTITUT MAR D'INVESTIGACIONS MEDIQUES (IMIM), Barcelona (ES)

(*) Notice: Subject to any disclaimer, the term of this patent is extended or adjusted under 35 U.S.C. 154(b) by 0 days.

(21) Appl. No.: 14/236,614

(22) PCT Filed: Aug. 2, 2012

(86) PCT No.: PCT/EP2012/065090
§ 371 (c)(1),
(2), (4) Date: Jan. 31, 2014

(87) PCT Pub. No.: WO2013/017645
PCT Pub. Date: Feb. 7, 2013

(65) Prior Publication Data

US 2014/0170662 A1 Jun. 19, 2014

(30) Foreign Application Priority Data

Aug. 3, 2011 (EP) .................................... 11382270

(51) Int. Cl.

| | |
|---|---|
| ***C12Q 1/68*** | (2006.01) |
| ***G01N 33/574*** | (2006.01) |
| ***C07K 14/71*** | (2006.01) |

(52) U.S. Cl.
CPC ............ *C12Q 1/6883* (2013.01); *C07K 14/71* (2013.01); *G01N 33/57419* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,981,606 B2* | 7/2011 | Emrich | C12Q 1/6844 | 435/6.11 |
| 2007/0048754 A1* | 3/2007 | Freeman | C07K 14/71 | 435/6.14 |
| 2009/0258364 A1* | 10/2009 | Goel | C12Q 1/6886 | 435/6.12 |
| 2011/0230360 A1* | 9/2011 | Stephan | C12Q 1/6886 | 506/7 |

FOREIGN PATENT DOCUMENTS

| | | |
|---|---|---|
| WO | WO2005085473 A2 | 9/2005 |
| WO | WO2008088860 A2 | 7/2008 |

OTHER PUBLICATIONS

Liu W, Innocenti F, Wu MH, Desai AA, Dolan ME, Cook EH Jr, et al. A functional common polymorphism in a Sp1 recognition site of the epidermal growth factor receptor gene promoter. Cancer Res 2005; 65:46-53.*

Wang WS, Chen PM, Chiou TJ, Liu JH, Lin JK, Lin TC, Wang HS, Su Y. Epidermal growth factor receptor R497K polymorphism is a favorable prognostic factor for patients with colorectal carcinoma. Clin Cancer Res. Jun. 15, 2007;13(12):3597-604. PubMed PMID: 17575224.*

Zhang W, Gordon M, Press OA, Rhodes K, Vallböhmer D, Yang DY, Park D, Fazzone W, Schultheis A, Sherrod AE, Iqbal S, Groshen S, Lenz HJ. Cyclin D1 and epidermal growth factor polymorphisms associated with survival in patients with advanced colorectal cancer treated with Cetuximab. Pharmacogenet Genomics. Jul. 2006; 16(7):475-83. PubMed PMID: 16788380.*

Siena S, Sartore-Bianchi A, Di Nicolantonio F, Balfour J, Bardelli A. Biomarkers predicting clinical outcome of epidermal growth factor receptor-targeted therapy in metastatic colorectal cancer. J Natl Cancer Inst. Oct. 7, 2009; 101(19):1308-24. Epub Sep. 8, 2009. Review.*

Spindler KL, Pallisgaard N, Rasmussen AA, Lindebjerg J, Andersen RF, Crüger D, Jakobsen A. The importance of KRAS mutations and EGF61A>G polymorphism to the effect of cetuximab and irinotecan in metastatic colorectal cancer. Ann Oncol. May 2009; 20(5):879-84. Epub Jan. 29, 2009.*

Genbank Accession No. NP_005219.2—Epidermal growth factor receptor (erythroblastic leukemia viral (v-erb-b) oncogene homolog, avian); Epidermal growth factor receptor; epidermal growth factor receptor (avian erythroblastic leukemia viral (v-erb-b) oncogene homolog) [*Homo sapiens*] (GI: 29725609, submitted Apr. 10, 2003, retrieved on Mar. 24, 2015.*

Carcereny, E., Castellvi-Bel, S., Alonso, V., Garcia-Albeniz, X., Munoz, J., Gallego, R., & Maurel, J. (May 2008). EGFR polymorphisms as predictors of clinical outcome in patients with advanced colorectal cancer (ACRC) treated with cetuximab and panitumumab. In ASCO Annual Meeting Proceedings (abstract, vol. 26, No. 15_suppl, p. 4124).*

Montagut et al. Identification of a mutation in the extracellular domain of the Epidermal Growth Factor Receptor conferring cetuximab resistance in colorectal cancer. Nat Med. Jan. 22, 2012; 18(2):221-3.*

(Continued)

*Primary Examiner* — Samuel Woolwine
*Assistant Examiner* — Olayinka Oyeyemi
(74) *Attorney, Agent, or Firm* — Peter B. Scull; Hamilton, DeSanctis & Cha LLP

(57) ABSTRACT

The invention relates to a new identified mutation in the epidermal growth factor receptor gene, leading to an amino acidic change which highly correlates with the resistance to a therapy regimen comprising cetuximab and the sensitivity to a therapy regimen comprising panitumumab. The invention includes peptide sequences, primers and probes to detect such a mutation, as well as kits for predicting the response of a subject to a therapy regime comprising cetuximab and/or panitumumab. In particular, the invention is useful in the therapy regimen applicable to metastasic colorectal cancer and to head and neck cancer.

6 Claims, 3 Drawing Sheets

(56) References Cited

OTHER PUBLICATIONS

Genbank Accession No. NP_005219.2—epidermal growth factor receptor (erythroblastic leukemia viral (v-erb-b) oncogene homolog, avian); EGFR (avian erythroblastic leukemia viral (v-erb-b) oncogene homolog) [*Homo sapiens*] GI:29725609, submitted on Apr. 10, 2003, retrieved on Sep. 18, 2015 from http://www.ncbi.nlm.nih.gov/protein/29725609?sat=24&satkey=45331.*

Genbank Accession No. NM_005228.3 *Homo sapiens* epidermal growth factor receptor (erythroblastic leukemia viral (v-erb-b) oncogene homolog, avian); (EGFR) transcript variant 1 mRNA GI:41327737, submitted on Jan. 26, 2004, retrieved on Sep. 18, 2015 from http://www.ncbi.nlm.nih.gov/nuccore/41327737?sat=24&satkey=6467075.*

Rychlik W, Rhoads RE. A computer program for choosing optimal oligonucleotides for filter hybridization, sequencing and in vitro amplification of DNA. Nucleic Acids Res. Nov. 11, 1989;17(21):8543-51.*

Mendelsohn J, Baselga J et al., "Epidermal growth factor receptor targeting in cancer", Seminars in Oncology, Aug. 2006, vol. 33,(4), pp. 369-385, Elsevier, Philadelphia, PA.

Gonçalves et al., "A polymorphism of the EGFR extracellular domain is associated with progression free-survival in metastasic colorectal cancer patients receiving cetuximab-based treatment", BMC Cancer, Jun. 10, 2008, vol. 8:169, pp. 1-11, BioMed Central ltd., London, UK.

Eisenhauer et al., "New response evaluation criteria in solid tumours: revised RECIST guideline (version 1.1)", European Journal of Cancer, Jan. 2009, vol. 45(2):228-247, Elsevier, Philadelphia, PA.

De Roock et al., "Effects of KRAS, BRAF, NRAS, and PIK3CA mutations on the efficacy of cetuximab plus chemotherapy in chemotherapy-refractory metastasic colorectal cancer: a retrospective consortium analysis", Lancet Oncology, Aug. 2010, vol. 11(8), pp. 753-762, Elsevier, Philadelphia, PA.

Loupakis et al., "PTEN expression and KRAS mutations on primary tumors and metastases in the prediction of benefit of cetuximab plus irinotecan for patients with metastasic colorectal cancer", Journal of Clinical Oncology, Jun. 1, 2009, vol. 27(16), pp. 2622-2629, American Society of Clinical Oncology, Alexandria, VA.

Karapetis et al., "K-ras Mutations and Benefit from Cetuximab in Advanced Colorectal Cancer", The New England of Medicine, Oct. 23, 2008, vol. 359(17), pp. 1757-1765, Massachusetts Medical Society, Waltham, MA.

Montagut et al., "Mitogen-activated protein kinase phosphatase-1 (MKP-1) impairs the response to anti-epidermal growth factor receptor (EGFR) antibody cetuximab in metastasic colorectal cancer patients", British Journal of Cancer, Mar. 30, 2010, vol. 102(7), pp. 1137-1144, Cancer Research UK, London UK.

Amado et al., "Wild-type KRAS is required for panitumumab efficacy in patients with metastasic colorectal cancer", Journal of Clinical Oncology, Apr. 1, 2008, vol. 26(10), pp. 1626-1634, American Society of Clinical Oncology, Alexandria, VA.

Pao et al., "Acquired resistance of lung adenocarcinomas to gefitinib or erlotinib is associated with a second mutation the EGFR kinase domain", PloS Medicine, Mar. 2, 2005; vol. 2(3): e73, pp. 0225-0235, NCBI, Bethesda, Maryland.

Lynch TJ et al., "Activating mutations in the epidermal growth factor receptor underlying responsiveness of non-small-cell lung cancer to gefitinib", New England Journal of Medicine, May 20, 2004, vol. 350(21), pp. 2129-2139, Massachusetts Medical Society, Waltham, MA.

Paez JG et al., "EGFR mutations in lung cancer: correlation with clinical response to gefitinib therapy", Science, Jun. 4, 2004, vol. 304(5676), pp. 1497-1500, Science, New York, NY.

Pao W et al., "EGF receptor gene mutations are common in lung cancers from "never smokers" and are associated with sensitivity of tumors to gefitinib and erlotinib", Proceeding of the National Academy of Science of the United States, Sep. 7, 2004, vol. 101(36), pp. 13306-13311, The National Academy of Science, Washington, DC.

Prenen Hans et al., "PIK3CA mutations are not a major determinant of resistance to the epidermal growth factor receptor inhibitor cetuximab in metastatic colorectal cancer", Clinical Cancer Research, May 1, 2009, vol. 15(9), pp. 3184-3188, American Association for Cancer Research, Philadelphia, PA.

Sharma S V et al., "Epidermal growth factor receptor mutations in lung cancer", Nature Reviews Cancer, Mar. 2007, vol. 7, pp. 169-181, Nature Publishing Group, New York, NY.

Chou The-Ying et al., "Mutation in the tyrosine kinase domain of epidermal growth factor receptor is a predictive and prognostic factor for gefitinib treatment in patients with non-small cell lung cancer", Clinical Cancer Research, May 15, 2005, vol. 11(10), pp. 3750-3757, American Association for Cancer Research, Philadelphia, PA.

International Search Report (ISR), International Application No. PCT/EP2012/065090 International Filing Date Aug. 2, 2012, Date of Mailing ISR Oct. 15, 2012, 9 pages, European Patent Office, Rijswijk Netherlands.

* cited by examiner

SEQUENCE LISTING

```
<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Thr Lys Ile Ile Arg Asn Arg Gly Glu
1               5


<210> SEQ ID NO 2
<211> LENGTH: 25
<212> TYPE: DNA
<213> ORGANISM: Homo sapiens

<400> SEQUENCE: 2

ccaaaattat aagaaacaga ggtga                                          25


<210> SEQ ID NO 3
<211> LENGTH: 19
<212> TYPE: DNA
<213> ORGANISM: Artificial
<220> FEATURE:
<223> OTHER INFORMATION: Reverse primer for amplification of fragment of
      human EGFR gene

<400> SEQUENCE: 3

gggacctccg gtcagaaaa                                                 19


<210> SEQ ID NO 4
<211> LENGTH: 22
<212> TYPE: DNA
<213> ORGANISM: Artificial
<220> FEATURE:
<223> OTHER INFORMATION: Direct primer for fragment amplification of
      human EGFR gene

<400> SEQUENCE: 4

cggtgactta ctgcagctgt tt                                             22


<210> SEQ ID NO 5
<211> LENGTH: 20
<212> TYPE: DNA
<213> ORGANISM: Artificial
<220> FEATURE:
<223> OTHER INFORMATION: Probe for detection of mutation in EGFR gene

<400> SEQUENCE: 5
```

-continued

```
cacctctgtt tcttataatt                                                20


<210> SEQ ID NO 6
<211> LENGTH: 18
<212> TYPE: DNA
<213> ORGANISM: Artificial
<220> FEATURE:
<223> OTHER INFORMATION: Probe for detection of wild-type EGFR gene

<400> SEQUENCE: 6

cacctctgtt gcttataa                                                  18


<210> SEQ ID NO 7
<211> LENGTH: 5616
<212> TYPE: DNA
<213> ORGANISM: Homo sapiens

<400> SEQUENCE: 7

ccccggcgca gcgcggccgc agcagcctcc gcccccgca cggtgtgagc gcccgacgcg      60

gccgaggcgg ccggagtccc gagctagccc cggcggccgc cgccgcccag accggacgac    120

aggccacctc gtcggcgtcc gcccgagtcc ccgcctcgcc gccaacgcca caaccaccgc    180

gcacggcccc ctgactccgt ccagtattga tcgggagagc cggagcgagc tcttcgggga    240

gcagcgatgc gaccctccgg gacggccggg gcagcgctcc tggcgctgct ggctgcgctc    300

tgcccggcga gtcgggctct ggaggaaaag aaagtttgcc aaggcacgag taacaagctc    360

acgcagttgg gcacttttga agatcatttt ctcagcctcc agaggatgtt caataactgt    420

gaggtggtcc ttgggaattt ggaaattacc tatgtgcaga ggaattatga tctttccttc    480

ttaaagacca tccaggaggt ggctggttat gtcctcattg ccctcaacac agtggagcga    540

attcctttgg aaaacctgca gatcatcaga ggaaatatgt actacgaaaa ttcctatgcc    600

ttagcagtct tatctaacta tgatgcaaat aaaaccggac tgaaggagct gcccatgaga    660

aatttacagg aaatcctgca tggcgccgtg cggttcagca acaaccctgc cctgtgcaac    720

gtggagagca tccagtggcg ggacatagtc agcagtgact ttctcagcaa catgtcgatg    780

gacttccaga accacctggg cagctgccaa aagtgtgatc caagctgtcc caatgggagc    840

tgctggggtg caggagagga gaactgccag aaactgacca aaatcatctg tgcccagcag    900

tgctccgggc gctgccgtgg caagtccccc agtgactgct gccacaacca gtgtgctgca    960

ggctgcacag gcccccggga gagcgactgc ctggtctgcc gcaaattccg agacgaagcc   1020

acgtgcaagg acacctgccc cccactcatg ctctacaacc ccaccacgta ccagatggat   1080

gtgaaccccg agggcaaata cagctttggt gccacctgcg tgaagaagtg tccccgtaat   1140

tatgtggtga cagatcacgg ctcgtgcgtc cgagcctgtg gggccgacag ctatgagatg   1200

gaggaagacg gcgtccgcaa gtgtaagaag tgcgaagggc cttgccgcaa agtgtgtaac   1260

ggaataggta ttggtgaatt taaagactca ctctccataa atgctacgaa tattaaacac   1320

ttcaaaaact gcacctccat cagtggcgat ctccacatcc tgccggtggc atttaggggt   1380

gactccttca cacatactcc tcctctggat ccacaggaac tggatattct gaaaaccgta   1440

aaggaaatca cagggttttt gctgattcag gcttggcctg aaaacaggac ggacctccat   1500

gcctttgaga acctagaaat catacgcggc aggaccaagc aacatggtca gttttctctt   1560

gcagtcgtca gcctgaacat aacatccttg ggattacgct ccctcaagga gataagtgat   1620

ggagatgtga taatttcagg aaacaaaaat ttgtgctatg caaatacaat aaactggaaa   1680
```

-continued aaactgtttg ggacctccgg tcagaaaacc aaaattataa gcaacagagg tgaaaacagc 1740
tgcaaggcca caggccaggt ctgccatgcc ttgtgctccc ccgagggctg ctggggcccg 1800
gagcccaggg actgcgtctc ttgccggaat gtcagccgag gcagggaatg cgtggacaag 1860
tgcaaccttc tggagggtga gccaagggag tttgtggaga actctgagtg catacagtgc 1920
cacccagagt gcctgcctca ggccatgaac atcacctgca caggacgggg accagacaac 1980
tgtatccagt gtgcccacta cattgacggc ccccactgcg tcaagacctg cccggcagga 2040
gtcatgggag aaaacaacac cctggtctgg aagtacgcag acgccggcca tgtgtgccac 2100
ctgtgccatc caaactgcac ctacggatgc actgggccag gtcttgaagg ctgtccaacg 2160
aatgggccta agatcccgtc catcgccact gggatggtgg gggccctcct cttgctgctg 2220
gtggtggccc tggggatcgg cctcttcatg cgaaggcgcc acatcgttcg gaagcgcacg 2280
ctgcggaggc tgctgcagga gagggagctt gtggagcctc ttacacccag tggagaagct 2340
cccaaccaag ctctcttgag gatcttgaag gaaactgaat tcaaaaagat caaagtgctg 2400
ggctccggtg cgttcggcac ggtgtataag ggactctgga tcccagaagg tgagaaagtt 2460
aaaattcccg tcgctatcaa ggaattaaga gaagcaacat ctccgaaagc caacaaggaa 2520
atcctcgatg aagcctacgt gatggccagc gtggacaacc cccacgtgtg ccgcctgctg 2580
ggcatctgcc tcacctccac cgtgcagctc atcacgcagc tcatgccctt cggctgcctc 2640
ctggactatg tccgggaaca caaagacaat attggctccc agtacctgct caactggtgt 2700
gtgcagatcg caaagggcat gaactacttg gaggaccgtc gcttggtgca ccgcgacctg 2760
gcagccagga acgtactggt gaaaacaccg cagcatgtca agatcacaga ttttgggctg 2820
gccaaactgc tgggtgcgga agagaaagaa taccatgcag aaggaggcaa agtgcctatc 2880
aagtggatgg cattggaatc aattttacac agaatctata cccaccagag tgatgtctgg 2940
agctacgggg tgaccgtttg ggagttgatg acctttggat ccaagccata tgacggaatc 3000
cctgccagcg agatctcctc catcctggag aaaggagaac gcctccctca gccacccata 3060
tgtaccatcg atgtctacat gatcatggtc aagtgctgga tgatagacgc agatagtcgc 3120
ccaaagttcc gtgagttgat catcgaattc tccaaaatgg cccgagaccc ccagcgctac 3180
cttgtcattc agggggatga aagaatgcat ttgccaagtc ctacagactc caacttctac 3240
cgtgccctga tggatgaaga agacatggac gacgtggtgg atgccgacga gtacctcatc 3300
ccacagcagg gcttcttcag cagcccctcc acgtcacgga ctcccctcct gagctctctg 3360
agtgcaacca gcaacaattc caccgtggct tgcattgata gaaatgggct gcaaagctgt 3420
cccatcaagg aagacagctt cttgcagcga tacagctcag accccacagg cgccttgact 3480
gaggacagca tagacgacac cttcctccca gtgcctgaat acataaacca gtccgttccc 3540
aaaaggcccg ctggctctgt gcagaatcct gtctatcaca atcagcctct gaaccccgcg 3600
cccagcagag acccacacta ccaggacccc cacagcactg cagtgggcaa ccccgagtat 3660
ctcaacactg tccagcccac ctgtgtcaac agcacattcg acagccctgc ccactgggcc 3720
cagaaaggca gccaccaaat tagcctggac aaccctgact accagcagga cttctttccc 3780
aaggaagcca agccaaatgg catctttaag ggctccacag ctgaaaatgc agaataccta 3840
agggtcgcgc cacaaagcag tgaatttatt ggagcatgac cacggaggat agtatgagcc 3900
ctaaaaatcc agactctttc gatacccagg accaagccac agcaggtcct ccatcccaac 3960
agccatgccc gcattagctc ttagacccac agactggttt tgcaacgttt acaccgacta 4020
gccaggaagt acttccacct cgggcacatt ttgggaagtt gcattccttt gtcttcaaac 4080

-continued

```
tgtgaagcat ttacagaaac gcatccagca agaatattgt ccctttgagc agaaatttat   4140

ctttcaaaga ggtatatttg aaaaaaaaaa aaagtatatg tgaggatttt tattgattgg   4200

ggatcttgga gtttttcatt gtcgctattg atttttactt caatgggctc ttccaacaag   4260

gaagaagctt gctggtagca cttgctaccc tgagttcatc caggcccaac tgtgagcaag   4320

gagcacaagc cacaagtctt ccagaggatg cttgattcca gtggttctgc ttcaaggctt   4380

ccactgcaaa acactaaaga tccaagaagg ccttcatggc cccagcaggc cggatcggta   4440

ctgtatcaag tcatggcagg tacagtagga taagccactc tgtcccttcc tgggcaaaga   4500

agaaacggag gggatggaat tcttccttag acttactttt gtaaaaatgt ccccacggta   4560

cttactcccc actgatggac cagtggtttc cagtcatgag cgttagactg acttgtttgt   4620

cttccattcc attgttttga aactcagtat gctgcccctg tcttgctgtc atgaaatcag   4680

caagagagga tgacacatca aataataact cggattccag cccacattgg attcatcagc   4740

atttggacca atagcccaca gctgagaatg tggaatacct aaggatagca ccgcttttgt   4800

tctcgcaaaa acgtatctcc taatttgagg ctcagatgaa atgcatcagg tcctttgggg   4860

catagatcag aagactacaa aaatgaagct gctctgaaat ctcctttagc catcacccca   4920

acccccaaa attagtttgt gttacttatg gaagatagtt ttctcctttt acttcacttc   4980

aaaagctttt tactcaaaga gtatatgttc cctccaggtc agctgccccc aaaccccctc   5040

cttacgcttt gtcacacaaa aagtgtctct gccttgagtc atctattcaa gcacttacag   5100

ctctggccac aacagggcat tttacaggtg cgaatgacag tagcattatg agtagtgtgg   5160

aattcaggta gtaaatatga aactagggtt tgaaattgat aatgctttca caacatttgc   5220

agatgtttta gaaggaaaaa agttccttcc taaaataatt tctctacaat tggaagattg   5280

gaagattcag ctagttagga gcccaccttt tttcctaatc tgtgtgtgcc ctgtaacctg   5340

actggttaac agcagtcctt tgtaaacagt gttttaaact ctcctagtca atatccaccc   5400

catccaattt atcaaggaag aaatggttca gaaaatattt tcagcctaca gttatgttca   5460

gtcacacaca catacaaaat gttccttttg cttttaaagt aatttttgac tcccagatca   5520

gtcagagccc ctacagcatt gttaagaaag tatttgattt ttgtctcaat gaaaataaaa   5580

ctatattcat ttccactcta aaaaaaaaaa aaaaaa                              5616
```

<210> SEQ ID NO 8
<211> LENGTH: 1210
<212> TYPE: PRT
<213> ORGANISM: Homo sapiens

<400> SEQUENCE: 8

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95
```

-continued

```
Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
```

-continued

```
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940
```

Met Ile Met Val Lys Cys Trp Met Ile Asp Ala Asp Ser Arg Pro Lys
945 950 955 960

Phe Arg Glu Leu Ile Ile Glu Phe Ser Lys Met Ala Arg Asp Pro Gln
965 970 975

Arg Tyr Leu Val Ile Gln Gly Asp Glu Arg Met His Leu Pro Ser Pro
980 985 990

Thr Asp Ser Asn Phe Tyr Arg Ala Leu Met Asp Glu Glu Asp Met Asp
995 1000 1005

Asp Val Val Asp Ala Asp Glu Tyr Leu Ile Pro Gln Gln Gly Phe
1010 1015 1020

Phe Ser Ser Pro Ser Thr Ser Arg Thr Pro Leu Leu Ser Ser Leu
1025 1030 1035

Ser Ala Thr Ser Asn Asn Ser Thr Val Ala Cys Ile Asp Arg Asn
1040 1045 1050

Gly Leu Gln Ser Cys Pro Ile Lys Glu Asp Ser Phe Leu Gln Arg
1055 1060 1065

Tyr Ser Ser Asp Pro Thr Gly Ala Leu Thr Glu Asp Ser Ile Asp
1070 1075 1080

Asp Thr Phe Leu Pro Val Pro Glu Tyr Ile Asn Gln Ser Val Pro
1085 1090 1095

Lys Arg Pro Ala Gly Ser Val Gln Asn Pro Val Tyr His Asn Gln
1100 1105 1110

Pro Leu Asn Pro Ala Pro Ser Arg Asp Pro His Tyr Gln Asp Pro
1115 1120 1125

His Ser Thr Ala Val Gly Asn Pro Glu Tyr Leu Asn Thr Val Gln
1130 1135 1140

Pro Thr Cys Val Asn Ser Thr Phe Asp Ser Pro Ala His Trp Ala
1145 1150 1155

Gln Lys Gly Ser His Gln Ile Ser Leu Asp Asn Pro Asp Tyr Gln
1160 1165 1170

Gln Asp Phe Phe Pro Lys Glu Ala Lys Pro Asn Gly Ile Phe Lys
1175 1180 1185

Gly Ser Thr Ala Glu Asn Ala Glu Tyr Leu Arg Val Ala Pro Gln
1190 1195 1200

Ser Ser Glu Phe Ile Gly Ala
1205 1210

<210> SEQ ID NO 9
<211> LENGTH: 195307
<212> TYPE: DNA
<213> ORGANISM: Homo sapiens

<400> SEQUENCE: 9
attagccagg tatggtgatg catgcctgta gtcagagcta ctcaggaggc taaggtggga 60
ggatcacctg agcctgggaa gttgaggttg cagtgagcca aggtcacgcc actgcactct 120
ggattgggca acagagccag accctgtctc aaaaaaaaga aaaattccat ggctctgctt 180
acattatcca tctgatctta catgttgcct attttttcca ttaaaactcc tagcctatta 240
atcatagttt ttttataatt aatactccga tgtgataatg tcttagtcca attactgtgg 300
ttataacaga atgccacaaa ctgggtgatt tataaacaaa agaagctgat ttaggctgat 360
ttagaggctg gggagtccaa gagcttggtg ctagcatctg atgagtgtct tcttgcttca 420
tcataacatg ggagagggca tcacgtgtga agagagctta ctcttataac atagccactc 480

-continued

```
ccacaagaat taacccaccg ccatgagagc catgtgaatt cattcatgag gacagcgggt    540
taagtttcca atatatggac ttttcgggga cacattcaaa ccacagcagt tagttgtaac    600
gttcgtgtca tgtctcattc tggttctgat gcttgtgcag tctcttcaaa ctgcgtcttt    660
gccttttagt gtgccttgca atgtggaaat gatatactgg gtaagaggag ctgtagtaaa    720
gaggcttcta gtgacgtagt gacaagctgt ggggagaggg agtgttgcac agtcctgccg    780
catgtcacag tcttccagtg agcctgtgtc cctggactgt gaacttcatg cttgcttctc    840
agcttcccca gcccccttaga tggtacagaa ctgttggagg ggggtggagt tgtatatttc    900
ccttgctctg ggtaggtcac cctctgataa aacaccaggt taggcctctg gtgaaataat    960
ttctcctgag ggcagacctt ctattaataa tagaatgttc caacctattt caaaatggtt   1020
cctcttctcc ttccactgcc agaagcataa tgagattttc cccctaatat tcgtggtaag   1080
gacctagcag agctccagga ggtaacactc tcaagtgtct catactaccc tgcaccatga   1140
ctgggctctg ctggagttct taatttgcag aactgcccac actgagcctc ccgcaatttc   1200
tcaattacag ggcaaacttt cccagccggc actgggtcct tggaggtttc tgtctgctgg   1260
tttcttcctc tggaggttgt gcttctgtgt ttgcctgtct ctccaatttg gggggcagtg   1320
gtttgcccaa tgacctcaat tctctgaaag agctaagaag aggtgttaat ttttcggttt   1380
gctcagcttt ctacttgttg ctagaatgga gcgccaatag tgcctcctat agtgacatgt   1440
aaccctcaac tctagagatg atgaagcata ctaatgacaa aggagaaatg cttcagcagt   1500
tttctgtcag cacattaccc cttgaaaaag ctgcttcttc cacattctgc aagagatggg   1560
tctcaactca gagctcaagg caaatgactt ccttcaagga gaaggaataa acagtctcag   1620
aaaccatgaa agcctgcccc caggagtgtc cctgaacctc agcaggggcc acacttacct   1680
tgcagaaata ggtgaggcat gctcctggta caaaatccca atggtacaga aggacaaatt   1740
gaaaaacaag tctccctcta aacccctgac cccgagctac ctagttctcc tccctagagg   1800
caaagctgtt accagattct tgtatctcct taacatatat ccttagaaga gctgtcaagt   1860
gaacacatgt ttaagtgaaa acctatttta gaagtgcatt ttcttaagga actttaggt    1920
tggaaggaac ctgtgtcagt ccttaattca caacctccat tagtacttat tgttcttgca   1980
caaaaatctt tctcaaaaaa gccctttcca ctctgacata gcttattcta cttttactta   2040
gctccaataa cttataaaac atatttttga aagtctaaaa tctgccacta tgttttttt    2100
tcctaatcaa tctttacttt gacctctaag ccagagaaaa caggtggtca aatgcctttt   2160
gcctaagatg gaacttagaa tatttgaaga cctcagatct tcaccctgcc aaataacgtg   2220
tttctcctcc cctttcacag agcatttggt tttaggaaat tcagagccac attccttata   2280
gacaagacta aactcttatt caacatactc agaaacttct tctaagagga taaccactca   2340
tcagaggaaa aaagtttctc atgtacagct ggcaaaggga tggaaccatc tgtgttatta   2400
aaattgacag acgcttatga gatttattaa gggaaatact agagtcttag tacatacttg   2460
ctaatatagc atacatgaag gctttatcta taattttttt ggccaagcag aaattttggt   2520
attactcacc ctaacaaatt tccaagacat tatgaaatag aattttaggt cctgacatca   2580
ccatttgtct caggttttga agcgttgctg gacaagaggg gtaaaacacg gctctgcctt   2640
ggattcaaag ttggcctctc atactagcaa gtataccttg gtatcctggt cacttctccc   2700
ggccacagca tcacattgct ataaaaggca gatacaagta ttaaccagct cacaggttat   2760
cagataagct tagtctgacc aatgcttaac acagcaactg ggccactatt gtcattcctg   2820
tggtggtggc acacacaccc agcctctgtc cgggccatgg tctaggacca ccctccacag   2880
```

```
aggctgtgag ctagagccct aactgtgcag ggccctaact atgccaggct acttatctct   2940
cttaagagga cttcattagt gcctgctcgg ccatacagtt ttttacttac caagtaacac   3000
agttatcagc acactccagg tactagccaa ggactacaaa atcaacgtga atgtcagctt   3060
ttgtatcaaa agctcaaagg agaaactcaa actttacata gatgtcccat gaagatgttc   3120
agcaaaccca ttcttctctg ttccctggaa tccatcccag tattgtgcta tgtgtgtgtc   3180
tagtaattct ttacaaaaag ctctgtttct tgtgatgcta tcagatcaca ttgaagaata   3240
tacaagccgt actatgaagg ctgttgtctc atatagtcct aacgtagtga gaactgatgt   3300
tcttacatgc tgtctttttg ggcactcaaa gaaattcctg tacagtctta caaatcagtt   3360
gtagcttaaa ttgatttgtg ttgtgacttg tacacacagg tcacattccc ttgacagaaa   3420
atatagttta aaaccaaatt tgcagccctt gttaagtgaa tgcacaggac tttattgtat   3480
tcaggtcttt tattgtaaga ctcactcctg tcttcatttt atgttccact gttgtgcttc   3540
ccatttgcct ttctctagtt ttgttttctg tgtttctacg gactgctctc agcccaggtg   3600
tgcaggaagc acacacatgc ctgcagagcc ttcatggcct ctgcattcag ggcatgactt   3660
caacgcacag tggctgtact gatttgttaa aacaaaggaa cagattactt ctcctaattc   3720
acagggaagt tccaggttgt gcgggcagtg agcagacctg tgtctgtctg cgcttgccct   3780
ggtgaaaaac cccaccgttc aggctgcagg gtgcgagacc caggcacaaa cattttgctg   3840
gatgaggagg aaagatgtaa ggttgctccc cttcagagac agcaaagggc aggtctgtag   3900
cttcacttac ttcaggattg tgatttttga cagagccgag agatcagggt tgttgaacca   3960
ggcctgaagg tcctagtgaa tctcgtgaag agaggagggg tctggctgta acatggacct   4020
agaggacatt tttactgcag gagaaggaac agtggggatg ggtggactt gccaaaggaa    4080
tatagctcaa gttcctgcag cccaaaaaag ctcagtttct tttggccaaa gcttccgcga   4140
gtttccctgg catttctcct gcgggagcta caggggcagt gggacactta gcctctctaa   4200
aagcacctcc acggctgttt gtgtcaagcc tttattccaa gagcttcact tttgcgaagt   4260
aatgtgcttc acacattggc ttcaaagtac ccatggctgg ttgcaataaa cattaaggag   4320
gcctgtctct gcacccggag ttgggtgccc tcatttcaga tgatttcgag ggtgcttgac   4380
aagatctgaa ggaccctcgg actttagagc accacctcgg acgcctggca cccctgccgc   4440
gcgggcacgg cgacctcctc agctgccagg ccagcctctg atccccgaga gggtcccgta   4500
gtgctgcagg ggaggtgggg acccgaataa aggagcagtt tccccgtcgg tgccattatc   4560
cgacgctggc tctaaggctc ggccagtctg tctaaagctg gtacaagttt gctttgtaaa   4620
acaaaagaag ggaaaggggg aaggggaccc tggcacagat ttggctcgac ctggacatag   4680
gctgggcctg caagtccgcg gggaccgggt ccagaggggc agtgctggga acgcccctct   4740
cggaaattaa ctcctcaggg cacccgctcc cctcccatgc gccgccccac tcccgccgga   4800
gactaggtcc cgcgggggcc accgctgtcc accgcctccg gcggccgctg gccttgggtc   4860
cccgctgctg gttctcctcc ctcctcctcg cattctcctc ctcctctgct cctcccgatc   4920
cctcctccgc cgcctggtcc ctcctcctcc cgccctgcct ccccgcgcct cggcccgcgc   4980
gagctagacg tccgggcagc cccggcgca gcgcggccgc agcagcctcc gccccccgca    5040
cggtgtgagc gcccgacgcg gccgaggcgg ccggagtccc gagctagccc cggcggccgc   5100
cgccgcccag accggacgac aggccacctc gtcggcgtcc gcccgagtcc ccgcctcgcc   5160
gccaacgcca caaccaccgc gcacggcccc ctgactccgt ccagtattga tcgggagagc   5220
```

cggagcgagc tcttcgggga gcagcgatgc gaccctccgg gacggccggg gcagcgctcc 5280
tggcgctgct ggctgcgctc tgcccggcga gtcgggctct ggaggaaaag aaaggtaagg 5340
gcgtgtctcg ccggctcccg cgccgccccc ggatcgcgcc ccggaccccg cagcccgccc 5400
aaccgcgcac cggcgcaccg gctcggcgcc cgcgcccccg cccgtccttt cctgtttcct 5460
tgagatcagc tgcgccgccg accgggaccg cgggaggaac gggacgtttc gttcttcggc 5520
cgggagagtc tggggcgggc ggaggaggag acgcgtggga caccgggctg caggccaggc 5580
ggggaacggc cgccgggacc tccggcgccc cgaaccgctc ccaactttct tccctcactt 5640
tccccgccca gctgcgcagg atcggcgtca gtgggcgaaa gccgggtgct ggtgggcgcc 5700
tggggccggg gtcccgcacg tgcgccccgc gctgtcttcc cagggcgcga cggggtcctg 5760
gcgcgcaccc gaggggcggg cgctgcccac ccgccgagac tgcactgttt agggaagctg 5820
aggaaggaac ccaaaaatac agcctcccct cggaccccgc gggacaggcg gctttctgag 5880
aggacctccc cgcctccgcc ctccgcgcag gtctcaaact gaagccggcg cccgccagcc 5940
tggccccggc ccctctccag gtccccgcga tcctcgttcc ccagtgtgga gtcgcagcct 6000
cgacctggga gctgggagaa ctcgtctacc accacctgcg gctcccgggg aggggtggtg 6060
ctggcggcgg ttagtttcct cgttggcaaa aggcaggtgg ggtccgaccc gccccttggg 6120
cgcagacccc ggccgctcgc ctcgcccggt gcgccctcgt cttgcctatc caagagtgcc 6180
ccccacctcc cggggacccc agctccctcc tgggcgcccg cgccgaaagc cccaggctct 6240
ccttcgatgg ccgcctcgcg gagacgtccg ggtctgctcc acctgcagcc cttcggtcgc 6300
gcctgggctt cgcggtggag cgggacgcgg ctgtccggcc actgcagggg gggatcgcgg 6360
gactcttgag cggaagcccc ggaagcagag ctcatcctgg ccaacaccat ggtgtttcaa 6420
aatggggctc acagcaaact tctcctcaaa acccggagac tttctttctt ggatgtctct 6480
ttttgctgtt tgaagaattt gagccaacca aaatattaaa cctgtcttac acacacacac 6540
acacacacac acacacacac accggattgc tgtccctggt tcaagtgtgc caagtgtgca 6600
gacagaacat gagcgagtct ggcttcgtga ctaccgacca taaacccact tgacagggga 6660
aacatgcctt ggaaggttta attgcacaat tccaaccttg agctgcgcgg gttccaagag 6720
ccaggcccgt acttgctgtt gatgtcattg gcttggggag ttggggtttg gtgcccagcg 6780
cggtcgttgg gggaggggca aggcatagaa cagtggttcc cagaccttgc tgcacattgg 6840
aattacctgg gattaaaaaa aaaaaaatca aaacaaaaac cagtgtctgg ctcccgcccc 6900
cagacattct gatttaattg gcatggggca agacctggac ttgggatttt ttttaatgct 6960
cttcatgtga tctgttgggc agccagattt ggggatcact agacggaaga aggattgtta 7020
aagtctccgg agatgttact tgccaatgct aagagctctt tgaggacatc tggaattgtt 7080
acaatattgc caaatatagg aaagagggaa aaggtagagt gtgattccaa taataaagga 7140
ttccgctttt cattgaagga actggtggaa aggtttcttc tctgctgagc ctgcaggccc 7200
gtcctgcctg cctggggtgc ccgggagacg cgggcctgct ccggagactg ctgactgccg 7260
gtcctgttag tcaggtgtca gccctgtctc tgccgaagag actcttctct ttattttaaa 7320
ttaaaccctc agagcaccac caaagcatca cttttctccc tccattggtg ttctcattct 7380
ttgatgttac ttgtttgaac accactatta gtagttggag atttgttcct gagaaaaata 7440
taaataccac ttaatttgcc tgtttgtccc gcattcactc aaaacagaat gctcctgaag 7500
acaagagaga gagtaggaga acagacgcta ttccattaca gtaacataaa agactggatt 7560
ttcaggggca aattattaaa ataggagatg agctctttta acagaaattt gtttaaggcc 7620

-continued

```
tgtgtctatc aaattcagtg gattttattc aagatgcact ttgtttagtg ggagttttgt   7680
ttggttctgg gacatgctaa cttctagact tgctgctctt agaggtaatg actgccagac   7740
accatttcat gagtcctaat ccccacatta agcataagag gtgcacactc tcctcctatg   7800
ggggaaactg aggtacgaag aactaaagtg actttcccac agctggtggg aggcagacgg   7860
gaaattcaca ccaggggctt ccaactccag atccctctct caacttccaa actccactgc   7920
cttgtccgag ttctggtttc aggagatcca aatcaggtgt gtgcaaatgt ctaatgtcag   7980
agctggcaag gggaaagggc ccagggagcc ggctcatgac gatgagcctg tctgaagctt   8040
caacgcgggc tgtccggcag tctgcattcc tgccgagttc ctcagccctc tgttgggtca   8100
ccttccatag aggcagctta gtcctcagtt cagtgagcat ggagtggaga ctgcttgagg   8160
ggtgctgagc aaagccctgc ctcttacagg atgaaggtgc tctccagaag ggacactgga   8220
aagtattcca aggcgagtcg aattcccaac tgagggagct ttgtggaaat aagcccgccc   8280
agccccactt ctggagacgt tcccattcag taggtccgag ctgtcttaaa gagaaaccaa   8340
agtggggata ttaatggtat ccaaagtgag atctacccca ccctccctcc tcaaaggagg   8400
tcagatcaag aaagcccaag cccggcctgg caattgggac ctttcttctc actccagccc   8460
agggtgaagg tggacaagtc actttgaccc ttcaggcttc tgagctgttg tttctgaatt   8520
cagtgaatat ttactgagtg catagaatat gctagatatt ctgggctaaa ggttgaaggg   8580
ggggtgagtt ttaagggttt ctgctcttgc ttccagattg ctttcaaatc tggaaaggac   8640
accagtggtt tgtgtgttag acccacactg ccgtagcaca gaatacaaga aactggctga   8700
gagctccaat aggcttttaa cagtaatttc tggcttcacg tatttagttt cataactcat   8760
gatttttcaa aaacttctgg tttgaagaca ccgattgccg aaagtccatt gtgctgcata   8820
attacacttg gtccacgtga cagcactaac atgttctgaa atgtttttag aagtagtctc   8880
agcaaagatg aaggattcct ccctgtttga aaagaaaata ttctttgttt tttctttgat   8940
ctaagctcta agactagcag ctagcatctg aaactttttt gacgagagtg acaaaccaac   9000
tctaatatta aaggcaattg atgattatgg gcactgaagg gaaggtaacc ccaggctggt   9060
gccccggaat agggatgggt cacaatgttg aggacatttc gcctgttgca gaacccacct   9120
gcaacacagt gtggcccttg ccatgtgact tgtgtgtgtg cctgtgtgtc tgtgtgtgcg   9180
tgttttaatt ttgacttcat aagtactcta gttatgagct tatttaacat tgggttttac   9240
taataggggt atgtgttgag aaaatttcaa agttttagaa tatggttcac ccacatgttg   9300
cttccctgta aatataattt ttaaaaccag attctgggcc gggcatggtg gctcacctct   9360
ataatcccaa aacgttggga ggccgaggca ggcgaatcat gaagccagga gtttgagacc   9420
aggctgacca acacggtgaa acccagtctc tactaaaaat acaaaaaaaa ttagctgggc   9480
gtggtggcag gtgcctgtaa tcccagctac tcaggaggct gaggcaggag aattgcttga   9540
acccaggagg cagaggttgc agtgagccaa gatcgcacca ttgcactcca gcccgcgcga   9600
cagtgtgaga ctccatctca aaaaaaaaaa aaaaaaaaca gattctgttc ctcagatcca   9660
ttccattttt gttttccttt atcacttatg gacatttgaa attatggtaa taaacattgt   9720
tagtctcagt taattattac tggtttattc ttgaaccact aatccataga gaatagagtg   9780
taaatcttaa cttgttcctg taggccatcc ccattaaaca tcatagtgtt ttctcattcg   9840
ttctttttcg ttttcctcct acaggaatga attttctaag aaaattccag cagttggctc   9900
tttggacgac atctctagat tgtcctccat tgggcccata ggcacaagct ggccagtttg   9960
```

-continued aatttgggca agaatccagg cattggaact tattcaaata actagtttgc ctgtaatttt 10020
cactttttca gagtcatctg ataaagcttt cttgctacac atttagatag atacactcaa 10080
tccagttgtc tagaaagttc cctgagccag ctgggagcag gaggggtagt tggggccagg 10140
aatattgggg gtgtgtttac tgagccccta gaaagtaagt gctagatttg acatttcaat 10200
ccctgaaggc cctgaagttc agtatcaaat gactggtcct gtggactgag catctgtgaa 10260
ttgcatatgc ttagagtaaa ttttactcct accagtttca gcagcttgct ttagcaagca 10320
gtatggaaac actaacatgg gggagtagaa tttctctctc tgatccaagt tttatctcat 10380
tctggtgggt tttcaaggag agactcggag tccaagtgtc ctttctgaat atatctggaa 10440
cttctcatta acaaaagact caagttataa tttaggggac aaggcaccca atgagaatgc 10500
cttgcaggca gccctaagta cacctgcaat tacaccatta ctagcgcggc agcacacatg 10560
gccctgactt agtttaaata attacgtaag tcaaccatga ttgtttgccc tttgcataga 10620
agggcaagta ttggtacctg ttacaactta ggcttttttt tctttatgtt tgagccatga 10680
tgagtgattt acactgttgc atccatatgt tgagatgtaa gaataaatta gacttggtaa 10740
ttgcccttaa gtgtctggaa gtcaactggg gaaagagagc tagagataat aagtgtgaaa 10800
caatgtcaca gaatcaatga cggaactctt cccaggacaa aggatgactt ttgagttcag 10860
tctttgcctt taattctaca tggggaggag agcacgttta gccacaaatg gaagggatta 10920
ctcatttgag ctatttggtt atatgattat ttccccagag aataggatgt gcagggcatt 10980
acacaagcag tgccaatagc agcaaagttc ttgagagtgc tagtaattca aatggcagga 11040
agagaaggaa taaatggtaa ggctacctac agttcacaga gagctccatc ctcactgtgg 11100
ctttggattt tgtcctgtgt gaaagagaag tgactgtgaa ctgacatgct gtgtttggtg 11160
ttttagaaag atggctgcag cagcggtttg gggaatggac tgcaggagtg gcattggaaa 11220
caggaaggtt catgactatt gccagagaca gaggatgaag caggagcaag gaagattcag 11280
gacaggggac tccggggctg atcaggaggc agaactggtt gataagtata tgtagcagca 11340
taagaaagaa agaatcccag attgacaccc aggcttctca cttggaagcc tggatagata 11400
ctgaatgcaa tcacaaaggc tgggaagtca atgggactgc agggaaggga agggaaggga 11460
ggagaagagg aagggcagga gggtccaata tcaatattca gcttttagat gtgttgagct 11520
tgaagtgctc agatggagaa gtccaggagg cagtagaata cggtggtcca gagcacagga 11580
gagcaatgtg gcttgagttg tcatttgctc acatatttcc gtgtcagtta cttgtcttag 11640
atcacagaac aagttctcct ctcacagttt cctggctcca cctgtctcat gctcaccgtc 11700
agcatcgaaa ttgagccaca ccaggggttc tggataccag cttctctcta ggtgaggctg 11760
ctatagtcag cagctgatta gttgcagtta tcagcaactg gtaatataat atattgtgca 11820
tataagtgta ccagaagtca tgtttatata ttgctgcaaa tactcggaat ggggatctct 11880
tgttccctgc ttaagaccac atcacattac ttggttttgt acgctagtgg ctgaaccaaa 11940
aaaagtagga gatgattttt tttctttttt cttaaagcag tagcttttga accttgacca 12000
tgctttctaa ccagctgagg ggcttttgaa aaagagggtg ccttactgtg ccccagacca 12060
ggacaatcag tatttctggg gaatggagcc tggcacacac acatttctta aagctccctt 12120
ggcaattctg aggagtggat tacatgttgt atgtagctcg taacgaaaga aatcttgtct 12180
ttgctctcag acccccattt cttactcatc tcatgagctc cttcgagatc cagaaacagt 12240
tgcatatttc attagtaaat cagttccaga gtcacatttt atttcacaag ttagtccatt 12300
aaaagtttcc tgcagtgagg aaatagccag aaagaacact ccacccctcc tcctttttat 12360

-continued

```
aactataggg tctggctcga cagagcagga gcatcgccat cttggacaag cccctcattc  12420
taaagttcac cttaataaaa aactgcctaa attcaaactg catcagccta atggctaagg  12480
tcagcatgac cataaaccac aaataacatc tccaaccgga aacattcgaa actcctcctc  12540
gaccagagac atgctagtcc cgagataacc cccctccagc agggaagatg ccagtctcgg  12600
gataacctct ctctggccgg aaagatgcct gccccaagat aaacttgcct cctcccagag  12660
atattccaac cctgccataa aacttctccc tcaaacagga acattccaaa attctgataa  12720
tctccctcac cctaaaacca atatatactc ctagtctgta agagaaagcg ctcttgacca  12780
aaattcacca ggagtgcctc ccaggtttta actaaagaaa acctctcttt aactgccaaa  12840
aaaaaaaagg gaaaaaaaaa agctttctgc agtggctttc agcgggccca gcatggcagc  12900
agcacctgag aacctgttgg agatgcacac tcttggaccc caccctggcc tctgagtaag  12960
acactggaag ggcaggcccc ggtctgtgca cacaagtcct cagggagatt ctgactgatg  13020
catgccagat tttgagaact gctgatatac tccaggcaca tcgcatgctg ggatctagat  13080
acaccaaggg aacaaaataa ctgcacttgt cctctgagga ccgacttacc ttttggaagg  13140
gctgagaaag agagacacat acaagatcac tccctgtaat gcaatgtttt ataacagatg  13200
tgatttggga tttcagtggg agcccaaaag agggactgac taattcagcc tctgtgacaa  13260
ggggagtttc tcagaaacag aatgcttagc tgggcctcca ggcacaggga caggaatgag  13320
gaaatacttg taggccctgt gctccttcag caaaaccctc agtttcttgt tatttttata  13380
aatgcaaaca tcttattaaa gtagatgcta aggcattaga atttcctgct ttatttttct  13440
aaatgaccat gaggaaacct ggaatgtcaa agataaagtg caacacattc tgcatttaaa  13500
aattaaaatg atccttttta aaagtagcaa ccagatgtga aaaattggac tggagtccag  13560
gttatagttg atagctttaa ctttctcccc aacagcaaca gcacaatttt ccctaaaatg  13620
tgttatgaat aagtaaaatg actacttcac atcctttaac tcttcctaca gaaatctaag  13680
agagaaatga aacaaaagtt tgcacagttc tagacacgat aaatacatgt gaaatcacac  13740
aactcagaaa atgtccctta aattaattga gccattggta cttgtgaatt agaagagaca  13800
tctatgttct gatccactgt tgaaagctgt acaatgttac ctatttattt gcagacatcc  13860
tttggaaaca aataggtaga tttgcaacaa ataaagagtg gagtacagct gctgacatta  13920
ccttgtatat tcatgccttt atgtaaaaaa aaaaaaaaaa atatatatat atatatatat  13980
atatatatat atatacacac acacacacat atggaggtaa agaccactgc ttgctttgca  14040
gttgttttaa gagcattcat gaaggatttt attttataag cagaaatgtg atatctgacg  14100
attttaccac tacatgcttg caggccagtg cacagcagat gacgtcatga ttgttttagc  14160
agtcctatcg ttttacttat gatgtcatta caaccctttg ctaaaatttc tttcctttac  14220
tccaggtttt ggataaaatt gatgcattgc acatagtctc tctgataaga caaactggca  14280
tttgtatgtg aaaaactgtg catgttttag tgtctctgct gatactcaaa ttatccatta  14340
ttttagtgct ggaataaaaa caaaccactt agtgaatttg tgcaggtcct taaggacagg  14400
caaaggtgtc ctgagatttt ctgatcattg tataccaaat tttagaaact ttttcaaaaa  14460
catttttta atttcaaaaa cctggttttg tttatttacc agcaatcatt gaatacctga  14520
aagctttcag gagattttat tacaatggtt tctattcact tacaaaatta tctcctagtt  14580
cattctcata cactgtaagc cattgtaaat gcttcaaatt gtgccgaaca agataaacta  14640
gacaaactat tttaagtttg ttctagtgct aacttgcaag atctaatggc tccaactaga  14700
```

-continued

```
tttttaaaat aaagtatatt ttaatatatt attagaaagt taagcaatta tctgtttata  14760
ggtaacaaaa accctggaac cccaatgtca gatgtcatcc acttttgatt aagtccaaac  14820
atatgacaga taaacaaaag atggttggct gggctcagtg gctcatgcct gtaatctcag  14880
cactttcaga ggccgaggcg ggcggatcac aaggtcagga gtttgagact tgcctgacca  14940
acatggtgaa acccgcctct actaaaaata caaaaaaaac agctgggtgc ggtggcacgt  15000
gcctgtagtc ccagctactc aggaggctga ggcaggagaa tcacttaaac ctggaaggca  15060
ggggttgcag tgagctgaga tcacaccact acactccagc ctaggcgaca gagcaagact  15120
cagtcaaaaa acaaaaaaaa agtggtcatt ggagaattat tgtgtcacct gttgtttttt  15180
aatgtactaa ttttgagagg cttttaaata gagtgcacta tagaactttt tcttggcttc  15240
aatttgctac aatgttaata gagaatcaga aaccttatcc ttatagatgt ttcttgattt  15300
ttttaatttc tggtgacatt tatgagtgag aatagtgtat tgccctgttt tctttcttac  15360
tccccttttct tcttccttcc ttgctttctt tcttcttccc ttccttcttt ctcttcctcg  15420
ctccttcttt tttacaagct gttatgaatt agccttcaca gagaaagaaa aatttttata  15480
aataactgga aatgaaactt tgcaaaggac tgcagatgaa aaactttgtc aaatgactgt  15540
aaaaatatac tatataattt tcaaaagtta gaaagtacca aacacactca gtattcatgg  15600
ttatacaagt atgcatacac atgtattgct ccctgaaaag tggtgttgtt aagggagttt  15660
ttcttagtac gcggcttaac atattttttt ctgtaatttg ttgttagtta taatggggag  15720
agaaaacagg ttagagtctc ccctctcagt ttcaccttcc ataaaacagc taaactagac  15780
gatcgtcaga ctccttccag ctgaaaacat ctgtaaaatt aaaaacaaat ctaaatgtat  15840
gcaagatatg tatttaaaca tgctggtaat aagtgtgctg tccctataat ttagatgcta  15900
aaacattgat gtcataataa taacaacacc tcgcatttgt acagcacctc atagtttaca  15960
caatgcctta acattcttct ctctcagcct cctacaaccc cacaggattg ggatagcttt  16020
ccagattggg aggtgaggga cccaggctca gagcgattct gctgttgtcc gtaatcacca  16080
ggctggtgat cagtgggcac tgggtgctct cctgctacac agcactgtct ctcaacatgc  16140
aggtcaaggt tacttattcc tccttcaaga cgtcattggg ttttttagct atggatgccc  16200
catcactttt agttctattt gtgaatcaaa ggctaaataa agtattcctc aaaatttgtt  16260
atacttctgt tactaatgct taatgtccct cacaatttct gtatatttct gtgtatttct  16320
gctctgtttt ggttcctttc ccaggtttct tttttgttat gaagtagttt ttagactcaa  16380
gtctcttctg tatgtgttat aactgcccat tccataagat acagggcagt gaatttgtga  16440
gccttgaaaa tatttacttt agaaatgaga agtatgactt ttcaacgttg tgtcatcaac  16500
ttctgtaaat tttccagacc tataaatact tgcagaaaaa aaatgaaagg agaaggcaac  16560
ttgatttagc agttgggtca gttagcaatg cctatggcaa gctgtagtaa ttcccttaca  16620
tagatttgta agactcattt ctatgattta aatgaaggca tacacttaac ctctttaggg  16680
tgtgaaacag cttttacaaa aagagacaaa cttaagaaac agtgtggccc tccaagagtg  16740
ttcattttcc atatcatacc atttgtaata agctattctg gctgggattt acttgcaagc  16800
attggctttt aagaagagat ggtttcacac atcaaattat tcacttggag gcactttctg  16860
ggttgaagga atggaatgga gagtgcggca gtgagtagat ctctcagtga cggtgatgtg  16920
cctctcccag aagaaatttc aaaatgcagt gttcattttc ctccacaaga aaggaagaaa  16980
ctgttttgtt attgtttatt cctaacatag tggaaacttt tcagtactct ggcagaaatt  17040
tcccaaaagc aattttctat ttcatgatta taaagtagca aaggaaaaag tcctgcactc  17100
```

cagctgagca atggatctcc agttgttatc taggtgctgc aggtttagag aggattgcca 17160
ggagaacaca tcgatttttc aggcctgtga tgacgtatct cttgttgaat aagtaaaccc 17220
ttccagtaaa cagacagtta gtatattgat ttcagggtgg ctttagccac tgaacctgta 17280
agtcttgcaa aggttacttg ggcaaaagca tcattatttt accttcagtc aacaaaaatc 17340
tacctggcca aggcagaaca gaaagttcag caatttgatg aagtgggaca acatgaagaa 17400
tcaggtgagt tgcctacttt ttcacttcac tttccacctt tagagattct tgtttagatg 17460
cagagtagtg acgtgcctgg tgtcagggag agagttgaat gagaaaagtc ccagaagggc 17520
agaagacttg ggtgattatc tgagtccatc tttccttatc acatgacaga gttcttgaag 17580
tcttggctag gaattctagg cttttagatt ctttgggcaa tggctactaa atgttcataa 17640
tgttgctcag ttgcaaaaac aagacattca aactatagcc agggagataa gtagtcacga 17700
actcaaggcc taaattctgc tgatggagcc gatgagaatt gggtgctaag gcaaagagag 17760
ttgccaatat tatattcttc ggggtttttt gtttttattc gcattttgga aaaggaaaat 17820
attagcattc ctctgactta atattgagaa gacattgggc actctttttc ctcccacact 17880
tgtcttcttt cactaggtga caagggaaga ggtagcatga ggtggtggtc acaggtgaga 17940
ggggctgttg tgagcacagg catgttgact gcacattggt cacctagtag aagttttgca 18000
ggcttggtga cttctgaaca ctgttttcaa ggttgatttt tagttgagag aacctctagg 18060
taccacgtaa tgttattaac agtagtactg atctcacaat cgccctatgt cccattcaca 18120
agatgttctg ccaagccata aaaggcccag ttaagtttaa gagaagtctc aaaagtaaca 18180
gatgataact aattaatacc cagtgatttt gaaatgtaga catcaaacat accaattcag 18240
tggtatcatc cttagaggca gacagaggat gattaaatca ttcagcccat ctctgtctga 18300
ggacgcagct tagcacagca tggtggaggc taaatgggcc ttaagggaaa aaatgatatc 18360
tgaagatgca atttatttca aaaagagttt gctcccgtga attttcactc tctatgtaga 18420
acggcaccag cacacacttt tcctgagcct ttgcatgtgt ggcaggcagc ggcctggcat 18480
cctggggaac tgaatgagga cgcagatgac ccggacgtgt tcacagtttg acacatctga 18540
ctcccagatc agggacagct agctttgctg gctggttaag ttgatgattc catctttgcc 18600
tggttctctg actgtctcat gctttctgtt attactattt tgcagcagat atttctgctc 18660
atttttcaat catatatgca tcctggatgg catagagttg attctcctaa caaatcagtg 18720
tccctttgta tttttttctg gccataagat agaatatata tgtcatttat taaaaatgga 18780
gaaaatgttc aggagtttct tgactcagag agggaaaagg gatactcagg gcactttttc 18840
agccaggaat ttactacctt tgcagggtaa aggggactca ccacgctgga agtcaaaata 18900
agccaccagt gccaagtgtt caaagccctt agaatcacaa tgctcttaaa gcaaagtctt 18960
caacaatgct tgaaaacttc cactggttct cagtatgtcc aaaattgtca tgtctatgaa 19020
tgattttctc aatctgaaaa tttttatagc aggctaaaga atgagatagg tcagtgtgat 19080
tctagaacta atcattaaca ttcaatagat gactatttta ttctagaaaa agcagcaact 19140
ttctatttac tctctatttt gagggtaaat tctctgtaag tagaaaaagc aaaatgtgga 19200
catgggacta acatatgaat atacaaagca aatgtaccga aaaaatctta agacctgcct 19260
tgtggtgttt tttgttttgt tttgttttca ttaaagtgac ttgttagcct cttgctccct 19320
gtgaagcaca gggaggtgac gtgatgtgca cagggcagac tctgccatat gccctggcct 19380
tgaactcagg gccccctggg gactgcaggg gatgctggcc atgctgagca atgcctgtgg 19440

```
gtgtcagttt cctcatctgc agaatgaggg taggcctggt gcttatttca tagggtcgca  19500
gaggggattc agtgacaggg tggtgtagag gctggagcgt gccccatgtg tgcacgacag  19560
ccttccaact aggggaggcg ggcctgggct ctcaccagag agcctgtgtt ctccatggct  19620
acatgacttt gccccagacg tccttcccgt ggtctggacc ctgggaagtc gccaagagcc  19680
agacaggaga aaggctccac ttggctctcc tctttggtga ccatcccttg cctccatggc  19740
gggactctca ggtgacatcc caccaaccct cactttgctt ccctggtggg tctcactttc  19800
cctcaagagt gttgcttttt tgtttcctgc atagtcctgg gccagttttg ataaccctct  19860
tcatttcact tcagaaaccc tgatgatttc ttcctgtgct ctttttacct taggactttt  19920
actatgacga ctgtgactgg cccatttctt gtttttttc tcttgctctg ctttctcccc  19980
catcatcact aaagcagaca tggcaatgat ggccatgcac actttccaag ggtccagctg  20040
tagatcttca tggttcccca ggtgcctgga ccatcttgtg aggagggagg caaacacacc  20100
ctgcctggag cacttggccc tttcggcaat gttttggctt cctcaagtga gaaaagaatg  20160
gatttgtatt ccccctctgc attattgttt ttgttttgtt tgtttgtttt gttttgtatt  20220
gagacagagt ctcacttttt tccccaggct ggagtgcagt ggcccgacct cggctcactg  20280
caacctccac cttccgggtt caagtgattc tcctgtctca gccccctgag tagctgggac  20340
tacaggtgcc cgccaccaca cctgactaat ttttgtatgt tttgtagaga cagggtttca  20400
ccatgttggc caggtgccca ttattatttg atctggaatt aactgagcta ctgcaggaat  20460
tgcttgattc actgatgact ggtgttgagc cagtacacac ccacacccaa ggactgtgac  20520
tgtcttctga ggtccatcct cagaaattcc tgtctcttca cctagtgtgt aataaggcct  20580
gcgcgtgtta tatggaactg taaaaaatgc gccaaccatc tgtccttcct ctttatctga  20640
ttacttatca ttgttctcta agttgcaagt taatagactg atcataaatt aatgcatgct  20700
ggagacttgc tgtttcctac tagcagcata taaaagttat ttttaaagtt gttttaaatc  20760
tgtgagtaaa aataaattgc tttgctgcaa gaaacaccaa acatggaaaa gctaacggtt  20820
caaagttaat aatttatctt atggacatca ctagtggcat agttgcttta aacagtgaga  20880
ggatttaata gatatttgat ttgcaagtgg gatgaagggt ggtctaacct ttgtcctgtg  20940
tttaccttcc atgagatcct agaggttgta cagcacagta gtggcatgtg acacacttga  21000
gagtgcctgt tctgtttgga aacctggaaa ctatgaaggg aagtggcctt cgagcttaac  21060
acataagact tgggaggcaa aaccttttat tctctttaaa tattcacttt aggataagca  21120
ttttttttagg tgttaggaac agggaaaact gtgtggttag gaaggaagaa agaagaaagt  21180
taactgttgt acattcccta ggtaatgttt ttaagcattg ttattcactt tcaaaacaca  21240
ttttatttat ttggacttaa tattttgatc ttattttttc aatttctttt aatttaacag  21300
acaggatgag ttttttata gttgtattac ttagaaatta tactaaaaat ggccgagtgt  21360
ggtggctcac acctgtaatc ccagcacttt gggaggccaa ggcaggtgga tcacttggat  21420
cacttgaggt tgggagttca agaccagcct ggccaacata gcaaaacccc gtcttcacta  21480
aaaaaaaaaa acaaaaaaaa aactagccac gcatggtggc aggtgtgcct gtaaccctat  21540
ctactaggga gactgagaca taagaatcac ttgaatccag gaagcagagg ttgcagtgag  21600
cagagattgc accactgcac ttcagcctgg gtgacagagc aagactctgt ctcggaaaaa  21660
aaaaaaaaaa aggataaaga aatcatacta aaaacaaaac agaatgctga ccaccttata  21720
gaaatagaaa tagtggtttg ctgtgatagc aaattttctt gttaactttt tatttttaaa  21780
gaattgcaca ttcacaggaa gttgcaaaaa atctactggg aggtcctatc cccttcccc  21840
```

caacctcctc cagtagtaac atcttagtag caaagttttg tatatttatt ttgatatcat 21900
tatctaagtt tgacatcatt atctaatatt aacctaagcc aaaagcccac tattttaatt 21960
atctagtgat gcagtgttat agaactcata gcctttcaca gcattatttg gaagttaatt 22020
ttcttaagtg aaatgttttt ggtctttaag gtttggaggc catggaggca tgaggagaaa 22080
tgggatgagg gagagagagc taagatagat aaagacagag atggggagat ccactgattc 22140
gttgaacaaa ccagatactt ccttatagtt tttggattaa cttacatgag ctaagtttat 22200
attctgttca gatcacaagt ggtcaagttt gtgtgtgtgt gggggggggg gggtgggtgt 22260
gtgtgtgtac cactctaccc atcctatatt tattgtcctg tatttggtct gttctgcctt 22320
ctttattttc aggataggtg tcctaaatga gggtctttgg aaagctggtg aggccatgtt 22380
gcccgtttca ggtgttccgt gctcaaatgt attcatttct tgaaaaattc agggagtgca 22440
cacttttgta cattttccta tgtgtatatg ataccattat ataaatctta aaaatatata 22500
tggttcacct gaatccccag ccatttggta gagaagatag aaaacctaca gaggaggcta 22560
agattttatt agaaaattca gcttctcgac ggaggtattg gctttaaagt caaggcaatg 22620
catctattct ttcttttgat ataactagct aaaagatctc ttaaattcaa agtggccctc 22680
atcttactgt tactgcaatt tactcttaat tacaaattat ataaaaatag gttttgaaat 22740
actgtagcga caaagtaaca tacctctgct ccattacaca gataaaacct ctaaggaaca 22800
cctcctctct taacaggcat taaccaactg cagaaactgc agaaggacag ggctatttgg 22860
gaataacaca gctcccttcc ttgtctgttc cctcccattg tcaggcttct gtggagccat 22920
attcagagca acatagggag ggggaagaga aaatcaaccc cttggtgaag gaaagctccc 22980
aattcacaga gcaaacatgg gtactcttgt ttgtgggagc tcccagggcc tcccagctca 23040
ccgagcattc tgagccctga tccttacact aattgtatta tgcaaccata aatgatgtct 23100
gctgtaccag cggggacagt ttattttaat agattggtat aacttggcag aatcttatct 23160
gcatgtttca tcttggattt ttagctcaat tcaactcaat aggcatgtgt caaatgtcta 23220
ctgcagactg agcactgaaa agctgctggg tacagggtta catggataga aaacgtagcc 23280
tctgacccct aaggagcctg taatccagat ccccattctt tccatcccat tctcccaagc 23340
aagaatttac ctaatgtggt ttgcgagaat ttaagagctg gaaaggtggt cacgagaagc 23400
cggaatgggt tcgctaaaat gtgtctatat gattaagcat aacgtagctt tgcagcactc 23460
ttcacagctt cctcagagcc ttccgcacgc ggtgtctcat ttgaatactt gtgtgaggat 23520
agcctcatac ccctcagtga gctcttcatg gagtgatgca gtagacagca agcctcacac 23580
ttctatgctc acggaagacc aaatttgcct tgaaaaatct ttatagtctc ttcacatttc 23640
taagttgaca tcaaaaatcg gttaccataa aatcctaata gttgaagaga tgtaatttca 23700
attatttggt aaacctgacc ttcattgtca aagcaattag tcaactcaga tttactttct 23760
cccagataat agattctgac ttcttttttt ctgattaaaa aacttaacac cttcctcagg 23820
agatctatct cagttctgaa tgctgattct aactaagaag gatatttggc tacatgctgg 23880
gaagaggggt actgaggcac gccgcgattc cactccagca tttccagtta gtcgggtgcc 23940
tctgcactcc cggtgttccg gcgcccagtt agttgtgtac tctgggctgt ccctatactg 24000
gagtcctaaa acacttacga ctgcagatag ggggaggttt ttcaaaacct tggtctgaaa 24060
agccatagaa gggagatagg aaagcggggg ggtggagcca cagtacattc aggtggatcc 24120
gtttttggaa atagtacaaa ctggaggtga aaccctggaa attgatctgt cgttcacatg 24180

-continued cttcatgccg agtccttgtg gacccacaga gacacactcg ccccagtttg aaggctgcta 24240
acttgattct gaggacacca gtgaggtggt agtgtgcaaa tgatgtgtga ggaaactttg 24300
gaggagtctc accctgcctg gagcacgtgg cccctaaaac agcgcagcct cccaaagaca 24360
gaagatgtgg actagtgaga agccaggtat ggtgactgct gctggatgaa gcttgtccca 24420
ccagaggctc gcttgtttca ttgagcacct actgtgtgct tgtgggatgc aaacacacgt 24480
gtggtccctg ccctcaggtt aataggcagg ggtggaacag ttatgaaact gctctaaagt 24540
cattttctca aactgggagt gacaaatgta tccacttgga aaagattgag aattttataa 24600
gatttttaaa tttttgttta ttcacattga ggagaatcta aattcttttg aacttatgta 24660
tagatttcac cattttatag taataaatca gtcctcctgt gtgtgtgtgt gtatgtgtgt 24720
gtgtgtgtat gtaaacctca ccttgcaata ttattatttt aaatagccac ttgcatctta 24780
aggaaattaa gaggacaaaa gaaaagctgc tgttttgtat gtatccacat atttaccagc 24840
tgcttccctg ccggcaggtg ctctggttct gcactgcctg ttgtcccttg cctgaaaatg 24900
gttgcctcca atattttgct cagttttctg attgtttaca gtggcagagg agggtagatc 24960
tggtaccagt tagtaattgc cagaggtgga agtctgtgga tgaaatttgt ataacatgga 25020
acgttagttc cacagttaat gctactcaat tggaacccat ggaaattatt ttttggtgaa 25080
aagggcccat gcgttatgaa atttgagatc catcacttta agtgaatgta ggccctggat 25140
acagtgggag ctcagaagag caaatcagtt ggtcaccttg ctcaacgtat tttactaagg 25200
gcatcagtaa ggctttctat gacctgctcc ttcaatgctt ggttgacatt tggggagcaa 25260
agataaacta aggattctaa gttctgtcct gtgatgctgt aaggggaatc tcaaacctct 25320
aggtggagga gtgcagagat gaccaggatg gtggaagcct gcaggagagc tgaacacctg 25380
aagacaccca gtgggaagac caggaccttt aacgcccata tctgctgctc aagactggca 25440
gagagaagag ggtttgtgat gagaaaaggt ggtgaaaggc acaaggaggc acagagcatg 25500
tcaggtccca tatcccaaaa ggaatgtgct tgggtgaggg agagctcctc catggctgga 25560
ggcattcaga gaccaggcag tcgcttgtgg gtttgtgatt agagtgaggt tcttttataa 25620
agggagtgag aagagaaggt ctgtggatac ttgagtgtat cggtaattaa gaaataaatt 25680
gtgtacatcc catttctttc cacattttcc tgggctgtca cagtggctgc aaagaaagca 25740
gtccgtgaac tgaactgtga tcccagacag gcaagcacac caggaatctc ttctcagctg 25800
ttgataatga gggagcgctg gggagagaaa tggggtcctc tttgagtttc ctctgtgccg 25860
ataccttttct ctttgttaaa acagctaatt aaacactgaa gcagtatagc tctcttacta 25920
tacactggta gtcatagttc tcttactgtt ctcttcactg acagttctct tactatacac 25980
tgatggtgac gcagaaattc agaattcccc gcatgtgtcc cggtttgaaa gccactgtgc 26040
tttgctgtgg attaggatca gacagttgag tcttgttcca acaaggaaag ttgcttattg 26100
gaaagttttg ctgcagggag ccttgagttc tgcatcaggc ttggaagtgg gctctgtgga 26160
ggtcagaagg aggatccccc acccgcagcc tcaagaaaaa tatgaaaagt ggattatgcc 26220
tctgtagcta tattgcctat aaactttctg cagaatgaca gtattcatat cctacatttt 26280
ttcaaagcga tattaatcct gagacctgca gctaaagtca agtagaattt agggataatt 26340
aataggagga aggtggggtt ggaagatctg catgattata gtcctctgat ataactggaa 26400
aattctttcc attagcaagg agctttggtt aatataaaat ggacagatta aacctaggca 26460
atttatttta ctcattgctg tatttttatt tcagagctgg ttgaaaatat tacaaagtaa 26520
tattttaaag tgcttatcta aactcttact ctgcatttta tcattgggtt atgaaatgac 26580

-continued

```
tggggaaaga cttttcttgc ttttatttct cagtgtctac ttataaacat gtttttttgaa  26640
ctactgtttt tgtgacaaca tgcctttttc ccagaaaatc tcaggttaac attaaatagg  26700
cactggatgt ttatctgatc ttgtttatag aaacacaaga aaattttaac cttgtatata  26760
ctttactcaa ttaactaggt aagaggtcat tgaaacattt agaattccac tctacatttc  26820
aataattatc aggtgaaagc tactgcatct acatcagaag atgtttgtaa tttatttaag  26880
aataaaatta gctatgcaag aaatagtatg tggagtccta tgtggaaatc acagaaaccc  26940
tgacaacttg atgatctttc cgcaagctaa aaatatcact ctggatcaca gcagtagagg  27000
actctgtaaa tttaatctgt gtgtctcctg taaataagtg cattagcagt acacaggtgg  27060
tgtcagagtc agtgatgatg gatagaaatt ctacataaaa tccaggctca gtggctcatg  27120
cctttaatcc cagcactttg ggagtctgag gcgggtggat cacctgaggt caggagttcg  27180
agaccagcct ggccaacatg gcaaaacctc gtctctacta aaaatacaaa aattagctgg  27240
atgatggcac atgcctgtaa tcccagctat tcgggaggcg gaggcaggag aatctcttga  27300
acctgggagg tagaggttgc agtgagccga gatcacgcca ttgcactcca gcctgggcaa  27360
aagagcgaca ctccatcgca aaaaaaaaag aagtaagaag ttttacataa aaacgtggag  27420
tgagcccaag gtgccattta tccagcccat acacatcgta ccatgtacag agtggacacc  27480
agataaatac attgactgca tgccacaaac atatatatgt aggcaccgtt gcattcaaat  27540
acacatctgc agccctaaca catctttatt tgctaacgag catcaatgta tttaaaaaca  27600
aacatgttta aactagtgaa tgattagatt ataatgatct taattcataa gttttctcat  27660
tggccttttg tatacttcaa ttgtaatacc tagaaaaaca gttatgtcca aaggagtgaa  27720
taggccttat ctgaaacagg tgagcgtgac aagtgttttc ttacttattt tacttttcag  27780
ataattcatc cttaaagtac attagtttaa aagtactgtt taaggaaaca gtacttggat  27840
taaaacttga atcattgtta aggaaaacta taccttaact tcatgtaatc acaattaaac  27900
ctcttcatat agaaggatct aagaattttc tgcagcattc accagcacca aaaagctcag  27960
agacatatat ttctttctct gtatatgtat tttaaattca agttagtata aattgacagg  28020
caggtcagag taatatatga tcttctgagt ccccttagta attaaaagaa atgattattt  28080
ttgcatgaaa tatgataaag tgattttaag tgcctgataa aaagtcttaa ccatgacaac  28140
cattaaagat tacatcaaag aaaaataagt ttgactttca tttaccttgg aaacagctat  28200
taactggtaa cctcaagaaa caccatgaag agtcagtttg ctccacacat gtcttgtaaa  28260
agtcaaataa ctggtggtta tccagtaatg acaagaggta gaagttacat ccttgctgtc  28320
tgattgaacc ttcccagagc tggcacaagg ctgggaagac cataggtgct aaatgaggaa  28380
ctacttaaag aaagaaaatg gaatttcacg gacaagaaaa tccatgtcca tttggttctg  28440
tgacccacat cctttgtatc ctatgctttt ttacacttgg tacatggttg caagattgcc  28500
cctgttttct acttatagtt ccatgcagca tggatgtggg aaaaagtctc ctctgcaaag  28560
ggggttaatg caggtcactc tacgtatgtg cacgaggtcg ttataaagct cgaaaatatg  28620
ggctcaccaa ccaggtgatt tttttaatta tccaaccaga agacataaca tataggggaa  28680
tcaaaagaaa tctctgagta aaataatgat aacaggtcaa actttgcggt cccacgtgag  28740
gctggagatg cgtattgtct tgactttgca tctacaagtt taacaaatga tgctttctca  28800
gtttacctct ggaaatggaa attagcattg caaatgactt catgaggagg tagaagctat  28860
ctgtgaattt cctttcgctg tgtttacgat agactctcac gtctagatgt gtcatgtatt  28920
```

atgttaaatt ggtatgtctt gaagttataa agcacagccc tctataagta tatatattcc 28980
acctctttca aatcggatgg tacctatcct tcaaactgct atttaatgac tgtctgctat 29040
gttcaaggca ctgctctcaa tgttaatact tgatgagatc gggcgcgttc aaggtggcat 29100
ggccgtagac tcaatgttag tatctgaaat atggcctacg agctgagttg tgaatcaagt 29160
taatagattt tcggaatgtt aaggtctaaa ccagtagctc ttaactgaga caatcctgtc 29220
ctcatctcac ctgggagaca tctggcaatg tttggagaac cttttggttg tcacactggg 29280
gcatctagtg agtagaggtc agggatggtg gtaaacaagt ttttttgttt gtttgttttg 29340
tttttgagac agagtctcac tttgtcaccc aggctggagt gcagtggtgt gatctcagct 29400
cactgcaacc tctgcctcct aggttcaagc aattcttatg cctcagcctc ccaagtagta 29460
gctgggatta caggtgtgca ccactacact cagctaattt ttgcattttt agtagagacg 29520
gggttttgcc atgttggcta ggttggtctc gaactcctgg cctcaagaga accgcccccct 29580 tcttggcctc ccaatatgcc gggattacag gtgtgagcca ccgtgcccag gctaacattc 29640
tttaatgcat aggacagccc ccaccataca gaggaatccc cagcccagaa tgttaatagt 29700
tctaaggttg agaaacccaa ggttaagcca agtcaactta tctatcttct ttaaaattgc 29760
ataagaatgc agtcctgttc ttcattcctc ttgctttgca gttaatgatc ctttgcctgg 29820
actttctaag tgcccagaag agcaacagcc agcatgcagg atggcattcc tgaccagttg 29880
cacttggcct agcattccaa cctcacctgc ctcagcttgt tcaacctgaa aacctaccaa 29940
gtgaaagcaa gagccacgtg aagacgcctt agttatatgc acccacccag acacttgctc 30000
agaaaggaat cagtggggcc ctggccttag aaactggctc cttcactgct gtagaaacaa 30060
cataaattta acataaaaca cgtgcttttc ttttttcttc ttactttttc ctgtcttggc 30120
aatgcaagga tgccattagg taaagaaatc cttcaccaca ctaatcctgc agagccagaa 30180
gagaaaccag cttgttctaa cccagctttg tcatggagag aaggcagctg ctccagtctg 30240
aactattctt tcttttggta gcagcctgcc caagggtgaa agtgtgttta atagtttgaa 30300
ttacacaagt gaacagtaaa tgtatgcctg tttctgcttt atgggacttt gaaataatgt 30360
tgtttgtgcc aaggttttag attactatac ctaacaacct agaaaaagaa atgaaaagga 30420
agccttctgc caggcagagg tcactacggg cctggagctg ggcacctgac tcagcagctg 30480
cccagatccc cagagctgag aagtcaccat gcatttgtgg tgcttcgagc gagttaccag 30540
agtcctggaa cagagcagca cacctgcggg gtgtcccctt ggcatttggg cagggcaggt 30600
gaccaagggt cttgttggaa ctgaagtcca gcttgaaaag caaatctggt tgtgagctag 30660
agtccagtaa cacttgtttc ccgccgcccc ccgcataact cgtgtgtcct aaaatacaat 30720
aatttcttga acttcagtca cttatgccta taagcgggca tacaacaggg gcacaataaa 30780
tgtttgttaa gtgaatgaat tctttcagaa ctagatggga tcttagtcca actctcttat 30840
ttaacgaggt ccacagaggt tctgcgattg tctaagaaag aaggctgtgt tcatggcctt 30900
tgttgtttac gtggccctgt gattctcttg gctccgtgaa agtcctgatg cagacattcc 30960
ggccatctag aaaggcatgc agacaagcca tccagctggc atgatcctga gtccagcttt 31020
ctttaaaaga gcttccaaaa ctgcttaagc tttgactgca caaaacctgc atcacctcca 31080
gttgagaaac tcaagagaat aagtaagtta tggagttgga gaccccagct taactactag 31140
ttttaaaata gtgaaatcaa cattttcaaa tctttgactt cactaagatt taataaagtt 31200
tattaatcat atattatgag ttattgctct ctctttatgt ctgtaatgca gttgctcctc 31260
tctgtataaa ttaataagtt ttagagatcc aaaatgagaa ttttaaaata aattacgtat 31320

-continued

```
attttaatca agtttaattt gactatatcc agctaaacaa ttgattgaac ttcacttgct  31380
tttctatgac aggtttttg ttcttagtaa aagaccccag ttttctcact tgtgaacaga  31440
aggggttaga cttcatgaca gctaaggttc cttccgtctc taacaaaagt ggcctgaaga  31500
gaggcttcta gactatactc acggtgggtt cttgggacct cagagtcagc tccatcactt  31560
aagtggctgt gtgattgagt ggagacacct caatctcttt gtgcctcagt ttcctcacct  31620
gtcgagtgtc aacatgatgg cacctaaagc tgttgagact tcagaaaggt aatgtgtgaa  31680
aagtgaaaag tgcctggcat ccaggaagta ctcaataaat accaactatt ttattgctgc  31740
agctgttctt atagatgtga tttctagaac attgccttct aatagggtag ccatgggcca  31800
caattgttgg ctgttcggtg tttcacatat ggttagtcca aactaagatg tgttgtgagt  31860
ctcaaataca cactggattg tgaagactta ggacaaggaa aacaatgtta ataaaatctc  31920
attgataact tttaaattaa ttacatgttg aaatgaaaat atttgggaca tattgagtta  31980
aataaaacag gagattaatt tcttctgttt ctttctactt tttttattag tgtggctact  32040
caaaaatgtg acattatgta tgcatctcgt attacatttc tattggacag cagcgctcta  32100
gacagtacta tgggtagtat ctgtggggag gttctcagaa acatgtcgca tgctctttta  32160
gaaccttaaa gtattcctag tctcctctac ttccagccct tggctcttgg gcctcagtct  32220
ttttactttt gcggctgtgt ttctctgaag gcttggcatt agtagattga aaagaataac  32280
catctaggga aatgtgaatt cagtttcttt ctgacattct gctctctaca aggggatatt  32340
atgtacacat aaacctactt ccaaaataat gaagtgaggc ctaattcctt actcttcaga  32400
gagcccactg tggaagtgtc actgaccttg tgtatgggct gcccttcatg gctctgggag  32460
tcattataaa gggcagcatt tggcgtggtg cgtcctaagc cagtgtttct cggctctgtt  32520
ccttagacat gtgttagtgt taatagatgt tcttggaaaa aaaaaaaaaa aacagcattc  32580
tgaggtcaaa catgctcaga aagcttggaa tctgcactac gcttctcgta cacatttcat  32640
attaaagatt ttggaaagtc ctgcaataca gagccctgtc taatattgcc acaacccaca  32700
attgctcaaa tgtaaataga tttgagttta ttcacattca gatcacctct taaggcccca  32760
cctcccaatg ctgtcacaat ggcaattaga tttccacatg agttttggaa gggacattca  32820
gaccacagca ggggaaagca gggtacttgc tgctttgcaa gtgtgtccac atctaattaa  32880
tagtacagtt cttactcttg gtgtgtccgg tgatattaaa aattaatgtg ccttatttag  32940
ataagtaaca taaaaatcac aaaatgtatg ccttagattt atatgtattt ataactagtc  33000
tatttcctga aaacagttga gacaccttgt aaaagttacc ggtacgatag ggccattcca  33060
acaaagctgt aaagtggtga taacacagtc ataaagaaga ggagatagct ctgggagaaa  33120
aggtggccca gaaaccagct ctgagcctca tggctgcagg caaggtctgc aggttcctgg  33180
tcctgattgc aggccatttg ctgccttgag tggtggttac acaaggccag ccctgggggt  33240
atcacccaga acacctagta cacgaatttc agtttagagg acgaagcatt actggagtat  33300
tgttatgcag gaaaactttt tcctaaaaat gccctgaaaa gagagtagcc taatgcattc  33360
aatcaaaatg tttttaagtg gaaaacatat tgtgtgtact tgatctggcc tgctgctttt  33420
aaaagattaa aactgggact gggcatggtg gctcacacct gtaatcccag cactttggga  33480
ggcagaggca ggtggatcac ctgaggtcaa gagttggaga ccagcctgac caagatggtg  33540
aaaccccatg cctactaaaa atgcaaaaag ttagccaggc ttggtggcgc atgccggtaa  33600
tcccagctag ttgaggggct gaggcagggg aatcacttga acctgggagc cggaggttgc  33660
```

agtgagctga gatcgcatca ttgtactcca gcctgggcaa caagagtgaa actccatctc 33720
gaaaacaaac aaacaaacaa aaaaacactg gggccaaaga actctgtgtg ctgtatcacc 33780
taaccacatt tcatgacacg gctagagaag aatcatgcaa ataaaaattt ccaacatgtt 33840
cgtaaactgg gaaagtattt cactggggag tgagcagaaa agtaatacta taacctctat 33900
atctagacaa atgtgaattc agtttcacat ataaatatat aagtgaaaaa atatataaat 33960
ataaataata tgaaataatg gttatctcac cactttctac atcttttgtg aatattttat 34020
agtgctcaaa tatattagtg cactagtata tgtacattac attaaataac taatcattta 34080
ttaggaggat gtgcttgttt tttgctaata aagatgataa taaaaaaatc cttagacccc 34140
ccctcggttt gttttcagtt aggaattagg gatatttata agaatatctt taaatgacac 34200
atgccttgct ctgggacgag gcatctgcat gggtgacaca tatgtgttgt gtgtacaggc 34260
tcccagcatt tccagggccc tgctcagaat gtaggcctta ctgattctta cagagttaca 34320
agcgctggtg aggttggcga agtttaggta aacacagctg ggaatgcccc atggcctctg 34380
ggtgactttg gacatcactg aactttaccc ttagagatgc atacctgcat ctttttttacc 34440
ctgatagggc cttccatgat gctttcaaag tgtttttgtc tgcttttcgg ttaatagact 34500
ttcacagtag ccaattgaat atattggtta aatgcatctc tttatacaca gactggattc 34560
aaactgaggt tgtgtctctc cctggctgtg tgacgttggg tatgatccaa gtgtcagatt 34620
actcaacttc aaaatgagga cagagccttt cccttctagg gctgccagga acattgaatg 34680
agagagtgct ggcagcttag tacaggtgtt cattgctctt gtatggtact gtctgtggca 34740
cggctagata aaatacagta gccactgatt caaatttcaa ctgaggagta aaataaactg 34800
aataacttag aaaagttttc ttcttttgaa tgactctaag aatttaagga gcatgtgagt 34860
gttgatggct ctaaaagggt aacagagccc aactagctca gttctcagca tgaaaatagt 34920
catatggcac agactcagtg gagtgggtgc acttcaataa ctggaagcac agatgcccta 34980
cagcagcatc aaagatggca ctctaaacta ctttcaatcc tttaaaataa atggaaacgc 35040
acatttagta tgcatatgac aacacgaagg acttcgattt tgctgatgca atacagtttt 35100
acaggatttt ttatactcaa attagtaaaa ttctgtattg catccaaatt ataaattata 35160
atatcatcta gattggacat aggaataacg accactggta tctgcccaga aagctctacc 35220
gcctgtttat aagctcctgc aggagacaca aaaagaagag aatttgaata taacttgaaa 35280
tgaccgtaat ctcctgcccc aactcatttc attaccaaac cgcctctttc ttcattattt 35340
ctcctgaagc acaaatctat agagaactca gctgccagtc tctcccactg cactcagcag 35400
tgaaagggtt aggcctaggc ttttcaaaca gaccagtgct tgtatcagcc cttaaacatc 35460
tctggagaag gaaatgggat ccttctttgg taattcattt ttgacagttg gggattaggt 35520
gttctgtatc tggggggcct tgctgtcttc tctcctcctc ctcccactgc agaccctctc 35580
ctcccctccc ctctccagct ctctgatgac tgcttcatgc tccttccacc tgaggactgc 35640
cagcacagcc tattgcagga acagccaatg aggggctggc tgtgctcttt tatttataaa 35700
attataaact caagcaaaat ctagactatg tgtccccaag atcagaggag cacaaatccc 35760
ttgcttacag attgcatggg gggcacattc tttaaaattg gtccctgatc tagactctag 35820
cctgagaatc atctttaagt tcagaatttc cactcatgac ctcacatctg tgggctccca 35880
cattgtcttc caaaacacac atggcatctg gcatcacctt cacccccacc ctcagagcct 35940
catctccctg caggtagata gtcaaggcaa cctcttcact cttctgccaa gcctcctctc 36000
ctcagctctt cccttcctct ctctttttga aaatattttt aattgtggca aaatatacac 36060
aacataaaat ttaccatctt aatcatgtat aaaagtggag ttcagtggca ttaaatacat 36120
tcacgttgtt ctatagccat aaacaccatt catctccaga gctcctttca tcttgcaaag 36180
ctgaaactct gtccccatta agcaatggct ctgttttcct ccgttccccc agcccctggc 36240
caccatcctc agttttctgt ctctgtgagt ttgattactc taagcacctc ttataagtgg 36300
atcatacaat gtatctgtct ttttgtgact ggcttgtttc actttccata atgtcttcaa 36360
ggttcatcca cgttgcagca tatggcagaa catctgtcca tttccaggct gaatggtact 36420
cttttgtacg tgtggaccac atttcattta tccattcatc cacgggaggg cacttgggtt 36480
gcttctgctt tttagctatt gtgaataacg ctgctatgaa catagctgta tgcctttgtc 36540
ttttaaagcc caaatctgat caagtcactc cccagcttaa aaccttccac tgctccccag 36600
cagtgggata aaggccagtc tcccctgtag gtctctcccg ccagccctgc tcagtcttct 36660
tgcttgtcat ccttggctag gccttgcatt gccatagccc tctgcctctg ttcacgctct 36720
ctcatcttgg agcatgagcc ttccatcatc tctaccagat gaactctcat ttcttctttc 36780
aaaaaataaa aaacccaaaa aacccagaga tcccaactgt cctggtgtct gcatagtctg 36840
cagcacacgc cccctccatg gcccttcctc cataagcaga atcactcctc actgttcctg 36900
cagcacctcc tgtgtgccca cacagctgtc ctgcggtggg ctgtgtgtgt gagtgtgccc 36960
cctctaggac ctgagctcct tctggagggt gggcacagca tccattcatt ctgggaatcc 37020
tggtcggcac catgctagaa cttctgcaag tgagtgcctt tggtgctggc ccatgggaga 37080
gctgttggta aggcatactt ttgcagattc cagttgctgc tgaggttgtt gctctttgca 37140
caagtttctt ctagtcacca gtgaagtgac atgtgtggca ggcatggccc agggaggctt 37200
tttcataaag aagaggttga atctttgggg ctgtggtttg aatatgtccc tcaagcttat 37260
gtgttggaaa cttaatccca aatgcaatag tgttaggagg tggggcctaa tcacaggtga 37320
ttaggtcata aggctctgcc ctcatggatg gcttaacatg tttagtgagg cagtgggtta 37380
gctattgtga gagtgggctt gttagaaaat tgagtgcagc cccctcttgc ttgctggcta 37440
ccatgctctc ttgcttttct gccttctgcc gtggggtgac acagcaagaa gaccctcccc 37500
agatgctggc accatgccct gggactttcc agccttcaga accacgagcc agacaaattt 37560
cttttcttta taaattaccc agtctgtggt attctgttat agaaacacaa aatggactaa 37620
gacaatcttc tttcatcaag ttagggtacc aacctttaaa gactgccagt ccaaggttaa 37680
aggaaacttt tcaagagcag tccaaacatg atctggccct cagctactct ccagggtcat 37740
gccaccctat cacccactgg ctcacacaga cgctgaccac tgcttagttt ctcaaactga 37800
agttttcctc ctcagagctt ttgcaaaacc ttttctttgc ctggaaaact ccccccacaa 37860
atctttagtt gtaggttcct tctcatcttg cagaattatt agtttgctct tcaaatagtc 37920
tctccagcta gactatcaac tccaggaggg cagagttctt cttcgcttcc ttcacccatg 37980
tgcccactga gtccagaact gtatagcagt ttgattgaaa aaatccacag ggtggaggat 38040
gagaggaccc tggatcccag cctcacagcc tcttacttca cctgtgtgat tttggtcaag 38100
tcctttattc ttcctgggct ttagttttcc cttatctaaa atatgagaaa agttcccctc 38160
tcctgggtat tctgggagac tcatgtaaaa ggcactgagc cagtgcagca catctatgac 38220
caggaagggt cagcttcctg ccttgcatga gacacacatt cccttcttca tgcacagtta 38280
ttcatgagtt aaatatgtat tgagaagtgg gttctcagga gatgatgcat ccacagcatt 38340
gtttgtatgc ctctgtcttt gatgtccctg cctgagtcgc ccactttaga gcccttctgt 38400

-continued

```
tcttcagaaa ccagactttt ctttcaatag tttcagtaat caatcgatca atcaatcaac  38460
caatcaacag tgataataat catgagtgag cccctgcccg tgctggctgt gtcctgctga  38520
aggcacacta agtgctgccc ttcccagaag cctcaggaag cttgcgaagc tcaggtgcat  38580
ggatgcctgg tggaatgagg aagggatgca gccaggtaga gaaatgccct gccatcactt  38640
gcatcagcat ctgtgaagag ctggccaggc ttttgctcac agtggttgac acagtcaagg  38700
agcaagggcc ccgtaggaga ggggagtcaa gggctccggg tgggaatgga gctgggggct  38760
gatgctggct tctggagcac tgtaatgtga ctgagaaagg tgaaggagcc gttctgaaaa  38820
agaagaaggc aggagctcgc acagctcttg actcatcttg acttcttttt cctgcttcat  38880
ccaagcaggt cgactctctc gtgatctcag agacagagtg aagtcatgag tgggaggga  38940
gcacagaaaa taagaccttg attcccagca ttgggagact ccctgctccc ctgagtctcg  39000
gaaaatagca cccttcaaat gttttaggga tccagatttg atgaagagat gttattttgg  39060
cttttagatt cttaggagag atttgtcttt ctcaggtcag gaagaaaatg ctgcccgctg  39120
cacattcttc gggacagact cttttaatta ttactagttt aatgtatgtt ttgcttagtt  39180
aaggaaaacc cctgtggttt cttgacgtgc ttcagtattc taactcacag ctgattcagt  39240
tcagggggct ggggagatgt cctcgacctc tggaaaggag ggtgcatctc tagaaataag  39300
gctaagtatg ccactgacac tgtctgcata aacgtgtgtg atctcaggtc caaaggatgg  39360
ggcctggtct aagccaggga cgtgggaaat cattttcctg tggcaacttg tgaagaccat  39420
tctgtgacct tggtgtctct gggccttctc ttagattttc taagttggct agtcagtgga  39480
gctgccatcc ctcctttgcc catgttctac tcccagagtt cctccaagaa attgcggagc  39540
aatgcctgtt tcatgagagc tgagtttgct gtgtcttcca cttagaaaca acactgtgga  39600
ccaggaggac acacagctcc cagggccatc accacacaaa gtgaaggctg gtgaatccga  39660
ggcttctagc ccttgccggg ccaggcccgc agcactccgc tccccaaccc agccgctgct  39720
ttgtcgcagg aacctcagca gggcagggtg tttcctagga ggacatccga ttcccagcca  39780
ttcctttcag tgaatcacct gagctcacat tcttttttct tttatttttg aagctcttag  39840
ccaatctgct tcgcgatgaa ccagttttgc ttgaagcaga caaacccgat tgtcaggaga  39900
cagtgatgat ttcttcagtc tctgaggaag agttttcatt ttccccaatt cgcaaaaaaa  39960
gtcaggtccc tccctccctc cctctccgta gaatattttc catgtgtgtt aacaatggct  40020
gagcgtggta gatgccagga atttctgtca accctcaaag aggaaagccc tgcctaatgg  40080
tctgcccgtt cttgttcact ccctgcccca ggctccccac ccgccttctt tctggaaggt  40140
ataaaggctc ctgcttatac ctggcactgc acgcttcgct ccctctgatc tcctgactgt  40200
catgcccagt gtctcagcct atcattctac ctctaactcg accttgagtg accttgagca  40260
agtttctcag gattccacct ccaagtcact ctccctttgg gatatgcagc actaagttaa  40320
gcttgcctgg aaaacatcac ttgaagctgg aaaaccactt ttaacacagc gggaaaagct  40380
atttgttcag acaggagtgg ggtgggtctg ggcagagcac tgctctaact tggccatgcc  40440
gtggcagcag ctcctttaat gccacttttt cctggcgcgc ccgcggggcc tggagctcag  40500
aaagagggga acgctccctc gtctctcaac agttgctcca gacaggtcag caaacatgga  40560
attcagaatg ttcattaaac actggctgtg tcttttgtgt tcaaaagcaa gacactctct  40620
ctgaaccatg gccccacaga gagtgcagaa tgtgtgaaac ctgccgggaa ggtctggacc  40680
ccttgcgggg cagtgggcag caccgtgcct ccgttcacac cactcacatg gctgtgcctc  40740
tgcttccttc tggcatggct gcttcttcct caggtctcaa ccatctccct cagatgctct  40800
```

-continued ttcccatgtt tgtggctaca ggtccccgtg acctgcagag gcagagcact caccagcagc 40860
ccagcctcgt tgcgcaccca tgtttgcatt tgcaggccct agaaccactc caagctccgt 40920
gtggcgagat gcaccctcct gcccttcact ggggagctgc cctcctgttc acagcggcac 40980
ctgagtcaca catctggagc catcctggac tgcctcattt ccccgatggg gggtttccct 41040
gacttcatcc atcctgtctt ttgggtcccc ataataactg acatgggtcg gcccgtacca 41100
gcccctgtga gaagggcttt aactgccttc ccaccccctg ctcatcttag agtctctcta 41160
tagtgctgct gaaagaatct ctaaatcagt ggttctcaac ctcagccgca cattgagaat 41220
cacctgggac ccttaaaaaa atcttaactc ttggtccaag aattctatta caatcggtct 41280
gggatggggc cctacaggta ttttttaaa gctctccagt tggtaatgca tagctagagt 41340
tgagtatcgc tgttctaacg tgcagatctg gtcatgttac cagcctttta ggtggtcttc 41400
tttggctttc tctatctaaa gttcaaaacc gaacatgtgc gcattcagtg cacccatttt 41460
caactgtgca ttaacacatt cagcccacca gcaagattta tgaaccattt tctgctgttg 41520
tatataacat atcatatgca taatggcata ggttattgtt ttcttcaaaa tatatgagat 41580
gtgagtcctt ctacgaactg actcacactg attgcccaac ttcctctctc gaggtctcat 41640
cctctttccc tgcagccgtc tccctcttgc acgcacacac acacacacac accacacaca 41700
cacacacacc acacacacca gggtcgatgc catctaccct ggacttcatc ttgaactcct 41760
tcgagtgtga gtcattactc ctttgtgcac ctctgctttc tcttctcaag atgttcacct 41820
gcttgaggtc agttccttga gcgtcttcca cttgccatgt tcaccacagt gctcaacatg 41880
cctgaatgca tggatggcga cttctcagat cctcagtctc ctcatctggg taataaggca 41940
ttgggttggc gggtccatct ggtttcttcc agctctgaga gtgcatttgc tctgtgattc 42000
attcgttcca caacacttca ccaattaaag agagggtaca aaaggtgaac atccttggct 42060
cccagcagat gctcctcaaa acctgaaaaa tcagataggt gagggaagat tgaatgaaag 42120
gcctcttatg attctgcagc aattttggtg gtttaagaac tctatggaaa aatcatcagt 42180
atttctggaa ttgaagtaaa atggatagtg agcctctgtg tatgtgaagg cccgcatctg 42240
gaacatgaaa gaacctgtct gatgtgttct agtcaggaaa gcaggtagcc aatactattt 42300
atagaattta cagaaactga agattttgtt tctactgatt ttcaaaatag tattatgtct 42360
gatttttttc ctcagaaata tacttcctgc tcttctcaac aaactcattt gaaaatatga 42420
ttagaacatg atagaatttt actcatttgc caactgcggt tcccatttca catattgtta 42480
gaattctgca tggtggcttt gccctttaac cactaactga taaatgatgt agttagcttt 42540
taaatgtgtg gaaaaatata atttcaggtt caaccatagg tcagaagtac acgtgttttg 42600
ttagtctatt tgtctctcag tcatctcatg gaaaattctc agcttttggt atggaaataa 42660
ttttcttgaa ggcaatattt gttgagtgac tgacggaatg aaaaacgcca gttgcgtaag 42720
tgtgaaaaag atctgggtgt tttcattgga tccaaattcc acatgagcca acaacagcgt 42780
ggtgtggagg ctggagcaca ttaataagaa cagtgtccta aattcaggag gtaatgctct 42840
gcccatgccc tgtgcagctc agacggtgtg tgcagtgcag tatgtaaccc agggcacatt 42900
tcaggggccc acagggagct gcagcttgta aggtggagtg cagccaacag agcagagagt 42960
cagaatcccc gcagagtggt tgaaggcaca aggatgcgca gcaaggaaga cagacttata 43020
ggtggtgcga ctgccatcct ctggtactga aggtgctatc atggagggag ggaagtagat 43080
tgaccctcct ggctccagag tacggaactc agacaaacgg tcagaagctt acagggaggc 43140

-continued

```
caattttgga tcaactttaa gaagaatttt ttaaaagcta gagcaatcct aaaatggaat  43200
ttgctcttta taaagttgcg aatgcctcac cctggaattg cttaagcaaa gttgggacgg  43260
gcagttgtga gtaatctcct ttccaatcca tacccgcaat caccagaaac gtggacttcc  43320
ctgacactga gcacctctta attaagcatc tcataagtga acaaaaccca gcccttcaaa  43380
gaagtcactt tatttatgtg tgggtctgca gcttggattt cttgataatg ttaaataaaa  43440
ctccatctac tcttccacaa acacttcaag aaacctaaga cttttggcca gagtaacacc  43500
gaggtttgag agaaaggata tgtgtgtgag aggtgtggtt tcattagaac atattatttg  43560
acttcatgtt gaatcaacac ttttgtgcaa aatgcagttt taccagcctc tttccttgtt  43620
ttggtcacat aatttaactt aacattctcg gtacttgatt ttctaacata aaatgggatt  43680
gagaggggaa ttttgaagtt cccatggtct gtcctctaca ttctgacagc tcattatctc  43740
tgcggtattg ttctcacatt taagtgaggt tagcggaggc agaggcctct caggcctgaa  43800
gatagcctct gttttcaggg aaatactaga ctgtgagatc tgtgacactg aagcactaag  43860
ttcatctcac aaaagcaacg tgctcttttt aaatggttga tcaaagttac tttcaaaagg  43920
aagtgttagt ttttgttatt agccgaaaca agagctgctt taatgtagta tatttaaaat  43980
catatctcaa ttaagatgtt attcaaatac tatttgaccc accaatctca ttactggata  44040
tatacccaaa ggaatagaaa tcattctatt ataaaaacac atggctgggc acagtggctc  44100
acgcctgtaa tcccagcatt ttgggaggcc gaggcgggtg gatcacgagg tcaggagttc  44160
aagaccagcc tggccaagat ggtgaaacct catctctact aaaaatacaa aaattagcca  44220
ggcgcggtgg caggcacctg taatcccagc tactcggaag gctgaggcag gaaaattgct  44280
tgaacgcggg aggcggagtt tgcagtgaac agagatgaag ccactgcact ttagcctagg  44340
tgacagagcg agactctgtc tcaaaaaaaa aaaaagaacc acttgcatat acactattca  44400
caatagcaaa gacgtggaat caacctaaat gcccatcggt gatagactgc ataaagaaaa  44460
tgtggtacat atataccacg aaatactatg cagccataaa aaagaacaag atcatgtcct  44520
ttgcggggac atggatggaa ctgcaggtca ttatccttag caaacgaata agaaaagaaa  44580
acaaaatacc gcatgttatc acttataagt gggaggtaaa tgatgagaac acaaggatac  44640
actggggcct acttgagggt agagggttga agggagagaa gcagaaaaaa taactattgg  44700
ggtactaggc ttagtaccag ggtgacaaaa taatctgtac aacaaactac tatgacacaa  44760
gtttacctgt ttaacatacc tgcacatgta cccctgaact taaaaaaatt tttaaaaaga  44820
tgctatgcaa taaaattctc aattaagaat ttaacttggt aaatgttcat ttaatgatct  44880
aaaaatatgt gtctggatgg ctctagcaaa aaaataaata ataagtttct cagagatggt  44940
aaggctgaaa taaatgggga aaaatctgaa ttgtaatcct ttttctgttg gacctggtgt  45000
tggggtttca cacttgtggg tgaatgtggg cctcctgtga gcaccagcac aaaagactaa  45060
actgaacaaa agattaaatg tcacctctaa aattctgtgc aacaagactt ccagccacag  45120
aatgtgcaac tcagatttcc aagtaaaaac acaccaggaa gcagatctta gatctctgtt  45180
atctccttgg caccagctgg tattcatcct caatgctagc tagagttgaa ataaagagtg  45240
aaagaacttt ctcttttatt acttaataaa cttccttttt tgagctgttt taggcttaca  45300
gaaaaattga gtggcagttt cagggagttc cagcacggcc cctgtttctt tctcatggtc  45360
cctgcaggtt tcccctatta ttaacgtctg tcattagcat ggcacatttg ttacaattaa  45420
tgagccaata ttgatacatt attcactaaa gcccacaggt tgcgttaggg gtcattcttg  45480
gtggtgtacg ttcttcaggt ctggacaaat ctataatgac atgcattcac cattactata  45540
```

tcacgcagag tcgtctcctg gccctacaag tcccctcctt ccccacctgc tcactcctcc 45600
ttcccaccct ccccaaactg tggcaaccat ttaacttttg actgaatgga tttattctta 45660
ttctgcctta ttgtatgtac accatatttt aataagataa aataatagtc tatagtagac 45720
ttctgtaaat actcaatgaa taaatacttg catgaatgca ggaaaaatca atcagtcttg 45780
caggatttct tatgcgttac atcgtcctta taagaaagca gtcattctca ccgagatgtg 45840
ctgagcagat actggacatg ttctgaccca gataagggct gggtggaagt agggctggag 45900
acacagagac ccagtgccaa cttccaggac ctcggaagaa ctgaaggcag agaggtcctc 45960
tcagtgtgga ctgggcctct gctggcagcc accagcgggc acagagctga tgtgtgttat 46020
gccacgtggg gaaaacctac agacgattct gagaaaggct cacagggaca ccctctgccc 46080
ctaaaagaac aatttaactc taatttattt ctgtcactct gcattttctg acctttccca 46140
agtgtacagt tttatatgca tttaactgcc aaattgtcat gtgagattat atggttatat 46200
ttcattaata tattctagtt tgttcagctg ttcttactgg gtgaatttgt gtggtttcct 46260
gacatttttg tttttagtag tgcctcagta gttttataca taattacgtt tcccttctgg 46320
attatttcct tagtatctag ttcaagaagt gaaatcgctg gattcttgtg gtaaattttt 46380
gaatttcaca gtataatgct gattttctca aagtctcaca ttctaagaaa gtataatgag 46440
gcaaaacaaa caacaaacat cttaagttga ttttttccta gcatcttttc cttccatctt 46500
tgcttgtaga atctagacta tttcatgaac ccaagatata atcagtatcc ttcttcagta 46560
tggccaaagt gagtttctca ttattttacc tccccttcag gaaatgactt ttcatcttgt 46620
gttttgggag ccatagatgg ttctgggcag gaaactggct ttggatagac ccagcatgta 46680
gatggctatt tggccttgct cccagtataa cgatgcagtt ccctgtgaaa gggtatgagt 46740
aggttttggg gctctggata ccgtgtggcc tgaagagaca agggctcaat gccaactctg 46800
cctgtttcca actgtgtaac catgtgagcg tcaaaaatca tggacgtgct ctggttaaca 46860
ctgagtggga gctcaacaaa ttattatttt taattgttac ttggacatgg ccaagttgac 46920
tacactttat gttctgctac ctgccagtct gaaagtgacg ccacagaagg tgaaccgcat 46980
gttgggagat gctcctcatc tgcttaaatg aggtgcaaac acagcccatg cgcctgctct 47040
tcatgactgt atctgtacca gcaatatttg tattggcaaa tcacatgccc cagtgggaac 47100
tacttaaggg gaattcaatg gatttcattc cttttatgta attggccact tagtaataga 47160
cgtgtaggtc tcttgtgtgg ataaggattc tgccttttat gtaagatatg tgttgcaatt 47220
cagctttcag gtcccagccc cgggaaggct ccaggccttc acaaactggc ccacccacga 47280
gaaggaaagc aattgtccaa atgtgggtag cttttcttcc cactgttgtc agctgcttcc 47340
aattagcccc catatacata atcccagttt gtgtctgtat cagtacaatt ctcccatgtc 47400
aatgtgaatt ttaagccaca gagggaaagg ggacagagaa tatgctttca ttcagctctc 47460
ctcgtctcac acctcttgcc ctgcatgcat ttctttgctc tgattaaacg agcattttat 47520
aagccacatt tgctgtgtga aaggcaaagt cttccctccc acggatgacg gtctccaggg 47580
atgtgtgtgt gtgtgtgtgt gtgtgtgtgt gtgtgtgtga gagagagaga gagagagaga 47640
gactgtaaac atatatctct gtgaaacttc attttccata tgtgaatttt tggaaccgag 47700
acaaatggaa cttagctaaa agatgggaaa ggtagactga ctctgactta atctacttaa 47760
cctaccaggc aatttataac ttgatggcct aatttttgca gcacccagaa gcaagcctgt 47820
ttcagcacgg caaaggctca gctgctaagt gggcagcatt gttggaggtg agcagcttag 47880

-continued

```
gctgactgtt catcaaagga ccaagcgctt gaggttcgct catcgctgga ggccagagtg  47940
gggagggcca tttaactgct caaggccatg gaactctact gtcagtttca gggaaatttg  48000
ggaccctgga gcacaaacca aaactccaat taaccaggag aggaactcga tccccaggag  48060
ataagtgaag agtaagaagt ctatctttag aaacaagaga tgtccaaggc tagaaagatg  48120
gggaaggagg gtggaactgt tctggaagtg ggtctcaatc tcagcaccag cagctctcaa  48180
gactttctag agaaggaaac ttcatttctg aattaaaatt agtcttcaat gacatggcag  48240
ggatttcggc acactctctt gcgtcatagg ccactgtgtt ggaggcagga gtgttggctt  48300
tggaggcata gagattaaaa ttagagtaac acgtgagcac tgaaaaggtt aaacagtaga  48360
gacatggagg actcccgacc cccatgtacc cctttcttaa ccctttaatt aagatcacag  48420
ccctagaaat agcttgcaaa ataattaact actgatcatt tataccttag tgcttctgtg  48480
agcatgtttt ctctttcatt gctgctcatc tgcatggaaa aatgtgcatg ggtttctgaa  48540
tataactcca tggtgcttgc ttccattata tttgtgccat ttggatcata actgataagc  48600
aaccaaagag tcccatatta ctgcacgttc ccatcgctat tttatgtgaa ggtggtcctg  48660
ggggctgttc tgaattctca gtttcctttt ttcccctccc cagttctttg aaaatatcag  48720
aaacggactt gtggcatctt tgaaaagcta cttaaaatgt gctgctgtgc tctgaacttg  48780
aaaatgtgct tttaatacaa agtttgtgca gcccttgctg ctcatacgag atgaatctta  48840
ccatgtggtg gatgcccgtc tcatgccagg cactgtgctc taagcccatt ggtttatttc  48900
agtgcttgaa attggctttc gagagaggca ccacggttcc ctttttacag gagaggaaac  48960
accagaggat cagagatgga gagtctttct ccacaaactc acagacccca aaggcaagct  49020
cagggttgtc agcttccaaa gtctgcctgc tccaggacct catgttgcat ctccattctc  49080
ttcactgagg gtcaaatgga aagaacacat gggggtcaag tttcagaaaa taagagaaat  49140
gaagaaatat gtgcccggaa gcaagaacga ccgacctcat taaactggct cccttcacct  49200
cctctcacat ctttttctgc cttttggcca agttttctct cccccgcatt tcctccttga  49260
tctcgtttga atcctcttcc ctggtgaagt catttaggtt caggctctta ttttactttg  49320
gtccataatt tagatcgaac cacatgtgct gatgtgattg aaacgatgtg gaattctctg  49380
gacagagata gaattatgga ggggttagtg tgtgtgttta agattaaaag accaggtgta  49440
tgggaggaaa tataatgaac aaaaaatagt attttaaatg aatactaaac ttgcactcat  49500
ggaaaaagtt ctcttcccat gaggttctcg caaagcattt taccatcagc acacgcagtt  49560
tttctcagtt ttctgagatg gggccatctt gaatccaaca gacaacacac agcatcagcc  49620
agactaacac aaaggacgtc atgggcatgg acgtaaatac tggtgtcaac actaggtctg  49680
cacctcgaga ggagtggagc aaaaggatgg agtggcagat gaaggtatgc tgttcagaaa  49740
ggaggcagaa atgaaaggaa gaccatcagt gcgctccaca gcttgaggac cgtcctggag  49800
ggcaaatgcc agctgctcac ttctgaaaag aaaaattcca gtgaaatgag tacagtcatt  49860
cttaggatta ctcacttgat actgtgtatg tctcttcttg gcttctcatc tccacacaaa  49920
accctcaggt ggtaaaaatc taattaaaaa aattatataa agtcttgtag atttattagc  49980
ctgaacataa tagatttttt ttaagcacgt taagtcttcc atggactaaa agaaaacttg  50040
taaacctaag agaacctcta tttttgatat acaaaataat acatttcctt aaactatgat  50100
cttgatacta gaattttaat taaaaaatac ctgcagttta tatgcaaagt tatagattaa  50160
tgcttaaaaa taggttgtat gtagtatcca caggtcatgt ttgactgtca aatagatgta  50220
attttaattc ataataattg tgtcgtgttc ttccccacta gaagccaatt atgcaagctt  50280
```

```
caccattcac acatggaaaa taatttaatg gagtactcat tgcaatttca cttatccaga  50340
attggctgtt gttctcagag cagcttgtgt tgccttgtta aggagaatat gttagtatcc  50400
agacatccag aaaggatcct ttactgtttc agagtccatt ttccccactt ttgaaataca  50460
cacacaaaca cccattcatg caaaccaaac agagattgta aagtgattcc actgacattt  50520
atgcacttct tttttctctt tggttcttca aactctcagt cagtgcgcat ttactcttaa  50580
tttagatacg gtttaaacct aattagaaac cagaagctct tgtatttcca caaaggatta  50640
tgacagcccc aagaaaagat agtgaaacca ttatataaca agataaaggc ttcttaacaa  50700
tacaaggatg gattttctca ttgatcttag ccttctgaat tttagaaatt gccatttcaa  50760
agtctaaaac aaaggaaaat cagggaataa aagaatggta agtagacaca aacctactgg  50820
ctccatcatt tctgttttag caaataacct gccacatata ccaatagccc aagagatggg  50880
catgtccctg catttcctgg tcaaggtgac aacactgcgt cctcctggaa gaggtctgcc  50940
actcaccata ccacaaacca aatataataa aatcagaagg cacactatag tgaatttttt  51000
agaggcatgt attgaaaagc atctcaaaaa gcattctcga agcttccaga agtcaactca  51060
agttatctga aaagtgacac ttttgatgat tgctcgctta atactgggag agccagatga  51120
agattcctcc ccacttcctc agatgtgcaa ctctggaatt tcttagtgtt actggagatt  51180
cctgctgcat tctgggcctt taatgcataa acactgagat gttctaagga aattactccc  51240
tagggaggag aggggtggac gaggagtaag ctttgctggt gactcatgcg ctgtgtggaa  51300
actccctgca caagtgagct gcgcagggtg agtctaaagg gttaatgcac tttcaaaagc  51360
ctctaatttg ttattccaga agagtaattt actcactaga agtatctggg tggctactaa  51420
cacatttgtg tctttaaaaa gatcagtttt attttaagat taaaaatata aagcaagagc  51480
tggaaagtca ctaaaaactg acagccagtt tcccattttc aagagtattt attaaaaggt  51540
tctggttgca gaaggaataa gaaatggctt gagatcatga cacagtgaat catgttgtaa  51600
acatgttagc tatggctgtg aattcaacca gcgatgagtt caagcgtccc cagaaggtgt  51660
tgggggaatt agggacatgg ctgtgtttcc ccagagaaaa gtggccattt tactttccct  51720
cttcactaac atgcttttga catgcatggc agagctgaag gcaaggggaa ggggacaaca  51780
tagtaagtga ctaagtggct tttttttttt tttttttgcc aagtgaagct gagtcatatg  51840
gcctctgtca ttccaaaact attctctacg gctgcattcc tttcgctctt gccttccttt  51900
agaaccctgg agaaggcctc ctgaagcctg gccctattat gtatcctgac aaagataaac  51960
ttttccaaaa agctgcatgt tgtttctagc acagtttttc ctcgcagtga ctacgtgatg  52020
aaagtaccat gcagaggagg tgtctgactg aggcgttcgt ggtgtgtgac agagtcccct  52080
gcacaggaca gccgcactcc cctcttgcgt cctttcctcc catgtttgca aagcctcttt  52140
ccctgtcagc agggggtgtt ctggcagttg acatttctga aaactacagc ctacattttt  52200
aaaaaatcca gtaagtgaaa actaaaaaat taataccgtg gtcataatag tgtggcattt  52260
gataactaat gaggcactgt cgtgccagct attattttca gacatttaca gtcctttttt  52320
aaatacaaag aaatatttgg tgtgaaatgt tccccgggag ctggtgcaag cagaggcgac  52380
agggcaaggg agcttgggtt gtagcctcga attcctccgg ccagggctac cgtcagcctg  52440
cggcacacaa gtaaatcaaa tataaaacca aaatttctgt aagcaaatca gtttctaact  52500
cactgtaacg aattatcttt cgcacatcac agaggcatct cttttcactg tcgagtttgg  52560
tttgcttggt tacaaaaagg gcagttcaaa agctttggtt gctattgtga aagtcagctg  52620
```

aattccttcc accgtgctgg ggtggggtgg ggttcacgca ggttctcttt tgtcaccagg 52680
ggtgctgtgg attcacaagt aagcaagagg ctcctcaggt caagcctctg gctgctccct 52740
gaggtcagct gcctagcttc tcctcctctg agatagacgg gaacaaagtc tttgatgtgt 52800
gcatttctca agcttgacaa tgatacagct acataaaaac ccatgatttc atatagatat 52860
tccaaaacgt aaaagtaaac catgcatcca cagagacatg gaattacaga actggatgct 52920
gagctggtca cttgggaggc aggcgtcctt gccattggtt tatgcctcag ccccaccatg 52980
cagtggctgg ccaggtgacc taggccagtc ctgcatcctc ggctcctcac ctgcctggtg 53040
ggacagtgac atctctcctg cagcactgct gtcagggtga gggaggtagg gcgcagtttc 53100
agaaaaccat tgggctgcac ctgcgtgagc acagctgcag gagcaaaagt cagaaaggtc 53160
agcaaaggat ttcaggagca aaggtcagaa gaaaccctca aggtggttgt gtctgcagga 53220
aagtgctgtc gtctcctgca atgctttcaa gactattcag aagcacagtg tgaagggaga 53280
gccggagccc atggggaaat gactccagag tgttccacgt gttggaaggc atctgttgga 53340
aaacggacat tcaagcaaat agttgcctgc atagacaacg cagaatgact gggaaagccc 53400
caacaagtta cctactggta aatgaggtga gaagcttaaa gtgagaaccc cattgctgcc 53460
tctttttcac tttaaaaaca tttaagtttt gaattatggt aaaatacacg taagatttac 53520
tactgtaacc atttttaagt gtacggttca gtagtgttaa gtatattcac attgctaagg 53580
aaccaatctg ctacttttgt ttattaattt tttcctgagg ggaaatattt ttaaatttta 53640
aaatatttaa ttgacaaata aaaattgtgt atattcaagg tgtagaacat gatttcatat 53700
gcacgtacat tgtatactca ttaccacaat caaagaaatt aacacatcca acccacccat 53760
agttgccatt gtgtgtgcgc ggatgtgcgt gtatgtgtgt gtatgtgtgc acgtgtgcgc 53820
ctgtgtgtgt ctgtgtgtct ctgtgtatac gtgtgtgtac atgtgtgtac gtgtgtgttc 53880
ctgtgtatgt gtgtctgcgc acgtgtgtat gcatgtatat gggtatgtgt gtacgtgtgt 53940
acgtgtgtgt gcatgtgtgt atatgtgtgt ctgtgggcac aggtgtgcct gtgtgtatgt 54000
gtatatgtgt atgtgtgtac atgtatgtac gcgtgtgcat acgtgtgtgt gtgtgcacag 54060
gtgtgtatgt gtgtgcctgt gtgtgtgtgt gcatgtgtgg tggggacact aaaaatctct 54120
catcaccttt ttagtcaaaa gaacagttgt tttggtttgg ctcttctgtt ttaaaatatc 54180
agaacaataa taatttccca cagacaaaat cctcaatcct caccatcctt ctatttccta 54240
tattcatcat aaacttcatg cttgatgttg aaattgtttt ctgaaaatag agaatacaaa 54300
gaggagattt taaaatgtca gtggcagccc cacactcctt tttaatctta tttcctgata 54360
tcttgagttt acttggacgt agagttttcc ttgactatgg ttatttctgg tagtagcagc 54420
tccagattag gcaatggttt tcttcagaga tagcttagag tgagccccag aacaaggtca 54480
atgcgaagat tgcttgtgtc tgcgtgtcca gggcacagtg atcctcatca ctagccgggg 54540
ggctccgtga ggatctgctc ctggtcgttt ctgttctgta tcttctctgc agcccttact 54600
gaagccgtta ccaactggca caattcaatt cctactgtac ccatcatgca cagatggctg 54660
aagtattgag aacgctccag tgaccgggag gcaatagtct gtccacatct aagaacacac 54720
ttggaataac cttagagaag agagagagag agagaatgca tggttagtag gttatcaaac 54780
tcctatgact tttcacagga aaagccctca tccacaccaa ctttaggaat gtgtagaaag 54840
aagggtcagg gacaggggtg agtggtgggc agagcagttg gagggcacag ggaaaaggca 54900
tctggtcatg tatttggagt aggaggtctt gctttactat tgaattgcag ggacactttg 54960
ggaacagtgt tcacttcttt ttgcaaccat ttcttcagag aaaagtcatg atactcaagt 55020
cttcttacaa agcagtttga ggctttgagt accagactga ttacagagat gagtatgaag 55080
cattattgta gtatttttaa gtgaaattca ctaaatgcaa ataaacctag caaatgctct 55140
atggttaatt tttttctaaa attcagataa ttaagacaat tcattctcct gaaactgctg 55200
ttcatgtaaa aaggaatttt atcgaggtgg cccttgagtg ccaaacagcc tgtcctcagc 55260
tgcaaaatga gtcgttgatg atcctccagc aagggatact ttttagctcg tgtggtgatt 55320
gctgcacacg ggatatgtgc agcaagtatc tgctgagcta ataataaaca gcctcagaca 55380
gaaagacagt gggcacaagg tcatgcttaa aaagacccct tgttctactg catcccagct 55440
ccccaccatg gggcctcaca ggccctggtg accaagcaca tcagacctgg ttcttgctca 55500
gtcctgggag ccacagaacc cagcacgtac tttacccccca agaccagact ccagcttggc 55560
ttttgtcctc ctctccagga ttggtgacct cctaggtcgt gaagctgtga tgagcaaaga 55620
cacactcctc tccattctcc caacttcagg tccctttgac agtgtcagca ggcatttaaa 55680
tagcagacca cccacagcag ggctggtaga tgcagtgaac tcaggaagat gcctgcatag 55740
actctagtgt taaagacaga atccttacaa ggaacccccca tagttaccta actgctgtct 55800
ccagtggtca tagaagtgtg ataacccact aatcatcatt ctctgtctct ctgtctttct 55860
catacacact tacacacaca tacacacaac cttgttgctt aattttcaga gagtctactt 55920
tcagaaaagc cttcaggaat acatcatgta caaaactgag aaattacctg aagtatcttt 55980
aaatttagta aaaagttgca ttgtttttttg aacatcacac ttgaaaagta catgaataca 56040
aacatactta ggaaaaaaag ctttaattaa tttaaaaagg agaacaatgc tatatgctgt 56100
atcccacctt tctctgaatg ttacattttc tcccctatcc caggctgcat ctaagaaaac 56160
tcagagggaa tatgctatct atcttttccg agcaatgaaa gctctgggtt ttttccttgc 56220
ttttcagggc acaatacttc tctttcttcc tggttagaca ggataagttc tgagtcccct 56280
ggtatcatca gcttacttct tctctgttaa atattcacaa aaaatcacta actttcatgc 56340
ctcagcaaac ctccactgcc taaaatatag tgaggtcatt catcttcgga caaattgccc 56400
caactacggt gggaaaagaa ccaatgtgtt ggactattta tctaattttt gtttagttcg 56460
gggatacaaa taaatgcata gatacataca aacatgcgta cataatagca gcagcagcct 56520
gtgaaacatt gacaagacct ggagttggaa gaggactttg ccatcctcca gtccaacagt 56580
tgcctgtcac agattagacg actgggatgt gcgcaggcga ttatttgcaa acggccctga 56640
gtcccccagt ttatgtctta attcgcagcc agggctgatt gtagaagcaa atttgcaaac 56700
atgtgcaaga agaaatcaca catcctagag cttggatttc ctcgtttctt gctatttcta 56760
tccgtagaca gaaccattgc tgagctgtta aatttgtctc cttcccctat accagtcttg 56820
aaaaaggaaa ggaagtggag caaagaaaaa gaaattaata aagccggcag atcctaggag 56880
aatcttattt aatccaagct ttgtaaagtt ttgctttatt ccatggcaac atgggtatac 56940
acatcccacc ggctgtttca gtggctcaga gcaggtaagg cctgtgccaa acgccgctag 57000
caggaggaac aacgtggaga cagccccaga ggtggaacgt tggcccttct gtggctccgg 57060
tgtctcagga cctccctaaa gcccagccct gacactgagc aagtttccac cactgttagg 57120
aagaagtaga aaggaatttg gagggttggt gttactgttc aagagctgga aggcttctgc 57180
ccccattccc attccattaa ttgcgtgagg tagagaactc atagaagata ggaacacata 57240
tgctgatttc caaaattgcc tttgtatatt ttcacgtgaa gactttaggg gcaaaagaaa 57300
agaagcaagc attttgaata tgtgtttcaa tttgccttct gttatataaa attgtatttt 57360
gcctattctt ttttcattat tcggaacctt caagaaataa attaagttct ctcaaaaatg 57420
tgttttttga aaagaggact aaaacagatg gcctggctgt gttaaacaca gggaccagac 57480
cagcacccac ctctccacct gccctgcctt cactggcaga attgtgatcc atcatgttct 57540
ctgttcaatg tcatcatccc tttcagagca tgggtctctt cctttctagg cagtcttacc 57600
aggatgcatg ggtgtgcctg cgtaggcaca cgcacagctc ccaaggactc taaaaaaaga 57660
tatttttctg cttatatact aataatatgt tagagattta tgtttcaaat tagtacagaa 57720
tcacatggtt ctctccaaat tatatttgag agagaaagaa tagaacaaaa tttattttac 57780
aaaaatactc agtacattta gggcatatac aaagatgttc cagaatgtag cttatctctt 57840
taaagacaat taacacagtt tctgggcaag gcaaggcaaa atattcagta acttagcaac 57900
accaacagaa gacagccaat attgcagcac atttttctct tggattgggt cagagagtac 57960
tgcagagaaa atggagtaga gagacctgaa atactttcgc acacactgtg gtcagtgcag 58020
cgtccactgt gtgccacagt aatactagaa actccctggt taggccttgg aatccagctc 58080
tcatttcgta tgtgacctgc agggaagtaa gttaaatgca cacgttttat caagttcaaa 58140
tgcaaactta attttaaatg tatgcaacat cagtttaagc gttgtagcta ttactagcaa 58200
ttgtacctat tactagtctg tactctgcac aactttggag tatactgcct actcaaggtg 58260
gattttagag ctctatttgt ggcattatat cacggacaaa agcacgttca tcagagtcag 58320
aggaatgtgg tgcaaatccc agctgtccca cttaccagct gtgggacttg agtaagctcc 58380
tgaagcagct gcacctgcat tttctggtgg gcaccatgga gctgtcagca gtgctttcct 58440
cagagggctg cgggctggat gaggtttgct ggtgcatgtg aagtgtcaat cattgctctc 58500
atgagtggtg atgctgatgc cgttcccttt tttagggaag tgatttttccc ttacaaagtt 58560 accaacagtt tcatgttggc ccatttttct attaattgtt tccactaata ggaccaacag 58620
tggtagtccc atcattttat tactgcttgt cgtagcacaa gcagttgctt cattgtgttt 58680
agataaatat tgacggctgc ttttaacagt ctgctgtttt gtctcctttt gaggtcctta 58740
aagtaatcct taaaaagata gtgcagatgg aaagatgtct ggagtcagtg aacctgcctt 58800
ctttcctgtg tgcttgtcag tttctaaaat gccatacaca aaggactttc atgatttctt 58860
tttaggtaca tgattacagt tcaattcact tcactgtctg gaaaatttcc ttataatcag 58920
gatgaaattt ctcatgttag cctttcacat ttcactactt ttagataagg aattctcagg 58980
ctttgctata tctgactgct cttggaggct gagcttttgg ctaactacct gactactttg 59040
tcgtttctct tcccttggaa tgaagcaaat atctaacttc tcactcattg tttctgctat 59100
tttaccattt agtcatctgt gatttttcta aatactgaaa gacttccctc aattcaaact 59160
atgtgccgga tcaaggaaag ggcagttgga tattgcagac agcatagtgc aattgtgaag 59220
agtgtctgct taccagccac gctgccttgc acaagttatc aagcctctca acccacttcc 59280
tcaatctgta aaataggtat gagtgtagga ccttcccagg ggattttttt gtgactatag 59340
aatgattctc agaagacttt caggcagtat gtgggtgagg cacatgctgg aaaggcttct 59400
gcaggtgcag tgatcaatgc ttttctcagt gtgtacatcc cataatacag acacgttacc 59460
agaaactccc tagccaggac tttgattgca gctcacattt tgtatatggc ccatagggaa 59520
atgaagtgtg tattttttat aaagttcaag tgttaactta atttggaatt tactatcaaa 59580
tctcagttgt tatgggcatt tatagctatt aatacttcgt cccatgtgtc ccatgaggaa 59640
accaaggaac agaaattaaa gttctttctg gagtcccctg aatctcgttc ctgttctttt 59700
gcaccctgtt aattacatag agacattcac agctcttctg accttatcag cgttaaggaa 59760
aacagaaaac cagcgtgcta tttgttctgt cccttagtca agccttctca acatatattt 59820
ttcttccaag attttgcatg tgcacaggga tgcctatcct ctacaagaaa cacattttag 59880
gcaaattata attaaaatgc tgtttacatc tcttcacctt tagaatttaa agaatgatca 59940
tttcttagat tgcatctcag acacaccctt cccctagtct ggagagggcg aggcccatgg 60000
gtactgcaaa cagcctgacg ttgtcagggg cggtctcaac ggctcattca ccacatctgc 60060
ctcgcgaagg ctaagccatg tgctgttacc cctgctgcgc tctggctcat tctaaggtac 60120
acgctattaa ccttgtgaga aaacaaagag gccagcccca cccttcctgc tcactctgag 60180
tcacggtgaa aatgtttcag gatctcgggt tcgaccatga gtcctgtcca ggtccaggag 60240
gaaattcgga aggaccacat gttcactctg agatcccact ttcatttccc tcctggttga 60300
gcagcattaa tactctggct agatttaaat tctggctttc tccagttaga actgaaagtt 60360
atgacaatgt aatcaaaata gaatgtgggt ttacagctgg ccccctggcc tggtttgtga 60420
acataaaaca gaaacagaaa gtgtaagtgg tgacatcata ttctctcatt caatgtgaaa 60480
ggccaccgaa gtctttccag aattattttt gagaataata tgaattttta aaaaatacct 60540
aattatttta aatatcgtct tgcttgctcc ccaaatacct actgttttca acttggatat 60600
acgacatgat taaagaatat ctaatatttg ggaatgcata ctttaacctt ataaactacc 60660
actgtaaata gacagactca ttaaagtgaa aggacatttt aaatcaatta gtaagcaaat 60720
caattaggtg gcaaagacaa gattattttt ccttatggta gttgaagaat aatgcttaac 60780
ctgtcattct aattaccaag cacggtgttc tctttggaag atcatttcaa caaaacatta 60840
ttttcatcca gaatttgaac cttgagattg catggtattt tagaaatcta ttttagaaat 60900
ctttggcaaa ggttactatt aaaacaatca cattcatgga aaatcagtat aagagcaact 60960
aaaataactc acaataccag taaaatcact ttgtcatctt cttaagactt ttaaagagca 61020
tttgtaagta actgaataga aggccaaagg gtgtgtaggt agcccagacc atcagtgggc 61080
agccagggcc agggcagggg ccacggttgc agcctgcatt cttctaaagg gcagagcaaa 61140
ttaaagttga agcaggagct aaaaaaaaaa aaaaaaatgt ttcaaagaat tccaccaacc 61200
agaggatact acctaggaca gtttgggcct aacttatctg tgaaggcctc cagcttcctc 61260
cacaccggtg gccacttttc attcactctg aacccttctt tgtatggagg tcattttatt 61320
aattgagctg tgaccaacat gacagaattt cctgttttag ggcttttata atatagatag 61380
tttatatcta atttcagaat atattcactg gggaatggac ttagcaacca ctaccacaac 61440
aatgcaacaa tgtgttttgg aacaaattta ccaatctgaa tttcccccta gattaggtca 61500
caggaacatt gcagctgatg tacagctatg ttcctcctga aacttggaga cacatcctct 61560
tgagctgggt tataatgggc cacccaaagc tcgagttcct gtaatggata cactcaggca 61620
gcagaaccta ccaccgtagt gaggacagca cccagagccc tcagaggcca tcacaagtgc 61680
accacagctg ccttctctgg cacgctcaga gctacacagt gtactctggg attggaactc 61740
tttatttttt tttcagttga tttgtaaata agattgcaca aaaatccatg cacatcaact 61800
ctccaaatca gaatttgctg agctaaaaag agcattaaat tagatgggct ggctttcaag 61860
gggtgggggt gcaatagtgg aactctgcac aacagttctt tacaaagaga caagcaagca 61920
catcgcgtgg aaatttccat tcaactggaa atgtccaagc ctgtttacct caattaattg 61980
tccttgttca cttgtccagc ctagcaattg tccattagta atttgttata aatgagacat 62040
ttggtattaa agcatctctt tgggatactg gtatggttta ttataacatt ctgttagtag 62100

-continued tgttgtacaa gcttgagatg tattaatacg aaatccaagc tgcatgaggg ctttattttt 62160
caagcctaca ccttgctgaa attctgaatt aaaatatgat tctcagtaca aatgaataaa 62220
tcaacagaaa tggtaacgca tgtcaaatat tcttaaaacc caagaaagcc ttgtaacttc 62280
cttcaatcta atgggaaatg caggcaaata caagactgat gtccttgagt tttattatca 62340
agactcaagg gcaccagtaa aatctagttt cattggttgg aaaaaaaatc ctgataagca 62400
ctgttaggca tattaacttt aatgattaca atttttagga cactctgtgg cctagactta 62460
gaaacacaac taatgtccag aaaaagattc ctctttttat tccatcatct gataggccta 62520
tttttacaca tacacaccaa ccaaaagtag ccaagcaaac aaaacaacat actcacaccc 62580
cttcgcctat tatcatctag gtgattttca atgctcattg caatgaaacc tacttattgt 62640
gcatggcacc caccccact gaggaatact gtagtttctt tccctttgaa cttcattagt 62700
agagcacatg gttcattcac tcctgaagag ttcttcgtat gtcagaatat atatactaca 62760
acataatttc catcagagct ctgaccaccc gcttatctat tttcataatg cctgccactc 62820
catcattagc tgttgtcatg taggctatca ataaatatat gacaaataaa acagttaggg 62880
aatgagggaa attgactagc agccaaagac ctaagccatc ctctgcttgg acattagaaa 62940
actgagttca ctacagtcat aagatacaca aaggcagaat gtaagccata caaaaatcca 63000
tgtcaatccc aatatgtgag tacaactatt gaacaccatg tactaatgga tgagttggta 63060
aatcattcaa tgtcttcatg aggtcaatta cagattatta tttagacccc aaagattcca 63120
aagatggtat ttcggtcaga tcttcatcct ttgtaagcct agcagaaaat atggcagttt 63180
tattgactac tattctttgc tgggtgtggt atttttaaac tgagacatca gtgtgcctag 63240
cacagggcct caagcacaca gaaaaattcc ttgataataa ttaaataaaa tttcagcaaa 63300
aaatatcatc ttaaggctgt gaaattatct tcctgtgtgg ctaaaatagt gaataaaatt 63360
cagcgcaata taaatcatag tacaatttca tcactaaatt ttctgatctt gatcttgtca 63420
ttttacattg gaagtaaaaa tgtgtcctcc tttttttctc tgacagtgaa aagtgtgtgt 63480
gtgttgtgtg ccctttttgca caccctgcct cacacttgct ggtctaattc cttccagcat 63540
gattatgata taattaaatg acagaaatgt ttacttccaa gtggaactaa gccagggtaa 63600
ctcagggtag ggcagctgct tgcaccgaaa gaccaagact gctagagaac taggaaacag 63660
gcggtgcaag aactccaggc tctcatggaa gagcgggagg cttctatggg gctgcagaaa 63720
ctctttggtg cttggggaaa aaatgggtta aatgctctta aaaaagaaac ctgggagagg 63780
tagtttccag atgcaggccc gtcttttctt ttaaacagag gcagctccga agagctggac 63840
attgaaccct gagcaggaac tggaggccgt cagcgcagct ttgtttggcg agcggagctt 63900
tgcaagggtg taatgctgca ccagggagac gctatctgca gggaccggtg acgccgtggg 63960
tgtggagggg gaggcagtgg ctggccctct tggggtaagg tacgcccagg aacagtttag 64020
aataacgtgc gcgagtcaaa gggaagaaga agctcctgca gaccttctgg gcactgtgca 64080
gggtttgctc ctgtccaccg tgccgtgttc ctgtcctggg gtatttgggt gtgtggcgtg 64140
tggggagggg agaaggagca aggcggcagg gaggggatga ggaccaccct gtccatggga 64200
caggccctgg gccccgcaca caccccaagc cccgcgtccc gcgtcctcac tgtcctggga 64260
caccccccac cccaccccac cgccacagcc cagagcggtg ccaggaagcc gcctcgacgc 64320
agccgtatct tgaggctcca gccccatccc cagggtacca cgccacgtag agacactatt 64380
tttcacttcg tgtttgtcac tcctaaagca tgtgtgctag ctgcaccaac cctgggatgc 64440
ctcggtgcat agggtttatg tgcgtcctcc tccttccctc tgagctggtc ccccgtgggg 64500

-continued aactgctgcc cagactgacc tgcgtccttc cgcacgtgca ggaaaatgtc cacgtgcact 64560
tgtcagggtg ggggccacac gggcaccacc actgatcatc tgtgggatcg agttactgcc 64620
catgcagatc ccacgtgcag ggcccagtcg ctttggtgag agagtggacg ctgtggtgac 64680
tccacggtct gtggctgtgc tcaggaggac agagagggga catcctgaga tggtttgggc 64740
agcccgcgga tcctgtgcat gtccccagag cgtccacttt ctccatggag cagtggagtg 64800
gcgttgctga gacagaaagt tcaggttctc cactccccat gcagccccca ctcccctgtc 64860
tccggccagg cacgcgtctg ggtggagac tcccggtgcc cggggccctc cagacctctt 64920
tccccacccc agggagcagg cgggtacttc tattccgttt ggcttcagaa gggaaaagag 64980
aacgtaagtt cagggagttc tcgtccattc ctctcccgtg ggccgggcag gcagcaggga 65040
cagccttcag gagccaggag gggctcgagc tgcgaggccc tggaatgagg caggcatggg 65100
ctgaggctgg agggaaagcc ccgctaaggc tgggcggggg cgggaaaact taccaccagg 65160
ggactcgaga tggggaagga aaggtcagaa gaggagaggc caggcacggg gtgtgggcgg 65220
cctgcagagc tggagcaggt gctccgccca gagccaggca tgcacactca gagtaggtgg 65280
cctgtgcagc ggggaagagg ggcgggtcgg cgtgctgctg aagatgcagg agctgcggcc 65340
tgctctgtgc gtgctgaagg tgtggtgaga agcacttaca aaaagaaatg gactgtgtta 65400
ggattgcaca ttttactttg tttctcccaa atacgtgttc tttgaatttt tttccttcca 65460
gggccaggac tggagtgatg gttgagacag gcacgcactg ggtcttgtct gcatttacat 65520
tttgagattt tgttcagcat ggattttatg gcgttttttt gtttgtttgt ttgttcgttt 65580
tcaaaatact gcacggttta tcgtgaagac agggtccttt gctgccgtct taagttttgg 65640
gcccaagaac gtgccccacc ctaggcccgg gcctgctggc ttcatagctc tcatcattcc 65700
cacggaacct taagacctga ggacagaaag gaaggaaaca agcccagtag tccgtgaaaa 65760
tccagggtcc cgccactcca ggtgtctgca gcagagctga acacacgtag gctcttgcca 65820
ggaggggcat ttgtatgtgc tgagcattcc ttatattctc aatatgacgc ctttgaaaga 65880
tctgtggttt gcaaatattt actctcagtc cataacttat ctttccaacc tcttaccagg 65940
ctcttttgct gaataaaagt tttaaatttt gaagtctaat atatttttaa ttttttttatt 66000
ttatggatca tactttttgt gtcaggtttg agaagtctgc accaaagtat gtcctgtggt 66060
tttcccttag gtcatcttca acaagtttca tagtattttg tttagatgta aatctgtggc 66120
ccattttgag ttagtttttg cacaagagtt gaggtcaagg ttcttttttt gcctgtgatg 66180
ttcagtggct ctggcaccat ttgttgaaaa catgatagcc aatgtcaaga cttaatagtt 66240
ataataatca ggagcttttg tttctttttg ttttgttttt agtaactgcc agtcactgct 66300
tgtggtatac atacacaatg gaatactatt cagtcttaaa aaaaaaaaaa gaaggaaatc 66360
ctgtcatttg catacctgga ggacattatg ttaagtgaaa taagccaggc accaaaagaa 66420
aaacattgca tgatctcact ccttcatgga atctaaaaaa ttgtattcag agaagcagag 66480
agtggaatgg tggttaccag ggctgggaa ggtgtgagct tggggagatt tggtgaaagg 66540
acatagaatc tcagttagac aggaggaata agttaaagag atctattgca catcatggta 66600
actgtagtta gtgacaatgt attgtataca tgaaaattgc taagagagta gattttaagt 66660
gttctcacca caccaaaaaa aggtatgtgc agtaatacag tcattaatta gcttgatgta 66720
gccattccac aatggataca tatatcaaaa catcatgttg tataccataa atatatactg 66780
tctctttatg taaatttaaa aataagataa aataaatgtt attcacttgt cgtggatgtg 66840

```
gtggggacag gtgtgggata gccctccctg tacaactagg acccaggggt gatctagtga  66900
cactagccat ttatcaggac gtatgggtgc cagtcaggat gataaagctt ccttttggcc  66960
actatactac ttagaaatgc cctgcaaaag gtgcacatca aagattgaaa gctcaatcct  67020
ggattttaag tgcttcaaaa gtgcacttaa ttgccacatt tttgtcaaac attttcccag  67080
gtagtatttt tcctcatgta aaacaacagc aatttaattt gaacagaaag cattttgaaa  67140
catacttttg gcagggttcc ttgcagatca gaatggaaat gattaacagg gcaattatca  67200
atcatggact tttggcggca gaaggaactg tattgtttgg tacagtctgg gccagggcca  67260
cacaccgtaa cggagatact ctattctgtg gacggttgga gggggctgtg ctgagcaggg  67320
taactgcatc ttttcctaga ctgttcacac tgctgccacg aaggagtctt gtttagactg  67380
gacctggctt tcttcttcgc aatgagtgtt gcagactccc gacaaaggcc aggtggtaaa  67440
gtgtggtgtc tgtgagcgag agcctgagat gcctgagctg acctgtcctc agccacctgc  67500
catcgtgcag aggtgagagc agcccctgaa ttctgcccct cggtctctcc atagctaaag  67560
caaaaccatc cttccgtgct cccaggacaa gcaggctatt accaaatcac ccactaaccc  67620
tgggcgagga ggggccatca ctgcacaatt catcagtgtc tgtgacagga agagattgtt  67680
ttagactggt tttttttttt ttatttgcaa gctttttttct ctctccaaaa cgtgctgtca  67740
gtgtgttcta atttactctg taaggaattc tggagctaat cataggctca caaaaagcag  67800
cacaggaaag tttcccagat aacatctatt tcagtggctt tcaaacattt ttgaccttac  67860
caaagtaaga aatacatttt aatatcatgg cacacataca gctgtatcta aactttcata  67920
atactgcctt tacgatatca ctctgatatt gtctattctt ttctgtttat ttttcttttt  67980
gttccttgtt atgctggttg tgacccactc cagtgatttc acaatgcagg ctgggtggtg  68040
tcccacagtt tgaaatccca atctagggcc ttcctctcac tgtacaaagt aggtaactgg  68100
ggacattagt ggatcagtga tcaaaccaaa gttatttgat cttaccaagt gatatcagga  68160
tgagaaagct gttagagtgt cagatatgtg aaggaacttg ggtcattcct gatacctcaa  68220
agagaaaaaa ggtagtcctt gaacacctcc tacttgtaaa ggatgcacaa tcctacatgc  68280
ccctcccttt cctttcctcc cctctgtacc ccacccctgc ccacattttc ttcataagca  68340
gctttggtgt tttggcttgt ttgtttccct tgtctcctac ctgtgacttt atagcctttt  68400
ggagactcac agcaatagtt gtatttaaac tcagtgggtg gcatccaagg ctaaaaagga  68460
gattgcctag acacaaaacc acccaaggga gaaagcagga cagcatctta ctatgattgt  68520
ttcttgtttc ttcctgtctc ataaggatta ttacccaggg ttttcatttt tttcatttca  68580
tggttcattt tcgctccagt gtagacatac aatagaccac tcgtccctgt ggctccgggc  68640
agcagcctca tctgagaccc tcctgagaca tctcgtgcag ggcagccgta gtgtgtggct  68700
tccccagggc tgctctaaca gatcaccatc cttgccatgg cttaagaagc tgcagattta  68760
tttgcttaca gctctggaag ccagaagtcc aaaatcaagg tgtcagtaga gtctctctct  68820
ctgaaacctg ctgaggatga tgcccctggc ctctccccag cctctggtgt tcccagcagc  68880
ccttggcatt ccttgccttg tagatgcaaa actccgatct ccacctctat cctcacagtg  68940
agttctcctg catgtctgtc tctgtgcctt cacattcctc tctgtgtgtc tgtgtttcca  69000
tctccttatg aggacaccca tcactgaatc agggcccact ctataccagt aagacctcat  69060
ttcaactcca ttacatcttc aaaaaacccca ttctcaaata aggttacttc acaagtgctg  69120
gaggttagga cttgaacata ccttattgaa caatccaact gatgacacat agtaatttat  69180
gcactcgttc ttggagacgt tgactttatt tagtagcatt aaccatggca atgtcaccag  69240
```

-continued

```
catcgctgac agcctgaagc atatgatctc cagaatgtat ttcaatcatc atgttcactt  69300
ccttggtatt ctttagacaa taactcagcc ttgaactcca gtaaagggtt tccctgggat  69360
tttcttcttg actcactcca ctgtggcctc cctcatccag gactgtaaca gacgcctgac  69420
gtcagtggtc tagacctctc tgctgaatgt catctttggt gaatgtctta tgagaaaaca  69480
catggttggt cactcttaga agggcatgaa agcctgtctg cagtataacc aaaacaggca  69540
catggcgagg cacactgtgc gcatgtgtgt acaattaata tcatggtttt aaattatttt  69600
caggccaagg ggagatcttt gctgcatcta ctgaagaaag cgaatctttt tcttcctgaa  69660
aaaaaatggc tacttattag tcgaatttgt gttttaaaaa tatgtgaact aatataatgc  69720
agacatgcat taatgtttaa atatactgga agtttttggt aaaatgaaac ccattgtctc  69780
tgttgattac tttgatgagt caagaagtaa catcctggga atgattggcc agtttaaatg  69840
agtgcctcag gtttttggaa tacaagaaat caagaggaag ggattagaac atataggtta  69900
gcaagattgg gatcctaaaa tacagaccca aatgaatgga acaaaatcag ggaatttatt  69960
aataacaggg tcaaggccaa atcagtaaca aatatcctga gtggaagaaa ggtggtttaa  70020
caaatgcccc tatgaaagat agagattggc ttaccatgat gagatgtaag cccaagttat  70080
gaggttggca cacaaaacca caaatgtcat agcttaaaac aacacacact tcttatctct  70140
gtttctgtgg gtcagggtct gggttctcag ggactcacaa agtatgtttt catctggagc  70200
tccaggtcct cttccaggct cataagggtt cttggcagaa ttcagtttct tgaggctgta  70260
ggactgaggt cctggctcct agaggccacc ctctccataa gcagttctta gcatggccgc  70320
ctgcttctcc aggcccagtg ggaaagcatg tgcctccagg agggctcagt ccattcttca  70380
tggcttttac ctggttaagt caggcccact caggataact tcattttgta ttaaatcaaa  70440
accagctgat ttgggatgtt aattacatct gcacaacttc aactttgcca tataacctaa  70500
ccatgggact gatatttatc atgcatttgg gtcaagttgc attaagagat ataataaagc  70560
tggacaagct tctgttgatt agaagagttc agttacaagg ctacacttgg gaggaatgtt  70620
tacaaactgg aatggtcaga ggatggggaa gacacttgag aaaagtcaag tgacggatga  70680
aggcaaatgt ggatatttat ctgggagaaa actaagagga gttataatag ctgtcttcaa  70740
atatttaaag ggcttttatt aggaagagga atttggcata ttggattttg ccttcagaga  70800
agtggagtcc tgagatgctc ttagccattc attccagcct ccagggctca cctgctgtct  70860
tctgtccagg ttctcggtag cagggcagta cagccccatc cgtgatcttc catagtcagg  70920
catattgtca cactcagtga gcggagagtc aaccgggagg aaggcacagt ttctctggaa  70980
tgacctacgg aatggtacgc tcaaatgcaa attctccttc ccttccccag tccttgtcct  71040
tcagatggta atttaggagc tgaaggtcag ggcaccagca gcctttggaa gcctacagga  71100
caacagtcag cctggctaga aaaaaaaaca atgtcacagg catgttgtgt ttaatcacat  71160
gaaggatatt tgcattgttt tccaactgat gccagcagac acattgtcag tggtatcatg  71220
cctggggtat cagagttgac attgggttgc cccttctctg aggcattcat gtaaatcctt  71280
ttaagtttat aaaacctcca tgtggctcct gcatgcttca tcatttgcat gtgtctcttt  71340
ttccagggga ggcagcatgg ggagcaggat gctggtgggc tccaggtgca gagagcaggg  71400
tgggcgtcag accccaggtc cactgtgcac gccctcttgt agagcccgtt ccgttgtcca  71460
tgagatgagg agtgttctta tctctaaagt attatcatga aaacctaaca atgtagaaag  71520
actaaagcac atgggtggtg cttcataaat agtatttctc ccactttctg aaaactcctg  71580
```

-continued

```
ctgaagtaac tgcacaagaa tccttgaaca tttagaattc tggttttagc cataccataa  71640
agtcagtagt gcgtggtgga attctgctaa cgaaaattgc gaaggatcaa ggcagagtac  71700
agagctggtg tgtagcgggt accttctgtc tgctggcact aggtatttta cacattaaat  71760
cagctcgttc tcacatcagc tcttttaaaa ataaggaaat gaggagccac agtggcccaa  71820
ctgatgcagt ggcagaagta gaatttgagc ttgtgcagat gtgcctccgt gttttgtctc  71880
ctgagcatgc tgccccaagt ttgacaatac caagatttgt actggaacat tccctcccat  71940
ccccaccccc tagaagcccc tcttcctccc ttagatttga cacatagttt gaaaccacta  72000
ttaactacct tatgagagcc actgtttgtg aagtgctgac tatgtgccag gtcccgtgcc  72060
gtgcaatttt tgtgaattat ctcgtgtcta cagtgcctca caatttctct gctcaatacc  72120
tccatgttac tgccgaggaa agggaagctc agagagagta agtaatttgc tcgagttaaa  72180
gagctggcca ggacagccag gggcttgcac cccggagcct tcatccacta cactgtcagc  72240
tggtatctca accagccatt acaggctgta aaaaaattat ataagatagt ctatggtaat  72300
gcagaaaagt gaggttattt tgctcccttt ccctttgaag aaaaaagccc tggaaagaca  72360
tatcacttga gtatgggaaa aaatgaagct gtggcttttc tgtgagtcaa ttctttcctg  72420
gcagcttctt ggaataagac caagtatagc agcagagttt tctgttttaa tttgagctgc  72480
agggtgactt tttttcttct atgctttcat ctctctgtgg cttcttttgc ctcgttaatt  72540
tcatgccctg cccaggcggg ctactgtgct gcccagtcac ccgggtctgg ggcggccacc  72600
gctggccagc aggcaggccc tccagaggca gaggtggcca cgcttaggtc gctcccgctg  72660
tggaggcggc acacttgggt ggcagcacag ctgtgatgtg gcggcagctg gcagccccat  72720
gggaaagatg tgtgaagtgt ggggtttgac gacccatggg agaacagact ttcttcctct  72780
tcttgttttc ccttcaaagc cgtgagtcaa cctcaaattc tctgtctttt ttctccaccc  72840
cctcgtgcct ctctccctca cgctctgcat ctctcattgc aagcttgcat ttttttgcac  72900
acaacactat cttaatattt ctcttttctg caggcaggaa atgagaagtc atttttcagg  72960
gtcattcagg aagtcatcca gagttataat ggcccattat ctactggtca gagtttactt  73020
aggctttcac tacttccact gcccacttga aacagggaaa aatattttcc ccccgcgctg  73080
tgagtgtgct atttagagct gaccacaagc ggggggaaga gaggatggct cggatgctgc  73140
atttccactg agaacacaag gctggcaaag cttgtctgct gcccagcaag cacttcaggc  73200
tcacaccatt ttaggttcac tttaagtagt ttctcaattg ttaaaaaaaa aacaaaaaaa  73260
aaaaaacctg tactctgagg atatgcttat aatcccatag ctaacccaga atttcttaga  73320
gaactgatca acatcagcag tggcacttac tgaaaatgca cattctcagg ccctgcgtag  73380
ggcctactga gttagaatat tagagagcag gtctcagaaa cattctatcc ggcagtctta  73440
ttctatgcac ccgaagggat aagagccatg ctttcatgaa acatgggttg tgtgtaaaat  73500
gtttaaaagg tatggcaaaa tgtgtttgat tggcaccaag gatttctggt tcctcctaga  73560
atcattaatc aaactttgaa ggagaaataa gagagtcggc attttcttgc acattctttg  73620
tgatgttgtg atgagttgga aacttcccga ttgggtttat tagagcatga acacccaggc  73680
acccagcttc tagccagccc tgtcaggcag agtctcctcg aagatgtgga aaggactgac  73740
caacagctga ggcctacagg aacctgagca ggcaagggga gaggcacccc ggaaccagga  73800
gcaatggcct tcccaccctc cctcgtcctc tcctcttctc cttttggagt tgcaggccac  73860
agaaaggaag tgacatgagt cactttgggc cttcttaatt ccttcatcaa aggcagcaca  73920
ggtgtgtatg tgtgttggtg gctaattgag gtaggcccac agaggagata acagatggac  73980
```

atactatttc ctttcttcca ttctgatata attcagggta taaacacaca cacacacaca 74040
cacacacatt ctcacttctt tggcatctac cacacctgcc ccagtgccca tttctctccc 74100
acctgaataa aaagccccca caaagcctga ggtacatgga aaggagcagt ggtctggctc 74160
ccaggagtgt gagaagcagc catgttttca gaggctgtat tccacttgga cttggcccta 74220
cgctgaaggt aggagcggat gggggaggcc cccttcgcac aaagagcccc atgaaagagt 74280
gcacagtcca gtctataaaa cagacgcaga aaatgtgtgt aggacttctt cctgaaaaag 74340
agcgtggtgc gtccagtacc tccatgttca tggaacttcc cagtctgcag tttacccttt 74400
tgtgcaactc ccttttggta aagccctggt cacacttctg gttgttcaga ttatacaggg 74460
ataattccag agtgatttta aagtcaactg ccaggcatcc gcacttgcaa attagatgcc 74520
tggcacatgc ttgtgttaag gtaataattc attacaatac aaattacagg ggagttcctc 74580
tgggcatgcg acctttcccg tcatttggct ttccctgtga ttatcagggg agcttccatc 74640
gtgctgctaa tgggacctta accatgtgtc aacccatggc tgtaatgctg acactgtttt 74700
ctttctggaa tgaaaggcct tcgcaattga aaccaaaatg ttatccaact cagtcctgtc 74760
cctttgacga tgaaaacatc aagttctgga gactggccat ccagcctccc tgcctcatct 74820
cccacgccct ccatcatttt ttgtctctac ttacttattt atttggctgt attttacgta 74880
catcatgcaa aaatattcct ctttgtaaaa agtataatga tttcaggaaa ttagagggta 74940
aaaagcaaga accatgcttt cactccactg tcaagagttg tggaagaatc cttccagcat 75000
tttttctgtg tattttacat acatacaaat atatgtacaa ataaaggtcg atcatttagg 75060
ttttgtttat atttttgtat atatgagctt atgtcattca tacatattgt tttgcctctt 75120
gctttttttt aacttaattt tactttgctt gagagctttt tgaactgaag tacgtgtaag 75180
tcagcctatg catgtaatgg ctccctcatc ttctgtgagg ctgtcactaa aaaggggatt 75240
tagcttgttc tgggctttgc agcccgtaca ctgggcactg ttcatacgta cttctctgtg 75300
cacgcaaagg agggcttgct agggaggcct ggcagagggt gccattcaaa taggattttc 75360
aatggaggaa tttttaaatt ttcagttatt tgaataagtt ttaatatata tccagaaccc 75420
caaatcatca agtttgtttt cttccacatc tgtccttcca tttctgaact attttaaggc 75480
cagtcatgtc tcatccaaga aatcccatcc tttcacacaa cactatctcc gtttcatggt 75540
tatgaatctc taaaagcatg atttttaaaa cataatcaca atgctgtcat cgaacttaaa 75600
aattagccat aaatctctta tgttacccaa caaccagcct actgacacat ctccagttgt 75660
ctcaaaaatg tgttttccat tgtggtttgt ctgaaacatg atccaaaagt cagacccacc 75720
tctcaccttt ccctaacctg ccggagccca tgtttctttc cagccaggct tggagaccac 75780
cacacgggat ttgcttcttg gggcctccct ctaaccagct atgcaggatg ccctctttcc 75840
tgtcaataca agctgctcaa aggactcatt cagttcaaat tcacctatgt gagcctaggt 75900
gatgctactt atttatttat ttatttattt atttatttat ttatttattt attttgagat 75960
ggagtctcac tctgttgccc aggctggagt tcagtggcat aatctgggct cactgcaagc 76020
tctgcctccc gggttcaagt gattctcctg cctcagcctc ctcagtagct gagattacag 76080
gcacgtgcca ccacgcccag ctaattttta tagttttagt agagacaggg tttcaccatg 76140
ttggtcaggt tggtctcaaa ctcctgacct cgtgatccac ccacctcggc ttcccaaagt 76200
gcttcatgtt ttcaggagct gtacgtgcat ttttagtttt gatgaccagg tcctttttct 76260 gtttttttaaa gaacttcaaa tgatctccag ggtacacagc gcttgtgtgc tgatgaaaaa 76320
gctggcagta caaaggccac cagccaaggt cacacagcca aaaagcccct gacctcgggc 76380
cccttcccag accctgggtc ttttgctgcc acatgaatct tcttcaaggt cctatgtgta 76440
gattttcttg acttggccat attatttagg attcagatat aataacaaaa tagatgttaa 76500
agcataacat gaaggcattt aaaagggtag aaagcacatg atttactaaa accataaatc 76560
ttatgacctg aaagtttcac ctaatctctt aaaaaatacc gtactaaacc ctgattgaaa 76620
atcagagctc agacatacag cctgagatgc caaaaaatgg ccaggcttgt ctgttgagaa 76680
agccatatgt aactaactgt ttggaaattc aaaatatatc ttatcatttt aaaaacatct 76740
ttcttctaaa gacaatcatc ttggcttcag gaatgaggct agtaaaaagt gaaatactcc 76800
tacttgtgga agaaatcctc attttaacca tgaagaactg aaaaatgcat tctgatgttg 76860
atggacccaa cctatatttg ggtattttat gatgtacaca atatactttt gtatatgaga 76920
ttgttattaa atgtgacttt gctttttcaa gacatacaat gttcctccgg gggtcaggca 76980
ctgtgtttag cactttgtcc tgacctcatc tgacttctca gctgtccctg agaggtacca 77040
gtgtgcaaga tcgctgagtt ggcaagtgat agtgacaata ttttcacccc aatttctaat 77100
ttaaagaccc cgatttctag ttttgttttg tattggattt gcacaatttc acgttctgaa 77160
agaggatgcc ctcaactttg caaaatgggc cttttgaatg aaaaggatca gtcatgtcag 77220
gaaaagcgct acaatgatga aatatgataa ataagtcagt ctttcatctg taattatcta 77280
ctatggggta aaaagtgatg aaaactacca tcttgaaagg ttctggtgat agtggttcct 77340
aatgcagtga aagatgtgta agtcaaagat ttgtaaccag ccagggaatg agaggcgaag 77400
ccatagctgg tggcgggggc cacatctggg tgtggggagg ccacagttgg gttgggggtg 77460
gggcctgcag ttatccacac ccctcccacc tcccttcgac agtacaggct tcctggttac 77520
cttccagaga gtaaggccag ggagagttga ataagttgag aaatgtcatg tcgaagctat 77580
tggtggaaag agttccatta attgacaata caagtcccta ctacattcta aaatctggtc 77640
ctgactagtg gcaagccggg cccaggagta gcacttaaac aatggcaggc ttgtgttgct 77700
ggcaggatac ttcagcctca gaggagctgt gtgcagctgg ggagactcac actcagagga 77760
tttcaaagca gagggcatct cgtagagcaa cttatccaaa ccctgaccca ctgtaaacac 77820
acacacacac acacacacac acacacacac acacacacac cctgagagag agaaagagag 77880
agagataact aaagagagag aactaaagtt tggcaaaata atacatgctc taatgaaggt 77940
ttattaatga ttaatctact cctagcattt cctagtccac tctatctcct taaaaaaaaa 78000
ttctggttgc agcccactaa cttgattgta cagctgctta atggatagca ggctgtaatt 78060
ttcagagaac tgtttaatgc gggctacctc tgttcttcca tgctgcttgt ggttcctgct 78120
ctgctcagga cagaatgggg aggaaaacag gctctgcggc acaatattgg caagtgaaat 78180
tttgtaaacc ggccctccct tccttttgca tttggtctga aaattcaatt agatgctgag 78240
tcctacaatg tatttgagaa gcccaggagt gccctagagg atgagactgg gtggctccct 78300
gtcaggttga acatttgcct taattacttt ggcaagattt gcatcagtgg tattagtccc 78360
tgcctcactt ggaggcctgc acttaagtgg ccacattcag gctccaattt cctggtgatt 78420
tcatagtgta gggcacttgc aatcaaaact aggcttaaag cccaaccctc ttacatttta 78480
cccacccccca caaatgcagc aaataaaatg actctgattt tcattcccta gacctctttt 78540
ctatatttat tacattattg ttaagacagt ttttgaagaa agctgtttta tttaacaaaa 78600
tagctttatg gaatcaactt catatatctt ctccgccaga tcaaaacaag ctcgtagtat 78660
tagatgtcac cgagcaccat gacaggcaga tgaacatcat ccctgtgccc ggctaatgat 78720
agctcggcct gccccggcgt cagccgctcc tggcagggcc agcgggcggt gtgggaccgg 78780
caccgtatct ccagcaattc gcagataaca aatatggttc tgatgatgtt actaaagatc 78840
tgtccctttc aagattggat tagacattag gaatttggag ggctttttat tgctagcatt 78900
tttaagaata accaattaga gtattgattc taaagtctga aagccacatg gacagagttc 78960
atgtaattgg ctactttatg tgcctcttcc tagattgccc tgcattttca aaacaagagc 79020
ctttctattt taatcaaaag aatccagaat gaaatgaggc tttgaaaact cagcctatgt 79080
ttgtcttgat ttccttaact gacatctaga agaaaatatg agctcagggg tccgctgggt 79140
tccttccagc gcctaagcct gtaagctctt cctgctggaa ccaagcttta aatgcacttg 79200
tcagtcatgt cccatgagaa tagatactgc cttccatgtt tttttgttct gatttccgtg 79260
tttgaaatga tgaaaatcat ttttctgtgc tttttaaaaa tggaattgct tttgtgttgg 79320
gaattgtgct gttcattttt actctacctc gttttggaat cactaatgtg gccaatttat 79380
agccaaaaat cagtatcgta gagtgagcaa tgaatggcat ggtgactgtg tgagcgaatt 79440
catgccctcc ctccccaccg ctcgccccgc gtctcagtcc tcagtgatgg taaacagaat 79500
gaggaccttc tcccgaccgt gatgcgcctc agccctactt cccttgtcct ttcctatcat 79560
aaaatcttct ttcatagaaa tggtcatttc tgttcatatc tgtggactgt aaataacaag 79620
gaagtcattt ttgaggtgaa aactgcactt agactcattc caattttgat ggaaactttt 79680
agctggtgga tggcattttg ttttgtctta gttttgcaag gagttatctt aatttaggga 79740
gatgaaacta gtctgtgatc cgaggtctca cttccataca tttctctcgg gcagtgtggc 79800
tgcctgaatc atgcctggat gccacaggtg cttagccagc tggtcctgtc gtaactgtca 79860
ctggtagctc agggagtgca gaggtgccag cagacactat gaaattggcc tcgtaaagca 79920
tcagttatgt tgtgatggtg gcaaagctgc aggcgagatg ggaagtgcag ccactgagaa 79980
ctcacagtag agcgtgtgta acgtaaaaag atgaaaccca ttgtacacag ctgtgtactg 80040
cctccttgaa gtcaaatttc ccccattacc aaggaaaagt tttttctgaa gggggctgct 80100
tgacaggatg acatctggtg atatcattta ttcctttgga aatcaatctg tggaagtgag 80160
tttccactga ctgatgagga gaaaaatgaa ttggcttcac ccagcatcca gcttcttatc 80220
ctgggagaga tagctcttgg tctgtcatcc acgcagctgc ctggtgcaag agccaagttt 80280
gtgcagcctg cagagcactc ttcctgagct gtgggctgcc aggtcggggg gcaggggggg 80340
cctcactgtg cagcctcctg ccacccactg atcatctggg gagactggcc tatcctgtca 80400
ggagacgcag ttgcccagac gttttcaagg gcctaagatg taggcagttg atccacagat 80460
ttttggagag tccttgagtt ggagattaca ggtgacctca gaggagggag tgagaacatc 80520
tgggtcatgg gtttctacta ggagtccaca gtgaaaacaa gaagaggaat ttacgacaag 80580
acagtccagc aacttccttt ctaacttctc ctttcacata tgctggatac tccaagactt 80640
tgcatttaca tggacatcac agatccactt tgagagaagt agggtaaaaa gaaataaata 80700
catagtgctt taggtgtatt tctatacatc ttaattgata tgggattaca ttttcacttg 80760
tgtttactgt acagactcta gacagatcct gctcttttgc aggtaaaaca aatatttctt 80820
aaaacctaga aagacccaaa acaatttaac agaaacattt tggaccattt tggaccttgg 80880
cagttaggcc ccagtgcagc agcggcaacc ataaacctct ccataggtgc tgaacccagg 80940
tgatccctgg caccggcagc cttatgtcag ggctctctta tcgctggttt ttatttctcc 81000
taataaaagt gattaaaaga ttcatctttt aaagaaagca aggacacaga ggtggattct 81060

```
ccctgacgct agcacagctc atgcccaagc cactcctgca gggctctggt ctaagtgcaa  81120
aagctggaaa agctgcaggt cccgcaagac acagagcaac cctgcaagcc aggtcacctt  81180
ccctcttctc tgctgtccga ctggccctcc accatgtgac attcaaaagc tcaagttact  81240
taacctctca aaactcagca tccttttctg tacagtgggg aagatactgg actgttgtga  81300
ggattaagtg aggagagtgg cccaatgagg ttgacagtta ttactgtcat tgtcattatt  81360
tgccttctca caggcaggcg tgccacagtc attttactga agctgcttca gtgggtcctg  81420
aattaggccc tgtcctttgg gagagacagt cctggttcaa cacacagctc cctgcccagg  81480
gcagcttggg agtgtgggcc agtttcgcct ttagaaccac aattctctga tatgtgcaat  81540
gagagaatta attatagact caaaggattg catgcagaca cacacagata caaacacata  81600
cacacaacac acagagttac acacagacat gctcacaata cacagaaata cacacagaca  81660
cacgcacaca gcacacagag atacacacag acacacacac acacacacac agacatacgc  81720
acagatgggc acacacagag acacactcac agagacacac agatacacac aggcacacac  81780
acagagagac atacacacag cccacaggga tacacacaga cacacagaga catacctaca  81840
acacacagag atacacacag tcacacacag agagacatac atacaataca cagagataca  81900
cacagagaca cagatacaga cacagacaga catacacaca gacacgggca cacacagaga  81960
cacacagaca cacacaggca cacacgtgca gataaggtaa tattagctag ttcaggagga  82020
gaaagagata aagataaagt aatattagct agttcaggag gagtgaaaga agccttgttt  82080
ttctccactt tttatagaag agaaagtgaa gattcgattt gaggtgagtt cagcacaaaa  82140
gcgtatccca ggccctctgg ctccaactgc agccctttct acctcattcc cagaccccac  82200
ctaagccttt tctcttcaaa atcttctcag gcacactgat acacatacct cagattttta  82260
attctccggt tgtgttcacc aggtgcttgg tcatgattaa gaattccgtg atgtgtaccc  82320
catgtgttta aatttgctgc tgagttaact ttgtggcggc ctgtggacta gacctctgca  82380
catgcaatgc agaacggcag ggccagattt gaaatcctgc tatcttttcg gctgccttgt  82440
aaaaataaca tcaggcgatg gggatacgat gccagaggtc acctgtgata agttctgttt  82500
atggccattt tacttctagg aagacaggaa gtgtcaggat ctcagggatc taggaagcca  82560
aaatgttttt ccactctgaa ataaagtgac tgaccaggag ttcccggcca cgcagccctg  82620
tgggaactgc cgcacggcca cttttatgaa gtggacacgt gttggtccca ctgaaaagaa  82680
actccccacc catggctccc tcacgctgca gcagaggccc tgccacagca cctgtcagcc  82740
cctgccagct tgcaggggcg caggcgcaga gcggtttgtg cccttgctgg agccagggaa  82800
gggcacaggg tccctcctgg agtcatggga ggtgcagccg aggttctata ttaaaataca  82860
gaggctagca catgtgcttg ggaatgcag ctacagtagt ggaatgaaag tgctgtccgt  82920
tccttacccc cccagctcct cacctgtcct ccacacgcat atccctggct ccctttccct  82980
agtaaggaga ctgaattgaa attgtggctt gcccgaggct gcatacctgt gctctttctg  83040
aagcccaagt cactggctct agaattctaa cctgtgagga agccactgag gatgtttgtc  83100
aaaatacata tttctgtgcc ttgccccagt tccacggccc aggaatctgc agttttcaca  83160
agcaccccca ggtgattctg gtggtgtctt tgcacttctt caaggcagta ctgcctggaa  83220
cgcagaatcc cagcctcctc tatcctcctt gcctaatggc ctggatgctc tcagatctac  83280
aggggaaggg aaggtcacac agtcatcgca atagtaacct cagctgataa atcctccccc  83340
ataaaactta ttccccagtg ttttttaata ggaaacaata aaactgtaac cagcccaaat  83400
atccatcaaa gagaaaatgg agaagtaaat catcgcacat tcacctggac cagatctatt  83460
```

gtaaagccaa taatactgaa gccccttcca aggccctggg agtcctaaca gtgcactggc 83520
agtgtctata atttatatta tgaaatttgc ataaggaaaa cattttgtct catttgtgca 83580
atttctcctt ctaaatatac gtgtcacttt gtacctgatt tctataagac ccaggaccta 83640
caaaccctgt gtctgcccct gcagccaccc agggaaggac tgcacagcag caagacagat 83700
tgccatggag catgttgtgc ccaactaggg acagcgcaga tagattctgt aatttgccta 83760
acaatgtcta taggatgatc ccatttgtca aaaaaaaaaa agaactgggc tttattgatg 83820
tcacctaaat gcacctaaac ttcttttttg ccccatgctc ttctgtactc ttgatctttc 83880
cccaaatttt taaaaacatg acactcattc ccttattttt cctacttaga aaagtgtaga 83940
tggttttatc ataggaagtt caaaaaaatt aaaatataat gaaaaatact caaatagtgc 84000
ctcacaacag taactactgc taacataaat aaaatccata tttcctctca tacagacccc 84060
agagttgctt tgcctgacag tgtagttgat ggagaaaata atctttatcc ttagcctcca 84120
tctggttgca gaccataaag acagggaaaa aatgagggtg ttggtagctt cgttagaaac 84180
tgaaagctca ctgatttttt caaaacctaa atagcctgtg tttctccaaa taactaattt 84240
gcagccttcg gcagccagga ctggcaggga tggggctagg gggactgggg agaactgctc 84300
tctcctgagg gtggtctgac ccgacagcac gcatgacctt cccacagtca ggaactgctc 84360
agagacgtga tggcaactcc atagaatgaa atactcttca gccagtaaaa tgtatttttg 84420
gataaatatt tgctttaaaa aactttacta tatgttgtta aatgaaaaaa aaaccttaag 84480
gcatcagaaa ttatgtgcag taaaatctca cttttgtaaa taaatatacc tgtttactac 84540
gtatgcataa aaagaatcct gagaaatata agtactgtat gcatattgtt gttaagtatt 84600
ttttctgttt gcttatctat aattctaatt ttgcttcaaa gaacaagtta ctccggcaat 84660
ataaaaataa aataactaat ttgtcttgtc atcaaacaga tagtaagaac aggcaaacct 84720
ggccctccac actgccagcc ttttgtgatt caaggcttca gtttcctcca cttgttaaaa 84780
agattcaaca aagtagttga aatagtatgt gaaccagtaa accctaaaag gtgtccagtg 84840
ttgtctgtga gctaattaag tgatttgatt ctgactcccc gagtcttctg atttcgaagc 84900
agtggggagt cagacaggag cctcaggtgg cctctcctga gaggccctgg aaagtgatga 84960
gaacctggcc tctggcagct cttcataaac gtccatgttt tccctctact ctctcactct 85020
tttcccaggg cctcaaacag aagatgaaaa tcaatttcta aaacagccct ctgtgtgctc 85080
tctcgtatct ctccttttca cacatcgtgg tggtggcttt ctctgtgttc ctctgttgat 85140
tcagtctctg gaattaacgg atcaggattc catgcccaga atgctacaaa gactgtgctt 85200
gagttctccc acatctcact caattacaca gaagtttcag attatgtaac agatgctgtg 85260
ctgggttagg cagagccatc tgacttgttt tgctttattt tagaccatga gatgggtgag 85320
tttttctttt taatgccaca ttcttttaag aattaaaaac ctccacttgg ctgtcagcat 85380
tggaaatcag agtgatggtg caagccctga tgaggacaat gtccttgtct atgaaaaggt 85440
gaaatcattg cttgaaatcg ctaagcagga catgcagtcc cagatggagg ggggaattcg 85500
ggagctggtt ggaaaagagt atttggcact ttgcagcctt gagaggtgca gaagagacac 85560
cgaggggttc accaccagag ccaccattgt cagagaggcg tccagctgtg tccacctggg 85620
actctgcctt cagggcttct tgcctggctg ggagctgcac aggcagactc ctgggacggt 85680
gtgccgacag ctctgggcac ccccttctag gatctgattc ctgaggaatc acaatgtgga 85740
tttcacaatc acttccagtg tcttttgcca acctctgtga acagatgtgc aattaaaaaa 85800

-continued

```
aaaaaaagaa aggggcccaa ttctcaacac tgtaagtgga aactttttaa tggaaaagga  85860
taggctaatg aattgaattt gaaatctgag acagaaccga tgcatcaaat gtgctggtgt  85920
ttacagataa tacaaggggg gctgcatctt atggtttcaa tcctttttta aatttttgtt  85980
ctgagagacc cagccagcag actgccgcca gtcttgtcag agatgtcagt ggtggccact  86040
ctgaatggaa agcagcatct ctcagcatct ctgaggcact gctcctcagc ggagactgtg  86100
gtggctttgc ctttcagcac gcatcctttc tacgatgcct gacagtgccc agggaatggg  86160
cagagctggg agctctgaag ccctttcacc taaaccaccc tgggtcacct gacctagttt  86220
tcctcccaat tttaattatg tcaggcactt cacaaaggcc tccttgggga caccatgagc  86280
tcactgtcat cagattgctc caatcacagc tgtggcttgc acacaaccgc catctctgcc  86340
ccagcagatg ctgtgtgtaa acagttgtat taattacatc tcaaaaacat ggttcttgcc  86400
agatcctcag gatttgggtg cagcctctga ggtgggtggg aggccctcga gggagaaatg  86460
tctgcaggaa attcttcccc tacgagaggt ctgttttcta agttatctaa gagctactgc  86520
agctgtttac tgcagagtga ccctgctcaa agctgtggtc acccaaggct ttgaaagggg  86580
acctccactt ccgccctggg tggagcaccg tgctggagac ccacgcctgc caaggcctca  86640
ttgtcatctc cacacgccgt ccttggggtg ggccactcct gggacacgca gacaggaagc  86700
cggccacctg agccactcgg aggctctatc cagagtcagc tgccaagcct cacgtcacac  86760
atcactgtta gtcttggagg gctggcgggg ccctgaagtc aattgaacac ttggatgaca  86820
gggaacttgc cactgccaga ggcaatatgc tccatttttt tgacagttcc aacaattttt  86880
ctttaaactg tcataaaaaa ttgctgctgt gaataccagt gtcggcgtcc ctgcctcacc  86940
tttacctggt gcttttccac cacacaaaac tgtttctcct cgtgctggcc ttgggcttgc  87000
agacagctga ttcttctcct cccgcggctg agcagcctcc tccgagcaac cctctgacaa  87060
ctctgctcct tctgacaacc tctgcaaggg ctgccagatg tgaacaaggg gcccgggcag  87120
aaggtatcca ggaagactgg aaactcgagg aagcctgccc tgtcctgtcc accagacttt  87180
acgcttgcgt cactgggctt tgggacctaa gtcctcgtca tttgttcctt ttgcagttcc  87240
tactgttctc agcacttcct tccagcttac tgaggtacac tcagatgtga tatgccatcg  87300
gtacagacac agttctgctc cagcatttcc ccgtgttctt tctgtcgctc tatttactga  87360
attaccgtga ggatgtggag cgaggctgag ttctgtattt taacaccatt ttaattctca  87420
cctactgaga aatccatcct cttatcactg tgcttttttt aacctgtcac gaatccatga  87480
aatcctatca gccagcctgc atacttcctt ttaaggtgca gttgaatcag gagaaacttg  87540
ccgcacatgc tgcgtccggg cacagcattg gctgaggctg ctgccctgac ctgtccgctt  87600
tgtagtactg cccagctatg aaacaggtta gccacacatg acctgcattt aggagtaaca  87660
agtctgtctg tacatgcaca tacagcaact tttttaaact gtctatattt tttcctgaga  87720
taggtattta taatatctcc atcttctttc ccattttgaa acttagaaca agtttgcctg  87780
tcaacagttc tccacagcat actgtgtatt ctaggatttt ctaaggttga gcaacggagg  87840
ttcagcaatt ttgacttaat ttcttcccat cccttttcca cgcagcccag aagccttgga  87900
tcacgtggtg aggggaagag gttgtgctat gtcgggaaac tctgtatcga agctcggctc  87960
agatcatgac attctcttga ctaaaaccct cagtttccat caaacttgtc actctggcat  88020
taaagcctgt cactgtgtgg ctctgaaaac ctctctgaac gtgttccctg cctctgccct  88080
gcaggtccct gtgctccaca gaagcccact tatgtgaccc acccccactc atcaccacct  88140
tccctcaccc agagcctcag ctccccactc ccacctgtaa gacccctact ggaaagattc  88200
```

ccacctgccc ctcaagatta atctccaagg acatttccaa attcctctcc ccatctctca 88260
gccagatggc tttgctccct ccaggaaccc cagccacctt cgacctccag cagggcactc 88320
cactccacat tctcctggtc tgtctggctc atcttacctg agccatgctc tccaggtgaa 88380
ggactatgtc taactcaact ctgctttaaa agcagctaac acattgctct ttgcatattg 88440
ttcactcact aagttgaact ggacttggac atgcacactg aactgcagcg tctgctgctt 88500
cttggtggcc cagctcgtca aaagaataag atttcagcaa aacaatgtaa caattttttt 88560
taccaaaagt aatgttaaca atatatggtt ttcccctgat gtttgcgtca aaatgctttt 88620
tggaaaaaac atttttcaac tctttagggt cagaattaag caatgaaatt tatataccac 88680
atgtataatg tgtatgttta tctaagtatc tgttcattta tatatcttaa atagaaattt 88740
taaaaatttt tttaaaactc ctgataaaca ttctcaggag gcacactatg taactgttgg 88800
ttgatatacc tagctagatg gtgaaatcag attttgttta aagcatggag gagagggaaa 88860
aattaaatct tgcagattct gcagtcctta acatctttga aagaggaaca tttcagacaa 88920
tgtaataaga aggccacgtg ctttgacttc tgtagatttt aaaaatactt ctgtatagtt 88980
tcttcttcct ttgaagaagt ttggggagtt tgggaagatg gagaaagata taagaataga 89040
ctccccatat gggtcatgaa ttatcttttt gcatcagaac tcttagtgca gtttcagtat 89100
tttcttcctc aggagggtga gctgcttccg aatgtcctcc ccttctttga ggcatcctct 89160
gttggtgaac tttgagagca tccatttatg aagttgatga cctttcccag tctctgcaag 89220
cccttcagtg tgtgtcctct ctgagcaaat ctgaattgtg tgcttaatac atggaaaggg 89280
atttgggagg gttgcttttt aaactgattt cttaattaat attatggttt agttaactag 89340
acagtctcat tgcagaagtg cataaccata atatgtcttc aaatatatct cccttcctaa 89400
caccctgtaa tatactttg taaagatacc cttacagaat gtgatccacc atttatgaac 89460
ctgcagcatt gcattcagag actaagtgaa aagctggcag attttcattt aaagcacaag 89520
ctaaggaaga aagctggtct agaaggagct acagaagggt aatgcttagg gagggaatga 89580
tgtgcctgtg ggtggtggta gttaaatcta accaaagaat gatgtcgtgg gtgtttggat 89640
attggatggt ccacattggg ccacattctt tcaaacataa gagtctgtag aaatatgacc 89700
tgtaaaagac tcttaaatat tctggaaact gtttcttcct tgtcacatcc ttatatatac 89760
ttgaacctat gcctaccaga catgacatgt gactattcat acagatttca tcatctctgg 89820
tttaagaata aaggatgctg catagaaggc tcacatcttt taattcacaa gactgaaact 89880
gttctgaaat gacattgttt ctaaaaattc attacttgca ttatattcat ttttattttt 89940
ccatgccaga agggtagaag ttcctgtgct catattaaga aacagcaatg tcaatcgagg 90000
cccaactcaa atccaattta taggagttat aaagggcgtg tgcctgtttt gtctagaagc 90060
agtgttgggc agcactgagt aggatagacc acctgttgct accgataaag gagcagcttc 90120
tcgaatgctc ctgtctggta ggcactatcc cgagtgcttt ggcccctcat ccacaatctg 90180
tgtggcaaaa ggcattgcag gcaattcagt gaggagaccg aggcatggag agcaagtgcc 90240
atggaattcc ctaaggccgt gcagggagca ggttgccaag ctgggttgaa accgtcctcc 90300
gtaggctccc aactccgccg tcgctgctac tgtgctggat gatgcctggt agatgcagat 90360
gtggagcccc atggattctg agacaggccg ggtttcagtc ctgccctagc tgcctattgg 90420
ctggatgacc ttggcaagtt gactttcgtg agcctcattt gtctcatctc tcaattaaga 90480
aaacctagag cctatctgtg ggggttatct gaaggattcc agggatgcat atggcactgt 90540

-continued

```
ctaccgcatg cggtaactgt ttcacaaatg atgaggagcg atttatgttc ttagtggaaa  90600
tatgtcggcg tgtgaagtcc caaagctctg ccctgcctgg cttgatccag tgcctaggca  90660
ctgcccctct tcccctctct cccaacccac tgtaagaggc taggctgcct cagtaactct  90720
gaggggcatt gactcttttc atccaaaaat tcatgttact gccccacatt ttttctgttg  90780
ttttacaacg cagtaggaag tgggcagact gtcaggaaaa gtgatttata gtcatgtatt  90840
gcttgtgctt tggcttcatt tgatccaatg cagatcagct gcactcagaa aactactcaa  90900
gtgaaagaga aaaagtaact gaagggggaa atctggatga gtaagaattc cagggatagg  90960
aatattaata gcaagctttt tgcctgatat agtcacttta tgctgcaggg gtgccccttt  91020
ataaagtgct tgtacaatgg atgtttgctt ttgattttgg atttggagtc taatgaatgt  91080
tctaaattat tattagagga gcttgcggtt gttacatgtc tgcctttatt gcttattttt  91140
agccatctcc cctgatgtca aatgctcagg caagaatgat acattcattt ataatgtggc  91200
tccttcagaa atataccaca taccttttgg tgtggtttgt ggctgagaag agtggggaat  91260
gcacaagtgg aaaactgcag aaagattatg ccttcatcac ttcaagtatt tgagatgaaa  91320
ctagatcatt tgctgttgct ttttattctc attctaagtg cttttcaaag tcagcgctaa  91380
gattttaaaa tggttttctg ttgttggcag agagggaatt actctattac tttctgataa  91440
aacagagtct ttcatgatca aagagaacca ggctctagta gttccagtat cctaacgtgg  91500
acactaattg tttccctcct tttcttcatg aaaacagctt ctgcacaaat gatagccttg  91560
tgaactagcc atgggcacaa ctggagaagc atttagggag ctttagtgca aattgagacc  91620
acctacacat ctgactctac agggtttgac aacatccagg gtgaatcaca aaacatcagt  91680
ctaatcaggg cttatataga aagagtgaaa gaactctgat ttcatcctaa agattattta  91740
tattaaccat tgttccaaat gcattaacta ttttaattta gttgttttga ttgttaaaaa  91800
aaacacatct gtttggtaga taagacataa tttaagacaa atgttctatt tgataagctt  91860
ttagaaacaa cttattttta ttctttcctg tgagataact cagatgtgga gaatgtgaca  91920
aaattttaag cataacatga gaagggctga cacacataga tttctgtgtg cttacttgaa  91980
aacaacaaaa tttaagaatt tggtatagga gttgtatcag gtagtgcaga gtccccagga  92040
gacctagaga cccaggtctg ggagcctagc ggcaagggct gaatgtggga tgacatcagc  92100
agaaactcac agccactgct attccaaaaa cccagcagca gctcagtgca gggcagtgct  92160
gatagtacag tgcctgcaat cctggagtgg atttggatgt gtcaggtacg cacacgctca  92220
ctgctccccc agcagtacgt tgaacagtgt gcgtccaggt gtctgtaggg cccctcgccc  92280
taactcacaa aaccattctg ggtcagaagc caccaatatt gtcatcatcc tcccttttct  92340
gagaacccta gtaagtccct ccagtggggc aagcccacct tttcccttca ttctgtggca  92400
atatgccttc atttcctaat cagttttgcc ctgctcattc aatgcaaaat ggatctgctt  92460
tccttgggca ccaatatgtc cagggattgt ttatcaatct tcagttctgt ttcctttaca  92520
tatccctcca aaaatcaggc ctgcactgcc tgtgcactcc acaatccaca ggcctgaagg  92580
aaatgttatc tttgatgtag agacttaaag taaaactctt caaattaatt atttcatgca  92640
aaaggctagt cctgactcta attctaagac atgtctccta aactctggaa gtctgatgta  92700
tcctattatc aacatttatc cttaatgtga tggtttatca tttatcctca aagctgcatt  92760
gtaaaatgta cactgtaaag tgtacatttt aaagtcggtt ttaaaaaatc atatttagag  92820
atcctggtaa aaatctatca agtcaagaca ttaccttatt acccatggaa ttgtcttcaa  92880
ctcttacagt tcaaatattc ctgaattggc tttcacaata aacatcctaa atatgtaagt  92940
```

agaaacatat atattgccaa ctttgtgcct tcccaagcaa aattaaaata caggaaaagt 93000
cagtttgttt tgcccataaa taaatatatg tgtgtgtgta tgtgtgtgta tacacataca 93060
cactcagaaa agatagaagc agcagcatat tttggcagca tctggtttat tggaactcaa 93120
acgttctgat tgtgcataca gactagttaa tgtggtaaca attatgtatt tcttccctgc 93180
tccttgcctt ctttccctcc ccagtttttt tcttcctgat agtaggtgtg tacttttttc 93240
ctatttccat tggcaagcca catgacaagc aaaacgatca ctcgaagaat attgttccct 93300
caatcaagaa aaatgcccat tgggttttgt tatttgatgt tatttgatga cagagaccta 93360
ttgtttttcc atttttcttt ttttgtttc cgtggcacct atggaattaa gcaatataaa 93420
aaatctatta tttcagatgt tcacgtctaa tgaatttcat gtgaaatact ggcagtataa 93480
ccccaaatag aggaaatttg tgaagagtgg atgctgcagg gcatgagaca tctgcacaga 93540
gttcatctct tccagcatct tgcatgtccc aagcactgcc ctgccaggca gagaatgctg 93600
cagatcacgg cagtgaattc cagttgttca gagcacattt gacttccaaa ttctcaaggc 93660
cacagatttg aggacagaac aatatttgca tttgaaattg gaagattatt ttttgcacaa 93720
gtgcctatat gctatataga gtttgcccac tctgcattat cttccccctg ttcccccgtt 93780
atctggcaca agctattcaa aagacacgcc tacttgtaaa ataaatggtt tgcaaactaa 93840
ggaaaatact taaatctcat gtaaatggta ctatactatg tataaaaatg tgaagaaaca 93900
cagaacagct catgaacacc tccactgctg tataaaagaa ccatcttttt tctggctcct 93960
attggatgcc ttagaaaaat ctgtatttcc tctttagtta ttgtgtttga aagatgaagt 94020
tgagacaaaa gttctattct ttttaagttg gcagaacttc tgaaaggtga tttttagctg 94080
cagtgtgact cattccaaat gcagaaatct ctgaccctga gttagtctat ttgtcatgca 94140
agagcctaga aaagccctga gtgataagaa atggccatag gccattccca cagaattttc 94200
aacaaaaata gaatcatgct tatgttctag tcatgactta gaacttataa ctcatgttcg 94260
gaactgtcca tgttcacgca caggggccgt atcactccgc cagagctgcc ctgggtgccg 94320
gtgtgcagag gggtccgaga gtgactgtct cttcctctgt tgtcgaatgt gtgggttatc 94380
tccataaatg gctgccatga gcatccttgt tcacacattt ttaggtactt gagtgagtgt 94440
ctgtggaata attttgggaa gtgaaatctg tggtcagagg tttgtgagtt ttacatgcta 94500
cattttcaga agttgagaaa tagcagtagg ctgaaggcaa gtcgccatgc ctggaattca 94560
tgaacactag ttgaaagaac tggcgtgagt tagtcatgac aggagagatg gggaagggag 94620
ttgcaggtag gagggccatc ttcaaattct caaagtatag tcactccaaa ccaaaattcg 94680
atttaatctg taggactcca ttctcaaagc acagtcactc caaaccgaaa ttcgatttaa 94740
tctgtaggac tccaggtggc agaataagag gcaatggatg ggtggaagcg aaacagggcc 94800
aaagtttgac ttcatgtgca acttcctaag gagtgatttg aactccacaa acatgaacta 94860
agcacctcaa cacaggctgg gcaagttgct gttcttttgg agcttacatc ttagtgggga 94920
aagagaaatg cctatgtaaa catataaatc agcaggatac attgtgagga cggtcattgc 94980
tcagtgagac tgcaatagag tgatacgctg gagggggctg caagggagaa ggtgggaggg 95040
acagcattta gcagaatgag cagcacagtc ccataggaag aagaatttat tgcctcctta 95100
ggcaaataaa ttcccaaacc ttgaacatca gaaaggaaat agattaatgt gcacagagga 95160
ttaaattatg tgatctgcaa agtcatttaa aatctatttc cacataaaac atattaatgc 95220
aacctaaaca aaaggggtct ggataccctc atcttcttcc caagcatcaa gtctttctat 95280
agttaaactg agatgctttt attcttggaa aattttaagg actatctaca gcaatggaag 95340
aatcgggtgt tgggatgtgt tcccaggtaa taatgactgc aggctgattt ggcccttgag 95400
gtgtggcctc atggccctct ccaaaaaaaa tcaaggacct gctacaaagc acaaagccga 95460
ctgcaatgct tgctgcttac tggttagggc agctcctctt tgccagcgac caagcagaaa 95520
gcaagacaag acaggttctg aagcagtaat tcaaagcctt cctcgctttc ccatgtgagt 95580
cattgctagt cagaatatta cctttgcaga gaggcttaat tccaaatttg ctcttaaagg 95640
gatatcctct cctggtttag gtataaactt ttgactcaca ggacaaattc tatcattcct 95700
ttgggcctag gattgcattt atttccatga caaaagggcc tgtctggtgt ttcagcaaat 95760
gaaaacaaaa atataaagcc catctccttt tgaatgagct ctaaaacagt tctccactgg 95820
acttcagaac aagagggagc tctgggctgc tggctggttg tgcatttgct gtgggttccc 95880
tccggcaggc gacctctccg cgctgagaag gttatccgga taaccaagta agaaagtaca 95940
tgaggaggca cagaaagaaa aatgtgagag ataacagcat aaacacacag tgtatgttgt 96000
tatgaggcat cacatgatga gatactgctg gggagggaag aagtgaggag attcctagga 96060
atcttatgag aatttccaga gacaacaagt tttgagcttt tttttaattt agaaaattta 96120
ccttattttt aaaagaatat gtaacatatc ccatgctata aaattctaga catagtagat 96180
ttaaaacagc ataatggaaa atataaatat ctattttctt ttcctattta tgtattctgt 96240
gccagtagga atgtagccaa aaagagagaa aaggggtctc tgcagacatg gatgtctctg 96300
tgacttgatc actgctaacc caagaagata ataaagcaga agcatgtatc caggttgctg 96360
cagccaagcc tgcccggtct gcggggcgtc ctcacacatg gggcagctct cccaccccac 96420
acactgggaa aggcggacag aggctgggca aagcccccaa ttttcgttgg cactgacccc 96480
gatgatttat aggcctttgt ttcccatgtt aaatgtctta cgatcattaa attatttata 96540
gctcaattag catgtgtcca aaaccaggaa gttcatagga gactgtgtga ctgggaatta 96600
aggagcaaag caactttcca gtctgtgatt tactgggttt ccattctgtt tcctgttcgg 96660
atccggaagt agaatttcaa atattgcttt tcatgcttta tttgggaccg attttagccc 96720
cgctctcctt tctcttgcca ttcgctggcc attagccacc agcctctgca caatgaccag 96780
ctggcccctg gcagatcttg ggcccaggtg tgaagtcgct ggagaagcat ttcagggcca 96840
agatgggagt gatttcattt tccattgaca ctatgcagaa atgaagggga ttcaagtgcc 96900
ttcagaaaag cttccttcca gcgaatggag ttttgggggt tttccagact tgcaactgct 96960
tttattcttg gaagcatcat tgttgctttt tcccccccttc catttatatc ccaggaactg 97020
attcagaaac catagaaatt ggatttggaa tcgctgaatg ctagcagaca gctgactgca 97080
ctcttcccaa gaaaccctgc cagctgggtt cgggtatcgc gcggtgtgtg ctctctctgc 97140
ctggcccgct gagtcctcta actctaatgg attccttctt acaccaaagt gcactagaac 97200
taaagtgttt tgcttcattc tttagacatt ttgtggttta gggctcaatc agccagggta 97260
tgatttgcaa tccacagtaa ccggtttcag agcagctgcc cagcgaggca ggtttcatct 97320
cgcttgctag acgttttgtt ttttttttt tctaaacctc acacctttta tttattagac 97380
ttggattcca gtttcctgag cctgtttgtg ccactgatta gacaggcttg aagcagaacc 97440
caccaggctt cctgaataaa atgcagcagt gattgtatta gggggtttta aattgctcaa 97500
aatactgtct aaaaaacact aaaaatcatg ttactttcta gattgaataa aatcctatag 97560
aaatgaattc ctggacttga tatgtagcaa gctggcattg gctcgggagt gagtgggctc 97620
agttaagtga gctaagatga gatggtgcac aggcgagcac ccacctgagg agtgtttgga 97680

```
tgttatgata gccagctcct ctgtaaagac ctgtccttct atgtcagcag cccagcagat  97740
aaatgacgtg taaataccac atttaggagg gcttatgatg atgccaatta atggagacct  97800
ttttgaaaca ggaaggaggt gaaacatatt cctttgcttc tacatcactg tgtgccaggc  97860
actgtttaca gcatctcgtt taaccagcag tcaccacctg acggatggct gatgtggggt  97920
ggggtcccag ggtgggattg cgtgatgggc ttggggtctc tggctgatgg gtgccagagc  97980
tgggactgga actcctggcg tgactgaggc agacacctgg gctacccagc ctcacccacg  98040
acgccctcac taagtgaccc acaggactca ccggaagcag ggcagcaagg tccccctaca  98100
gaggtcccca ctgcaaaccg atacccagct tagacagcag ttctgcagtc ggcgtctcac  98160
cccttcgggt ctcattgtga ctcactttga tagccacacg atttaagggt ggttcagtag  98220
tgatttgatg agtgctgtgg ctcagggtca ttcccctgcc caagcatttc aaattccaga  98280
agttcatgcc ctgcatggtg ggtgaaaagt ctcaggccaa ccatgagcac acagcagcca  98340
ggcgactgag gcagctgccc ggggtggcac gttgctcaaa cccatcattt ggagtcaaaa  98400
caaacagatg attagctggg gtggtcactt tcaatcaaga gttttcacat cgcctagaca  98460
tggcctcaga atcaggcctg gtgtggccag gggctgatct cacagtagac aggaagtgtg  98520
gcccgagggc catggctgcc ccctcagaag gccctgtgga gtggctggcc gagcctcagc  98580
agcctcctgt gaagcgagga agggtcttcc tgccggcctc tggagatcag tatgggaatg  98640
cacaagtagg aaacgctgga tgggaatccc tctgccctgt gataccaagg cagtgagttt  98700
gtagactatg gaattgctgt cggagggctc tgtaaccggc caaggtcaca caggtagcca  98760
ttggtagagc agggactgga atcccagacc cccaacttcc aggactgtgc acctttcttt  98820
atcccataca gccttacagt caagtgccag tgcaacacct gattcccagg ttccagcctt  98880
tgtcttttat aatgggaatc aaccttatct tgacgatcca gagatagtca tcaaggaaga  98940
ttaaattatc cccttagact cagagtgacc atatcatttt ccctccacac aaggacactt  99000
ttgagaatga aaaggaggag atgtctgtac cagacgctgg atgacaggca ccgacaggct  99060
gtctgccagg ggagcagcga ttcctgtatg ttgtagaaag tttttcaaaa gtcaccttgg  99120
aaagaggttt tgttccttaa ccttctgtta aataggaagc tccgtgaatg aaaacaactc  99180
ccttccctaa acattctagt aatgacccaa cactgccaag cctgccagct ctgcctcatg  99240
gtcgtgttga ctgtgtgaga ctatgtgagt gcctgctaca cagtacgctt tcagtaaaca  99300
tggtattgcc tcgataatcc cacaaaaatg tcctattcaa atcacctggc acccaggaaa  99360
tttccttctt ttttttccca ggtgaaatat acagttgaaa acacctgaca gcaattcccc  99420
tctcccatgt gtttgcagga tggtggtttt ggttcctcca tctttgatgt gtacaagtgt  99480
gatgttttcc ccccacagac aagtaaacca cattctcttc acattcccaa tgttttgtca  99540
atgtacctcc ttcaatagag gatcgataag gaaaaaaatc attgacaatc tcaattagat  99600
tcactatttc atccaaaagc atagcttaga actctagttt ttgttcaaca ctcttgccct  99660
atgagtgcac agaactttaa ttctgataca aacatccctg aatgtttagc tttgacagag  99720
attccaaggt gatttgataa gaagcagggc tgtgtttggg ctctgggagt tttgatatg   99780
gtttcaagcc ccatccaaaa cccacagacc tctagaaagt aggtgcctgc cttcctgcag  99840
cagccctgga gcctgctggg ggctttgagc agctgctgcc aagccaggcc tcacccgaca  99900
ctctgatggg cacggccatg gtggcagggg cttggacgct gccaggtgac tctaacttgt  99960
ggccagggtg ggaagcactg ctccacagag gtgccaaaac caggttcctt cctgtgttct 100020
```

-continued cacatttcac agcctcaatg taaaaagtaa gacatgggca ctctggaata ttacaaaaat 100080
atagaaaagc atgttatagt aaataaaagg ctcacagaat tttgtcattt aggaacaatg 100140
attattaata tattagtgtg tgtttttgct cattaacagt atatcctgag atatttccta 100200
taccatttaa tattttaaaa gatgtttaca ctggccacag tagctcatac ctataatccc 100260
aacactttag agggcaaggc aggaggatca cttgaggctt aaaaattagc caggtgtagt 100320
ggcacatgcc tgtagtccca gctactcagg aagctgaggc tggaggatca cttgagccca 100380
ggagttcaag gctgcagtga gctataattg caccattgca ctccagccta ggtgacacag 100440
tgagaccctg tttctaaaat aaataataaa taaattaaaa catttaaaaa tacatgatgt 100500
ttaattatta gaggactcaa ttttatatct atgtatacaa taatttttaa gtttcttaat 100560
attggacttt tagtaccttt ttaaaaatac tatttttaaa aaaatctgta tttctaactt 100620
tttataacaa ggaacctttg gctttgagat gactggggaa tccattcttt cctatagtat 100680
ccatgtccaa tggacttaaa gtattaatca atgtgtttat gttttgttat ttttctggca 100740
ttacaaaaaa ttctaaatat attgttaccg cctgtataaa tatcagcttt tgagagaagg 100800
acattgtgta gaaataatga aacactgcaa cttgtatttg tattattctt tttttttttt 100860
ttttttttga gatggagtct cgccctgtca cccaggctgg agtgcaatgg tgcgatctct 100920
gctcactgca agctccgcct cccaggttca caccattctc ctgcctcagc ctcctgagta 100980
gctgggacta caggtgcccg ccaccgcgcc gggctaattt tttgtatttt tagtagagac 101040
ggggtttcac catggtctcg atctcctgac ctcatgatct gcccgcctca gcctcccaat 101100
gcactgggat tacaggcatt atattattct ttaaattcac atgagaattt agtatggctt 101160
caaaaaatac cataagttaa aatatcacca agactctgtt cagacaaaag tatcagaaaa 101220
gtgagccagg cactcacata gtttatagtt tataaaagtg agacaggcat gatctcttaa 101280
cctcactata gtcctgtgaa taaggtttat ttacatttca ttttacctgc caggattatt 101340
gtaaaaacgc caagcacatt gcctacacaa actaaatatt cagtcaatgg ctgctatttt 101400
catgagttcg ttttaacata tatttattgt cctctactgg atttaagaag ttatatttat 101460
tatcatctaa gattttagct attccttctc ttaaaaatag attttataat caatggcagt 101520
aagggagagt aactcgcagt tctctgaatc tcaaggggtt cctggaagcc ttcctgaagg 101580
tatagtgaaa tttcagcttc acattcccat ccatgagctc cctgcaaata tcccggtctg 101640
ctctcaggac ccagtgactt acctatgcag aggctgtaga tagcacctgg agcttcctgt 101700
gtgccctcct caaactcagc caatgccgtc atacagtagc aggcaggtgt ctttgctggg 101760
tagttggact ggatgtccct gggattgcag aactggaatg gggagtgaca tcaggaaact 101820
ataatcatca ggacaacatg gtttgccata actttaagtt ttaagcgacc gcagattatg 101880
cggagagaga tgcatgccca cagccatgct tcccatgtaa ctggagaggg gtctgaagtt 101940
tgaaacaagt gttcctaggc acgggttaca gtgtttgtta tcatcatact tgatttagaa 102000
tggggcacaa catgtggatt catggtaact gttacaacct tactcatttt aatacctgaa 102060
aacatgcttt ccccatgctg ggaatcgaaa gattctccta ggaaaagaaa ggcttgacaa 102120
catcgattca aaaagggcat gcattttcct catttaaata actctaatgt gcaagtagat 102180
cccctgacct caagctcaga agagtccagg ccttcacacc ttctctgctt ctgctctggg 102240
gccagctatt gagattcctg tgcccacgca atgcgcacat cccacccctg gccgctgtcc 102300
acaagaaatc cagttgcacc aagcacccca ctttttgcac ctctcattta tgtactccta 102360
agagcctcac cacaactccc ttctaaaaac atgagttcct gactgggaat tcgatgctgc 102420
ccaggcagct ttgctcagag ggagcagcct tctagaaatg tttcaagtaa actttcaagt 102480
ataactaaat tcaaaaaaaa cacatacaca cacacacaca cacacaagtc aaaggtgtgt 102540
aatttggcca atatcacaaa ccaattagcc ctttgtaagt ggcacccaga tcaggacagc 102600
tgaccatacc agcaccctag aagcaccccg tgctgcctcc tgggacaggg ctaccaccat 102660
cctaaggcca gcacgatggg ccagctttgc ctgctgttga attttgctta catagaatcc 102720
tccagtaggt actcctttgg gtcaggttct ttcactcaac attatgtgtt gatatttttc 102780
catgctgtgc tgcaaaattg tatttcttgc attccataac tgggcagttc catcatagga 102840
gaataccaca ctgcgttcgt ccattctacc gccaatggac atatgggttc tttctctttt 102900
cttgcagtta caagtttatg aatattgtcc cacgtgtccc tggtgaactt ttgtttgcat 102960
ttctgttggg tacctcagag tggcgttgct gggtcagagg gtactggtcg ctttagtagc 103020
tttgaaagat attgccaaaa cattttccag cgcagttata gcaaattata caccaccagc 103080
agtagaaaac atctcctaat tgctcacagt aaaccccccaa agattgccac atacatcttc 103140
catatcaatt acttaactat tcagcaaatt tgaagggaaa tatatttaat ctttttattc 103200
aaatagttta taaagtggaa tagagatgtg ggtaaaagtt gtcttgccac ctttttagat 103260
cggtaaaagt ttgttgaatg caggcaagaa aagatgagaa ataatggtac ccaatgaaag 103320
acatagcagt ctacaaggag gggcatttcc cggggtgggg gggacccaca ctctgtaact 103380
cccacattca attagcatgt tataggtaag ctgcagaaaa cgaggcagct tgtcaaagag 103440
gaacggctct tggccatggt tgctgcccta ggaggatatt tgatactagc agagctgggg 103500
caaccctgga ggaaaccacc tggaatgatg ggagaactcc tccagggaac atggcccttt 103560
aatagatctc tgttataaaa aataatccca aagcagccac cagggcatac tgctgcgatc 103620
aagtcctagg cggtattccc ttctgcgcca tagaccctgt gcagagtgcc ctcaacgaag 103680
gagcaaggaa gaccaagtct cccgagggtt tgcatatgtg tatgtgattc tgcagtcatg 103740
gtgaatgaca cagtcagggc tgcggaaaag cattggtaaa gtgtatattt gaggcttcag 103800
aagtttgaaa aggctagatt tcctaggcca aaacactgaa aatttgcaat tagaacttca 103860
gtgctgatgc tgggaagact ggagttagtt tgagacatgc acctgtgcag aactgggccc 103920
ccagaaaagg agaaggaagg gaatccagac cagagtaggg cctgacacca ctcagactcg 103980
gcgtgtctat aaattagaat tgcgttacaa ttacactttg acattttagt ggtttttaaa 104040
gtgcccagca caagttaatt tttcattaat gaatccttta ttcataaaat gcttagatgg 104100
agattaccct tttgagcatt ttgccagtgc ttctgaaatt aatggggacc tcctgttgga 104160
ggacacagtc tgttgcaata ggtgaccact gctctgaatc tatgtcacct ctccaggacc 104220
acgggcacaa ccatcacctg aggcatgttg gagatgcaga tggtcaggcc ctcctagaat 104280
ctcagaatct gcattttagc aaagtcctgg gtaattccta tgtccattgg agtttgagaa 104340
gcactggtaa tctcaaatac tttaaaagat tactagagta agataggctc agtaggtacc 104400
tgaaggcacc atcccaaaga ccagagtggt agaagcaggt ggaccagcct ctgaacacat 104460
ttctccccca ctccccggct gtgtggaagg ttgccacctt tggggtagtc attcaacaaa 104520
cacgtgtcaa ctgtccacta tgtgtcaggc caccactggg cactggctgt ggctagctgg 104580
atagacacca tttctgccct ccagaaatgt catgtccact ggcacatgac aagtcactaa 104640
gtcattcaga gccatgggtg acagctccag gggccgacaa aggagctgtg atctcacaga 104700
tccacagaga agtgtcccag ggcgggcggg aaccaggact gcacagggag gggtgaagtg 104760
acacataaga agtcagccca tcagcctgaa atgctccccc aaatcttccc attcagtgtt 104820
ttctcagtag caaactcgtg ggaaaattgg ttattttact taaaaaactc atactagaaa 104880
gctagtttaa ctttaaaaat aaattttaaa aacattttta ttaacaaatc ctacctttcc 104940
tccaaagtca aggagaaaag aatagaagtg aacaatggac caagtaagcc taaaactctg 105000
ctctttcccc tgctcatttt acagttcaag tgccattcaa tttatcctgg caagaagagg 105060
aaggcatcat caagacctta attttctaat acatctgatc tgagaagaat gtgaaagcta 105120
taaaattaat ttttgatcaa taactacagg ccttttgaga gagtgccctc ctaatgaatt 105180
gagtacctat ttctccatac acagtgtcta tcatgaccta caaacccttt tcccatgagg 105240
tgtaacagag agagattaca gccttggaac tggatgtcag actctcctgg tttaagacaa 105300
taagccatga catagagcct gaaaccaaca caatcttccg agtggttcca gaaacatata 105360
ggggataatg ttggctctga tgctgtacat ccccaacaac catcaactat ttggaaacta 105420
gaatttcagc ataattggag ttggtgttac cctagcaaat gctgtgggaa gagagtctca 105480
ctgtgtatct tctcctgttt aaagcctgaa tttgttcaga atgtaatatc tctgtttagc 105540
cactctactg aaactgatct aggaaatgtt caaaaaaagg tatcccaagg atccctttgt 105600
agctacatct gtgggattcc cctcgctctg gcgtggcctg gcccctctgc atttgacaat 105660
acggtcctat gcttttgtct tcctgggctg cgtgaaccca ccctgccctg gttcacctct 105720
cctcttgacc catccttatc agtgtcttga aaggtccttc tattggagga cacattctgt 105780
tgcagcaggt gaccactgcc ccaaatctgt ttcacctccc cagggccatg ggcacaacca 105840
tccctggagt gtgttagaga tgcagttggc caggtcctcc aaaatctcag aatctgcatt 105900
tttgcaaagt cctgggtaac tcctatgtcc atgagagttt gagaagtact ggtctcatga 105960
gttcctgaca tacaaatagt gctgaggcca gtatgctgac tgggtagcca gatacaagtg 106020
aaaaccttcc tgtttttttgc aaacctggat ggacccgagg ccgctgacgt gggccaggac 106080
aagctactct ttttcagtgt ttctgttgca tcgctgtgtc tctctgtgat caggtgctgc 106140
cctccctggc aggaggactg cagacaggat gaccaagagc actctacaca gcctgctctc 106200
cagtgttggg ggacgccacc caccctcgtg gttcctgttc atctgcctac acgtggaggg 106260
cccaagaggg ctaatatgtg actatctcca cttcctggta ccctgtgtga ataacttcac 106320
ttactaaagg gatgttgagc aactttatta ataatgaaga aagcactttg gtttgacaaa 106380
taatcactcc attttttcat ttgaaagtta actcttgtta gtagagaaag caatgtatta 106440
caaccacaag gacgtttaca tggaaatgaa ccatctgcaa agcatccccc attttccttt 106500
taaatcagcc aatgggtggt ggtgggagaa atattcacca gagtatttaa catctatccc 106560
ccttcctaga ctgtcagctc catccgggcg gagactgttg gtatctccac agcacacaca 106620
gggcctggca cacatccggg gctcagtgag cacttgctga atggtgaaca gattagctct 106680
cctgggaacg ttgttgacac atctcataac actggtttgg agtggagggc attcatcggg 106740
ctgcatattc ctatttttaa ttgtattctc cactggttac agcacctaca gttataaaga 106800
cattgttaac attgcttata ggaagacatt tgatggaaat gagtccaaag gcattacggt 106860
tagaaactgg ccaggtgtca tttttgagag attagataac tgttttccgg tagagtgaat 106920
tgcctgtttg ttgcaagttg ggactttgct gggctggttt acagggccaa ggggaaagag 106980
ataagtggat cttctagtga gaggtcatct gttttgaaag cctggaagat tccatgaact 107040
aaatccaagt cttacaacac agggaagtgt gtcatactgt gcagggatga agtctccaat 107100
ttagcatgaa aacaagagct cctcacactg tcctcttcag aaagcccata caatccaaac 107160
ttctgaatgc ttagctgctt acaaccatac atagattgag ggataaaact ctgatatgga 107220
agagaaggta aacatttttt ggcagacatt cccaggaaaa ggcggctctc ttctctcatt 107280
gctgctgctc tttcagaatc catttcaaca gaggaggagt caatgggagc cccgtgcctc 107340
tggcagatat catatggcgt ttcagtggca ttgtgtgtta cccttcttag gtaacagctc 107400
agccattaga agaatgtcct acacaccttc tcattttctg tgatgagagg aatgtgaggt 107460
actgcccttc gagagctgtc atttgtccta gtagccagca gcgtgactgt gctgtcttct 107520
gctctgtctc cctgtcagcc ttctgcccag ccaccaccac tatagttttg ttctctccat 107580
tggaactcct ggttcagaga attaccataa aaaacagacc cctagacata caacactcta 107640
tcacataatg gtgactttgt cttctatttt ggattactga gctttcttgg gtaacttcca 107700
ctaaatcgaa gttaatatta gaagaacttc ctcttactag aatcgaaaag catttaagtg 107760
atgcagtcaa gtttgtacca taagtaattc agtcatttaa caaatatata tggcctctgt 107820
gcgacagtga ccttgactgg gaatgaagct gtcccatgtg gggcctgttc ttcaaaggca 107880
gttccctgct gcccagttca gtccagtgga tctgggcatc tctctttaat ccgcattagg 107940
ggctctttac tgattcttca ctatccaaaa agacttggag gggagacctg agcccacttc 108000
tggaaggaaa tgataacaat ttatttagat aatctttgtg caacaagtca attcactgaa 108060
gagatctgct ctctaggagc ctctgtgacc ccaccataac tgggaaggct ctacctctcc 108120
agtcttcggg ccacatttct ctctggcctg ctgtcttccc agcactctca gccttgctca 108180
tggagcactc tagtcctccg tcgaccttgg cctttggtaa cgtgattttt cacctggcag 108240
ctcccatctg gtctcactcc ctctttttgt ccagtctgca tgacacagcc tcacatcgtt 108300
agtgttccct cactcccctc ttactgccca acctgcaaag tccatgcctg ggccagtgca 108360
gcatgtgtcc tcaatgggct gctggtggca gtggggggaa ccgcacagcc acgctgtgtg 108420
ctgctgaaga aatgcacagc ctcctaccct cgccctcaag aggcagccat ggctgcgcat 108480
ttctgccctt ctgagctccg ctcacttttg gcagcagccg ttccaacctg catgggatct 108540
tcactctctc acagatgtgc tgactcctcc tgctgcctcc cctctctgtg ccttctcact 108600
ctctgttccc tttgcccttt ctcccctttt ctcctctgcc tacctccaag ccatccatca 108660
caggacagct caagcatcag atcctctggg acactttcct tagttgttca gtctgatgag 108720
gtgtccctca tcctctctta gctgaaaatc agcagctgcc tcaacttctt ttccagcatg 108780
tctcatgagt attgccacaa cagcatctgt cacaatgtgg ggtagtggct gacttgcttt 108840
tctgccattc aactgagttc cctcagtgct ggggccagcg tgcagtgtct tgtattcagt 108900
atatagctga ttaattgatg aattgattaa ttaatggttc acactagcac agtgcaacct 108960
tcaatgcaaa gatctcatca aaataattca catggtggga tattttagaa ggatgaccag 109020
gctagtttgt agtaagaaaa aatcaacaag actaggtcag gaattctttt tttgtctaca 109080
ggcttgctat agaagatatt gaaaatcatc tacctaatta cctttatttt atcaggttgt 109140
gtattaaata tcacgtctgg gggaagaaaa tgtgatatgt gattacagac ctttcctggt 109200
acaacatagt acgtttcaga ttaactcaag gtattgtggt gatattgcgg tcaaagccag 109260
gtgattaaag agtcattctt tgaaacaaat atctgtgcaa tcaattaaga aattaatttg 109320
caaattttat ttgcttagag taattgatat atcattcctt ttacaaacaa atataaagaa 109380
aacttaacta aaaatactgc atatctcttt cagattatat atcccagaaa ggatatattt 109440
ttctcctttc tggtcttcct ttttggtgta gcatctgtag gaaatgcatt tcttcatagc 109500

-continued taagtgtacc tccttgtgaa atatcttcag agtctactgg tgcacataag caattgctgg 109560
cagcagcttg agggtctcca tctcacattt atcatatgcc ttattgcatg aggctttgca 109620
agaggaggtc tagagctaca atatctcatg gatatgaatg tcaattcaaa tcccagtggc 109680
agtttatgag gggaaagcc tagaagagaa gaaacctaga ggaatcaagc aggaggggag 109740
agtaataaaa gactagagca gcaggttttt cttaactcaa actagaatta aatctctgtg 109800
tgtgtgtgca tgtgaatgtg cccgtatgtg catgcatgca cgtgtgtaaa tggatgtgtg 109860
tgtgtgtgca tgtgtgtgca agtaagtgtg tatacgtgtg tgggcatgta ttgtgtacat 109920
gtatgtgtgt tttatgcatc tgtttgcaag tatgtgtgta tgcacataaa agtgtgaatg 109980
tacatgtgtg cttggtgtat gtgtgtgtat taatgtatgc gtgtagttct agagtctagt 110040
tagagaaagt gcataaagaa atagggaaat taacaagaaa gctatagctt aaattatagg 110100
aaaaactttt ctccctatca gtcatggttt taaaatgttc agacttgata tgtttcccag 110160
tgctattgtc agaaaatgtc cctatgacat tccatactac ttcaatcaaa tctaaaacct 110220
ttgttccaac atgttttatt gatatgagta tatttcaaat ttctaccagg tttttggaga 110280
ggtattttgg ccataaaatt gactaaatta ttcaaaataa aaaatgaata agcctgggcc 110340
aaggcttgga gacttgctta actcagttct taaattttca gattttcaaa attacaaatt 110400
taagctctaa aatcatggtg ctgtgtatga tattctttga ttgcaactta tggttgaaaa 110460
actatagagg gctttatgct aagagttgtg gatcttagga ttttcatgaa atctgcatta 110520
tcatcatctg caagtttaga tggggcataa ctgatccaaa ggatggatcc ctcgggggca 110580
attcaactgg ctgattccag ccaagatgac aacagtcagg atccgttccc ttctgatcat 110640
ccattgggtg ccctgatttc ctctacagcc ctagctgaaa gaccagacac tatctcaggc 110700
tggctgcccc acatgccttg ctccacacca aattcacagt ctataaacct gagcctccag 110760
tgctcctact accatactca ctcgaacatt cccgattctg acctggagat gtcaacagct 110820
acttgatgcc actctcttct atctttctgt agctaagcca tccccaagtt tgtcgattca 110880
ccctctttaa cccctgtcgg ggtgtccatt gtgccccttc accctgccat ctccctggtg 110940
cactgttttg caaagttcag catacatgag cgtcacctgg gaaccttaat aaagtgcaga 111000
tgttgattca gcaaatctgg gatgccctcg ggctgcattt ccagcaggct cctggggatg 111060
tccccgctgc tgtgctgcag atgacactct cagtggtggg actccaggct ctgctgtcgc 111120
ctcctagggg tttctccaca ctccctggag gcctaatggg cccttctcca catggcagta 111180
agatctgttt ttgtgtttgt gtttcaagtt gggagaagga gattatttaa tactaaaatg 111240
tgcaacatgg gattgagaaa actaattatt agtcataagt tgagtatgca acattgaaac 111300
cacatgcttt aaaaaattat aagaaaaaat catagtattt gaaagttaca agctattatg 111360
gctaactcca tttatctcag ttagagaaga agagtcacct gtcaccaggg cactgccaga 111420
agccaggctc atttccaaca gcactgggtg ctccagcttt ggggtgccag ctcctcccat 111480
aaagcaaaca catacctagg gatgatattt ctttgcaagg gctctgccct acagcttgta 111540
catctcaaga agttatgtaa ttaaactgtc tgttttgaga aaattgtaga ttcacacata 111600
ctagctgtaa gaaatgatgc ggataaatcc agcgtaccag ctttccccac ggagacgtct 111660
tgcagcgtca cagccaggat gaggcattga cccaggcgaa gtccagagca cctgtgcgct 111720
acagggcccc ttgcactgtg ctgtcacaga cacgcccact tccagatgcc atctaggacc 111780
ccctccaaaa agcagaggca ttcttaaaaa cacacatctg cacatgttcc tcttcatttg 111840
aatctgtcag tggcttctca gtgcctttca aatgaaatct aaagtcctta caagccttgc 111900
agcaggaacc tctccatccc acttcccctc acactctcag cttcatctct gctaggctct 111960
gttcagccag gcagcctttc acagtccctc tcctcctgcc ctgccaggaa ggtcccctgc 112020
ccccaactct tccccacatg tggcggggcc ccgcttgtcc ttagaagccc agctgaactg 112080
cttcctgaag gaacccctcc agaacctctc agaccaggtc aggtttctgc actcttagat 112140
catccccatg gcataatcac agttgtgatg ttgtgatgat tcagtgaatg tctgtctccc 112200
cactggatgg taagcttcct gagggcagga acagcattgg ttccagtcaa tgctatgtcc 112260
caggactgtt cgtttttgca catactaatc ctaaaaggac gatgacaaca gcaaccactt 112320
acatgaccta gatgctcttc tgggtgttgt gcaaatatta acaatttaat ccttgcaaca 112380
atccacgagg gaggcattct tctactccca cttaacagac aaggacagtg aagctagtaa 112440
agagaagtca tttgcccaag gggaccccac tactgttggc agagctgggt gcaaacgcag 112500
gcttgtgaag ccaggaccca tgcattcaaa gaccatgcca ggtgccccca ctgcacacct 112560
catccccaca taccagtgag ggggagagaa atgctcctgc actgcctctg attaactgct 112620
ttcctagaag tcacacatat aaaagggatt taattctagt gggattgaat ctcaatagtt 112680
tccttattag gttgatttct gttaatagtt taagtactgg atatacatga attagaaaat 112740
ctagattatt agcaaatgca aactataaag tattttataa atgttatctt gtttgtcagg 112800
ggatgagtga gatattcatt atacaaaaag tagtgtggat tttgaggtag aaggtttact 112860
aaggatcata ccgtagtatg aaatagccac aaacattcag tgaaaccaaa cacccccgct 112920
taacctcaaa ctaacactaa ataataagga atagacttgg gggcagtgca agtgtatttc 112980
taatggtgaa aaccattccc cagtgaaaac taatgtacca tctagttaat aagagctcct 113040
ctgacccacg cacatcaata cttacatccc aatggtgatg tgacattttg ggttttgtat 113100
ttcttttgca aattgagcta gcatttttga tgagtggcag ggctctgcta cccaaccttt 113160
ggacagtttc caagcataaa atcacaattc cagataattc tgtcacaaag atctgggtct 113220
cattaggaag gagaggaagc tgggagatga tccagtccaa cctcccccaa accaaacatc 113280
acggccttct cagttgtttc accaaccatc taaatgtttt agtaattcta aaaattgatg 113340
cgctttttcc acgaaaggaa gtgttaccac attttccaag tgggaggcat ctatatcctt 113400
actccttcat cctctccttc ccaccccctc accccccacc acccacacaa catctgcaat 113460
tcttaaacta aagcacaaat tgttacaaaa gttaattgca ctttcaaagg aatgcttgta 113520
tagaaacttt ctcggcttca aggaaaaata atacgctttg aatggctgtt caacagcata 113580
gaaattagct gagtagaagg cactcatata gccattagga ccaatccttt ctgccgccaa 113640
caccccccctt ataaagactt gacagtgggc cagaataaac aacttcagga tgaattcagt 113700
tgagacacaa agtacacact tccagttttt cccttctctg gttactggcc tcaataacca 113760
ggcagtcaac ttaaaaagaa aaacaaaagc ttgcttcaga ttacagattg cagacttctt 113820
ataatatgtc catttcacca ggccccgctc tcagccccgg gaaaggccac tggaaaccac 113880
ctcacatggt agggccttgc gggagccagt aataacctta tctccgtcaa catgttctgt 113940
cagattgaat ggggcagcca gagaagccag agttggcaca ggaaccaaaa caaaggcttc 114000
ccatcctcct ggagtgagcg gttgagcctg gattggtgct tagacctata atgggtgcaa 114060
gcagcgttca ttcatagtgg ctttctagac ccagggactt ggccccagcc ctgctgctcc 114120
actcctcttc ttgcttcatt accacgagtc tcctagacca ccgaacgatg cctgcatttg 114180
aaagacactt ctgctgatca aagcagctga tgtgtccctt tgcggttcat ttctaattgt 114240
ccccaaggag gagaaattca aatagtttat tactgagagt taaagaaatc cactgaaata 114300
ttctttggtc taaaattact gtcatggcgg agcagcttca ccttagtcat tgcccttaaa 114360
tatgaaagct atttaagaaa gtttgccctt aaatatgaaa gctattttaa aaagtttaat 114420
gaaagaagag aatcacaaaa cattttcaaa aagcaaaaga aaacctaaga gaaaagttga 114480
aagtaggaat tttttaaaga atatacgacg tgtgttctgt gactcacccc tgcaagttat 114540
ttgtgtgtat tcccttgcat agtaattaat aatgaagcaa agcatggcaa tgatatcttt 114600
tcttgtctag tattctagaa gactccatgt ttttggaaaa tatcactcta gttagatctc 114660
aaatatattc aatcagaaaa tgggttttct acaagattct atatctgtag tcaatagcaa 114720
atataattct attaagctag taggatgtga taggaaacta aaacctaggg gagaccaaag 114780
caaggaaaaa tacttcctca tccaaacttg agagcaattt accgtcaggc ctactattaa 114840
tagatggaat acagattcca ttttcattac tcaactgcca tattcattat tacactgtac 114900
agaaaaggga atcacatctg ttgaaaactt atatatgatg ttcatgcatg cattccagta 114960
attcaacaat ttttatttat ctttttattg cttgctaatt tttcaaaata ataagctaaa 115020
gaaaacaaaa tgtttgtgct gttctcagat gacatgttat ctctttaaag gacaaaatgt 115080
gctgtgaaat aatagaatgc tttcagcact caagtgtgag tgagtgctca tacatgagag 115140
aaagccgtgg ggactacaga agccaagaag cagatctagc tggggaggcc tttgcagagg 115200
atgtagttgt gtggagaggc cacacacgtg gaattcccag gagggctgtg gaggcgggga 115260
atctgcagga aagcactggg gtgagaaacg tgatgagaaa caattattgt cttaaaatat 115320
ctgcagggct gtaaggtaga gaagcaatac gttgcatctg tgttaagtca aacaaaatta 115380
tcaagggact ggtttcagct taacataagg aacaattatg tgatagggtt gtcaataaca 115440
agagtagact gcttcttcac acactcctag tcactcagaa tggtccagga ggagtggaca 115500
accatttggt agagtatggg aaggcagggg ccctgggtgg gagtggtgag ggtagggagt 115560
gagtatccca atctagaagt aaattgtgcc cagcacggag ctgcaacact gccctgcaca 115620
caaacacaca caaataacaa tccccagccc ctgcatttcc ctctccggtt tcaggacctt 115680
gtatcttact tcaattcctt tatttagctg atgatgaaat aggaagagct tagcactaag 115740
aaaatccttt tggagtttgg ccttggggga aaatgaatca ctccaaccag gtctgtcttc 115800
tagaaagtat aggatgaaag ggctcctcat cacatacttc ctgacctcct gctaggcctt 115860
tccctaaaac aggggctggc aaagcacaac ctgtgggtca cgcctagcct gccacctgtt 115920
tttgcaaata aagttttatt ggagcatgac tatatgtatt tgcttacagt ctgtggctgc 115980
gttcacacta tcccagcaga gttgaataat tgggacaggg accatatgat gggtgaagct 116040
gaaaacattt actctctggc tgtattcaga ggaggtttac tgagcccttc tctgagacat 116100
ggcaagcgct gcttcaggct catgcttcac tagattcagg cctggggcag taaagagcca 116160
gctcaggata gcactcccga ctcactcatt ttttcaggca ggggagccat ctaatgtcaa 116220
gtgcctacgt gcaggaactg gtctgttaat tagcagctct cctcatggaa gggataaatat 116280
attctagaaa caggagtgcg gccctattgc aagaatgtcc tgagccaaaa ttaagattct 116340
tctatggcag aaacttggct ggggcttctc ctgagttaac ttggtagttg ttagtgattt 116400
ttgagtcagt ttttccttgt caacgacccc aggaatgagt ttgggattac agggtagcca 116460
gggaaaggga aagcttcacg cccgcccccg ggacaaggtc tgtcttcaca ctgctacatc 116520
ccttcaccca ctttaaaatg aaacttaaaa ggaggatttc agttgagtag gaagtgagaa 116580
gagggctcat tttaaaacaa gcgttaaatg aaaacccaca cacactcaga gcacacaaat 116640
ccaaccacgc ttacaaaacc atcacagagg gtcaggcgag gcccttttct aaatgaaaaa 116700
gaacaggggt ggagactgtt ctgagagcat gctgggttcc ctgaagggaa ttctcagctg 116760
tatgtgcccc gcacaggatc cctgctagac acaaggccag ctgccttcct ttcaagccgc 116820
agacgcatcc ctgtgtccag gcgggctggt cagctgcggt cagcaccagc ttccccgctc 116880
catggtgagg tcatcacaac atgtgagcag gagggcaggc cggcaacctc tgagtgctta 116940
gagaaaggga cgggattcct cctgtgcaac ccctctagtc tcactcagac tcaagtctga 117000
ctaaggggcc aggtgctttg accagggact ctcccctctc acttccctcc caggagtcac 117060
aggtacatga gtccttgttt tacaaatgaa gaaaacagac ccaacatgat taagatgttg 117120
ccttcatagg ggtggcacca ggattccaaa ccatggactc cactgagccc agtgcccact 117180
gacatgtgcc agtaacagtg cagctgcctg tggttctgtc gactaaactg ccggcagagg 117240
ctggctttcc accttctttt ttttttttc actcttcaaa cactttatga catgaacata 117300
aactactggc tgcatcgttc tgctgacaac atgacatgtt tctataactt gaaaaaagca 117360
agcagtggac tgctcattgg taaaattgag tcagtaatct tttaggaagg ttatttttct 117420
tccttttact gcttctcatc tgttccccgc agtaaagagg acaagatgac gacgactcag 117480
ggaacacctc cagcctgaag cagcaccatg cgagcttaga ccttagggtc ggcttagaaa 117540
ccacaggcgg ggcggcttgg gcccctcgga cactccctct cgaagctgct tctccccaag 117600
ctaccccaaa ggcactgagc gccctctgcc ccccagcaat tcaattcact ggctgtcctg 117660
ctcctgtcag tactgagagt tgcatgtttg accctcgggg gaaaagtcca gaggccctgg 117720
ggtgtccagc atgctctgag gtccctgctg ctgacccctt gcgctgtcag cattcagaga 117780
cattcacaca gcacagcctc ccaggctaac agctgtcatg gaacagtgga gcagctagac 117840
gtggccattc tgtggcccag tgctgcagag gtcaaaggga caagcgcagg gagcatcttt 117900
gctttcagaa aaaaaaaaaa aaaaaagaag cacactggtg cactgacctg ctcctggtgt 117960
ctttgtgatt gctcttttct ttcgattttt ggttgtcttt ttttttttga aagaggggct 118020
tttatgcttt tttcctaatg ttcatgggta aaccaatgta aatgtgtgta tgtttataga 118080
gatggcttta aatcgcaatt ctgcagtaga gattgatttt ttaaaaaaca tgggtaaaaa 118140
ttgaagaaaa attttaaaag aacatttaaa ccatcttggg ctaggggtgg atatgcacca 118200
ccccacggaa gccaaacaaa atctctctgc agataaacat ttgcaaaaag aatttccaat 118260
cccaattttt gagtcagaga tcttttattt ccttgcaaat tacatatctg tttcaggatt 118320
tttgactata agaagaatga atgaagatgt gtttcttaca gataactatg aacaaaccag 118380
gaaggataat aacttgtatc ccccaattcg aatccagagg atgggaaggc ataaaaaaaa 118440
gaaatggaag aaactttatt tttagtggta aatggtggga ctatgtattt tacgtatggt 118500
gaagtcacca agcccaacac ttggcacttg taggcaaggt agtcttctaa tctgaatgtg 118560
aagtattatg ttttcatttg cttggtaatg aggaatattg gtgctttcgt cccagttctc 118620
gagctgactg acttctcttt ctgacgtgtg ttcctttagc acacctctac actgcatggc 118680
tctgagatgt cctgtgactg tttcatgtgt aaagttgcct ccccaaagga ctcacatatt 118740
ccttcagggc agtgagtact tctgattcat ccttagcagc taccttcgcg ctactttact 118800
agatatgttg tagttgaatt aatgaacaaa agaacaagca actttggtgc ctggtgtgca 118860
tctcagagca gggtggagtg agcctggcca aagggtcatc atgcaacctc tgtggctgac 118920
tccatctggc cacggagctt ctcagccatg cttggtattc acatgacttc tagggcgaca 118980

-continued gctcaaccag caaataaaca gcttcatatg ggaaatatta ctcagccttt gtcatcaagg 119040
agtgagtcac gggcctgaac tgaatagaag atagaggaga aaaggtgtgt ggactgggtg 119100
agacagcgcc cagcgaggtg aactcccggc agccctgcct gtctttacct gcacatcacc 119160
ttgctagggt gccttcggtt gtgagggcct gtctaggaag agaagagttg caccctggca 119220
ggcagcactg agctgtctca tgcaaagctg aggaagaaag agtgagctgc ccagtgagcc 119280
tgctggggtg gtggaggctg ggctgggctg tgcagtctgc agcccccagc agcccttggc 119340
acctttctac tgcctggtgc tcaccagctc tccagtaaca aagagggacg tgaagtcaga 119400
ggggaaggga ggtagcacag ggcagtcttg actttgaaca aagagctggc ttcctgaagt 119460
cagctggccg ggttttgaag ccgattttcc agcagtgatc tttgatgcca accccattta 119520
ggaattctgt atctcccccct accttctacc agatgtctct gagctcacct ttggtgataa 119580
tcatgcaatc tccgtcatcc ccacgtccac actgccccat tctgtcccac cccgggttct 119640
gtggtgctgt cggctcccca gcgagccagg aagggagagg ccagctctgc tggggctcct 119700
gccgccctgg ctctgcactg cccttctctg gcaggtctga ggcgccactg gaggagccac 119760
acggccctga agcagcaagg cagatgccct ggacacagtg gaggcacaga gtgcaagcac 119820
cggcctggcc cacagacttt tggaggggaa gtggtattat tcagttcaaa agtatgcctg 119880
tgtgtaaaga gagagcccct gaacatgagt aagcaaaagt ctcagcgcag agattagaca 119940
agtagaatgc tggcccgaga ggaggcgttt actcaccctc tgtctaggaa ggaaagccag 120000
gcccagcacg ctcactgcta tctatcctct cacacagagg gattttgaat cgaagccagc 120060
atcctgtcct ttctccaatg tcccctgctc aggagtcagg actcagcaag gcccacccca 120120
gccacacaca gatacagttc caggactcag aactcagcga ggcccacccc agccacatgc 120180
aggtccagtt ccaggattca ggacacagtg aggcccaccc gagccacatc caggtccagt 120240
tccaggactc aggattcagt gaggcccacc ccagccacac acaggtccag ttccaggact 120300
caggactcag cgaggcccac cccagccaca tgcaggtcca gttccaggat tcaggacaca 120360
gtgaggccca ccccagccat atccaggttc agttccaggt aaatcatctg ccttcctccg 120420
tccaaaagcc ttgtttcctg tgtgtccttg tgtttaaaat ggaaacgtta tgagaaactg 120480
cctgccaggg caaagggtgc tgcccggcac acagtaggga ctcaaaatga aactattgta 120540
ttgaatacat aacagatcaa cgggtattgc tttctgaaat cttttttagc ccaattttgt 120600
ttcttatagt ccaataacag gtcaaattca tttctgattt actagccatt cagttgccca 120660
taaaaaatgg aaagtgattt aagattatta gtttaaaaac caatgaaggt aaaacagtta 120720
tcattgaagg cacataggca gaaatagatt gcaatagttg ctgccatgtg aagcctcagt 120780
gtcatgctcc atatttagag agatctatga tttctgaggc cctttcatgt ccatgatctc 120840
agtactgctc acaactgccc tgtgaaattc gccgagctgg ccccatgtca atcagagtac 120900
actgagcact gagacccagc atgttgagat aactggctag agatcatccc ataatggtac 120960
catcacaatc ttcacactgt agaagtttga tgatgtcact ggaagcatat tccacagtcc 121020
cttgtgaact ggccttcctg tgatcagaag catcagtgaa ctcccaagag ggtgggaact 121080
cccaagaggt attctcactc tacttagtgt atattttaca aatcacaagc ttggctttgg 121140
attcttttaa tggctagaag gagaatcatg gggttggaag tccaccagtt tgggtattct 121200
gttccctaac tcaaaataaa gagatgttat tttcaagtct tctgcttgtt aacttaatta 121260
gagatacatg agtttgcagc tgtgctgggc atgccgcagc ttggcatgtt tagtccagaa 121320
ggcatattat aatgtacatg gaagattgtc agaaattcaa aaggactttt tgagtatcac 121380
atgtgtattt tcaagttcca atatagattc acattcagtt tgacaggtat ctttggatgc 121440
ctatcagtta agaactattt attagttgtg gaataaaata gggtaaaata aggaacaact 121500
gaggaaaaaa cataaaattt gctttgtgaa taaaagttgt cttcaaaatt atgacttttt 121560
ccatcccaca aaagttttga ttaaacccac aatgaaaatt taaataagtg tatttacttt 121620
ggtttaacca cttatttcat tatgactcac aactataggt tttctagttt ccattattac 121680
aaactattgt gtggtttaaa tcaatttcat agactagtct agttctatag tcacaattta 121740
taaaattttt ttatgtggta aattgagtgt cttcatagat gtacatgatt atttctcaat 121800
ttttaaggaa tgtatttttt aagatagcct tctttagcct tctttaacac tgatttttgt 121860
aaatttttta cagatttttt taaatttttg gtaatttttt agcataaagt aatacatggt 121920
cactatggaa aacataaaaa cacaaaaact atgaagagta aataagaaaa acacccagaa 121980
atttaccatt cagaaaaggt cattgttaac aacacggtgt atcttcctcc tgtcatgctt 122040
ccgtgcattt gagcacattt gagatgtgta tacatgttca ctttgagatt ttagtatagc 122100
aaaagaaatg accggtcctg attcaatgaa acctctggca aactcgctat attttcctta 122160
catattttta agttcatcct ataaatgaac tatccattca tcttatttga gatttcttta 122220
aatctttcag caagaaagcg ggaaaaaaat cctcctctgg cctttaaagc ctaattaaat 122280
atatgactaa gctagaaata ttttataatg accaaccaga aagtggcaag gactgtcact 122340
cttcccatac agcccacctc ctcctctatc tccctcaggc acacggaaac gagaaaggca 122400
gagaaaccca ggacaagtca tccaagactt tggtcacatg gccatccatt gctttcacaa 122460
caaaaatata aatccaacat gtgtgtgtgc atttcatacc agtaggtcca ataagctatc 122520
tatatataca catatgtgta cacacacaca cacacatcct tacagacact ccccagctta 122580
ctacagtttg acttaagatt ttttgacttt acgatggtgt gaaagcaatg cacattcaat 122640
ggaaaccata cttctaatgt tgaatttttt atcttttctt gggttagttg atgtctgata 122700
tgttactttc ttgcgatgcc aggcaatggc tgggagccag agctcccagt cagccatgca 122760
atcaagaggc taaacagctg atactataca gtggactgtg tcaccagcat tttggggata 122820
ttgtgttttg tgtttttgaa tcctatcatg tctacaaaat gccattttcg actgctattt 122880
tcaatttagg gtgggtttat caggacataa ccctatggaa agttgaggac catctgtata 122940
tctggtaggg aaagatggat aacaaattca taggcaaata ataatttcat gattattatt 123000
aagttattcc tacttaataa taagtagtga tcactgccag ggagcagaga atgcaggata 123060
atgtgacaga tgtaatggtg ggtacttaag ctaatgtagt tgcagaacag gcttttctag 123120
agggtaggcc tttaagcgta cctcgaagat gcaaaggaag caaagatgcg aagatctggg 123180
ctggggatgg aagcagagac aacttggagg ccaaggggag agactgacaa cagcccagct 123240
catacctcag cagcctttaa tgcatagcta agaaaacaac aaattaaaac aattatagtt 123300
tacttagacg attctaagtg tctaagtgga tttgggcaaa tctggagaaa cttgttctaa 123360
tactgtgtct taataagtaa tatagatttg cccaggcttg tgggcagagt ggtatacacc 123420
ccataatagc agaggaaggc cacagggcct accctacaaa accagaggca tttaaaaact 123480
taaaggaggc agattgcttt tattttcagt taaaataaag tgaggagttt ctcaagaaaa 123540
ataataacga gaccaccggc ccgccctaga tgtccaacaa gaatgcacag ataacttcgt 123600
atatccactt tcctgaacct gcccctgaca gccaagtgga gcacaacaac agagatgaac 123660
ctcaaaacta ctgtgctgtg acataaggct tgctcaagag gacagtgtgg tgtgagtcca 123720

-continued tctatgttct aaagcaagca aagctattct gtagtgaaaa tggatcagga cagcagttgc 123780
ctctggtgta tgggggcagg gatcgactgg gaggggcatg agggatgaca gttagggttt 123840
cgatcatgac aggaattcag attactccag catgtgcatt tgttaaagct catcaaatgc 123900
tacacttaag attaatcctc tcacagtttg tggatgttac cttaaaaaca acaatgatga 123960
ctgcaaacta atattgaact ctggttagtg atataccaat gtgaagtata gtgatatctc 124020
tactttactt taaaatgcat ccaaaggcag actagaggac catatctgac agacagaaaa 124080
atagatatgt gataaggtga atgtagtaaa atgctaacat aaggatgttt gcggtacaat 124140
tctttcagct tttctataca tttataaatc ataataaaat tttaggacaa aaagttagtg 124200
ctttgaagtc ctaagtcata gggcctgctg ctcttgatgc agtagaattt gtcttcagat 124260
ttgcaaaggg taaggcaaac cactagcatt ttgtatggaa cttgatgcaa atacttttaa 124320
ttgtctggtt ttcaaatgta tagacttaaa gtaatatcaa ctctttcttt gaatcaacta 124380
ctgaaatacc tagtcttaaa taaatatttt tatgtaatcc ttaaagtact atgtattcat 124440
ttttctttct tctttctttt ctggtttgat aaatattcta taaagtaact gtgtttaatg 124500
gccaacattt gagtaagtcc atatgcagat ccaaacatct cagtttagac aataacttaa 124560
gacaatatag agtggctgac atcccctaac gtgggtccag atgcatgtta tgttatgttt 124620
ctgttgcatt ctcaatagtt aactttaata aaagaaagtc aaaagcttat atattttttc 124680
aatcttcaaa acatttctgg gaggttgtct tagttaattt tatgttgcta tacccatatc 124740
acagactggg taatttataa agaaaataaa tgtatttggc tcatggttct ggtggctggg 124800
aagtccaaga gcatggcatt ggcatctgct tggcagctgg tgagggcctt catgctgtgt 124860
caatctatgg tggaaggtca agagagcatg catgtgaggt ggtggggaag agaaaaagcg 124920
ggtttaactc atccttttat cagggactca ctcccgtgat agctaaccca ttcttacatg 124980
aatggcatta atccattcct tagggcacag ctctcatgac ctaattataa tacctcttaa 125040
agtttccacc tctcaacact gttgcattgg tgattaagtt tccaataaac gcactttgga 125100
aaacacattc aaaccacagc agagatcaac gttattgtca ccattttcat atttgaggaa 125160
agcatggcac agagagcttg gagaagtact tcaaggtcac ccaatgagga agtggctaaa 125220
caaaaacctt atcttaaatt aattaaaaac ctcttgctct ttgcagtttt gtcttaaatc 125280
tacctaattt gtgactgtaa tttttaagta atttactcat ataagtggtc tcacattaaa 125340
ttttctcatt gctttatatt tctaacatga gatatttggt ataaggatgg aaccaagatc 125400
ataccttgtt ttaattagaa aacctagacc aagtcattgt gatcctcatc ctagatttca 125460
gttaaatgct gctgtctcct tttgggtatg tgacagggga aagcctcaga agaaacaacc 125520
ttatgtgttt tcttttgata ctttagtaat taacccagga tagtattcaa gattgacatg 125580
ccttatattg aatcaaatag catatcaact gccttcttat tctcaagtat agacatgttg 125640
ggtaattggg catttaagtt tctttgcaat tttttccatt attaacaaaa ttaatgagca 125700
acattctgca taaggtctgt ttcctcagaa tacgtttccc aaagtggaat catcatgacg 125760
tagaatttaa gcatacttac ttgtttaaac aaattgtcca gttgcttccc aaaatgtttt 125820
gtgaattaag atttacatca agaatatgta atgttgttac tgtctcccaa atacaggatc 125880
tttttctgaa tataaaagtt atacatgcta attgtagaca atgaagggtc attatcctca 125940
tagataatga agtgcttcta atacttgtgc ttttattcat ttattcaaaa agtgctaaat 126000
aagccctgaa ggggcttttg gggggtcatt tggggcttat ttagcacttt ttgaataaat 126060
aaataaaagc acaagtacag tttttttaaa atactgtttt ctataataga ttaatcttaa 126120

-continued atggcatgtt ttcctttatt ttactgacaa aagttactta ctctgtgatt gaataataaa 126180
aattctttgg ttcagctgag agaaacttgc aagctgacgt ccttgattat ttaaaatgaa 126240
agcagctgcc tgttttcatc tctctgcatc ctgaggaaac tcttctgcaa cgtgttccag 126300
ccctaggttc tagctgaccc tgttcatctg tttggcacga ggggcccaac taacacttgc 126360
ggctacctgg acgacagcca atctagttgg aatgagagtt agaggccata gtctgtcagc 126420
tgggaaagca gcttttattc caaggtgtgc caaccgaaag gccacatgtt attgtcacaa 126480
cctggtacct acatcagtgc tgacatcttt aagaacctta gaattgggaa atcagtttag 126540
ccctatctgc atgtgtagcc gacaaccaca caattgttcc aacttgaggt tgcattcaga 126600
gcaacctcat ttcccccata ctcctgagga aaagcagacc agagacgctg ggtcaatcca 126660
gagttatggt tggaaaaatg atggaataat tctgcccctg gtgataggag agagggactc 126720
catcttgtca actgtcatgg ttcccatgtg aaagctatca ttatcactga aattgaatga 126780
gaacacagaa gggaagaaca gggaaatccc cacagagtta aagaggatgt gaagattgct 126840
tcatgtttaa tgtttgtgta agtgctttgg gttggttatg tgctgtctga acatgtgctc 126900
atttccatgg ctcattgaga gggcagacag tccaatgata ctctttagaa tcattcccat 126960
ggggaaggaa caaagaagcc tgtaaaatag aaatgcacat gtaaaaagca ttgaagaaag 127020
tgccagtgta ttgattttgg ccatggtttg tgctctacca cctggttact gtgattgcag 127080
aagtgccttt gcagatgagg aagaacctgg ccaaggctca atccaacatc caaagccaga 127140
ggccatattt cttcactctt aagataattt gggttcaaat tatagtccct ttacacactc 127200
tctgcctcaa aaggcccaag actctctttt gttatgcttg cctaaacatg cctttcaaag 127260
aactagttct gtaaatacaa ctttattata aacctctcct ttgcttttaa aaatggatca 127320
ccacgtccat ttctatggtc caactttgtc ccttaattta aaattttttc ttggattaag 127380
tttgatgcct tgaaacatta ggaactcaag catacaagat tgtatgctgg tggtgaggga 127440
agtaactgtg cctccgcctg tgctgggtgg atcaacatgg agtgtggacg agcataggga 127500
tgtgtgggtt tctcactagc tgagagtgtt tttaaatgtt gtattttgat gtttgttatt 127560
ttctgaatat tctacagtta gacctttgat ttattctttg atgcattcat ttgaataata 127620
tttttaatct ccagccagtt aggtttttaa tttacacttt tgtccctgat tttaggtgta 127680
gtgttgtgta cactactgcc cagtgtatgt tatgtttgta aacattcatt gcacgcacaa 127740
caatgtgact cacaatattt ttgagaagta aaaagttcat tatatagtta ttaactcaac 127800
cctacagtta tattcgtgaa ataccttgtg aaatttattt tttgcctact ggagctctta 127860
caggttaatc ctgtcttcaa gattttcata gaattttcat ctaccaccca ccccttttaaa 127920 tttcaacatt tttttatttt ggcattttaa tgcaattcaa tgcattatag ggacaagcta 127980
tctcttatta tgaattgcac cttatataaa cttaaagatc ttttatcaca aatttctttg 128040
ctgtgtcctt tagtgagaat ttgtattatc agtcactaaa gctcactaag ttagtaagct 128100
ttgcgcccag atgacctggg caggaatggg tgagtctctg tgtggagaga gtgaagaaac 128160
tgctaccctt aatacctgga ccttgaggga ttgttttatt ttagtttttc tgcatttctc 128220
agtatttcat gtgatatctg tctttttctt ccagtttgcc aaggcacgag taacaagctc 128280
acgcagttgg gcacttttga agatcatttt ctcagcctcc agaggatgtt caataactgt 128340
gaggtggtcc ttgggaattt ggaaattacc tatgtgcaga ggaattatga tctttccttc 128400
ttaaaggttg gtgactttga ttttcctaca caaataaaat tggagaaaat ctaagtggag 128460
aaaggcctgg gcagaattcc acttgaagtg tgtttatttt tgctatggca atgacaagtc 128520
ttacagagct acaaacgaga gttttatgag aaagccattt taccagctaa tgtcaagtaa 128580
taactagaaa aggatatcaa atagaaacag gctaatctgg agttccatgt catcatagac 128640
actgacgttt atccctgacc attacctcag tcatgatgtg ctgccatact cgctcttaaa 128700
aacttttttt aaaagccctg ctttgcacca tttgcctatt cccttagtgt aaatactcct 128760
actatagctg atttcaaggt accaagtttc actcagctgg tcacagaatt cttatttcac 128820
gataggcgct aatgacccca taggagccag ctctgaaggc ttcagagttt cactgaattt 128880
tggatggggt ttacttagcc ttcttctgtt tttcttttac ctttcctttt taaataagaa 128940
ataatgcaag acagatacaa agtaattctt tttaatttcc attttcactg gagagtgttg 129000
aaccccgtga ggcatgagag cacagtgttc cagaacaatg cttactgctc attatcacag 129060
gggtcaaagg ctaacgtgca gggattgttg cagatcgtgg acatgctgcc tcctgtgtcc 129120
atgactgcaa tcgtctacct attttacagt tgttgagcac tcgtgtgcat tagggttcaa 129180
ctgggcgtcc tagggctccc tggacccatt ttagaccttg agttcttgag ttcctcaaaa 129240
gagaaatcac gcatttatgt tttctcttct tagaccatcc aggaggtggc tggttatgtc 129300
ctcattgccc tcaacacagt ggagcgaatt cctttggaaa acctgcagat catcagagga 129360
aatatgtact acgaaaattc ctatgcctta gcagtcttat ctaactatga tgcaaataaa 129420
accggactga aggagctgcc catgagaaat ttacagggtg agaggctggg atgccaaggc 129480
tgggggttca taaatgcaga cagcagttcc gatggctccc agcgagcttg tcactcaatt 129540
ccacctcgga gaaggctttt atttttaccc agtacacgtg cactgagtgc cggctgtgtg 129600
taagatactg caggggaagt tactgagaag atggcagata ctggaatggg aagatttaag 129660
cggggtacca gtgtttacat ggacatgaaa aaatactgag agatagtaag aaatcgtaaa 129720
gattctgagt aaaagagagt atgaccaaac aagctgagca ggaatcgtga atctatgtgt 129780
gtaggcagtg aataaactgc cagtcttatt acctggacct caaggataaa agacatacag 129840
taaaaatcaa cccacattga ggacagtttc gagagtcgcg ctgctacaca gaaagccctg 129900
tgtaagttaa ggatagagaa tgaggtgttc tagaactttg aatttttgtg agcaggactc 129960
gtgaggttcc tgtgagagga aacaatgaag gatgatagaa aagaagggaa attgatttta 130020
aaaaactgga gatagcagtg attgtgcctc actgtgcagt gggtttgggg ccaggaatgt 130080
taaattggta acttcattta acgcccacaa cctttcttca aagtaggcac tgtacagatg 130140
ccccttgact tatgatggca tcctatctgg ctggaccccg ccgagggtga aggcgtcatt 130200
aggtcggatt tcagggctaa ttgaatgtat attgccttca caccatggca aagtcgaaaa 130260
tctgtgttaa atcatgctaa gccggggact ggctgtgctc tgccatcgta caaataaata 130320
aatggaagtc aagtaactcc cttgagggcc ccagctagtg aatggagagg ccagctatgg 130380
ccaccactct ctgccccagg gcgctcaacg cccctcctgt gccatgcagt tctgacaggg 130440
aggcagtgct ggtaggaaag gggtgtgatg aaaggggtgc ccagcagagg gagtcatatc 130500
cggagtgaca ggagcccaac aggggtgcag cgctggaacc caagccagca cctctggtca 130560
tggctcctca gttcaccgcc tataaaattg tgtggttccc ccacacccct tgctgctcag 130620
agcagccgcg cacatgcttg tgctgtgcgt gcctcctgtg agatggcctg gtacaccggt 130680
tcctacagtg cgcctcacac gctgtctcgg agggaggcag cctgtgcggg tgcctggacc 130740
tccgagccag accctctggg ttcctgcctg gccccgtccc tcagcagcca gatggctcgg 130800
gagcacattc tccaatccct ccgtgtctct gtttcgtcat cttcaaaaat gtggatggca 130860

-continued tagctgctaa aaaatggtga catacttcct aggtggtgca gaaaattaag tgactgtagg 130920
aacaggcctc agcagctcct tccacttcct tggtatgatt gtttttaaa ccaaggctgg 130980 gattgtatag atgcagatta gttaatgtga taccattaat agctaaccta gtgcctgctg 131040
cagggtgagc ctcccctaag ccaccgggaa gcggctcctg cagcctccct cacgtgtgct 131100
ggccctcctc tggcagtcat tgcctgtggt gtgctgaagg cccagctctg actgtgcctc 131160
tgtgctctcc tcgccccgcc ccctgctctc tctcaggtct ttggtctgtt gtccgagctg 131220
ccacagcagc ctggacatcc ctgttggtgt ttccagccct gtcctctcct gagttccatc 131280
cacctgtgca tggctttttc atgagtgttt tcacggatgg ttctgctgtc atctccaacc 131340
tgataaacaa agcaccacga ttcagccctt atgaccccaa gcttccttcc tcagttcctt 131400
gcttctgtgc atccactgaa gaagcctgtt ccactgtttc cctgcactgg gtctcctgtc 131460
tgcaggaagc cttcagccct cacttccaca ctcctctaag atgtgtgcct gtgcccttct 131520
ggggaagctc attttcctag cagcctccag gatcttcagg ggtgaatccc tcctttccca 131580
cgttggtact ctgtacacac aacatgccca ttccctgcct ggggagctgg gcattgcttc 131640
atgaatcaga ggtcaatttt ttctctatta aagtcacaga tgctcattgc accattgtga 131700
gaatgaatga agatagtgct tataaatcag ccagcaaggt acccagcctc actgtgtcag 131760
ggtctccctg ggcatgaggt ggttagagtg tgtgacatgt ctgtccccaa gcctgtcagc 131820
tcccagatcg aagccagtgg atctcattca tcctcgcagc gcccacagca cttgcacagg 131880
gttttgtaca cataagtcat tctgtcaatg ttcatgttta atgtcatcag tggaacactc 131940
ccactttgta aagacttgaa tgtgttcatc cctgactttt ccacatcttg ttagttcttc 132000
tttggaaaca gctgtacagt ttcaccatcc tgtgcatccc tggagtctac ctgtctctgt 132060
catacattca gattcttctt gtttcgtgtc actctcatat ccttttctct aatgaaaagc 132120
tccgcctggg catgcaaggt ggagccctgg atgccagccc ctcacctggc atccagggct 132180
gtagcactca ggaactgcct ccctgccctg cctacccct acatcatgcg accattccag 132240
tccagccaat cagccccttg ggacccagct taccacatgc atatcattta tgctgtgacc 132300
actgactaaa ccattctctt ccttcctccc catatttcta aatttctaat cattgctcaa 132360
agcccaattc agagaaaacc ctagctcctc catggcacca tcattaacaa ttttatctgg 132420 ccgcccccg ggaagttcac tgggctaatt gcgggactct tgttcgcacc atggcatctc 132480
tttagcagaa cataaatgcg aagagcacat gcatccttca tgggaattta aaggagctgg 132540
aaagagtgct caccgcagtt ccattctccc gcagaaatcc tgcatggcgc cgtgcggttc 132600
agcaacaacc ctgccctgtg caacgtggag agcatccagt ggcgggacat agtcagcagt 132660
gactttctca gcaacatgtc gatggacttc cagaaccacc tgggcagctg taagtgtcgc 132720
atacacacta tctctgcctc cagctcctat gggggacagc tctacagcac tggggcaggg 132780
gagagaagcc atgtttagta agtcacatta atcagaaaca aaaagtagta agcaaaatat 132840
ctgaccacta gaaaagcatg tatttaccac ggacatagag atcgtttttt tgtggcgggt 132900
ggcagcccag ctggttggca gtgcaggcca ccggaggcag atcccctgca gggacagcag 132960
agcacttgtg tcctgagaag agctgctgtt catggggctg gcagcaccag ggcctctcct 133020
agcctgccct gctgacactg gccagactcc tacatgcttc tgagtctcca gaggctaccc 133080
ggccctcctg aagcaccagg gctgaatcca cccccagctg agggcatgaa cactgccaca 133140
tggagtcaca cacacagctg ggcactgcca tggagaggaa gtctgtccat gtttccttga 133200
atactggtgg cctggtccct gtcccattcc ccagtgaggc agcctgtggg gaagcctggc 133260
agggaaccag gcgcaggtca gcgtggcgcc ctgactcagg ccagcactga tgggggactc 133320
tgagacgcaa gctcacactc acccagctcc cctgggctgc gcccgttcct gatcgcttgg 133380
actttctgtt ctttagagta agaagtgatc accatttcct gcttctttgt ttctccacaa 133440
ctgtgcagtg gatgcctgtt tgttttctgc cctcagaaca aaaaaaaaaa aaaatagagc 133500
tgacgtgaat cttcaaaatc atcaactaca gggctttgga tttttgtgta tttgttttat 133560
tttcatttta tggatggatt gtgatgaaat gcccgtaata caagattttc catcttaacc 133620
attgtaagtt acaatgtcag tggcattata catccacatg ggtgtgtggc catcaccacc 133680
gtccacacac agaactcttt tatcttgcaa agctgaaact ctacccatta gacagtaact 133740
ctctgctctc ccttccttcc cagcctctgg ccctggcagg caacagtcca cttgatgtct 133800
ctatgaattt gactgctctg gggctctcat acaggtggaa tcatgtagta tctgtccttt 133860
tgtgtctggc ttatttcacc tagcaaaatg tcccgaaggt ttatccatgc tgtagcacgt 133920
gttaagaatg tccttcctct tcatggctga ataatattcc attgtatgtt gacactacat 133980
tttgtttgtc cattcaccta tctacagaca ctggggttgc ttccatcttt tgactgtttg 134040
aataatgctg ctgtgaacat gggtattgag gctctttgtt tttatagacat attattccac 134100 cagataccca tcctgacacc tactatgttt gcaagaaact gaaagcttta ttttacattg 134160
caaaatttca tattatgaga tcaaggttag catttcctca gctgtctggt ggacaatggg 134220
gaggttaaac tgtgcacatt ttattttttt ttaatgaacc tggaacggtt atggggccag 134280
tgtttgccat ggatcaggtc aggcagccca caatggcagg tctccatgtt ctgtacaaca 134340
actgtgggaa agacccacag agaaagtgct ggaaagggga atgatgggta ggttcatgca 134400
gtaaaaagat tcaaatacta cagggcattg aactataggc caatatagca ttgctttaag 134460
aataaacaaa aaataagaca gtaagaataa gcctagcaaa atcaaaagtc tataaagaac 134520
tgacatttca agccaataag agaataattc cttattcaat aaattgtctg gaatgactta 134580
actattaggg gtgaaaatat caaagtgaga gaactataaa gggtttttaa aaaggaatta 134640
ggtatgttgg gttagtcgca ttggagagtg caaattcacc atcgacctga tacctgaaat 134700
ttcctcctta ccatctagag gcaagttggg aatgctgcca ggctcctgtg gtaaaggaag 134760
ctcctctctt gactggtgct ttatggctac acgttcctgc tcagaatgga tctcatttag 134820
tcttcaccaa aaaaaaaaat ctcatgagat gatttaagtg ttttatggac aagatgtcta 134880
aaactcagaa aaatttcaca gtgtgcctag cttttatgtt tatgttgaag ttgggcatta 134940
gaagttagaa tgaatgggtt tacttcagag aaaattaaat ccatcaccca ctccttgtac 135000
tatgaattcc aaatacatat taaatacata taataaaata tttaatatat atgtaagtgc 135060
cagaaggaaa cataaatatg aatattttgt aatatcaagt tgaagaaaag ccaaaatctg 135120
acatcataaa agaaaacttt caagtaaaat atgttaatgg ctaccaggaa aatattgtgc 135180
aatgtctgat tgccatgaag agggttaata tccttgctat atcactctgt gaagtcatct 135240
ttaaaagact aagaaaaaga tgaatctctt aataaaaacc tggcccagaa catgagcagc 135300
ctctctctct cactctcact gtctctcttt ctgtcacaca cacacacgca cacatacaca 135360
cacacacaca aatatggcca agaaataaag taaaatgtta tttctaatgt aataagtagg 135420
tcaaaataga aaaagaaagc atcacacctt cctttgcaaa gtatttgggt tccttttgct 135480
tttaaacacc tgggtcagct ggggtgtcga gaaacagaaa ttctcacgtt ctgcttgtgg 135540
gcatatatgt taataaaacc aagcttggca atatgcctgc aatatgtatc taaagcttca 135600
aagtatgtat agctttgacc aatcaatatc acatttcgga ataagagaaa aagaaataat 135660
gaaagtgaaa atcataagag atgtagaaac atattcttat acaagaattc cttgcagcct 135720
tatttataat aaattttgtg aacaaattat atatctaaaa ataagagatt ggttgaaaaa 135780
attatgcagc agccatgcta ttgataatca tgttagatag aagcatattt aaaggcatgg 135840
aaaaattgcc atgttttata tgggttttta aggttataac acaatgtata gtgggattcc 135900
aattcctgta tatacataga cttatatgtc tatattgatt aactctggat gagtctcatg 135960
tcttcttttt gctttcttct attatccata ttttatacga tgtgcctgca tttctttttt 136020
gtaacagatg gtcaatacta gaatcataaa cagatcttgt ttgtttattg gcaaatgttt 136080
cccgttagaa aaagatgcat ttttctttta aatattttta ttttatacaa tgattacaag 136140
cttataatag aaatttgaaa attatatgtg agtacagggt aaaaagttga aagaatggga 136200
ttgcacgcta cagatctagc tgcttttagc acgcctgcgt aggaccttgc tttctctaga 136260
cctctgttgc agtctctctg cctacctcct cacaacgtcc atcccccgcg gtcactgtcg 136320
tgatgccagc ctccccggcc ttcatgtctc taaggagcac cagcgcggca attagcgccc 136380
tttgccttgg tggtattctg gcttcacagt cacatgggag atcaatcgtc agcttttctg 136440
tttgaaatct aaattcttcc tgactgcagg ggacctcggg acccatgaac acctctagtt 136500
tactatgtct tcacagtaaa agatatctgc atgactggac tctttaacaa atttggtggt 136560
taacctactc tttctatata gatatagcac ttcgaccttc agacttctca atactgataa 136620
aaagaaaaca cgacagatga caggaaaacc tttgcagcta taatttgtaa tcggccaatt 136680
ataaaaactg caaaaattga ccagatagct aaggttttac acagtcatga aagtgatctg 136740
cactgttaac atttcaccct ctgtgcacca ttctgtgctt ctctctggtt tggagtctag 136800
aaggttttat ttacaggcta tgacttaaca atcccagaac ggctgacaca tgcagtcact 136860
caagactgga cacagcaagg aagtagtggg tccatgccaa aggctcagcc agacgagaca 136920
ctctagctgt ggcaggagat gccagggaat gctccaagcc taagcagatt gtaaacaagg 136980
aacctcaaat tcatgaaaaa ttcttgctta tgtggcccat gtcagtaatt actctctgcc 137040
tcagtttccg cagctgacat gtaaataaaa gcagttcatg gttcatcttc ttttcttatc 137100
ggggtctcaa gtgattctac aaaccagcca gccaaacaat cagagaataa gttgaaaaga 137160
ttgtcttcat ttattgaatg tgcttaactc aggcccggga aagggcgtca tcagtttctc 137220
atcatttcac tgagatatgc atctattact tttacatttc aggccaaaag tgtgatccaa 137280
gctgtcccaa tgggagctgc tggggtgcag gagaggagaa ctgccagaaa cgtaagtcag 137340
tgaacagcct cagacccatg tgtgaccgcc cctctcttcc ttcacttgct taggtgattg 137400
gatttgtttt ccctctgaag actccaaaga gttactttat tacagggtca gatgtgaacc 137460
agtaggtgaa ggacagtctt gcaaatctca ccgcatgcag ttaatccagg gtgggctatt 137520
ttgggagctt cagcctatca caaataagtg aacatcagca ggggctgggc gcggtggctc 137580
acccctataa tcccagcact ttgggaggcg gaggcggtcg gatcacgagg tcaggagatc 137640
gagccattct ggttaacaca gtgaaacctc gtctctacta aaaatacaaa aaattagccg 137700
ggcgtggtgg cgggcgcctg tagtcccagc tactcgggag gctgaggcag gagaatggca 137760
tgaacctggg aggcggagct tgcagtgagc cgagattgtg ccactgcatt ccagcctggg 137820
cgacagagcg agactccgtc tcaaaacaac aacaacaaca acaacaacaa taagtgaaca 137880
tcagcaagta ccccagccct gtcctctgaa cacagcacac tttcccagga atggaagact 137940

-continued tgctcctgtt gacagcagtc accagacttc ttgtttcctc tccctccctg gctttctttg 138000
gtacccacct acacagaagc ctgagcacgg gttctcatgg ggacttttcc atgtggaccc 138060
tgctttacga tggagagggc cattctccta ggtatggttg tctggctcag cctctcagtg 138120
gccaaggaac ctggggacat gagctcaaaa acggacacta tgtccttaag ctgaattgtg 138180
ggggggctgt taggcccttc taaacactac ttcccagcag gtatttttgt tctttgtatg 138240
tgctttctgc attgcccaag atgcatctaa ttatttagca ggtctcaaag tctagacttg 138300
atctcatgag ttctcttaag tgattaaaaa taaatcagga gaaaaaagag gcaatcagaa 138360
aagggcatgg tttgacttag tttgaatgtg gtttcgttgg aagcaaatgt gtcttcactt 138420
tttcatgaaa aagtctgcaa gtgctctgcg acatccctgg gaaatgatcc taccctcact 138480
cttcagctca cagggaacct ttgctctttt tcagtgacca aaatcatctg tgcccagcag 138540
tgctccgggc gctgccgtgg caagtccccc agtgactgct gccacaacca gtgtgctgca 138600
ggctgcacag gcccccggga gagcgactgc ctggtaagat gcccctccag cagcctccct 138660
ggagcaggct ggggctgcac ccgccccacc cacaccagga cagaagactt cctgtggggg 138720
agctgtcaat tagcatttgt cataacagac aggatattgc cctctgcctg gtgacaaagt 138780
atctttagta tcctgcctcc accactcact gagaccttgg gaaaatgatg ggactaccat 138840
gcctccattt ccttacctga caatgatgca taacaaagtc tctcccagtt gaatgcttaa 138900
atgatgagat gcctgtgatg tccgtcatta ggacctgggc acagaacaag cactaaatac 138960
tacatgcaag tatttgtcat gaatgtgcct tgttgccagc agcacactct ctttattgtt 139020
tgacttcggc tatacctcta gagacttgac actgtgaggt ccctaagaga cccatggaga 139080
gccacacagg tcttgctggc tggggctggg ttagggcctc ctgacacgga tccctcggct 139140
cctccaccac tgctcaggca cctcctgagc tgcaccctgc cctcaagggg tcctgaagta 139200
ctcactgtcg ccccattgct ccagaaagtg ccagcagaag ccttgctgcc ccagcgggct 139260
ctgagcagca ctggagggta caggtcagaa gcgtcttgga agtcctggag acgccaaggc 139320
tggtggatgt gactcctgga gtgggagctg gtgtgacgaa gcccttccta agactaaatc 139380
cagagcactc tgtggtttca gagaagattc ctaaattcca gagtttggac ccagacccag 139440
gaattgtgac ttggttggcc tgagctgttt ctaatgtgag ccccagggag aagactgtgc 139500
gtggggttgg tcctaggaaa agccctcgct gtattgggtc tggctccttt acacggcatt 139560
gttctagcaa ggctttctgc cattcagcaa tacattataa aatataccct caattgtact 139620
ttataaggga agcccaatgt cctttataag ggaaattaaa cataatttca ttccatagtc 139680
accgctataa tgtgtgaact ccatcatcta tacgttagta aacagacgta tttttatcat 139740
aatccataaa ttatgatagg tgggacagtg cacctaagaa aaaaatggac tttttagaga 139800
agggtctttc tgactctgca gagggcgcca gctgggtttt cccacactag tggaacacta 139860
ggctgcaaag acagtaactt gggctttctg acgggagtca acaccgtgct gcgcttcctc 139920
cgtgtgtggc gctgagtgta cttacctcac ttgcccagcg tgtcctctct cctccatagg 139980
tctgccgcaa attccgagac gaagccacgt gcaaggacac ctgcccccca ctcatgctct 140040
acaaccccac cacgtaccag atggatgtga accccgaggg caaatacagc tttggtgcca 140100
cctgcgtgaa gaagtgtccc cgtgagtcct cctctgtggg ccctctaact ggtcaggcat 140160
ccttgtcccg ctctgtctcc tgctgagccc tggagtatcc catcttggag agtctttggg 140220
tggatgtgtt tgccttgctt ggaggaggcg accctgtgcc cgtccaggca cacaggcgag 140280
gggaggggct ggcttgctac cgaggagcgg gcaggtggtg gccatctcca cccatggggg 140340
ctgctcagtg cacagggcag atctgggtgg ccaggccacc tcacaggaga aacacctgct 140400
gctcagccct caccactcat ccagcagcca cagccgtggg tattcagttg tctgctgggc 140460
acaaagccgt gggcatgcca ctgtttagtg cttgtgccaa gcaggtattt aatacaccga 140520
aatcagagag tctatcagaa gacctgcctt cttgagtggt taaaattcta gtgaaagtta 140580
tgcctcttag gagtattgca gaggttttgt ttttgttttt attttgtttt gttttaatgg 140640
tttgggtttg agttttgctt gtttgtactt acatttgtac tggtggctcc agggtttagg 140700
gaaattgtga cataaaataa ttcctgacag agaaagcaaa actttgtcta atgaaagagt 140760
tttagaagcc actcttgatc tctagaaggg gagattaact gagaaaaaaa attgaaagaa 140820
caattatgag ggggagattt taccctgcca gatttgtgta catgaaaaat tttacattcc 140880
gtatggaaaa aaaaaacaca aaataataag ccattataag gtaaatgaca aacaaagcta 140940
aagaaaaatg tgccacagtg atgacacaga tatatctttg agatagggct taacagagct 141000
ttaaaatcca taggaaaaca cttcgagcct gagataccaa gagcagatgg ttcacagaag 141060
aatcatcaat gtcctataaa tatttttgag gatcttcttg gggaacttaa aacaggaaca 141120
ggccaggcac agtggctcat tggctcatgc ctttaatccc agcactttgg gagactgaag 141180
gggctggatt gtctgaggtc aggagtttgg gaccagcctg gccaacaggg tgaaacctcg 141240
tctctactaa aaatacaaaa attagccggg cgtggtggcg cacgcctgta atcacagccg 141300
ctcaggaggc tgaggcagga gaattgcttt aacccaggag gcggaggttg cagtgagctg 141360
agatcacacc actgcactcc agcctgggtg acagagcaag actccatctc agacaaacaa 141420
aaaaggaaga catagagctc ctaaaaataa cgcagaagtc tgctattaat acaaatgaat 141480
tactttaaag gtgagagcag gtggaggaga gggctgaggt gcctgctggg acgcaaaaca 141540
gctggcccct caagggaccc agtgtttcct gccatgatga aacacctgta ttgtccacat 141600
tgcggcctag aatgttatta aactcttgaa cgggattcct tctctatttg caacctttca 141660
ttctttgtcc ttaaagtaaa taaagccaaa ggaggatgga gcctttccat cacccctcaa 141720
gaggacctgg accgcctgtg tgaggcccga gcacctggtg ccaccgtcat caccttcctt 141780
tcatgctctc ttccccaggt aattatgtgg tgacagatca cggctcgtgc gtccgagcct 141840
gtggggccga cagctatgag atggaggaag acggcgtccg caagtgtaag aagtgcgaag 141900
ggccttgccg caaaggtagg aagcccgccg gtgtgcggac gaggcttgtt ctcggctgct 141960
gaggctgggc tctcatgcca cctccaaagg aacacatctt cctcttctca ttaaaaaaca 142020
actatacata tcgtttcttt aaaacagaag ataaagctgt aaagctaggt taggcaatgg 142080
gaaggcactg aaggttgtga cggggtgggg ggctctgatg agaacagtca cagagccagc 142140
cccgctcagc agctgccagg tgcccagccc tggggagaat ccagggaagg cagagctgga 142200
agcagtgcag ctccaagcgg cccatgggaa ataatgagga gaacgcaagg tcagtgtgag 142260
gtgacaggga tggcatctcc tacaccgccg tagccccaaa gtgtactata ggtcctggtg 142320
tccccccttc ccgcctgcac tctccccagc cccttcagtg tttgttgagt gaatgaagga 142380
tgatgtggca gtggcggttc cggtgaccgg aattccttcc tgcttccctc tgcctgtgga 142440
tccctagcta ttcttaatcc aacaaatgtg aacggaatac acgtctctct tatctctgca 142500
gtgtgtaacg gaataggtat tggtgaattt aaagactcac tctccataaa tgctacgaat 142560
attaaacact tcaaaaactg cacctccatc agtggcgatc tccacatcct gccggtggca 142620
tttagggggt gagtcacagg ttcagttgct tgtataaaga aaaacaaaat ctgccttttt 142680

-continued aactggtaga gattggtgat caataatcac cctgttgttt gtttcagtga ctccttcaca 142740
catactcctc ctctggatcc acaggaactg gatattctga aaaccgtaaa ggaaatcaca 142800
ggtttgagct gaattatcac atgaatataa atgggaaatc agtgttttag agagagaact 142860
tttcgacata tttcctgttc ccttggaata aaaacatttc ttctgaaatt ttaccgttaa 142920
tggctgatgt tttgatattt ttcaaaagtg cagtttctcc tgcaggcaaa aggggacacg 142980
ttaagtccag gcttgggtca ttcactgcgg tgtaaacacg ctttctccct cccgcccggc 143040
cccagccagc tgccttggtg gcccataacc cctgagggta gagggagggg acaggggtag 143100
gtgacaggca gcctgggcct caggcttttg aaactggacg ccagagcctt gtggggccac 143160
gggcaagcct cgggtctatg actgccgcct gagctccgct tccttcctct ctaaaatggg 143220
aagattagac caaaataaca agactgtttt aaggttggaa tcaaataagg aaaatttgta 143280
aagctccttg tatgtgatac cagatccaca attggcagat aatcgcagca ggagcctctt 143340
cggggtaatc agatacgcgg cgcagcaggg gtctcagggc cacagccagg ggggcggcgg 143400
gagacatgcg gaatcgcagc ggaaggcggg aggcagctgt gaactgtggc tcggcctgcg 143460
tccgccctgc gcatgtacac tcagagaaga tgataatgaa aaagaaagca aatccaattt 143520
tcccacttac tgttcatata atacagagtc cctgagagtc tagagtaatg tctcatacaa 143580
aaaagaaact cctacgtggt gtgtgtctga agtctttcat ctgccttaca gggtttttgc 143640
tgattcaggc ttggcctgaa aacaggacgg acctccatgc ctttgagaac ctagaaatca 143700
tacgcggcag gaccaagcaa cagtaagttg accacagcca aagcctggta gattacattt 143760
gccttttag ttggaaatta ggcttaacag gagagttgct aagatagggc acagagctcc 143820
tgcatctctc gccggcattc ccaaatgcta tctcacatga gcaggcacag ggagcaagac 143880
tgcacgacca ctggcacagg ctgtccgcta aaccacagac ttctcagcgc tcgccagtgc 143940
ttctgcttct gtgtccactc cagatcccac attgcactta gttgtcaaat cttttcagtc 144000
catttctaac ctatattagc tcctgtgtct ttccttgtct ttcacggcct tgacacttac 144060
aaaacgtgtg ggtcaggtac tttgcacact gtctaaccat gtctgttcag ctggtgtttt 144120
ctcaggatgc aattgaggtt atgcacatct tatcacaggg accagagaga ctttttagca 144180
ccactcttca agaatttcca ctttttcagc tttgacagtg gaatagacat gcaggtgctc 144240
acacacaagc atctttaata tggtaatggt aatcatcagt ttagtggtgt ggaggaggag 144300
atgggaatct cttagtgaaa cccgccttgg aagcagcctc gttatgagaa ctgctgcccc 144360
tacttgactc ttaaagcact agataatact gtgcaacatt aaagagaata agagtgcgtg 144420
aaatatgcat tgcctcccat aaactccctt ggctctgaat ctctgatact aaatatgtgg 144480
ctaccgttgc ttcccagaaa ggccttttg ctctgaattc tctggaatgc tttctttgac 144540
caagattctt ataaaaataa gagatttaga gcaattttct tggatggctg gtatgagcca 144600
gttggcttag ttgtagggat ttaaacaaga taagggttac ttacttttca catttaatga 144660
gaagtctggt gattccagct cctactgaga cagggtggcc acacgttcca gggtgtgact 144720
cactgaggcc ccagacctgc cctgcaagga aaacctggct ctgccctggt gtcctggcct 144780
ccctgggcat atgtggggga gaattcctaa tggtattggt tacaggctcc tatgcgagac 144840
cactcatctg tgtaggagaa aggaaaaaga tgggggaaag aagagcagca gggagaggag 144900
aagcctctgg atgatactct aaccccctgc catccaacac ctgaacatca gtctcttcat 144960
ccagtgctct cagctggccc agcccccagc ctggggtcag atgagagctt cctgcaaatg 145020
cagatctctt tcctgtggct ccttctcaat tacagacagc tcctccacaa ggtgcactct 145080

-continued ggccttgtgc tccctcccca aaccagccca gccctcccag cctgcatcat cgtggtcctg 145140
taggggctag aggttctcac acccatcgtg gtctggcaga ggctggtggt tctcacaccc 145200
atcgtggtcc ggcaggggct tagtggttct tatacccatc gtggttcagg aggggctagt 145260
ggttctcaca cccatcgtgg tctggctggg gctagtggtt ctcatgtcca ccgcgtgctt 145320
tcctgctcct ccaggtggct gaggacatcc ccccttcggt ctgaatgact tccatccagt 145380
catctgatat acacattgga ccacccaata gcatcctagt gtcatgttgg atggtgaaga 145440
aaatgccaca gttactgctt tcagggcctc acaaccttgg gcatagcttt ttggaggaag 145500
gccccacttc ccaggcatcc ctcccagacc tggtcagagg cccctgctct ttgcttccat 145560
gttgcccaca ctcactgtgc tcttcacacc ggctcaaaat gatctgctta cggggttgtg 145620
tcaccaccag atcaagcgtc ctggagagga ggaaacatat ttaacctgca cagaatttgg 145680
gacagagaac ctctagtgtt tgttcaataa atatatgaat ggatagaggg acaggttggg 145740
tggtggatag atggatgaac ccacaccttt gaagtgtatt tggctgtttg agaggttaga 145800
atatgttctc aatttccagg caaaatgaaa atggagaaaa tataatgaca ttaaggcatt 145860
ttattcatcc tccccatctg ccactgggtt aaagatacta aataaacaag gaactatctt 145920
ttgcctggag gaactttaaa aacacctgca gttttcaaaa ggtgcagtgt gtgcctccca 145980
cagcatgacc taccatcatt ggaaagcagt ttgtagtcaa tcaaaggtgg tctggagaaa 146040
caaagtttc agggatacat tgtttttata atttttcacc acatgatttt tcttctctcc 146100
aatgtagtgg tcagttttct cttgcagtcg tcagcctgaa cataacatcc ttgggattac 146160
gctccctcaa ggagataagt gatggagatg tgataatttc aggaaacaaa aatttgtgct 146220
atgcaaatac aataaactgg aaaaaactgt ttgggacctc cggtcagaaa accaaaatta 146280
taagcaacag aggtgaaaac agctgcagta agtcaccgct ttctgtttag tttatggagt 146340
tggttctaat gggtccttta tttgtattta gaatattgaa gggctattcc catttaaatt 146400
actttttca gttccttaag aagcaaatta aaatcttaag attcctaact gtgaaattac 146460
catgtgaatt ccattaaaac tttttccaga tcattaccat tcaatgggat gaatttaccc 146520
tgaggtttag gctaccaatt atttgtaatg taagtaacta aatttagtat tagttatatt 146580
acctttagt tgtaggtcac tctctgctca tttcagcctg taaagactac agctacacac 146640
atacacacac agaggaatgg aatgagcact ttacatcaac acttcctgtt ctggctctag 146700
agcctcagct tttgaagctg gtgagagcct ggcctgtgct gggccttggc cacgggcagc 146760
gtcagctttg agtcaagtgc tggtctggcc tccctagctt tgagcctctg tcaattccct 146820
taatctgttt aggctttggc ttcctcatcc atagaatgga gatatgaatg attcctacgc 146880
cgtagtgctt tgagagaatt cagtgaaatt cctgtgtgta aaacccttcc atggtgccta 146940
gcacacagca cacagccaat ggcccaatgg ctcctatcag ctgtgggatt tgtcatcaga 147000
acaccaccag ctctgctcca ggctgccctg ggtaccatca aaacacaccc tgtgcccagc 147060
agcacctgct cctctgcaca cctggttcct tcagcagggg cagtggccgt gggagcacag 147120
aaaacatgga gtcccatctg gtttaattga tgccattgcc aaaggggagg actcacggca 147180
ccccctctcg ggtgccaggg tgcctggctc ccaccaggag gaagacctgt cctccactgt 147240
caggcacatt tcagtcttcc cagcagccag cacaactact ttgtccttcc agtcacggtc 147300
ggcctctggg aagcccagtc tgtgtcctcc tccttcaggg gtagccagca tgtctgtgtc 147360
acccaaggtc atggagcaca gggcccctcc cgggaaggtg ccgtctcctc cggcccctcg 147420

-continued ggtccctgct ctgtcactga ctgctgtgac ccactctgtc tccgcagagg ccacaggcca 147480
ggtctgccat gccttgtgct cccccgaggg ctgctggggc ccggagccca gggactgcgt 147540
ctcttgccgg aatgtcagcc gaggcaggga atgcgtggac aagtgcaacc ttctggaggg 147600
gtaggaggtt atttctttaa tccccttgcg ttgatcaaaa ataaggctcc aggttgttgt 147660
tatagcttta caggcattct gtttgatttt ctcttccttt tattctttgc ccttggcttt 147720
tggaggtttt gggttttctg tggggagacg ggaagttgtt tgattgcgtt atttttggca 147780
aatttaagca caataggaaa taagcaagta ttattgccta atataatcca ataatttata 147840
gaatctcttt tcctggaagt atcttaaatt tttctaagct acaaaaagtt cctaagacaa 147900
atgagacagt catcaatggt tcatctagcc aacaccgtgg ccatttgggc ttttctttgt 147960
agtgcccgat tcctggtgtg tgaaaataaa ttaacacaaa ttatattgcc aagttaatat 148020
ctgttttatg tgcccccagc atgtgttgaa catcaaacag taccagggac tttaaatata 148080
cccacggaca aagaaataat tcataatgat gtttgttgaa tttagttgca atcaataaaa 148140
agtgcagttt gtgaatgctc tgaggttctt gatattgatg taaggctttg aacgacaaat 148200
gaggacaaaa cataaatagg aaagtaaaac tgaaggatag aggccaaggc catgttttag 148260
aagatttaaa gaaaaaggga aatttggtga gcaccatagg aattacagat ggctgtagga 148320
attcttcctg ttttactctc tgggcatgga ccacagcttg gatccagaaa tatttaggag 148380
caggataaga ggaccaagtt caattctata ggaatccttt agctgatagg ctcagaacaa 148440
atcacataat tgatagtgct gcttcaactt caagtaagga atattgatgc aatccttaca 148500
gctacaaatg gacagtggtc tcatgttttc agttttcaag tgtttcttaa gaggcaaggt 148560
gatgaaaacg cccacgtggg gagccccatg tccttccatt agtgtagaga aacctggtgt 148620
ccagcagcac ctgctccctc tgcaagccca gccccccttca gcaagggcag tgacccagag 148680
aagaagcaca gaagacacaa ccctgtatca cattttgttt aatggtgcca ttgaccaaag 148740
gggaggatga aaggcacaca ctttttttgtt gtttttttgag acagagtctc acgccatcac 148800
ccaggctgga gtgcagtgat gtgatctcaa ctcactgcaa cctctgcccc ctgagttcag 148860
gtgattctcc tgcctcagcc tcccaactag ctggaattac aggtgtgcac caccatgtcc 148920
agctaatttt ttgtagtttt agtagagacg gggtttcacc acgttggcca ggctggtctc 148980
aaactcctga cctcaagtga tctgcccgcc tcggcctccc aaagtgttgg gattataggc 149040
ataagccact gcacctagcc aaggcacaca ctttggagaa taaacactcc ttgttcgctg 149100
ctggagggta gaactatgct tgactactag gcagagtcca gtcttactga caaacagccg 149160
tacatctgtt ctgtcttttc aatcaaacat cagcttcttg cttaacattg atgtgtacat 149220
cttgagggat gtcaaaatat tgtaagctaa gtttttcata cctgtgttcc acactcacca 149280
tttttagtaa taaccattga gcgagttcat tctccctcct tcctttttct atcacttaat 149340
ctaaaattat catttttcca gcttaatttt gataaccatg aatctggtat tagaggcagg 149400
gaacacctcc tcaggactat cttttctttt atcatttggc ttgcttaccc aatatgcaaa 149460
aactatgctg tagaaaaagc agaaaagata tcttgattat gaatgaagct cctgtgttta 149520
ctcagagaga agatgaccca ggattcagtt aacaaaatca gctgattata ttactatata 149580
gtcctggagt cccaactcct tgaccattac ctcaagttat ttggaatttt gaagaggtga 149640
tttgtgttcc tgcaataatg tctcaggggt gggctgacgg gtttcctctt cctcctctca 149700
gtgagccaag ggagtttgtg gagaactctg agtgcataca gtgccaccca gagtgcctgc 149760
ctcaggccat gaacatcacc tgcacaggac gggtaagagc cccttgctgc tatccacgtc 149820

-continued

```
catttcatgg gaagggcctt cacagaagcc gaacagtgat gatggcccag ggcatcctgt 149880
gtgggcagga cggccatcag agccacttcc cagaggagac ggcaggcgct gacagcgctg 149940
tccgggcagg gtgtcggtga cattagcaca cacattagcc tgcgatgaac attcactctt 150000
tctgctgaca cccccaacct tatctaagct tatcaaatcc tcacatttaa cggaggctgt 150060
tttcacctgg tttcccccat ccctgaccta gtcagcattg ctttatcgct ttcatcaaac 150120
atcctcaaat tcttaacatt agcttgtaat taattgaaga atttttaaag aaattgctag 150180
caaaactttt taaactgcac aactttgtat ctatatgttc aataacatat agatacaata 150240
ttctttacaa taatctttta aagaatatga gtgagaattc gggcccctct cacaccaaat 150300
gtcctgatgt tgttaattct caatgttatt atatagggag ctctgttttc ttgtgagctt 150360
caacagccag ttctaaatct actaactgaa aacatttttt agacattctc taaattgggc 150420
agaagatgac aggactgtgt tttgagggat aggctgccag cgtggctgct tacaaagtaa 150480
agacttggtt tataggtttg catggtgttg ggttaaattt ctgtcattaa aataattggc 150540
gatattgaca tagtcatcta attatgctgg ctctgggcac acacagccct tgagtggaca 150600
aaaccaacat gagagaactt agccaagggg aaagcctttc cctgctggtt ttatttctgc 150660
tacttctgaa gtgtggggca cacaacctga gcagtgcttt tatttgagtc ccaatgcttt 150720
tatttgagtt ttgcaaggtt attccaagtt ttacaaatag aaggtagcgt atgactcagt 150780
ccttgatatg ccaaccactg cacagagact tgccaccttc ctgtcactgg agaaacactc 150840
atgtgggttt tcttaaattt gcctccctct gagcttccct ttaacttcaa ctataatatg 150900
caagaaagac tatctgacca taaatacaca tttgggccaa tcaagatggt tttgccaagg 150960
aaagatgccc acaatggtta agcagaatgc aataatgtag agaatatcat ttctttcatg 151020
ctggtgtata tcatatgcat tcaaaaacag ggagaacttc taagcaacta acagtgacca 151080
tatcaagcag gtgcaatcac agaataactg gttttctcct ttaagaattt ttctatcatt 151140
tggctttccc cactcacaca cactaaatat tttaagtaaa aagttacttc cattttgaaa 151200
gagaaaagaa agagacatgc atgaacattt ttctccacct tggtgcaggg accagacaac 151260
tgtatccagt gtgcccacta cattgacggc ccccactgcg tcaagacctg cccggcagga 151320
gtcatgggag aaaacaacac cctggtctgg aagtacgcag acgccggcca tgtgtgccac 151380
ctgtgccatc caaactgcac ctacgggtga gtggaaagtg aaggagaaca gaacatttcc 151440
tctcttgcaa attcagagat caaaaatgtc tcccaagttt tccggcaaca aattgccgag 151500
gtttgtattt gagtcagtta cttaaggtgt tttggtcccc acagccatgc cagtagcaac 151560
ttgcttgtga gcaggcctca gtgcagtggg aatgactctg ccatgcaccg tgtccccggc 151620
cgggcctgtg ttgtgcaatg ctgcacatca caacaggagg gtagggggac aaaagagcac 151680
aggtcctggc agctgccaca gtctccaggg gcttttgcgt ttctctccag atttctaagg 151740
ttaacatggg gattagctgt tttgcaatga ataaaaggta acattgcctg gaatgttgct 151800
taaagacact tttttaaagc tagttgattg ttaagctgtt gctacttaaa ttaaaactac 151860
tttgggccag acgcagtggc tcacgcctgt aattccagca ctttgggatt ccaaggcagg 151920
cagatcactt gaggtcagga gcttgagacc aggctggcca acatggtgaa accccacctc 151980
tactaaaaat acacctgtag tcccagctac tcaggaggct gaggcaggag aattgcttga 152040
acccgggagg cagaggttgc agtgagccaa gatctcgcca ctgcactcca gcctgagcac 152100
caagagcgaa actctgtcgc aaaaaacaaa aacaaaaaaa aaagctactt tgactggaat 152160
```

tagcagaagc actctgattg tgtgtatctt atttactgga ataataaagc tgtcaatcaa 152220
actggatccc actcaacaat cagaaagaga agttgagctg tcatatagta gttcacactt 152280
acttctgttt ctcaaaatcc tcagctttgt ttggaactgt tactcattct ttctctgaat 152340
ccatctgtat gagttgtgtg cccttgggca agggtcttac cttctctgtg cctcactttc 152400
ttttctgtaa attgggataa taatgctgca tagctcacag gatttttatg accatgagtt 152460
aagatatgtc atatacttaa aatggtgcct ggaaaatggt gaatactgag tcaatgatag 152520
catcattgat ggtgggatgg tgatgaggag gtgggagtca caatggtggt gttgatggtg 152580
gtgatggtgg tgaggaggtg ggagtcacag tggtggtggt gttgatggtg gtgaggaggt 152640
gggagtcaca atggtggtgg tgatggtgtt gatggtggtg aggaggtggg agtcacaatg 152700
gtggtagtga tgatggtgtt gatggtggtg aggaggtgag agtcacaatg ttggtggtgt 152760
tggtggtggt ggtggtgagg aggtgggagt cacaatggtg gcagtgttgg tggtgaggag 152820
gtgggagtca caatggtggt agtgatgatg gtgttgatgg tggtgaggag gtgagagtca 152880
caatgttggt ggtgttgatg gtggtgatgg tgatgaggag gtgggagtca caatggtggt 152940
gatgagggtg gtgatgatga tgaggaggtg ggagtcacaa tggtgtcagt gttgatggtc 153000
cgatggtgat gaggaggtgg gagtcacaat gttggtggtg ttgatggtgg tgatgatgat 153060
gaggaggtgg gagtcacaat ggtgtcagtg ttgatggtgg cgatggtgat gaggaggtgg 153120
gagtcacaat ggtggtggtg atgacggtgt tgacagtggt gacgaggcgg gagtcacaat 153180
ggtgtcggtg gtgatggtgg tgaggaggtg ggagtcacaa tggtggtggt ggtgatggtg 153240
gtgatggtgg tgaggaggtg ggagtcacaa tggtggtggt gttgatggtg gtgatggtgg 153300
tgaggaggtg ggagtcacaa tggtggtggt gttgatggtg gtgatggtgg tgaggaggtg 153360
ggagtcacag tggtggtggt gatgagggtg gtgatggtga tgaggaggtg ggagtcacaa 153420
cgttggtggt gatgatggtg ttactggtgg tgacgaggtg ggagtcacaa tggtggtggt 153480
ggtgatggtg gtgaggaggt gggagtcaca gtggtggtgg tgttgatggt ggtgatggtg 153540
gtgaggaggt gggagtcaca gtggtggtgg tgttgatggt ggtgatggtg gtgaggaggt 153600
gagagtcaca atggtagtgg cgatgatggt gttggtggtg aggaggtgga agtcacggtg 153660
gtggcgatga tggtggtgag gacgtgggag taacaacagt ggcagtgacg gtgattgaga 153720
catgatgatg atttgtcaac tttctaggaa aacaatcata taatctccaa cagtgatatc 153780
ttaatatctt ttccaaaagt atcagatcat attataaggg ccaagtttcc agaataatat 153840
cagacataat gacagtggac atcagagctt ggcatctaaa ggtaatggga atagctctaa 153900
tgtctcagcg tgaaaaacaa catttgctat tagtctgaga tactaattat ctagttaagg 153960
aagtactcac ctatacctag tttttaactg ttttttaaaa tctggaattg attttgaatt 154020
ttaacaaata tttccctggg aacaatgtaa gattcttcat attttcgcct ttgggtatac 154080
caacatgcca gctctgttgg ccactttgtg agctcgatga agcatggtat aaaagatgct 154140
ttgctagtgt ttcacgtaat ctatttctat aagcaatttt ggagctaagc ctctgaaaca 154200
gaattatatt atctgtatag aataaatgtt ttatcttccc ccttttcttt cttctggaat 154260
agatgtgcat cagtatctct gcatcaatat ctctatatca gtatctctgt gtcagtgagc 154320
atatgttgct gggcttaggg gaggtccaga aagtgattgg gttttggcat tttcaataca 154380
cttactttgt ataagaaata gtttgccaaa tatagaaaga ggggatttag tcaagattta 154440
aattaaaaat gttagtggtc atttttctaa tgtctttcta ttttttccca ggtcctaata 154500
aatcttcact gtctgacttt agtctcccac taaaactgca tttcctttct acaatttcaa 154560
tttctccctt tgcttcaaat aaagtcctga cactattcat ttgacatatg gaattttata 154620
aatattttct ttagtatgtg tgattacatt cctgattctg agccttttta gatgagtata 154680
tagtttgata taatcttgtt attgccacct gtgtcttctc ccaaagccat taattatata 154740
ggaattacac gatagaaatg ggtttaattt ttaaaatacg gccaagtgtt gatgagaggg 154800
aaaatttttt taatttcttt cactgagtat ttatgacgtg cacaacattc ctgaatatat 154860
tgtctctctc atttctcaga tgggatgtat tgccttctcc atttctattg ttaaagaaac 154920
acttacaggg gtttctttaa caacttgtga acagcagcat cagagcccag actacagcat 154980
aagcagctgc tgattccaaa agccctacct tccaaccggg caggtgcagc cacccagacg 155040
agggggagga accctggagg aatagctatt tctttttttt ttttgtcgag acggagtctt 155100
gttctgtcac cctggctgga gtgcagtgcc gtgatcttgg ctcactgcaa cctccacctc 155160
ccaggttcaa gcaattctcc tgcttcagcc tcccgagtag ctgggattac agacacctgc 155220
caccacgcct ggctaatttt tgtattttta gtacagacag ggtttcacca tgttggccag 155280
gcttgtcttg atctcctgac aagtgatcca cacaccttgg cctcccaaag tgctgagatt 155340
acaggcgtga gccactgcgc ccagcaggaa tatctatttt taaatggaac tgtgttttca 155400
tagtacacgg tgaggagaaa gttgctttga aatctttatc ctaataaacc aaataatatg 155460
aaaatttgcc tattttaatt atatgtaaca aagtttagtt actgctataa ttgcaaatat 155520
gtataaattc cttaccaaaa aaaaaagaat caagtgggag ccagagaata atttttctga 155580
cagaattaaa taacatgcta tagctgcttg agttcatact caatagtcat ttctgcagag 155640
ttaccgaggg cctcatcagc gtcagcagga gcccctcgcc ttctgacgct ctcacatcct 155700
tctctcctgc agccccgtcc tgccactgtc cttgtccagc ttctcttcaa gggtcaactg 155760
gtctaccttt ccctacaagt ctgtcacagc ttcttgttag caatccctat ggttgcccaa 155820
aagcattttc agagcctgca taagactgca tcttgtagaa aatttgcagt ttcaatctgc 155880
cctccctctg ccgggtgttc ccattgtatt gcattcagca ggcagggaga gactgctatt 155940
aggtctgttc ctgagtgact gctttctgtc tcagactgtt tggtgtctgt aggaggtagt 156000
ggggtgggca gtaacgaggt ctcctgtata ttccacccct acgaagcctg tgtgtttggt 156060
ttatgaacta agctcaaaag caccacaggg gtaagactgc agtacatgac accatggaaa 156120
agagggagca cccagacccc caaattaaga agagcagtgt agagaacaga gacctggaga 156180
gcagagatag aaactgttag gatcagatta tagtgttaca ccagggctcc ccaggcctct 156240
cacatattga aatgtacttg tccatctttc tccaggccag gaaatgagag tctcaaagcc 156300
atgttattct gccttttttaa actatcatcc tgtaatcaaa gtaatgatgg cagcgtgtcc 156360
caccagagcg ggagcccagc tgctcaggag tcatgcttag gatggatccc ttctcttctg 156420
ccgtcagagt ttcagctggg ttggggtgga tgcagccacc tccatgcctg gccttctgca 156480
tctgtgatca tcacggcctc ctcctgccac tgagcctcat gccttcacgt gtctgttccc 156540
cccgcttttc ctttctgcca cccctgcacg tgggccgcca ggttcccaag agtatcctac 156600
ccatttcctt ccttccactc cctttgccag tgcctctcac cccaactagt agctaaccat 156660
cacccccagg actgacctct tcctcctcgc tgccagatga ttgttcaaag cacagaattt 156720
gtcagaaacc tgcagggact ccatgctgcc agccttctcc gtaattagca tggccccagt 156780
ccatgcttct agccttggtt ccttctgccc ctctgtttga aattctagag ccagctgtgg 156840
gacaattatc tgtgtcaaaa gccagatgtg aaaacatctc aataacaaac tggctgcttt 156900

-continued

```
gttcaatgct agaacaacgc ctgtcacaga gtagaaactc aaaaatattt gctgagtgaa 156960
tgaacaaatg aataaatgca taataaataa ttaaccacca atccaacatc cagacacata 157020
gtgattttaa ttatttaaga gtagtttagc atatattgct ttatgattta attaaaaatc 157080
tccaaaatat atgccaaaga agtagaatga gaaaaatgta tatttctctt tcacttccta 157140
cagatgcact gggccaggtc ttgaaggctg tccaacgaat gggtaagtgt tcacagctct 157200
gtgtcacatg gacctcgtca agaatgacca cactgctgtg ggtgaagatg ctttcctgca 157260
tttctgactg tcctctgtcc tgatcaagtt tctatggctc tgggccagcc taccctcagc 157320
cagggtttct gcagagactg cccagctggt tccacgtggc tccacgtgcc aactttgtcc 157380
tcagtggagg gaaagttgga cacacagtgc tggggctgct ccctgctccg ccgttgctcg 157440
atgcatggcc tgcctctgaa ttccttggtt ccactggttt tgctgggtcc ttctgtgcct 157500
ctagctcctc tttttttctg tccacttacc ccattggtcc catcacaagc ctgtgtgtga 157560
gtggcctttc tgttcgatga caacctccag catagggggag tgtttctcct tgctttcttt 157620
cccagacaca ctgcccagca aaggcaaaag ggcttccttc aacatcagct ctggccagtt 157680
tgccagagca aagccctgag aaaagcaagg ttgaaaagtc ttattcaaac tcaccaggaa 157740
agagtggtgt tactctcgat ggcgtctagc caggaatcat ggaattatac accgagcacc 157800
tgtttgccat tttggatgtt tccaaacatg aaccaaactt ccaggcccct ctgccatctc 157860
tggtaacatt tacaaagtcc cttcctcacc actgcccttc cttcattttg gcatgctcct 157920
ccgcccccga gttgacagcc atagctctct ctcctgccac cagtgtcaca tgatcgagga 157980
agaaggcaac ttcaaaaaga ctgggtcccc ttccactccc atctcttcag tgagctgcta 158040
ggacacccag cagaacttcc ccactccaca ctgcaatctc agggatctta gtcacggggc 158100
tttccaccat gtctccacct ggaaaccagt catggccatt ccttcttaca tctgctcttt 158160
tccatctttt tcttctcctc ctgttcaccc gcccttactc ttgtggcgcc ctatggatat 158220
gcgctccata gcaaatgatt ctttatatct tacggtattc tagtgagctg gcacatgtgg 158280
cttctggttt cctctctctg gaactagaca tgacctctgt gggagggagg attaaatgca 158340
ccctacagtc tgaggctgca tgatgacatc actcatcaca atgatgcttt ctatgtctga 158400
atcctattcc tttataaccc ctttcaagct cgttcagaga gtatttcaca caatccatgt 158460
gctcatctta aaagccaagg acccagagga gtctcagcat tgccaaaaag tcccttcacc 158520
cagcctggcc agaggcagtg cctggtccat gtgtatggac tatggcactt caattgcatg 158580
gaaatactct tggaatgaac aaaataccaa tccatgaaaa agcattattg aagtctaagt 158640
tattttttga atcatatttt gttaatcaac aaattgaaaa atactcatta tatggagagg 158700
tccagataaa gcctcaattt taaaaaatga ggaaaagtgt gcctggtagg ggactgggga 158760
gagcttgaga aagttggaaa cgttgcctta gaagcctgtt ttttctcctt ttagaagcta 158820
catagtgtct cactttccaa gatcattcta caagatgtca gtgcactgaa acatgcaggg 158880
gcgtgttgag tgccaaggcc atggaatctg tcagcaacct caccccttcct tgttcctcca 158940
cctcattcca ggcctaagat cccgtccatc gccactggga tggtgggggc cctcctcttg 159000
ctgctggtgg tggccctggg gatcggcctc ttcatgcgaa ggcgccacat cgttcggaag 159060
cgcacgctgc ggaggctgct gcaggagagg gaggtgagtg ccagtcctgg gtgggctcag 159120
gagccctcgc accccgacag gaacaagggc cagccccgag aacgggccat tagcagttgt 159180
gtatgttaga tacataattg tattatgatg cagaaagaat ctctgaatgt gcagttatac 159240
ccagttggtg acatgttggt acatccatcc gaggaaatgg caatgtttct aggctgcacc 159300
```

cttcaatgtc cacaaagctg tgtggcatct gcttaggacc cggtgcctgt gtgtgcatag 159360
gagggaggcc aggaagcctg gctgttgatc ccatgctggc actgtggcga aggcgagaga 159420
ttcctgcttt ggaaaacacc attgtccaca cagtggcttt gtccatgatg gacttcgcca 159480
cagcccagtc ctgtgctgga agccatgttc tctggaaaga gcaacccagc ggctcataag 159540
cataagcgcg tgtgatgtgc cccaaccaaa cgaccgccat gcacaacttc cctaccggag 159600
ttttcaatcc agttaatagg cgtggaaaca gacatagaaa ttgtgtttgt tgaaaggtag 159660
ctgttcagtt aaagaacacc tgtatcagag cctgtgtttc taccaacttc tgtcaagctc 159720
tgtagagaag gcgtacattt gtccttccaa atgagctggc aagtgccgtg tcctggcacc 159780
caagcccatg ccgtggctgc tggtccccct gctgggccat gtctggcact gctttccagc 159840
atggtgaggg ctgaggtgac ccttgtctct gtgttcttgt cccccccagc ttgtggagcc 159900
tcttacaccc agtggagaag ctcccaacca agctctcttg aggatcttga aggaaactga 159960
attcaaaaag atcaaagtgc tgggctccgg tgcgttcggc acggtgtata aggtaaggtc 160020
cctggcacag gcctctgggc tgggccgcag ggcctctcat ggtctggtgg ggagcccaga 160080
gtccttgcaa gctgtatatt tccatcatct actttactct ttgtttcact gagtgtttgg 160140
gaaactccag tgtttttccc aagttattga gaggaaatct tttataacca cagtaatcag 160200
tggtcctgtg agaccaattc acagaccaaa ggcattttta tgaaaggggc cattgacctt 160260
gccatggggt gcagcacagg gcgggaggag ggccgcctct caccgcacgg catcagaatg 160320
cagcccagct gaaatgggct catcttcgtt tgcttcttct agatcctctt tgcatgaaat 160380
ctgatttcag ttaggcctag acgcagcatc attaaattct ggatgaaatg atccacacgg 160440
actttataac aggctttaca agcttgagat tcttttatct aaataatcag tgtgattcgt 160500
ggagcccaac agctgcaggg ctgcgggggc gtcacagccc ccagcaatat cagccttagg 160560
tgcggctcca cagccccagt gtccctcacc ttcggggtgc atcgctggta acatccaccc 160620
agatcactgg gcagcatgtg gcaccatctc acaattgcca gttaacgtct tccttctctc 160680
tctgtcatag ggactctgga tcccagaagg tgagaaagtt aaaattcccg tcgctatcaa 160740
ggaattaaga gaagcaacat ctccgaaagc caacaaggaa atcctcgatg tgagtttctg 160800
ctttgctgtg tgggggtcca tggctctgaa cctcaggccc accttttctc atgtctggca 160860
gctgctctgc tctagaccct gctcatctcc acatcctaaa tgttcacttt ctatgtcttt 160920
ccctttctag ctctagtggg tataactccc tcccccttaga gacagcactg gcctctccca 160980
tgctggtatc caccccaaaa ggctggaaac aggcaattac tggcatctac ccagcactag 161040
tttcttgaca cgcatgatga gtgagtgctc ttggtgagcc tggagcatgg gtattgtttt 161100
tggtattttt tggatgaaga aatggaggca taaagaaatt ggctgaccct tatatggctg 161160
ggatagggtt taagcccctt gttatttctg actctgaaac ttgcattcaa ttcactccac 161220
caagttatct catctttgaa atggcttttt ttaaaggtgc ctagaatatg atggcgtgca 161280
gtctataaac tgttgcccac cttctgtact ttctctcaga ataattcaca ttcttctcca 161340
gtgtctgttg attgttactt tgtggaataa gttcttggaa aattccacaa gattattgtt 161400
atcttcttac taccaattct attgaacttt ctccaccttc tctgggcctt ccccagccag 161460
tggtgggaag atgctggctg gagtctgaca gagcctcttc tacactggcc tgggcttgct 161520
gtgagttggt ggaaaccttt gctcttgtcc caacacagag caagtgaaag aggaggtcaa 161580
ggggctcagg cagcggacta gggaagcaga atcgaggaaa aggaaaaatg gctgacttat 161640
tacctcaaaa ctctagagaa tttagttgat cttacagcca agaaggacaa aagccagaga 161700
gtaatatcct ccgcctcatg tctaacccac agaatacata gcaagtaaag agaacatggg 161760
cctttataaa aatgtcttaa gatacaattt tttaattgga ggaaatctac agtttaattt 161820
tctctgggca gcttttcttc cttttattat agtaggggaa atcccatgtt gatatacttc 161880
taaatgaaag atgatgaatt gatataatac aataaaaaat ctgtaaaatt gatgatatac 161940
ttatcaagaa aaattagctt tcattttaac ggtttacaaa ttgagtcaag tcctagtaac 162000
aaaatgttaa gtctattaac ataaccacaa gaaatacagg aagacgggca atctgtgaag 162060
cctttcactt acaatctctg gcccctcacc tgtgctgtgt aggaaaatct ttgtgcacaa 162120
tttgcttcct taattcattt tttattcatt caacacattc taataaatta tacaaaatca 162180
tgttgaaatg tgaatttcag tggtatttat aaatgcagtg tgaggagggt ttggatgtat 162240
tctaagacaa tagttgtgct ttgggaagga agcagtgttc actgaaaagt gcccccagga 162300
ccttttaatt ggaggaaata tgcttctgtg gagttggaaa tggggtagaa gatagataag 162360
gtcaaggctt aaaagttaag tgcacccaac atctgaagcg tccatgggcc tggcatggtg 162420
gctttcgcct gtaatcccag cactttggga ggctgaggca ggaggatccc ttgagcttag 162480
gagtttgaga ccagcctggg caacatactg agacccagtc tctacaaaaa ataaaaaatt 162540
agctgggtgt ggtgtctcat gcctgtagtc ccagccactc aggagatggg aagatggctt 162600
gagtccagga gatctaggct gcagtgagct aaaatctcac cactgcactc cagcctgggt 162660
gacaaagcaa gaccctgctc aaaaaaatag ttagatataa atattaatat agatacctat 162720
atatatctga atatagatat ctatatatac tctgtatata gttatttaga tatataaata 162780
tatatgatat atatttagag agatatatat ttagagagat atatatttag agatttatat 162840
atattttata tatatttaga gatatatatc tctaaatata tatctctctc taaatatata 162900
tatatctctc tctaaatata tatatatccc taaatatatt aaataaataa aagaaataaa 162960
agaaagctca gtttggcctc ctgcttgtcc tgtctcctca tcccctcttc cccctccatc 163020
attttatttc cttgccccat gtttcttcac tgcggccatg tccccccctcc tctccaatga 163080
tggatgtcat gtctgctgca gtcagagggc gacaagcctg gagtgttccc tgaagcctgt 163140
ggtttgtggt ttgtcctgca gctcaggctg cccaggcctc accagcaatc ctggcgggca 163200
gggcaccaca ctgggatgga gagggggaag ctggaggagg cactttctgg taaagaaagc 163260
aaaagccagc agtgcccagg ccaatttcaa cagggagtta aatagcacct taatcctgtg 163320
gcaggacagc tcatggggcc atgtgtgctc ttagaaagac tcacatgcac gcatgcacgg 163380
cagcaatgac tccatactca cgttcccctg cagacaccag gcccccacag ccggcacaca 163440
cactgcagcc ccagttccat gttgctagca gtggcttagt gaatgagtaa agttcttaaa 163500
atgcagggga cacctgccct tcattcataa ggctggacgt acacctctcc ttaaggagtt 163560
caagagctag tggaatccca attcatacgg tagagccatt cacagatgag agagacaagc 163620
cagaaggaag gaaccaaaag tcatgtcagc agttaggaca aaataacagg ctttcaaggt 163680
cacaaagcct cagggacact cctgcggtgg gactgggcta ggagccatgg gggctccaac 163740
tgtgcgctct gcctgccagc ctgtgggtgc tggggctcca cgaagattgt tgtggaatac 163800
caagcatgct tgctgtaggt cacggtgcac gtttactact tccaagacaa acagccgaga 163860
acaaagctcg ctttagcttc tgcgtacacc gaacgggaca cacgactgaa cagcgttccc 163920
attgtgcctg ctgggtgggg aggaagtgat ggcccagtgg gtctatcaga tgttagtagg 163980
atggggcctg gcggggctcc aggctctgtg tggccgacac ccacgccccc cgctctgctc 164040
cccattccca gccccaggtc agccctgcga ggccctgcag cagatgggct gctcaaactg 164100
ctctggtttg cagatttttc ttccctctca aatgaataca atatgttttc aagtctcaac 164160
cagatcttga gaaaatagga agagccagag ggtttctttg gtgttatggt tgtacagctt 164220
cccagactcc gggggagaga tgtgatttgt gctttctggc aatcccatgg cgtattaaat 164280
tttcataggc tttccagttt aaatttaggg taggcaatgg aagggaacgc aaaacagatt 164340
tctaggtgta ctgtgtgtgt gtctcccacg tctaaagtct gttaactgga gcacccaaca 164400
ggccccacag gctgccttca cacagaggac ctggggcgcc tccgacccat tggggtgagc 164460
agtgggccat ggagggagcc agggtcagga gacctggttg tgggcctgac ctgaccctgc 164520
tcagggtggc ctcaggtggg ccgttcacct cgtcagcctc agcttaccct ctgactacag 164580
tgacctcaga caaaatacgc ttcctggccc tgtccagttc tgacttttta taaacaagca 164640
cttatccaag ttaaagggat attttcaata tctactgagt ccacagatat taaatatctc 164700
ctctcttctt taaaattgtg gcattatctt tagaatataa aaggaaaata acacacactc 164760
tccttgaaaa tagagagcct aaacactctg caggaaatat ttaaagctat agtttttgtt 164820
tgtttgtctt gaatgcaagt ggcctggact ttgacttgct ttgagtcttt gaccttcatg 164880
acttcagtac agttcaaccc tgacagtttt gaagtaggta tgtgcctaga tctgccctag 164940
tccctgctgg aatgttgaag aagcaaaggt ccaggccctc agagcacttg ccacgtactt 165000
gccaacagat acggggcgga gacttgagtc aacgtaagag caagtgtgtg ccgggtgatc 165060
cgacactgca gagcgccagc tagaccctaa gcgtgtgcta ggggctgacc aagccgttct 165120
ttcctcaaaa acttggtggg gagggtattt ttaaaatcac acaaatattt aagtacagat 165180
tatgatgact gcctcaaagc agtggctctt cagcttcatc aagcttcaga gtccagaggg 165240
tttgttcata tggaaggcta ggcctgtctc ctgcatttca ccctcttggc ctgggggcgg 165300
gacccaagaa tgtgtggctc taaaaggttc ccaggcaatg ctgaggctgc tttctgaagg 165360
aaaaactgca agataccagg agagtttcat ttagattgaa gagtcgagga aggctcctct 165420
gagaaagagt ctgctaagga aggaggaggt gggttctggg gacagaggtt ctcccgtggg 165480
taagggtgga gggaagctct cctggggaga aggtgggcag gaggaccaga ggctggaggg 165540
aggagggcag tcagcctcgg ggcttcccag gaacagggac ggccagggca gggtttaggg 165600
caaggaaagc gtgtgagcat atttgtattt tagtaaatat ttacagtttg ccctccatgt 165660
ctgcagtttc atatccatgg attcaatcaa ccacaatgaa aaacgttggg gaaaaaaatt 165720
gcatcggtac tgaacatata cggacttttt ttcttgtcat tattccctaa acaatacagc 165780
ataacaatta ttcacatagc atttgcactg tattaggtac tataggtaat caggagatgc 165840
tgtagatggg aggatgtctg taggttacac acaaatgctg tgccacttta tatcaggggc 165900
ttgagcatcc tcacattttg atatttaagg gaggtcctgg aaccaattcc ccagatactg 165960
agggtccact gtctgtgtcc cctcgcccca ccttgccttt gtctcctgtc tcctatctcc 166020
accctgcctc ccgccagcct gttgctcctg acctgcccgg gcaccctgga gcagcaccct 166080
atctcagagc ctggctcagt gtgttcactt ctgcagagaa actaacttgc ccaagtccac 166140
actcaaaaca taggcattgc tgagatgtga aaagcagctg tggatgcttt ctgctacagt 166200
ctgtgtgttc ttttccatat ctgaataaaa ggtcaccacc atttgtattt taaagagaaa 166260
gagaatttat gggtggaaat tggggattcc ctcattctca gtcagacaga aaagagggcc 166320
ccattgtgtg cctgattgca aataaattta gcttcctcag cccaagaata gcagaagggt 166380

-continued taaaataaag tctgtattta tggctctgtc aaaggaaggc ccctgccttg gcagccagcc 166440
ggaattagca gggcagcaga tgcctgactc agtgcagcat ggatttccca tagggagcct 166500
gggggcacag cacagagaga ccacttctct ttagaaatgg gtcccgggca gccaggcagc 166560
ctttagtcac tgtagattga atgctctgtc catttcaaaa cctgggactg gtctattgaa 166620
agagcttatc cagctactct ttgcagaggt gctgtgggca gggtccccag cccaaatgcc 166680
cacccatttc ccagagcaca gtcagggcca agcctggcct gtggggaagg gaggcctttc 166740
tccctgctgg ctcggtgctc cccggatgcc ttctccatcg cttgtcctct gcagcaccca 166800
cagccagcgt tcctgatgtg cagggtcagt cattacccag ggtgttccgg accccacaca 166860
gattcctaca ggccctcatg atattttaaa acacagcatc ctcaaccttg aggcggaggt 166920
cttcataaca aagatactat cagttcccaa actcagagat caggtgactc cgactcctcc 166980
tttatccaat gtgctcctca tggccactgt tgcctgggcc tctctgtcat ggggaatccc 167040
cagatgcacc caggaggggc cctctcccac tgcatctgtc acttcacagc cctgcgtaaa 167100
cgtccctgtg ctaggtcttt tgcaggcaca gcttttcctc catgagtacg tattttgaaa 167160
ctcaagatcg cattcatgcg tcttcacctg gaaggggtcc atgtgcccct ccttctggcc 167220
accatgcgaa gccacactga cgtgcctctc cctccctcca ggaagcctac gtgatggcca 167280
gcgtggacaa cccccacgtg tgccgcctgc tgggcatctg cctcacctcc accgtgcagc 167340
tcatcacgca gctcatgccc ttcggctgcc tcctggacta tgtccgggaa cacaaagaca 167400
atattggctc ccagtacctg ctcaactggt gtgtgcagat cgcaaaggta atcagggaag 167460
ggagatacgg ggaggggaga taaggagcca ggatcctcac atgcggtctg cgctcctggg 167520
atagcaagag tttgccatgg ggatatgtgt gtgcgtgcat gcagcacaca cacattcctt 167580
tattttggat tcaatcaagt tgatcttctt gtgcacaaat cagtgcctgt cccatctgca 167640
tgtggaaact ctcatcaatc agctaccttt gaagaatttt ctctttattg agtgctcagt 167700
gtggtctgat gtctctgttc ttatttctct ggaattcttt gtgaatactg tggtgatttg 167760
tagtggagaa ggaatattgc ttccccccatt caggacttga taacaaggta agcaagccag 167820
gccaaggcca ggaggaccca ggtgatagtg gtggagtgga gcaggtgcct tgcaggaggc 167880
ccagtgagga ggtgcaagga gctgacagag ggcgcagctg ctgctgctat gtggctgggg 167940
ccttggctaa gtgtccccct ttccacaggc tcgctccaga gccagggcgg ggctgagaga 168000
gcagagtggt caggtagccc tgcctgggtg ctggagacag gcacagaaca acaagccagg 168060
tatttcacag ctggtgcgga cccagaaaga cttctgcttt tgccccaaac ccctcccatc 168120
tccatcccag tcttgcatca gttatttgca ctcaacttgc taagtcctat ttttttctaa 168180
caatgggtat acatttcatc ccattgactt taaaggattt gcaggcaggc cctgtctctg 168240
agaatacgcc gttgcccgtc atctctctcc gacagcaggg cagggggtcc agagatgtgc 168300
cagggaccag agggagggag cagacaccca cccggcctgg gcaggtcctc ctcattgctt 168360
gcatccgcct ggttagcagt ggcagtcagt cctgccgagt cattcgtgag gcgctcaccc 168420
aactccaggc agatgtaaaa ggtgacctac aagaagacaa acaaaaacat ctggagcgct 168480
cttatgccag catctgccct tgacaccacc aggcaggctg ttgctgggag ccgtggtgct 168540
tgggtaagct ccttcccatg gcagagctcc tgggacgcat tgtagaagca gggaccacct 168600
cccaggataa ccagatagca gcacaccctg cacagcccct tttactccag catcatcggg 168660
cattgatatc tcagctgcag ccacaggcgg cccccagcac cccaggaagt ggggagcgct 168720
catgcttctc tgagcacaaa aatcactgaa tatttttgcc attctcatgg tcataacccg 168780
ggccacagag tagaacactc ctatcactgt tgttagacag tggtcctggg agagggtctt 168840
gtgtgcctcg gatgccaggg cctcttttta ttgggaggtg cttgttattt ctgtgtgtgg 168900
ctgcatttgt ttcccaagac tgccacaaca aatcatcacc aacttggtag ctcaacatag 168960
cacagcttta ttccctcctg gctctggagg ccaggtgtct aaaaggccat gctcccacaa 169020
tggttctgag gaggatcctt cctgcctctc tggcttctgg tggctccagc atccctgggc 169080
tgtggctgca cctccccatg tcaacctccg tcttcacaag gccttttcct gtgtctctgc 169140
aaccacaggc ccctctcctt tctcttaata aagataccag tcattgagtt tgaaaattgc 169200
taagagagtc tgttgtaaat cttcttagca caaaaaaaaa tgacagatat gtgaagtggt 169260
agatatatta attagtttga tttgatcact ccgctatgtg tataaatgtc aaaacaaaca 169320
ttgcactcca taaatatata tattaaaaaa gatcccagtc attgcattta ggacccaccc 169380
taaatccagg atgatttcat ttcaagactt ttaactagat ttgcaaaacc ccatttccaa 169440
ataaggtcac attctgcagt tttgggtaga cgtgaaatgt ggagacactg tgcaacccac 169500
tgtcttgggg agggggtggt cagcctgggg cagatgttgc tgggtgtgga gctacatcca 169560
ctcatgccct gacctggaac ccagacctgc ttccccagct ctcctcctgg ttatctgaag 169620
cagggaatgg agagcactgc cctccttgcc caggcagtct ctatcacctg gttttagttt 169680
cttcttagca catattgccc cagaatatct ggttggttta tggcttactt gagtttgtgc 169740
ctacctgtcc caaccgggag gtgagccctg gctattcccc aaacccggcc ctgcatgtgg 169800
gagctgccct tcctccgttc atcagagggg gccaacagtc cacagctgtt cttaatcatc 169860
tcccagtaac ccccagctcc acaaaggtga ctccttacat ggtggagagg tggtcgggcc 169920
atccgtgtga aatgtgtatg tgaccgtttt ccttaagggg cacgtagtct tggcaggttt 169980
cgctcaatat aggatgagct caggactcca gtggactgtg gattcagatc tggattctgg 170040
cgcattcgcc gtgtgaacgg gggcacgttg ctggcctgtc tgcgcctcgt ctcccgactg 170100
tggagtgtgt tctgcccctt gtctttctgg gaggtaggga gggcagtgag ccccttcgca 170160
tcgcccacca caggcccagc acatggctga tccccactga gtgttctttt cctcctttga 170220
tccccctttgg ctgacctagg ttggagcagc cactaaaata tacccagaaa catcttccta 170280
atctacatct gtgccaaccc tcattccctg gcgcagcatg accatcacat gcccgccatt 170340
gttcctgatc tctgctgctc atgacctgct ctccagcgct ccttctcatg ctcacattcc 170400
agttggcctg acctagataa gtggaggttt atttgacccc aaaaattagc cttctacaaa 170460
cgaatataat agtgtccatt acagagaata aacttagtgc gtgtcccatt taagcagaag 170520
ttactgaaag cctgagttta agtttccagg gcctgaaagt tttccatgac agttttctgc 170580
ataatattac ctacaatttc aatctgttat ttaaagccat tcttgtgttt gttgtacttt 170640
gattagcttt attttgattt gaagtccttt tacattacgg gcagttaacg ctttgtctct 170700
gttagatttg ctttttagtt cacaagagaa acctcattcc tctgtatttg aatagttgca 170760
atgatggaac agctgtccct ggagggaaat gaaaacagtg attccccaaa ttgtgacaat 170820
agaaatttgc tcttgggtta cttacaatgt atctgagtat taaaaaattt tctttttaaa 170880
cgtttgaagt aaaactaccc agaaacactt agtggctgac cagaaactaa actcctggca 170940
tcctcaaaat gggatttatt ggcttataaa tgtcctgtgt tgactcacaa aggcacaaac 171000
tatctaggta agttttcttc taaatgttga tgggagagct ggccactgtt atgcaagttt 171060
cattgtcctg actaaactgc caaagagatt acataaaatt atatcaacta gacaaaagga 171120

-continued aaaaggaaaa aaaacagagg tgtcttggga ggaatccata tgagaccagt agaccatgag 171180
agagacatcc cttgccatct acaaggaaaa tggattttgt tctccatatg caaaaccatc 171240
tcaggagctt gcggagacac cacttgctta ctagccagaa agagcaggtg cctcctaaat 171300
tccccacaca ggagctcaca gtggctttca tgcactggga ttaagttaga cttaagaaag 171360
cctgtctact cttcctggga tttacaagcc agctagtaaa tcccagaata aatcacacgg 171420
cacagtcatc caaagatccc gtcatccgtg ccgtttggaa agccctgctc ctgtgccacc 171480
ctctccccgt ggagcctccc atgcccagga ctgcagagtc ctgccattca gactgcaact 171540
catctcacat tcttccaaac tatttggaca acagagcttt ctcatcacct aatgcagatt 171600
acagtctcac agaattgagt gttcaggcag acactgatgt ggttctgtag tacagcaaac 171660
aatatcagtt tacagtcctg aggccaggcc tggtgaacaa cgcacggtag cggtggggca 171720
gggttctcag aatgaaactg gcttacacat ggcactctct gaccacaact gtataagcac 171780
caaactacac ttagttccat ctatgaggta aaatttaatg cagatgaaca tcaaagaaaa 171840
cgtcaaaggc tcctttttac aagtacgtgg gctacttaat ttggtccaag tccattttaa 171900
aaagccctag gtgctttcac ggctctgcta ctgacaagaa gccccagtgc ctgtgagctg 171960
ctaatgggag ggagaggaag atgagctgag tgggccgggc tatcccgtcc acaccgggag 172020
acagggaagg agactccaag ctggtggtgc cagcacattc caggccactc aggcctattc 172080
ctaggtgcca ggtcacgaaa accacgctga cagatcgtgc tgtgtgcgtg tcatagcaca 172140
caagcaggac tgtgagagag tgaaagtgac actgggtgga gcactgagga agggccacag 172200
tgtgttggtg gagataggct gtcatggaga agagaccctg gcttgctcta cattgcttcc 172260
aatgcaactg caaggcaggt cccagagggc tccggccttc gtcatccagg tttgctccct 172320
cccctcatgg ctttcccatc ctcagatgag gactcggcag agcctacccc tgctgactaa 172380
ctgtggcccc agggtggtga ctcagccctg cacctcctga tcccgtctgc actgggccag 172440
agaggatgac ttacccagca cgttcacatc acacagcttt gtggattcct aggtccaagg 172500
accagagatt tcagttatgt gagttatttt ttttatttgt tcttgcgtat tccacaaagg 172560
gtcgcagcta aacttaacct aatgatcact ttagtatatc actaaaaaga caaagctcac 172620
agtgctgttg aagcacattc atcatcttta gacattttga ctagttattt cttaagcatt 172680
tacctgctag tgttaagcat cacatgaaat acatatagaa gtaagacaaa atttcttatc 172740
tccccaagtt tgccaacaaa tacagagcag gaagggaagc aggtcagagc aggaggcgca 172800
gctatagtga ggccaccatg caaggcacag ggagggtgag ctccaagttt gaatggaatg 172860
ggtctgtcag ccaagccccc tggctctggg aagatagcag tgaacaagcc agatggcccc 172920
tcaccctcca gagccgtgag tcctgcagac caaacagcgt gacaggtcct ttccctgtcc 172980
aggaggcctc tgtgggtgag agttggctgc ggacagggcg tgaaggcact tgagggtggg 173040
gaagtgactc tgactgggag atgctgagga cagggaggaa accaccagat aagggacact 173100
ggggaggagg ggtggacccc tcagggccaa gcacatggag cctcatcaca aaggcaagat 173160
ggtggccaaa ttcaaggtcg ctgcaaaagg aatggagaag agagaataga tttggcattt 173220
ggaggaaatg gtgacaatca tgagcaccta cccgggactc tccatgggtg ctatctctac 173280
ataaactcat tccaccctct gattaatcca ttctacatat ggggaaacaa aggcatgcgg 173340
tgtttacgtc acttgccaag atctcaggat ttgatccagg tggcctggtt ccatggtgca 173400
gcctctcagc ctgcatggat gccccagctc agagcatgac tctcaggaca ggggtcccag 173460
cagccctccc tccctgagca gcagggtgcc cgtgctgcac cacttctgtc taggaatagg 173520

-continued acattctgac actttcctgc ctcttccgag gtctagcact tactctatgc ctgcctggga 173580
aggtggcaag ctggcctgag gaacagactc ttccattttt tagggagctc aaggccacag 173640
atgctctgag atctggagtc cagagacagg agcggaggct tctcctggtg accactctgc 173700
ttaaaaactt catcagatcc gtagtttcag agcccccctg aaccccatcc cttacctcta 173760
ccagttgcag gtgggtctct ggggtggggc tgccctcccc accagcaccc caagggctaa 173820
aaggttgagg ggagaacacc atcatttgta caggggggatc ctggaagatg aggcctgaga 173880
aagccctgcg gggcccctca ccttctccct agctgtggcc aagagtgtct ggccttgcct 173940
gcctcaggac cagcccaaag tggaggtgag aggtgagccc cagcccccag gggaagggtg 174000
atggtggtct tggtctcagc atggttctgg tagaggtggg ttattttgaa gatgatgaac 174060
cttaagcctc tttctgatct tgctttaaat aaatacttct gaacaacagc aacaacagaa 174120
tagtgttgat aggaaagccc tccactccac cagaaccacg cggccttctc gtcctcccct 174180
cctccacttc cttcctaagt cactgctcca tgagctcttc cacaggagat ttacaaaata 174240
gaacacaaac aatccagttc ccgcctctca ctctgaactc ctcccaagac tcgtggggtg 174300
cggcagcccc tgggaacacc cagcccttca aggtcaaaca cagcccccgc ccctcactct 174360
ggggtaccct gccagaataa gccccgacag ccatgtggag cagagccttc tttttgtaa 174420
gtggaagttc caggctggct tttcaaatcc ccttttaacc tcagtgctgt atttcaaaat 174480
tcattccagt tttcctgtag taattaacaa aaataaatat tttaatttca attaaagtga 174540
gggtctcgga gaagaagcag gaactgagtt tcctgagagg ccccgctgag gctttgttga 174600
tatttcttcc tgcgacctct gctcggaccc tgggagctca caggccgtat cgcagctctt 174660
atctttgggg accagttaaa gcataactgc gccaggcaca gagttgtcct ttcaaatgtg 174720
ccggcagtgg gacggagacc catgcgtcaa gtctcctcta agttcacatg ggattctctc 174780
cttgtcccaa agctgtctct gacttaaaac cctccaactg attacctgaa ttccagaata 174840
tgtcctgtgc tctctgccct ttcccacgcc tttggtgaag accggtgttc tgaggaaaca 174900
gacactgtgt agaaatggct caggtccttt aaagccctgg tgtgaggagt ggggaagggc 174960
tgggccagag gtcagctgga tttgttagat tgacagagtg acgcggactt ccccagaggc 175020
acgggaccaa ggtgcatgct cacgctgtct catgctctca cacataatgt gtgtgtgtgt 175080
gtgtgtgtat atatatatac acatatacat atatatatat acacacatat gcatatatat 175140
aaaaccccaa gcagcctctg gcttagcagg tgcatttccc agcagggcaa ttaaagccat 175200
ggtcccagta gtggtcttgg ggtctcaggg tatttggtct gtgcagccac atgcttcagt 175260
ctctggaccc caggtcatct aacgaggtgg tcgtgtgggg actgggatag aaaaggtgtc 175320
tgcacggacg tgtgtgaaag ggctggcaca tcgccagtgc tcagcactgt cagctgctat 175380
caccagtcat tcaatcattc attcattcag ttgttcattc ttcaacaggc cgttttaaaa 175440
atgtgcccag tataccaaaa tctccgctaa gcatttaaag aggcagaatg aaagttagca 175500
gtggtggtga aacgaagctg ggaatgtgct ctgagggcct ccttgtgggc ttaatgaata 175560
tgtagaaacc acgcatttta aatagagagg gagaaaggga gaggttcctg gtcctctgca 175620
tggggacttg tgtgtggctc tttactgtag gcctgtgcca ctcctgctca acagctacca 175680
cagaggacgc cttcaacaaa tgtgaagaac gaacaaaagg tacaaatgtg aagaacgaac 175740
agggtagaaa gaaaggagaa agcaagggtg agggtgagaa atcaagggac agagaagaga 175800
gaagaggaga tagcctggga gttcacacag ccaagaaggt agacactcag ttgaaccagc 175860

-continued

```
aagaggctga gcctaactct ccctttcgaa tgggcaggag ttcatgatat ttaataaaca 175920
gaggccttgc tctgtaagag acagggtacc aggcagagag caagtcagca tcgcaggagt 175980
caaacgaggc agacagcggg ggcagggagc ttgcctctga aggagaccca ggctgccaga 176040
gtagcaggga gtctgggcca gtcctctttt gggaagcgct tcctcggctt ctgccccccc 176100
tctcctctcc ctttccaccc accatcctga cataatactt cctaatctgg aagtgttgtc 176160
cagagaagaa cctgctcatt tcctcttaag taggcaggga agcactaacg tccagcagca 176220
tcggaaaccc gtaggagcgc tctcggcagt gcagggtgag gggacagtcc atgtagtcat 176280
gagacgtggg tgtcaggcaa gcgtctcttt tccaaaagag aaaaacatta aaggcctcac 176340
aaacggcgcc caaagactaa ttctgcatag catctttgcg agaccctagg ttcttatgat 176400
gactggtttt gcctgagaaa gaaaaaattt taattttgct ctgacatgcc aattcaacaa 176460
atcattttca cataatattc atgcaaaaaa aaaacaattt gccagaaaac ttgggaatcc 176520
atccacatct acagcttttc cctgcagtca cactacagtg ggatccctcc atacaggagc 176580
ggcagagtgg agcaggctag agatgcctgt ttgtttctgt ttgctgcacc gcagcaagca 176640
tttctgtcgt gcccactctg tactagaaag tacatgaaca tcagccataa agggaactag 176700
aaaggtggcc caccctcttg gtggagagag aagagagtgt ggtagaaaca ataataagaa 176760
gtctgcagaa cttgacccct cccagcctct cccacctgcc agcctggccc ttgcagagag 176820
atgcaggctg ccattcttag gccaaagcct gggacagttg ggctcagcaa ggtaggcatc 176880
cgtcaagcaa ggaggagcag gggtcagcag tgaccccagc agccagcagg gagaaaggtg 176940
catgtgacaa ggacaccaga ggccgtgggt caggatcagc cagggtcagg gtagcatttc 177000
taggaattca ctctgttggg cgctgtgctg gctgcttctc acatattatt cctttcttac 177060
tctcagagca gagatttcaa ttgcagcgag attgtggagg cagccaggga ggtggggagg 177120
gtggtgtctt ctaaaagcat tttcagtatc catgtggttt cagtaataat aataataata 177180
aaccagtgaa aagtaaaaca ggacaaaaat cttcataggc agtgaaccat atcagagagt 177240
ccaagaaagc acaatgagag tgtggcttaa aaaccctgaa cgacattcct ttgcaccagc 177300
ttggtgagga gggcatggtc cccgccaccc cccaccccca ctttgcagat aaaccacatg 177360
caggaaggtc agcctggcaa gtccagtaag ttcaagccca ggtctcaact gggcagcaga 177420
gctcctgctc ttctttgtcc tcatatacga gcacctctgg acttaaaact tgaggaactg 177480
gatggagaaa agttaatggt cagcagcggg ttacatcttc tttcatgcgc ctttccattc 177540
tttggatcag tagtcactaa cgttcgccag ccataagtcc tcgacgtgga gaggctcaga 177600
gcctggcatg aacatgaccc tgaattcgga tgcagagctt cttcccatga tgatctgtcc 177660
ctcacagcag ggtcttctct gtttcagggc atgaactact tggaggaccg tcgcttggtg 177720
caccgcgacc tggcagccag gaacgtactg gtgaaaacac cgcagcatgt caagatcaca 177780
gattttgggc tggccaaact gctgggtgcg gaagagaaag aataccatgc agaaggaggc 177840
aaagtaagga ggtggcttta ggtcagccag catttttctg acaccaggga ccaggctgcc 177900
ttcccactag ctgtattgtt taacacatgc aggggaggat gctctccaga cattctgggt 177960
gagctcgcag cagctgctgc tggcagctgg gtccagccag ggtctcctgg tagtgtgagc 178020
cagagctgct ttgggaacag tacttgctgg gacagtgaat gaggatgtta tccccaggtg 178080
atcattagca aatgttaggt ttcagtctct ccctgcagga tatataagtc cccttcaata 178140
gcgcaattgg gaaaggtcac agctgccttg gtggtccact gctgtcaagg acacctaagg 178200
aacaggaaag gccccatgcg gacccgagct cccagggctg tctgtggctc gtggctggga 178260
```

-continued caggcagcaa tggagtcctt ctctcccttc actggctcgg tttctcttag ggaccctcac 178320
agcactaagg ggtgcgcgtc ccctgtcagg ccctcgaatg ccctcccaca gccaggcccc 178380
tctgaggttt cactctggcc tgcttggctc ctagcagcca ccaacccatg atgctgggcc 178440
ctgaaaacac acgcagacct ggatgagtga ggccactggg cacaaccagg gctcccagct 178500
caccagagca gcctgggaca cagagggtgc tcagaaacct accagagcag ccctgaactc 178560
cgtcagactg aaatcccctg ttgccgggag gaggcgccgg gcctggggga cgggtcctgg 178620
ggtgatctgg ctcgtctgtg tgtgtcactc gtaattaggt ccagagtgag ttaacttttt 178680
ccaacagagg gaaactaata gttgtctcac tgcctcatct ctcaccatcc caaggtgcct 178740
atcaagtgga tggcattgga atcaatttta cacagaatct atacccacca gagtgatgtc 178800
tggagctacg gtgagtcata atcctgatgc taatgagttt gtactgaggc caagctggct 178860
tttattgtta gttaatttac attatatcct ctgacatgca agtattttct ttcgagataa 178920
tgactaatga taatgtaatc attgctgtct atctattgta ctgagaaaac acggcagagg 178980
aaatcgagtc cagctgccgt ccaaaagtca ctggagattg caatgagctc gtctggcagg 179040
gtggggggta tgggagggaa agagcttagg aaacggctct ccctgcaaag tccaaccaaa 179100
ctttaacgtt aaccaaacca ttaatgttgc catgaatttg aagtgaacca gagggaggtg 179160
gcagaagaag cttaatgggg aatagttccg gtagagaaat gaggcttaag atgaactacc 179220
ctggccctta tgtgtcagag agaacggctt gacaaacaca cactgaggat gtctgcaggg 179280
ataaaagaag aaagggagat gacccttgct tctcgctctc gggaggacca tctggtccgg 179340
ccctggggat tctctgtttc ctcttctgaa tcccagtgtt gcccagcact ggcctgtacc 179400
catcctcacg agggccgctc tcctcacccg gccctaggtc cctgccctgt cctgagccta 179460
caggggcctc ccatgttgag aaagtgttgc tgacacattg tctctgaccg ctgtgccagg 179520
cattttctgc tgaattaccg cacttggtcc ttgaatttca cccagcaact tactgaaagg 179580
ctggaaccca tgaacctacc ccttcactga ggaaaataag ttaccccagc catctacagc 179640
gacaggagca agggaggagt cgcctcacct ctctagaaat gtgtatttga ggagaacact 179700
attgaaatga atttccaaga ataatctagt cagtattaca aaagcaaaat tatttgggat 179760
atcgtccttt tttacttagt attttttctt tttcctatag cattattaac tttctgattt 179820
tccaaataca tacacatttt taaatttcct gagtctttat ctcttctgtt aaaatgtaag 179880
atttatgata caaaggcaga gatttgtgtc catgaataag tgaagtttgg tgtgcacctg 179940
tgagctgagc cacctcaatt aatggaacag ataaggaaat aaaggtctgc tgatgcattg 180000
ttatttacag ccattttcag aatgtatctc ctctccacga gggaactgca gggtcctgcc 180060
ccaagccatt tattttgtcc tcaagcagcc cgcccctccc actccaggca cagcccggtc 180120
tcctgctggt ctcccctctt cccacttgct ccccctcatc tatgctccag acagaggcca 180180
catatatttt ttaacttttt tttttttttt tttgagacag agtcttgccc tgtcacccag 180240
gctggagtgc agtggtgcag tctcggctca ctgcaacctc cacctcccgg gttcaagtga 180300
ttctcctgcc tcagcctcct gagtagctgg gattacaggc gcacaccacc atgcccagct 180360
aattttttgt atctctagtt gagacagggt ttcactatgt tggccaggct ggtctcgaac 180420
tcctgacctc atgatctgcc cgcctcggcc tcccaaagtg catatttttt aactttatca 180480
gacttttcat tctctgctca acatctttct ttggtcctcc aggtatgttc agataaaacc 180540
tgagcacctg gccatgactg atgggttgct gggccatctg gccctggcaa ctctcccgtc 180600

-continued caccaggtcc ccctcccgtc acgctccagg catagcctgt gtgtgccagc gcaatgccca 180660
cactccatgc acaagtggaa gccctctcaa agtcagtggc ttagtgcctt gatgtggtca 180720
cacccattct caggaagtcc gttcccactg aaaacattgt gtgttttcaa catcattgag 180780
gctgccacgg cagattataa tcactggcct aggcagccca ctggaactac cagaccatga 180840
gcctgaattt tttgtttaaa aatcatatcc tgttttctct actctctagt ctctagtcaa 180900
ggtgaattat tcaatttaat aaattagggg cctagtgtgt tgtaccaagg agctaaaaag 180960
agagaactcg caacaccttc cagcccattc tccacctaac actggctata ctggctctcc 181020
tctctctcgc tgtttgttcc aaaatctaat aacctgtctt cccactagaa ttcatcatac 181080
atgtttaaaa acctagttaa atagtagtta aactgactgc atagatctgg aaatgagaca 181140
gtctttcttt tacaaatcca tatagactat gagttggggg caggggatga cacaagaatc 181200
tattttcttg cccccaaacc attgctttcc ttccaatgtt aagcttgtat tctgtgtatt 181260
aattcaggtg gttccgtttg ggaatggcct ctgttaccca gagatgggag ggccatcaga 181320
actcggggtt gtctgaaaaa acactggttc taaaattatc actgctttca cttgttttta 181380
accatcatag ttgtttgatt ttgaaggaaa aacatgaggg tttttattct atgcttgtta 181440
tatctatatt gtggtttcgt attttttaga ttttagtacc tgacattttt ttaactttta 181500
ttttaggttc aggggtacat gtgcaggttt gttatatagg taaatttgtg tcatgggggt 181560
ttgttacaca gattatttta tcacccaggg attaagccta gtacccatta gttatttttc 181620
ctgatcctct ccctcctccc atcctccacc gtcctataga ccccagtgtg tgttgttccc 181680
ctctaagtgt ccatgtgttc tcatcattta gctcccactt ataagtaaga acatgcggta 181740 tttgatttc tgttcctgca ttagtttgct agggatgatg gcctctagct ccatccatgt 181800
tcttgcaaag tacatgatct cattctcttt tgtggctgcc tagtgttcca tggtgtatat 181860
gtaccacatt ttctttatcc agtctgtcat tgatgggcat ttaggttgat tccatgtctt 181920
tgctattgta aatagtgctg cagtgaaaat acgcatgcat atgtctttat ggtagaatga 181980
tttatattcc tttgagtaat gggattgccg ggtcaaatgg tagttctgtt tttagctatc 182040
tgagaaattg ccacactctt ttccacaata attgaactaa tttacattcc caccaacagt 182100
gtaaaagcat tcctttttct ccacaacctc accagcatgt gttgggattt tttttttttt 182160
ttacttttca ataatagcca tctgactggt atgagatggt atctcagtgt ggttttgatt 182220
tttatttctt taatgatcag tgatgttaag ctctttttca tatacttgtt ggctgcatgt 182280
atgtcttctt ctaaaaagtg tctgctcatg tcctttgccc actttttaat gggattgttt 182340
aattttttct tgtgaattta cttaagttcc ttatagatgc tggttattag acccttctca 182400
gatttgtagc ttgcaaaaat gttcacccat tctgtgggtt gtcttcactc tgatgatagt 182460
ttcttttgct gtgcagaaga tcttcagttt agttagatcc catttgtcaa tttttgcttt 182520
tgttgcaatt gcttgatgtg ttttcatcat gaaatcttag cccattccta tatccagaat 182580
ggtattacct aggttgtctt ccagggtttt tatagtttgg ggttttacat ttaagtcttt 182640
aatccatgtt gagtttattt ttgtgtatgg tgtaaggaag gagtccagtt tcaatcttct 182700
tcatggctag ctagtcatca tttattgagt agggagtcct ttattcattg cttttttttt 182760
tttgtcaact ttgtcaacga tcacatggtt gtaggtgtgc agccttattt ctgggctctc 182820
tattctgttt cattggtctg tatgtctgtt tctgtactag taccatgctg ttttggttac 182880
tgtatccctg tagtttaaag tcaggtagca tcatgcttcc agctttgttc tttttgctta 182940
ggattgcctt ggcaattcag gctctttttt ggttccatgt gaatttttaa attgtatttt 183000
ctagttctgt gaagaatctc attggtagtg tgataggagt aacattgaat ctataaaata 183060
ctttgggcag tatagtcatt ttaatgatat tgattctttc tatccatgag catggaatgt 183120
ttttccattt gtttgtgtca tctctgattt ctttaagcag tgttttgtgg ttcttattgt 183180
agagatcttt cactttcctg gtttactgta tttctaggta ttttattctt tttgtggcaa 183240
ttgtgaattg aattgcattc ctgatttggt tctcagcttg actgttgttg gcatattgga 183300
atgctaatta tttttgtaca ttgattttgt acaactgagt cttcactgaa gttgtttatc 183360
agcttaaggg gttttgggtc aagactatgg ggtttttctag atataggatc atgtcatctg 183420
caaacagaga tagctgtttt cctctcttcc tgtttggatg tccattattt ctttctctca 183480
cctgatttat ctggccagga cttccaatac tatgttaaat aggagtgttg agagagggaa 183540
tccttgtctt gtgtcaattt tcaaggggaa tgttttcaac ttttgcccat tcaatatgat 183600
gttggctgtg ggtttgccat agatggctaa tatgttgagg tttgttcttt aaatacctag 183660
tttattgaga attttaaaca tgttgaattt tattgagagc cttttctgca tctattgaga 183720
tgatcatgtg gcttttgtcc ttagttctgt ttgtgtggtg aatcacattt attgatttgc 183780
atatgttgaa ccaatcttgc atcccaggga tgaagccgac ttgattgtgg tggcttaagc 183840
tttttgatgt gctgctggat tcgatttgcc agtattttgt tgaggatttt tatgtctatg 183900
ttcatcagag atattggcct gaagttttct ttttttgttg tatctctgcc aagctttggt 183960
atcaggatga cattggcctc atagaatgag ttaaggaaga gtccctcctt ctcaattttt 184020
ttggaatagt ttcagtagga atggtaccag cttttttttgt acatcttgta gaatttggct 184080
atgaatccat ctagtcttag gctttgtttt ggttggtagg ctatttatta ctgattcaat 184140
tttggagctc attattggtc tgttcaggga ttcagtttct tcctgaggtt tttattttta 184200
tcaaatggaa cttaagcttt ttcatttcca atttttttat gatctaaaaa tgtgcagttt 184260
acagccctgt tcagaatctg catcttcctc attctgcaga tacaggtccc tcagagcagg 184320
tgactgagtg tgtatcctgt ctggagcata atacttatgc tagtagagtt actgttgtct 184380
ttattgttaa ttaccaaagt ttaccactta tcagtcactt actacttgct gggcattgca 184440
ctaagcattt cagttgtatt atcttgttgg gtccttacag caatcctgtg aaacagatac 184500
tgctattacc ccactttata gagaggtaga ctgaggcttc cagcattgaa gcaaattgcc 184560
caagactaca gaaatgtagg tttctaaaca tcaagaaaca gtaaccagta atgatgacta 184620
aagcaaggga ttgtgattgt tcattcatga tcccactgcc ttcttttctt gcttcatcct 184680
ctcaggggtg accgtttggg agttgatgac ctttggatcc aagccatatg acggaatccc 184740
tgccagcgag atctcctcca tcctggagaa aggagaacgc ctccctcagc cacccatatg 184800
taccatcgat gtctacatga tcatggtcaa gtgtgagtga ctggtgggtc tgtccacact 184860
gcctagctga gccttggtgg ctgctcttag ccaaacagct gaggcctttg catccctgga 184920
gaaatgtcat cacattactt aaggcaggca cacaaatcca gaaacatctg taaatacccc 184980
ttcaagcatt cttttaaaga cacttcttga ctcattgggc agtatgacct gacatttgcc 185040
catgtttgca agcaaataaa taaaactaaa gtcttccgca agccattaca ccaaaatatt 185100
ctattcgctg agttactcaa tgaaataccg agttgcccta tattttgaag cctgttacca 185160
gagagactga atgtttttaa atgcatggca gtgagtaaca acataaggct aatagagtca 185220
acatttctgc tttgacttaa accttttaaa ccagtggatt tatgtgaagt ctctgcagtg 185280
tggcatttaa acatttcaat ctaaataaga gtgtgtaatt tgattgatgc tattattcta 185340
ccagattcac gagtgcagtg ggctctggag gtagcattac atgcatggga tgagcatttg 185400
caaaagaaag ttgtataggg aatatgacag agccaagtta atgtaaatat taatgccttt 185460
ctgaactcta ggccacagag ttgatctttt ttaacttcct tggtttgggc taaggaagct 185520
gtgatccaga gaagccacgt gatttgtcta aggtcacata gcagtctggc ctaaaatagc 185580
ttgatatgct gtggatggaa aataaatgtg atccctcaag aggcatgagg atttccaggc 185640
agtagccata cctccaaatt gtttaatctg gatttagatt gttgggtagt cacatgcagc 185700
agcacagtta acagtgtgtc ctcctgtgga agttgccagc acagccagcc ctctcacttg 185760
catgcatgcc caccagcctt ctcacttgca tgcatgccca ctgggtatgt gctgtactgg 185820
agacgccggg ggtaggggcc cagtcccaac cccaaattct ttaaagccta tttttctaag 185880
ttgcatctgg tttcctacct gaaggaatgc taagggtgga tgttgagtga ggaccttggt 185940
gcagggcacc ctgcagtcag gatagttcat ggagagcaat tgtacagacc cacactgctc 186000
catcccctca ggcgtaacac aggatgctga ccccaggaag agtgggcgta gaaaaactag 186060
agggcattat tgttattctg attcaaatgt acagtgctgg catggtcttt aaacagtaac 186120
cagtactagc tggccaagac agaaaagtct accacaaaga cttggttctt tcatcactta 186180
tttgactgga agtgtcgcat caccaatgcc ttctttaagc aatgccatct ttatcatttc 186240
ttccagtgtt ctaattgcac tgttttttct cattccttcc ccaggctgga tgatagacgc 186300
agatagtcgc ccaaagttcc gtgagttgat catcgaattc tccaaaatgg cccgagaccc 186360
ccagcgctac cttgtcattc aggtacaaat tgcagtctgt gcttccattg ggaagagtcc 186420
ctctaatgag catctcatgt cactgtgttc tgtcacatgc cagcctggcc tccctgtgtc 186480
ccagatcgca ttattaaacc ctccagcgca ttagagcaag cctcagtaag gcgcaggcca 186540
catcgtgaac taagcagcat ccgtgagtgg ggcccaccca actccatctc cccctccccg 186600
tctgaactct cctctggtgc tcgtcctcac tgtccggcta gccaaagcct cagctgggtc 186660
taagagagaa gcatggtcta ttgggctttg gtgtcaggca gacgtggctt cacacccctg 186720
actctccact tcttcgcatc acccaggcag ccgatccacc tatctccttc cataacacag 186780
gaataccaaa accaagctca caggattgtc tcaaagattc aataaaatat gttgcaaaat 186840
acgctcccta acacctcaca gcaaggtgca cactcgatga atgctgcagc ttcttccctt 186900
tctgtttcct cagaagctat ttgaatctca tgtaggggct ttcaagcatc aaaggatggt 186960
tcatgtttta ttttaaggca cccacatcat gtcatgaggg gaggcagcta taatttagag 187020
aaccaagggg gatttcatta taacaaaatt ggcaaacaca caggcacctg ctggcaatag 187080
acccctgctc ctatagccaa gaagtggaat agcatctcta cgggccattc taatagcctc 187140
aaaatctctg caccaggggg atgaaagaat gcatttgcca agtcctacag actccaactt 187200
ctaccgtgcc ctgatggatg aagaagacat ggacgacgtg gtggatgccg acgagtacct 187260
catcccacag cagggcttct tcagcagccc ctccacgtca cggactcccc tcctgagctc 187320
tctggtatga aatctctgtc tctctctctc tctcaagctg tgtctactca tttgaacaaa 187380
ttgaatttta gggaaaataa ccatctagtg aaactcacat ggatatgaag tcaattttaa 187440
ccaaatggta aaatcaaaat caaaataaat taagtgtatt aattattttg ttgcattgca 187500
acaacttgat tgtaagcctt ttaggtccac tatggaatgt aattaaatca aaactaaacc 187560
tagttgctct aaaactaacg attaagacaa aaattaaaca ccttcacaat ataccctcca 187620
tgaggcacac cacctgcatt caggaaaagt ggatgagatg tggtacaagc attccatggg 187680
caacttctct gtttcttttt cagagtgcaa ccagcaacaa ttccaccgtg gcttgcattg 187740
atagaaatgg ggtatgtatg aacaccttat aagccagaat ttacagctct ccactatggc 187800
tctattttac atggaaaatg ccttaaccta aataatttta acccagataa tcttgagttt 187860
tcttcctgtg tgggtttttc cctgcacggc tgtcacgcct cacagtgccg ttcaaagcgt 187920
gactcctgga ccagtagtag catcgcctgg ccttgttaga aacgccattt ttcaggccac 187980
tgccccagtt tgaccaaatc aggacctctg gggtggcac ccagtagtct atgtttgagc 188040
cactttccag gtgatgctga tgtctgttga agtgtgaggc cgtggtctag accgcactgt 188100
gccatgcaga aaccactagc cacatgtggc tacttcaact taaatgttaa tgagttaaaa 188160
tgaaataaaa tataaaattc agtttctcac acatgtgaag tgtccagtag ccacacgtgg 188220
ctagtggtga ccgtattgaa gagcaccgct catagcacac ctccctcact gcggaaagtt 188280
ctgctgtaca gcacccagca cagccctgct gcccaccctg cagcctgtgg cccagtagca 188340
ccagcaccca ccagggtgca gactctcagg cctgcccaac ctactaatca gaaccagcat 188400
ctcaaggaga tctcgggtga tttttgcaaa cactgaagtt ggggcagccc tgaccggagt 188460
aaccttccct catttcctcc tgcagctgca aagctgtccc atcaaggaag acagcttctt 188520
gcagcgatac agctcagacc ccacaggcgc cttgactgag gacagcatag acgacacctt 188580
cctcccagtg cctggtgagt ggcttgtctg gaaacagtcc tgctcctcaa cctcctcgac 188640
ccactcagca gcagccagtc tccagtgtcc aagccaggtg ctccctccag catctccaga 188700
gggggaaaca gtggcagatt tgcagacaca gtgaagggcg taaggagcag ataaacacat 188760
gaccgagcct gcacaagctc tttgttgtgt ctggttgttt gctgtacctc tgttgtaaga 188820
atgaatctgc aaaatttcta gcttatgaag caaatcacgg acatacacat ctgtgtgtgt 188880
gagtgttcat gatgtgtgta catctgtgta tgtgtgtgtg tgtatgtgtg tgtttgtgac 188940
agatttgatc cctgttctct ctgctggctc tatcttgacc tgtgaaacgt atatttaact 189000
aattaaatat tagttaatat taataaattt taagctttat ccagatactc ataacctgct 189060
aacacacaca catatacaca cacatacaca tacacacata tacacacacc acacacatac 189120
acagacacca cacacatacc atacacagac acatacacat gcacacacat atacacacac 189180
acctcaaata catacacacc acacacacat acatgtatac acacatacac acaccacaca 189240
tacaccacaa aaaccccaca cacatacaca tatacacacc acacacacca catacacaca 189300
cgtatacaca catatataca cacatacacc atgcatacat acacaccaca catacataca 189360
gacacaccac acacacgtac acacaacaca caacacagac acgtacacac actacagaca 189420
tgtatgcaca catacacaca caccacacat acatacacac agacacatat acactacaca 189480
caccattaca tacacacgta cacatacacc acacacacca cacatacaca caccacacac 189540
acatacgcca cacacacacc acaaaaaccg cacacacata caaacatata cacactacac 189600
cacacataca cacacacacc acacaccaca cacacacata cacacaccac acacaccaca 189660
catacacgca ccacacatac acacacgtag acacaccaca cacaccacag aaacacacat 189720
taacacacca catacacata tgtatgtgca tatacacacc cacaccccac acacacatgt 189780
ataaagattt agatatatat aaaacatatg ttatatatat gttgatgtaa tatctaatat 189840
ctatatatct aatatgtagt ttattagcta tctaatatct atgtcatata tatcaaaatc 189900
tttatatata aaaatatgta gaaatcttta tacatatgtt atatgtatat aaagatttag 189960
atatataaca tatgtaagtt atatatatgt tagtgtaata tctaatatat agtttattgg 190020
ctatctaata taatataaac agattatcaa tattataagc tattagaaaa atgcaagtta 190080

-continued aggcagatga tatacctctt tacacaccaa ctacacacac caactacaca cacacataca 190140
cacagacaca cacgacacac accatacaca tgtacacaca caccacatat acacaaacgt 190200
acacacacac cacacacaca tacacaccac acacacacca cacatacata cacatccaca 190260
caccacacat gtacacacgc cacacacaca catacacacc acatacacat atgtatgcac 190320
acatacacac caacaccaca cagacaccac acatgcataa acatatagac atatacacac 190380
cacacaccat atgtacacat gtacacacac accacatata cacacaacac acacaaatac 190440
acacaccaca cacacaccac aaaaacccca cacacacaca aacatataca ccccacacat 190500
acgcatatat acacacacac atacacacca cacacataca caccacacac acaccacaca 190560
tacacacacg tacacacacc acacacacac cacagacaca caccacacat acatacacat 190620
acacacacca cacacacgta cacacaccac acacaccaca gacacacata gacacaccac 190680
atacacaccc acaccacaca cacacaactc ataccacaca tacatacaca atagacacat 190740
acacaccaca cacaccatac atacacacgt atacacacac cacatataca cacacgtaca 190800
cacacaccac acacacccac atgcacacac cacacacaca tacaaatata caccacacac 190860
acatacacca cacacacggt gcacatacac acacatatac acacaccaga cacacatacc 190920
acatacacat cacacatata tgtatacatg catacacata cacacacaca tacacacact 190980
ctcctcaagg cagtttatcc tctgagaact ttaaatttac aaaagacaca tatgtccatt 191040
actttgagaa ggacaggaaa gaacccactt tcttttgcag caacagcaag agggccctcc 191100
cgaggctcct gctccctgtc ataagtctcc ttgttgagga cattcacagg gttcagaacc 191160
cagggatcct gcatgggatg gtgctttgct gattacttca cctctgattt ctttccactt 191220
tcagaataca taaaccagtc cgttcccaaa aggcccgctg gctctgtgca gaatcctgtc 191280
tatcacaatc agcctctgaa ccccgcgccc agcagagacc cacactacca ggaccccccac 191340 agcactgcag tgggcaaccc cgagtatctc aacactgtcc agcccacctg tgtcaacagc 191400
acattcgaca gccctgccca ctgggcccag aaaggcagcc accaaattag cctggacaac 191460
cctgactacc agcaggactt ctttcccaag gaagccaagc caaatggcat ctttaagggc 191520
tccacagctg aaaatgcaga atacctaagg gtcgcgccac aaagcagtga atttattgga 191580
gcatgaccac ggaggatagt atgagcccta aaaatccaga ctctttcgat acccaggacc 191640
aagccacagc aggtcctcca tcccaacagc catgcccgca ttagctctta gacccacaga 191700
ctggttttgc aacgtttaca ccgactagcc aggaagtact tccacctcgg gcacattttg 191760
ggaagttgca ttcctttgtc ttcaaactgt gaagcattta cagaaacgca tccagcaaga 191820
atattgtccc tttgagcaga aatttatctt tcaaagaggt atatttgaaa aaaaaaaaaa 191880
gtatatgtga ggatttttat tgattgggga tcttggagtt tttcattgtc gctattgatt 191940
tttacttcaa tgggctcttc caacaaggaa gaagcttgct ggtagcactt gctaccctga 192000
gttcatccag gcccaactgt gagcaaggag cacaagccac aagtcttcca gaggatgctt 192060
gattccagtg gttctgcttc aaggcttcca ctgcaaaaca ctaaagatcc aagaaggcct 192120
tcatggcccc agcaggccgg atcggtactg tatcaagtca tggcaggtac agtaggataa 192180
gccactctgt cccttcctgg gcaaagaaga aacggagggg atggaattct tccttagact 192240
tacttttgta aaaatgtccc cacggtactt actccccact gatggaccag tggtttccag 192300
tcatgagcgt tagactgact tgtttgtctt ccattccatt gttttgaaac tcagtatgct 192360
gcccctgtct tgctgtcatg aaatcagcaa gagaggatga cacatcaaat aataactcgg 192420
attccagccc acattggatt catcagcatt tggaccaata gcccacagct gagaatgtgg 192480
aatacctaag gatagcaccg cttttgttct cgcaaaaacg tatctcctaa tttgaggctc 192540
agatgaaatg catcaggtcc tttggggcat agatcagaag actacaaaaa tgaagctgct 192600
ctgaaatctc ctttagccat caccccaacc ccccaaaatt agtttgtgtt acttatggaa 192660
gatagttttc tccttttact tcacttcaaa agctttttac tcaaagagta tatgttccct 192720
ccaggtcagc tgcccccaaa ccccctcctt acgctttgtc acacaaaaag tgtctctgcc 192780
ttgagtcatc tattcaagca cttacagctc tggccacaac agggcatttt acaggtgcga 192840
atgacagtag cattatgagt agtgtggaat tcaggtagta aatatgaaac tagggtttga 192900
aattgataat gctttcacaa catttgcaga tgttttagaa ggaaaaaagt tccttcctaa 192960
aataatttct ctacaattgg aagattggaa gattcagcta gttaggagcc cacctttttt 193020
cctaatctgt gtgtgccctg taacctgact ggttaacagc agtcctttgt aaacagtgtt 193080
ttaaactctc ctagtcaata tccaccccat ccaatttatc aaggaagaaa tggttcagaa 193140
aatattttca gcctacagtt atgttcagtc acacacacat acaaaatgtt ccttttgctt 193200
ttaaagtaat ttttgactcc cagatcagtc agagccccta cagcattgtt aagaaagtat 193260
ttgatttttg tctcaatgaa aataaaacta tattcatttc cactctatta tgctctcaaa 193320
tacccctaag catctatact agcctggtat gggtatgaaa gatacaaaga taaataaaac 193380
atagtccctg attctaagaa attcacaatt tagcaaagga aatggactca tagatgctaa 193440
ccttaaaaca acgtgacaaa tgccagacag gacccatcag ccaggcactg tgagagcaca 193500
gagcagggag gttgggtcct gcctgaggag acctggaagg gaggcctcac aggaggatga 193560
ccaggtctca gtcagcgggg aggtggaaag tgcaggtgca tcaggggcac cctgaccgag 193620
gaaacagctg ccagaggcct ccactgctaa agtccacata aggctgaggt cagtcaccct 193680
aaacaacctg ctccctctaa gccaggggat gagcttggag catcccacaa gttccctaaa 193740
agttgcagcc cccaggggga ttttgagcta tcatctctgc acatgcttag tgagaagact 193800
acacaacatt tctaagaatc tgagatttta tattgtcagt taaccacttt cattattcat 193860
tcacctcagg acatgcagaa atatttcagt cagaactggg aaacagaagg acctacattc 193920
tgctgtcact tatgtgtcaa gaagcagatg atcgatgagg caggtcagtt gtaagtgagt 193980
cacattgtag cattaaattc tagtattttt gtagtttgaa acagtaactt aataaaagag 194040
caaaagctat tctagctttc ttcttcatat tttaattttc caccataaag tttagttgct 194100
aaattctatt aattttaaga ttgtgcttcc caaaatagtt ctcacttcat ctgtccaggg 194160
aggcacagtt ctgtctggta gaagccgcaa agcccttagc ctcttcacgg atctggcgac 194220
tgtgatgggc aggtcaggag aggagctgcc caaagtccca tgattttcac ctaacagccc 194280
tgatcagtca gtactcaaag cttggactcc atccctgaag gtcttcctga ttgatagcct 194340
ggccttaata ccctacagaa agcctgtcca ttggctgttt cttcctcagt cagttcctgg 194400
aagaccttac cccatgaccc cagcttcaga tgtggtcttt ggaaacagag gtcgaaggaa 194460
agtaaggagc tgagagctca cattcatagg tgccgccagc cttcgtgcat cttcttgcat 194520
catctctaag gagctcctct aattacacca tgcccgtcac cccatgaggg atcagagaag 194580
ggatgagtct tctaaactct atattcgctg tgagtccagg ttgtaagggg gagcactgtg 194640
gatgcatcct attgcactcc agctgatgac accaaagctt aggtgtttgc tgaaagttct 194700
tgatgttgtg acttaccacc cctgcctcac aactgcagac ataaggggac tatggattgc 194760
ttagcaggaa aggcactggt tctcaagggc ggctgccctt gggaatcttc tggtcccaac 194820

-continued

```
cagaaagact gtggcttgat tttctcaggt gcagcccagc cgtagggcct tttcagagca 194880

ccccctggtt attgcaacat tcatcaaagt ttctagaacc tctggcctaa aggaagggcc 194940

tggtgggatc tacttggcac tcgctggggg gccacccccc agtgccactc tcactaggcc 195000

tctgattgca cttgtgtagg atgaagctgg tgggtgatgg gaactcagca cctcccctca 195060

ggcagaaaag aatcatctgt ggagcttcaa aagaaggggc ctggagtctc tgcagaccaa 195120

ttcaacccaa atctcggggg ctctttcatg attctaatgg gcaaccaggg ttgaaaccct 195180

tatttctagg gtcttcagtt gtacaagact gtgggtctgt accagagccc ccgtcagagt 195240

agaataaaag gctgggtagg gtagagattc ccatgtgcag tggagagaac aatctgcagt 195300

cactgat                                                           195307


<210> SEQ ID NO 10
<211> LENGTH: 1210
<212> TYPE: PRT
<213> ORGANISM: Homo sapiens

<400> SEQUENCE: 10

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285
```

```
Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Arg Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700
```

-continued

```
Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
```

```
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210


<210> SEQ ID NO 11
<211> LENGTH: 20
<212> TYPE: DNA
<213> ORGANISM: Artificial
<220> FEATURE:
<223> OTHER INFORMATION: Direct primer amplification exon 12 of EGFR
      gene

<400> SEQUENCE: 11

ttgcagtcgt cagcctgaac                                                  20


<210> SEQ ID NO 12
<211> LENGTH: 26
<212> TYPE: DNA
<213> ORGANISM: Artificial
<220> FEATURE:
<223> OTHER INFORMATION: Reverse primer amplification exon 12 of EGFR
      gene

<400> SEQUENCE: 12

ttaaatggga atagcccttc aatatt                                           26


<210> SEQ ID NO 13
<211> LENGTH: 25
<212> TYPE: DNA
<213> ORGANISM: Homo sapiens

<400> SEQUENCE: 13

ccaaaattat aaggaacaga ggtga                                            25


<210> SEQ ID NO 14
<211> LENGTH: 25
<212> TYPE: DNA
<213> ORGANISM: Homo sapiens

<400> SEQUENCE: 14

ccaaaattat acgtaacaga ggtga                                            25


<210> SEQ ID NO 15
<211> LENGTH: 25
<212> TYPE: DNA
<213> ORGANISM: Homo sapiens

<400> SEQUENCE: 15

ccaaaattat acgcaacaga ggtga                                            25


<210> SEQ ID NO 16
<211> LENGTH: 25
```

-continued

```
<212> TYPE: DNA
<213> ORGANISM: Homo sapiens

<400> SEQUENCE: 16

ccaaaattat acgaaacaga ggtga                                          25


<210> SEQ ID NO 17
<211> LENGTH: 25
<212> TYPE: DNA
<213> ORGANISM: Homo sapiens

<400> SEQUENCE: 17

ccaaaattat acggaacaga ggtga                                          25
```

MUTATIONS IN THE EPIDERMAL GROWTH FACTOR RECEPTOR GENE

FIELD OF THE INVENTION

The present invention is directed to a mutation of the human epidermal growth factor receptor gene, as a marker for determining response to monoclonal antibody treatment.

BACKGROUND ART

Epidermal growth factor receptor gene (EGFR) is a transmembrane tyrosine-kinase receptor that belongs to the epidermal growth factor family of receptors (ErbB family), which includes four closely related receptor tyrosine kinases: EGFR (ErbB-1), HER2/c-neu (ErbB-2), Her 3 (ErbB-3) and Her 4 (ErbB-4). Upon ligand binding, EGFR activates intracellular signaling pathways, mainly the RAS-RAF-MEK-ERK cascade and the PI3KAkt pathway, that regulate key oncogenic events such as apoptosis, cell growth, angiogenensis and metastasis. Aberrant activation or overexpression of EGFR has been reported in several types of cancer (i.e. Mendelsohn J, Baselga J et al., "Epidermal growth factor receptor targeting in cancer". *Semin Oncol* —2006, Vol. 33, pp.: 369-38). Mutations in EGFR gene have been described in lung cancer. Examples of such mutation are disclosed for instance in the document of Lynch T J et al., "Activating mutations in the epidermal growth factor receptor underlying responsiveness of non-small-cell lung cancer to gefitinib", *N Engl J Med*—2004, Vol. 350, pp: 2129-2139; or in Paez J G et al., "EGFR mutations in lung cancer: correlation with clinical response to gefitinib therapy", *Science*—2004, Vol. 304, pp.: 1497-500; or in Pao W et al., "EGF receptor gene mutations are common in lung cancers from "never smokers" and are associated with sensitivity of tumors to gefitinib and erlotinib", *Proc Natl Acad Sci USA*—2004, Vol. 101, pp.: 13306-13311.).

Metastasic colorectal cancer (mCRC) is the second leading cause of death from cancer in the Western Countries world.

A therapy based on monoclonal antibodies (moAbs), e.g. cetuximab and panitumumab, which are directed against EGFR, provides significant survival benefit to patients with mCRC and are now standard components of therapy regimens for these patients, i.e. either alone or in combination with other antineoplasic drug(s). One of these moAbs, cetuximab (Erbitux) is also indicated for the treatment of patients with squamous cell carcinoma of the head and neck, also named head and neck cancer, in combination with platinum-based chemotherapy.

The moAbs bind to foreign antigens expressed on cancer cells. Once bound, the cancer cells are marked for destruction by the patient's immune system. In addition to targeting cancer cells, moAbs can be designed to act on other cell types and molecules necessary for tumor growth. For example, antibodies can neutralize growth factors and thereby inhibit tumor expansion. It is possible to create a moAb specific to almost any extracellular/cell surface target (such as cancer cells). In summary, moAbs can be used to destroy malignant tumor cells and prevent tumor growth by blocking specific cell receptors. Therapeutic moAbs cetuximab and panitumumab bind to EGFR and prevent the activation of intracellular signaling pathways driven by EGFR (i.e., the RAS-RAF-MEK-ERK cascade and PI3K-akt pathway).

Unfortunately, not all patients with mCRC respond to a therapy regimen comprising moAbs. The lack of response of a patient with mCRC to such a treatment could be primary, i.e. since the beginning of anti-EGFR moAb treatment; known as primary resistance. Moreover, all mCRC patients that initially respond to anti-EGFR moAbs invariably develop secondary resistance, i.e. acquired resistance to anti-EGFR moAb. In both cases, the result is treatment failure. The mechanisms that contribute to the acquisition of such treatment resistance in mCRC patients is still not fully known. The same resistance to anti-EGFR moAb therapy (primary or secondary) is observed in patients with head and neck cancer.

KRAS (also known as V-Ki-ras2 Kirsten rat sarcoma viral oncogene homolog) is an EGFR downstream effector, and a marker of primary resistance to anti-EGFR moAbs. KRAS has a significant impact on the optimization of treatment of mCRC patients. Forty percent of colorectal tumors harbour a mutation in the KRAS gene and these patients do not benefit from anti-EGFR moAbs. In current clinical practice all mCRC patients who are being considered for anti-EGFR moAb therapy should undergo KRAS testing, and patients should be excluded from cetuximab or panitumumab therapy if a KRAS mutation is detected.

Nevertheless, a fraction of mCRC patients with wild-type KRAS tumors still do not benefit from anti-EGFR moAbs. The response rate to anti-EGFR moAbs in wild-type KRAS patients is approximately 60% when combined with chemotherapy and less than 20% when administered alone in chemotherapy-refractory patients, as derived from Amado et al., "Wild-type KRAS is required for panitumumab efficacy in patients with metastasic colorectal cancer", *J. Clin Oncol* —2008, Vol. 28, pp.: 1626-1634.

Activating mutations of other EGFR downstream genes such as BRAF (serine/threonine-protein kinase B-Raf) and PI3K (phosphatidylinositol 3-kinase), as well as loss of expression of PTEN (phosphatase and tensin homolog), and alterations in other EGFR regulatory proteins are being evaluated as potential candidates for response to anti-EGFR therapy with inconclusive results so far. Information regarding the association between the mutations in theses genes and the response to anti-EGFR therapy can be derived from the documents of De Roock et al., "Effects of KRAS, BRAF, NRAS, and PIK3CA mutations on the efficacy of cetuximab plus chemotherapy in chemotherapy-refractory metastasic colorectal cancer: a retrospective consortium analysis", *Lancet Oncol*—2010, Vol. 11, pp.: 753-762; or in the document of Loupakis et al., "PTEN expression and KRAS mutations on primary tumors and metastases in the prediction of benefit of cetuximab plus irinotecan for patients with metastasic colorectal cancer", *J Clin Oncol* —2009, Vol. 27, pp.: 2622-2629.

The studies carried out so far to elucidate a potential role of the EGFR as a marker of response to anti-EGFR moAb are inconclusive. EGFR protein expression, as detected by immunohistochemistry, is not a reliable predictive marker of response to anti-EGFR moAbs. However, there is increasing evidence supporting EGFR gene copy number as a potential biomarker of response to anti-EGFR moAbs. Regarding the association of nucleotide changes in the EGFR gene with response to anti-EGFR moAbs-based therapy, the state of the art, in particular Gonçalves et al. In "A polymorphism of EGFR extracellular domain is associated with progression free-survival in metastasic colorectal cancer patients receiving cetuximab-based treatment", *BMC Cancer*—2008, Vol. 8, pp.: 169, describes a polymorphism in the extracellular portion of the EGFR gene, resulting in the amino acid substitution R521K associated with cetuximab benefit in mCRC patients. The polymorphism or single nucleotide polymorphism is the one identified as the variation CM942312 from January 2011, retrievable from the database Ensembl (www.ensembl.org). It corresponds to the codon change at position 521 AGG-AAG in the mRNA sequence identified as NM_005228 version 3, available on 26.06.2011 from GenBank.

Additionally, also document WO2008/88860 discloses that patients with metastasic or non-metastasic gastrointestinal neoplasm or malignant tumour having the polymorphism R497K in the EGFR gene are likely to show responsiveness to single agent anti-EGFR moAb-based therapy (e.g. cetuximab or panitumumab). This mutation is the same disclosed by Gonçalves et al. (supra), but being identified with the ancient designation. Finally, document WO2005085473 discloses the association of 12 polymorphisms in the regulatory region of the EGFR gene, which induce over-expression of the EGFR protein, with decreased efficacy of an EGFR-targeting therapeutic agent for the treatment of cancer in a patient.

In summary, the results showed in the documents comprised in the state of the art are not only inconclusive, but also do not fully clarify the fraction of mCRC patients with wild-type KRAS tumors who still do not benefit from anti-EGFR mAb-based therapy.

In view of the above, it is therefore necessary to identify additional predictive biomarkers of resistance to anti-EGFR moAb therapy in patients with mCRC.

SUMMARY OF THE INVENTION

The inventors have identified a mutation in the extracellular domain of EGFR (domain III) that correlates with resistance to the treatment with some moAbs used in the cancer therapy. In particular, the invention is based on the surprising identification of the serine by an arginine amino acid substitution in position 492 of the EGFR protein. Mutated protein has the amino acid sequence identified herein as SEQ ID NO: 10. Wild type protein has the amino acid sequence SEQ ID NO: 8. The mutation is known herein as S492R.

Individuals with the mutation showed resistance to the treatment with cetuximab, thus rendering usefulness such a therapeutic approach, and making enforceable other drug strategies.

Thus, a first aspect of the present invention relates to a peptide sequence comprising SEQ ID NO: 1 (TKIIRNRGE). This amino acid sequence is a fragment derived from the entire amino acid sequence codifying for EGFR, corresponding to the amino acid sequence SEQ ID NO: 8, wherein the serine at position 492 has been substituted by an arginine.

Advantageously, the mutated peptide comprising SEQ ID NO: 1 is still sensitive to anti-EGFR moAbs other than cetuximab being relevant for use in cancer therapy. In particular it is sensitive to moAbs useful in the therapy of metastasic colorectal cancer (mCRC) and chemotherapy to head and neck cancer.

In a second aspect the invention aims an oligonucleotide comprising a sequence coding for SEQ ID NO: 1.

A further aspect of the invention is a set of primers consisting of SEQ ID Nos: 3 (gggacctccggtcagaaaa) and 4 (cggtgacttactgcagctgttt).

This set of primers allows amplifying the genomic region comprising the portion of the EGFR coding region wherein the nucleotide changes resulting in the mutation of the present invention are located. They are thus related with the novel amino acidic mutation identified by the inventors.

In particular, the invention is based on the surprising identification of the serine by an arginine amino acid substitution in position 492 of the EGFR protein (mutation known herein as S492R). This amino acid change is the result of the nucleotide change CA at position 1722 (also known herein as C1722A) of the mRNA variant 1 of the EGFR gene. The amino acid change of the present invention may also be the result of the nucleotide change AG at nucleotide position 1720 (also known herein as A1720G) of the mRNA variant 1 of the EGFR gene. Finally, the amino acid mutation of the present invention can also be the result of each of the following nucleotide(s) changes in the mRNA variant 1 of the EGFR gene: C→G at position 1722 (also known herein as C1722G), A→C at position 1720 and C→T at position 1722 (also known herein as A1720C/C1722T), A→C at position 1720 (also known herein as A1720C); and A→C at position 1720 and C→G at position 1722 (also known herein as A1720C/C1722G).

Another aspect of the invention is an oligonucleotide consisting of SEQ ID NO: 5 (cacctctgtttcttataatt).

This oligonucleotide of SEQ ID NO: 5 is complementary to the mutated region of the EGFR coding region wherein the nucleotide changes resulting in the mutation of the present invention are located. Thus, it hybridizes with a fragment of the nucleotide sequence carrying the mutation. It allows detecting the nucleotide change CA at position 1722 and/or 1720 disclosed above.

As already indicated above, each of the above nucleotide changes refers to the mRNA, transcript variant 1 sequence of the EGFR gene (also known as ERBB1, PIG61, proto-oncogene c-ErbB-1, avian erythroblastic leukemia viral (v-erb-b) oncogene homolog receptor tyrosine-protein kinase erbB-1, or HER1). The sequence of the mRNA, transcript variant 1, of the EGFR gene is that corresponding to SEQ ID NO: 7 (or GenBank accession number NM_005228.3, available on 26.06.2011) as well as any variant thereof, wherein said variant codes for the EGFR protein. The EGFR protein corresponds to SEQ ID NO: 8 (GenBank accession number NP_005219.2 version of 17.07.2011) or any variant thereof that maintains the basic structure of the EGFR protein.

Also another aspect of the invention is an oligonucleotide consisting of SEQ ID NO: 6 (cacctctgttgcttataa).

This oligonucleotide of SEQ ID NO: 6 is complementary to wild-type region of the EGFR coding region wherein the identified mutation is located (in case of a mutation exits).

Both oligonucleotides are suitable probes allowing detecting the presence or not of the mutation leating to the arginine by serine change.

Another aspect of the invention is a kit which comprises the oligonucleotide as defined before and corresponding to SEQ ID NO: 5.

Advantageously, this kit is a usable tool to detect the presence of the S492R mutation in an easy and fast way since it includes the probe complementary to the mutated EGRF coding region.

Also another aspect of the invention is the kit as defined above, for use in the prediction of the response of a subject to a therapy regimen comprising cetuximab and/or panitumumab.

Further, the invention also relates to an in vitro method of identifying the presence or absence of an arginine at position 492 of the amino acid sequence corresponding to SEQ ID NO: 8 in a sample taken from a subject, comprising determining the amino acid at position 492 of SEQ ID NO: 8 by means selected from the group consisting of genotype methods, and/or protein sequencing methods. The in vitro method of the invention allows identifying a peptide sequence comprising SEQ ID NO: 1 (TKIIRNRGE).

Finally, another aspect of the invention is a in vitro method of predicting the response of a subject therapy regimen comprising cetuximab and/or panitumumab, wherein the method comprises: i) determining the presence or absence of an arginine at position 492 of the amino acid sequence corresponding to SEQ ID NO: 8 in a sample taken from the subject, as defined in the method disclosed above; ii) correlating the presence of the arginine identified in step i) with resistance of the subject to the therapy regimen comprising cetuximab, or correlating the absence of the arginine identified in step i) with response of the subject to therapy regimen comprising panitumumab.

The put into practice of the in vitro method of predicting the response of a subject to a therapy regimen comprising cetuximab and/or panitumumab, implies the advantage of accommodating the more suitable therapy for the subject, and avoids wrong or not useful enough therapeutically approaches incurring waste time, which is an essential aspect for the subject and the success of the treatment, especially if the subject is affected with cancer.

DETAILED DESCRIPTION OF THE INVENTION

Figure 1:
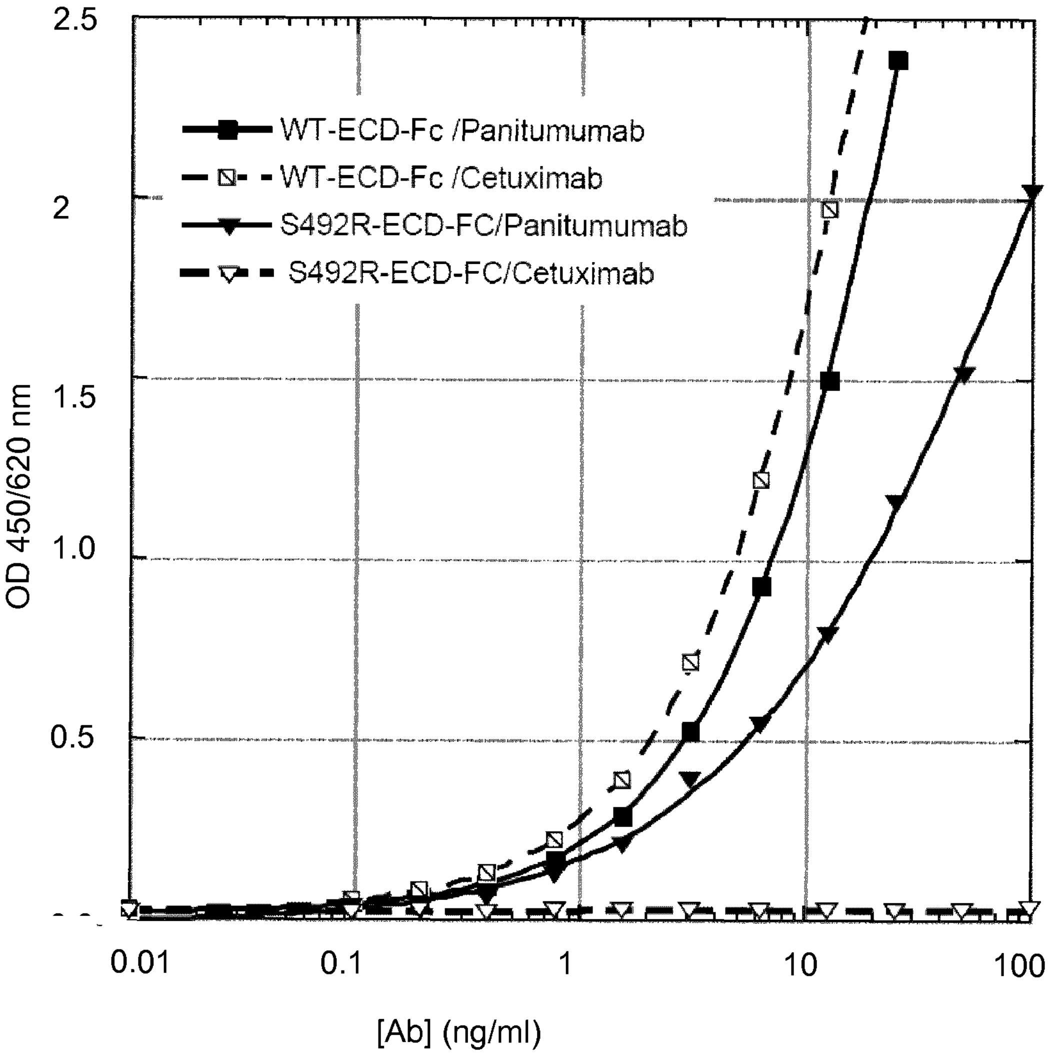
FIG. 1, related to Example 3, is a direct binding assay, showing interaction of cetuximab and panitumumab to interact with wild-type EGFR (wt EGFR) and S492R EGFR. WT-ECD-Fc means extracellular domain Fc (fragment crystallisable); S492R-ECD-Fc means extracellular domain Fc (fragment crystallisable); [Ab] (ng/ml) is the tested antibody concentration in nanograms per milliliter; and OD 450/620 nm is the optical density.

In general, the following words or phrases have the indicated definition when used in the description, examples and claims.

The term "therapy regimen" as used in the state of the art and also herein refers to any therapy intended to prevent, slow, arrest or reverse the growth of a precancerous lesion, cancer or a cancer metastasis. It includes chemotherapy, radiation therapy, immunotherapy, monoclonal antibody therapy or other methods.

By "response" is to be understood any kind of improvement either clinical or non-clinical selected from, but not limited to, measurable reduction in tumour size or evidence of disease or disease progression, stable disease, increase or elongation of progression of free survival or reduction in toxicity.

"Progression free survival" indicates the length of time during and after treatment that the cancer does not grow. Progression free survival includes the amount of time patients have experienced a complete response or partial response, as well as the amount of time patients have experienced stable disease.

"A complete response" to a therapy defines patients with valuable but non-measurable disease, whose tumour and all evidence of disease disappeared.

"A partial response" to a therapy defines patients with anything less than complete response.

The expression "genotype methods" includes all those methodologies and processes suitable for determining the genotype or, which is the same for identifying the nucleotide in a given position. Examples of said methodologies encompass Sanger sequencing, pyrosequencing, allele-specific PCR, denaturing high pressure liquid chromatography (DHPLC), Allele Specific Primer Extension (ASPE), DNA biochips/microarrays and dynamic allele-specific hybridization (DASH).

For "protein sequencing methods" is to be understood any technique allowing to determine the amino acid sequence of a protein, as well as which conformation the protein adopts and the extent to which it is complexed with any non-peptide molecules. The determination of amino acid composition may be performed by hydrolysis or separation of the amino acids. Known technologies include the Sanger sequencing, Edman degradation and mass spectrometry.

As already explained above, the teachings according to the state of the art suggest, on the one hand, that mutations in the regulatory region of the EGFR gene that result in the over-expression of the corresponding protein are associated with decreased efficacy of an EGFR-targeting therapeutic agent for the treatment of cancer in a patient (cf. WO2005/854732); but also that a nucleotide change in the coding region of the EGFR gene is associated with responsiveness to single agent anti-EGFR mAb based therapy in patients with metastasic or non-metastasic gastrointestinal neoplasm or malignant tumour (cf. WO2008/88860). These are contradictory results that moreover have not been further confirmed, e.g. by analyzing, at least in vitro, the effect of the nucleotide change identified in the coding region of the EGFR gene, hence, affecting the EGFR protein. Consequently, it is not clear whether the nucleotide change identified in WO2008/88860 is a mutation causing the responsiveness, or on the contrary, another mutation in linkage desequilibrium with it, and located in another gene, is causing the responsiveness.

In contrast with the findings disclosed in the state of the art, the present invention is based on a novel mutation in the coding region of the EGFR gene. The novel mutation of the present invention is useful to predict the response to moAb-based therapy of a patient with mCRC and/or with head and neck cancer (squamous cell carcinomas).

As already indicated above, each of the disclosed nucleotide changes lead to the substitution of a serine to an arginine at position 492 of the protein sequence corresponding to SEQ ID NO: 8.

Serine 492 is located within the extracellular domain of EGFR (also known as domain III). Arginine is an amino acid with a bulky side chain, whereas serine is a polar amino acid. The present invention, hence, is based on the finding that the substitution of the amino acid located at position 492 of the EGFR protein (i.e. serine) by a bulky amino acid (e.g. arginine) interferes with the binding of the mAb cetuximab to EFGR. In other words, that the amino acidic change of the present invention located in the epitope of EGFR that binds to cetuximab specifically disrupts the cetuximab-EGFR interaction.

Furthermore, and even more surprisingly, the amino acidic change of the present invention, which results in cetuximab resistance, does not affect the EGFR binding of another moAb, namely panitumumab, which is a moAb widely used for cancer therapy of metastasic colorectal cancer (mCRC).

Accordingly, this invention provides methods to select the appropriate therapy for patients suffering from mCRC, wherein the appropriate therapy comprises administration of the effective amount of cetuximab and/or panitumubab.

The isolated peptide comprising SEQ ID NO: 1 is the key product leading to the detection of a mutated form of EGFR protein of great interest in the field of cancer therapy. This mutated form of the protein is also detectable in the form of an oligonucleotide comprising a sequence coding for SEQ ID NO: 1.

In a preferred embodiment the oligonucleotide coding for SEQ ID NO: 1 comprises a nucleic acid sequence selected from the group consisting of SEQ ID NO: 2, SEQ ID NO: 13, SEQ ID NO: 14, SEQ ID NO: 15, SEQ ID NO: 16 and SEQ ID NO: 17. All these sequences can be schematically represented by the generic sequence defined in formula (I):

```
ccaaaattataXYZaacagag-        (I)
gtga
```

wherein nucleotides XYZ are nucleotide combinations selected from the group consisting of: AGA, AGG, CGT, CGC, CGA and CGG.

The detection of the nucleotide changes in the EGFR gene disclosed in the present invention is preferably carried out with the following method: After amplification of the target DNA sequence corresponding to SEQ ID NO: 9, the amplicon is analyzed using a mutated probe (SEQ ID NO: 5) and a wild type probe (SEQ ID NO: 6). SEQ ID NO: 9 corresponds to GenBank accession number NG_007726, version 1 (NG_007726.1), available on 19.06.2011.

In a preferred embodiment the mutated probe is that corresponding to SEQ ID NO: 5, whereas the wild type probe is that corresponding to SEQ ID NO: 6, these probes are labelled in the 5' end with 6-carboxyfluorescein (FAM) and the label VIC®, and with a Minor Groove Binder (MGB) that includes a non-fluorescent extintor of fluorescency at the 3' end. Schematically, the probes are as follows:

```
wild type probe (labelled SEQ ID NO: 6):
VIC-5'-CACCTCTGTTGCTTATAA-3'-MGB

mutation-specific probe (labelled SEQ ID NO: 5):
FAM-5'-CACCTCTGTTTCTTATAATT-3'-MGB
```

The probes may also include other suitable labels allowing the specific detection of the same once hybridized with the target fragment of the EGFR gene. Examples of other labels include chemiluminescent labels, radioisotopic labels, colorimetric labels, etc.

To the best of the applicant's knowledge, the specific portion of the EGFR genomic region wherein the nucleotide changes resulting in the mutation of the present invention are located has been of no interest in the state of the art, since no mutation with industrial applicability has been identified therein. Consequently, the state of the art does not disclose primers which hybridize and amplify said genomic region.

Therefore, the novel primers disclosed in the present invention specifically designed to amplify the genomic region comprising the portion of the EGFR coding region wherein the nucleotide changes resulting in the mutation of the present invention are located, are clearly linked with the novel amino acidic mutation identified by the inventors.

The preferred primers used for the amplification are those corresponding to SEQ ID NO: 3 and SEQ ID NO: 4. These primers are located, respectively, on nucleotides positions 146318-146297, and 146253-146271 of the genomic sequence of the EGFR gene, SEQ ID NO: 9 (corresponding to GenBank accession number NG_007726, version 1 (NG_007726.1), available on 19.06.2011).

These methods are not limited by the technique that is used to identify the nucleotide changes of the present invention. Any technique known in the art suitable for the detection of the nucleotide changes of interest can be used in the methods of the present invention. Suitable techniques include but are not limited to amplification reactions. In a preferred embodiment, the amplification technique used is the polymerase chain reaction. In a more preferred embodiment, the PCR is a real time PCR. The amplification conditions can be adjusted as necessary, and easily, by one of skill in the art; an example of amplification conditions suitable for the methods of the present invention are provided in the example section.

Alternatively, the mutation of interest is detected by a sequencing reaction, such as the Sanger sequencing, which gives the information of the codon or amino acid present in the region of interest. Examples of suitable methods to detect the mutation encompass Sanger sequencing, pyrosequencing, allele-specific PCR, denaturing high pressure liquid chromatography (DHPLC).

Thus, the in vitro method of the invention for identifying the presence or absence of an arginine at position 492 of the amino acid sequence corresponding to SEQ ID NO: 8 in a sample taken from a subject, is preferably carried out using genotyping methodologies. In another preferred embodiment the presence or absence of an arginine at position 492 of the amino acid sequence corresponding to SEQ ID NO: 8 is carried out at the protein level by means of protein sequencing methods.

In a preferred embodiment of the kit according to the invention, the kit comprises the oligonucleotide consisting of SEQ ID NO: 5 (cacctctgtttcttataatt) and further the oligonucletide consisting of SEQ ID NO: 6 (cacctctgttgcttataa).

In a more preferred embodiment the kit further comprises reagents for detecting mutations in the KRAS and/or PIK3CA and/or BRAF gene.

As above exposed, these genes are related with the resistance to the treatment of cancer (namely mCRC) with moAb (KRAS), or they are codifying for EGFR regulatory proteins (PIK3CA and BRAF) evaluated as potential candidates to drug target therapy.

So then, in a more preferred embodiment, the kit also includes tools and means (reagents) to detect the mutations in KRAS selected from the group consisting of G12A; G12C; G12D; G12R; G125; G12V; G13A; G13C, G13D; G13V as defined by Karapetis et al., "K-ras Mutations and Benefit from Cetuximab in Advanced Colorectal Cancer", *The New England Journal of Medicine* —2008, Vol. 359, pp.: 1757-1765. All these mutations are placed on codons 12 and 13 of the protein sequence of K-ras identified with the GenBank accession number NP_004976.2 from 24.07.2011 (named GTPase KRas isoform b precursor) and NP_203524.1 from 24.07.2011 (named GTPase KRas isoform a precursor In another preferred embodiment the kit also includes tools and means (reagents) to detect mutations in exons 9 and 20 of the PIK3CA gene that codifies for the PIK3CA protein with the GenBank accession number NP_006209.2 from 17.07.2011; and/or the V600E mutation placed on codon 600 of the protein sequence of BRAF identified with the GenBank accession number NP_004324.2 from 24.07.2011.

The kit of the invention, for use in the prediction of the response of a subject to a therapy regimen comprising cetuximab and/or panitumumab, is in a preferred embodiment for predicting the response of a subject to a cancer selected from the group consisting of metastasic colorectal cancer and head and neck cancer. Preferably the kit is for the prediction of response in case of metastasic colorectal cancer.

In a preferred embodiment of the in vitro method of predicting the response of a subject to a therapy regimen comprising cetuximab and/or panitumumab, the subject has already been treated with a therapy regimen comprising cetuximab.

In another preferred embodiment, the in vitro method of prediction is applicable to a subject affected with cancer. Preferably the cancer is selected from the group consisting of metastasic colorectal cancer and head and neck cancer.

The in vitro method of predicting the response of a subject to a therapy regimen comprising cetuximab and/or panitumumab is especially suitable for subjects affected with cancer. In particular preferred cancers are selected from the group consisting of metastasic colorectal cancer and head and neck cancer.

The invention further provides methods of treating subjects affected with cancer, preferably mCRC or head and neck cancer, comprising: i) determining the presence of the S492R EGFR mutant of the present invention; and ii) administering to said subject an effective amount of cetuximab, or a composition thereof, if the mutation is absent, or panitumumab, or a composition thereof, if the mutation is present.

The anti-EGFR moAbs, cetuximab and panitumumab can be administered alone, as a composition, or in a therapy regimen including other compounds, such as chemotherapeutic drugs.

The anti-EGFR moAbs, cetuximab and panitumumab, or compositions thereof, are administered or delivered in an amount effective to treat the cancer (mCRC or head and neck) and with any suitable formulation, e.g. including a pharmaceutically acceptable carrier. The formulation can further comprise one or more preservatives and/or stabilizers.

The in vitro method for predicting the response of a subject to a therapy regimen comprising cetuximab and/or panitumumab, is carried out in a sample comprising the tumour, in which the nucleotide changes in the EGFR gene of the present invention can be detected. In cases of mCRC, the sample can be used directly as obtained from the source or following a pre-treatment of the sample. The sample may additionally comprise normal tissue adjacent to said tumour. Accordingly, in case of mCRC the sample is selected from a primary colorectal cancer biopsy or a biopsy of a metastasis thereof. In other words, the sample may be a biopsy from colorectal cancer samples, including primary tumors and metastases. In a preferred embodiment, the metastasis is in the liver tissue.

The subject includes any mammal, including, but not limited to, a human or non-human mammal. Preferably the subject is a human.

Patients having the S492R mutation of the present invention are likely to show response to a therapy regimen not comprising cetuximab as measured by any suitable clinical or sub-clinical increase or elongation in progression free survival.

In a preferred embodiment the therapy regimen is cetuximab alone or in combination with a chemotherapy regimen based on irinotecan, oxaliplatin and/or 5-fluorouracil (5-FU or 5FU). In a preferred embodiment the therapy regimen is panitumumab alone or in combination with a chemotherapy regimen based on irinotecan, oxaliplatin and/or 5-fluorouracil.

Throughout the description and claims the word "comprise" and variations of the word, are not intended to exclude other technical features, additives, components, or steps. Furthermore the word "comprise" and its variations encompasses the expression "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. Tumor Samples and Patients

Tumor specimens were obtained during diagnosis or from surgical procedures on mCRC patients. Biopsy was obtained from the most accessible malignant lesion (either primary tumor or metastasis).

When necessary, biopsy of tumoral lesions from patients that demonstrated tumor regrowth (disease progression) after initial response to cetuximab-based therapy was collected. Specimens from matched normal tissue were obtained as control.

DNA extraction and mutational analysis of KRAS (codons 12 and 13), BRAF (V600E) were performed as previously described in Mutational analysis in the document by Montagut et al., "Mitogen-activated protein kinase phosphatase-1 (MKP-1) impairs the response to anti-epidermal growth factor receptor (EGFR) antibody cetuximab in metastasic colorectal cancer patients", *Br. J Cancer* —2010, Vol. 102, pp.: 1137-1144.

Mutational analysis of PIK3CA was performed as with the DxS PI3K Mutation Test Kit (DxS, Manchester, UK), as disclosed in the Procedures of De Roock et al., "Effects of KRAS, BRAF, NRAS, and PIK3CA mutations on the efficacy of cetuximab plus chemotherapy in chemotherapy-refractory metastasic colorectal cancer: a retrospective consortium analysis", *Lancet Oncol* —2010, Vol. 11, pp.: 753-

762. by the Amplification of EGFR was assessed by fluorescent in situ hybridization (FISH) using the LSI EGFR/CEP7 probe (Abbott Molecular Inc., Des Plaines, Ill.), as previously described in Pao et al., "Acquired resistance of lung adenocarcinomas to gefitinib or erlotinib is associated with a second mutation in the EGFR kinase domain", PloS Med 2005; 2:e73.

Analysis of EGFR S492R was performed by direct sequencing. Briefly, the region of EGFR exon 12 containing the mutated region were amplified with primers 5'-TTGCAGTCGTCAGCCTGAAC-3' (direct primer or SEQ ID NO: 11) and 5'-TTAAATGGGAATAGCCCTTCAATATT-3' (reverse primer or SEQ ID NO: 12) in an Applied Biosytems Veriti Thermalcycler with the following conditions: 95° C. for 10 minutes; 40 cycles of 95° C., 1 minute, 60° C., 1' 30" and 72° C. 1 minute; and a final extension of 10 minutes at 72° C. Sequencing was performed with BigDye v3.1 (Applied Biosystems, Foster City, Calif.) following the manufacturer's instructions and analysed on a 3500Dx Genetic Analyzer (Applied Biosystems). The sequence data files were analyzed using SeqScape software (Applied Biosystems) and all mutations were confirmed with an independent PCR. Real time monitoring of PCR amplification of DNAs was done with Taqman Universal master mix (Applied Biosystems) using 37.5 nM nM of each probe and 37.5 nM of each primer, in a ABI Prism 7500 FAST (Applied Biosystems). All determinations were performed in duplicate to minimise intra-assay variations.

Example 2. The S492R EGFR Mutation and Primary Resistance to Cetuximab

Cetuximab (Erbitux) and Panitumumab (Vectibix) were obtained from Hospital del Mar's Pharmacy, both monoclonal antibodies were ready to use. Gefitinib was obtained from Selleck Chemicals (Houston, Tex., USA) and was dissolved in DMSO and aliquoted and stored at −20° C. Purified EGF recombinant protein was purchased from Calbiochem (San Diego, Calif., USA) and was dissolved in PBS 0.1% BSA, aliquoted and stored at −20° C.

The EGFR extracellular domain was sequenced and KRAS and BRAF mutational status in primary tumor specimens was analyzed from 83 metastasic colorectal cancer patients prior to administration of cetuximab-based therapy. As a group, these patients had been heavily pre-treated with other therapy regimen before receiving cetuximab. In eighty-two percent of the patients, cetuximab was given in combination with irinotecan. Significantly, a CA nucleotide change at position corresponding to nucleotide 1722 of SEQ ID NO: 7, resulting in the S492R amino acid change in the corresponding EGFR protein (SEQ ID NO: 8) was detected in the specimens of two patients. Both tumors were KRAS, BRAF and PIK3CA wild-type and did not display EGFR gene amplification. The S492R EGFR mutation was not detected in matched normal tissue available for said patients.

Example 3. Presence of S492R EGFR Mutation and Resistance to Cetuximab

To establish whether the S492R EGFR mutation of the invention was responsible for the observed resistance to cetuximab, full-length wild-type EGFR and the S492R EGFR mutation was ectopically expressed in cultured NIH3T3 mouse embryonic fibroblast cell line that lack detectable endogenous EGFR expression.

EGFR was stimulated with its natural ligand EGF in the presence of cetuximab or panitumumab in transfected cells. In wild-type EGFR cells, both cetuximab and panitumumab inhibited EGFR activation, whereas in cells carrying the S492R mutation, panitumumab, but not cetuximab, effectively blocked EGF-induced EGFR activation (FIG. 2B).

Figure 2A:
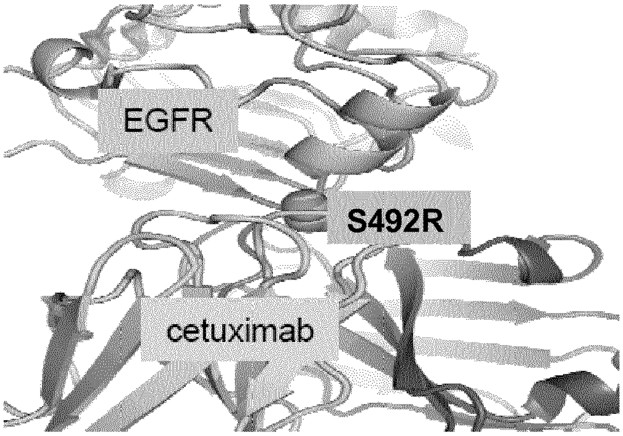
FIG. 2A is a structural modelling of the interaction between EGFR domain III and cetuximab, confirming the position of the mutation of the present invention (arginine at position 492 of the EGFR protein) at the interface of both molecules.
Figure 2B:
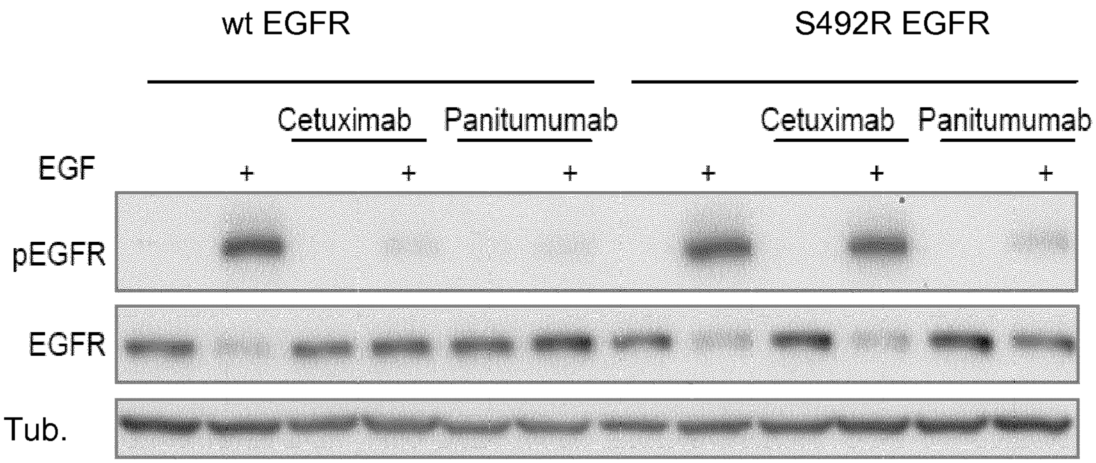
FIG. 2B, related to Example 3, is a Western blot analysis of total and phosphorylated EGFR (at Tyr1068; named herewith pEGFR) NIH3T3 cell lysates overexpressing wild-type EGFR (wt EGFR) and S492R EGFR mutant cultured in the presence of cetuximab or panitumumab. Tub means tubulin.

These conclusions were derived from the assay in FIG. 2B, which is a Western blot analysis of total and phosphorylated EGFR (at Tyr1068; herewith named pEGFR) NIH3T3 cell lysates overexpressing wild-type EGFR (wt EGFR) and S492R EGFR mutant cultured in the presence of cetuximab or panitumumab. NIH3T3 cells overexpressing wild-type EGFR (wt EGFR) and S492R EGFR mutant were cultured in the presence of cetuximab or panitumumab (10 μg/ml), after 2 h cells were stimulated with EGF 10 μg/mL for 15 minutes. Cell lysates were subjected to Western blot analysis of total and phosphorylated EGFR (Tyr1068 from SEQ ID NO: 8) to determine the activation of the receptor. Cetuximab was not able to revert ligand-induced activation in S492R EGFR mutant cells, as observed in the band corresponding to the pEGFR when the assay was performed with this moAb.

To collect lysates, cells where washed with PBS and scraped in lysis buffer Nonidet P-40 buffer (Tris-HCL (pH=7.4) 50 mM, NaCl 150 mM, 1% NP40, EDTA 5 mM, NaF 5 mM, Na3VO4 2 mM, PMSF 1 mM, Leupeptin 5 μg/mL and Aprotinin 5 μg/mL). After shaking for 30 min at 4° C., the samples were centrifuged at 13200 rpm for 30 min and the supernatant was aliquoted and stored at −20° C. until use. Samples (30 μg/lane) were subjected to SDS-page and transferred to nylon membranes. Western blotting was carried out according to standard procedures using horseradish peroxidase-conjugated secondary antibodies for signal detection. Target proteins were visualized after enhanced chemiluminescence treatment of membranes and subsequent exposure to X-ray film. The following antibodies were purchased from the manufacturers listed bellow: phospho EGFR (Y1068 or Tyr1068), EGFR, were obtained from Cell Signalling Technology (Beverly, Mass., USA).

Figure 2C:
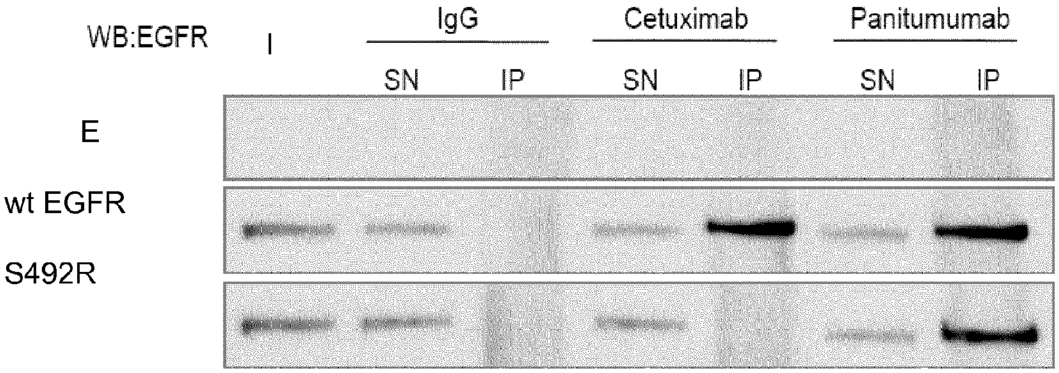
FIG. 2C, related to Example 3, is a Western blot analysis of total EGFR of lysates of NIH3T3 cells expressing wild-type EGFR (wt EGFR) and S492R EGFR, immunoted with cetuximab and panitumumab. E means empty; SN supernatant and IP immunoprecipitated; and I means input.
Figure 2D:
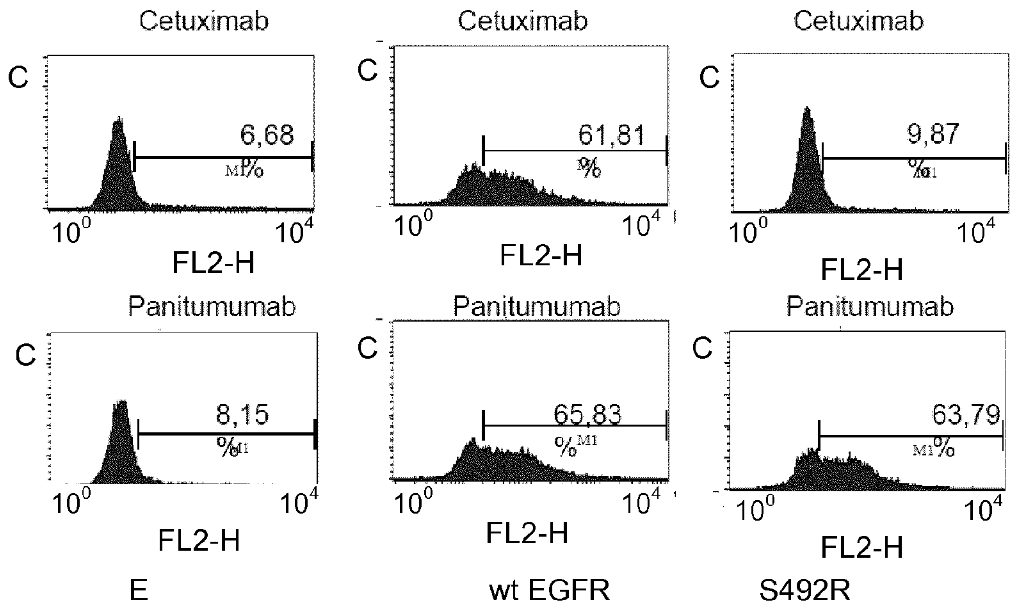
FIG. 2D, related to Example 3, is a Flow cytometry binding analysis of trypsinized NIH3T3 overexpressing wild-type EGFR (wt EGFR) and S492R EGFR mutant incubated with cetuximab or panitumumab as primary antibodies and using a secondary antibody conjugated with phicoeritrin directed against human IgG. C means counts; FL2H denotes the maximal signal intensity in the second channel of fluorescence detection with a band pass of 585±21 that is used to detect the phycoerythrin (PE) fluorescence; E means empty.

Moreover, flow cytometry as well as biochemical binding assays and immunoprecipitation showed that in cells expressing wild-type EGFR, both cetuximab and panitumumab could bind EGFR; however, in cells expressing S492R EGFR, panitumumab was able to bind to EGFR whereas cetuximab-EGFR binding was not detected (see FIG. 1, FIGS. 2C and 2D).

FIG. 1 shows the ability of cetuximab and panitumumab to interact with wild-type EGFR and S492R EGFR mutant in vitro by direct binding assay.

As above indicated, this assay was performed to further verify that the S492R EGFR directly impacted binding to cetuximab. The in vitro biochemical binding studies were performed using purified recombinant forms of the extracellular domain (EC) of wild type EGFR and the S492R mutant (FIG. 1).

The competitive binding assay was performed as follows: Anti-EGFR Ab binding to wild-type (WT) and mutant extracellular domain (ECD) of EFGR was compared in a competitive sandwich ELISA. Recombinant EGFR ECD human Fc fusion protein (WT, WT-ECD-Fc; or mutant, S492R-ECD-FC in FIG. 1) was immobilized onto a plastic surface overnight. The plate was then blocked with PBS containing BSA. Anti-EGFR Abs and a negative control hulgG Ab were serially diluted and mixed with an equal volume of biotin-labeled panitumumab or cetuximab at fixed concentration, the mixture was added onto the plate. The sample was incubated for 2 hours. The plate was washed and streptavidin-horseradish peroxidase (SA-HRP) conjugate was added as detection. The substrate tetramethyl benzidine (TMB) was added to the plate, and the reaction was stopped with acid. The plate was read at two wave-length values (OD 450/620 nm) and the Ab competitive binding results from WT and mutant ECD were compared.

Consistent with the cell-based assays, the biochemical binding studies confirmed that the S492R EGFR mutant is selectively defective for binding to cetuximab, but not to panitumumab. No detection of biotin-labeled cetuximab is observed at any Anti-EGFR Abs concentration in the experimental with S492R mutant, which means that no binding exists.

This was also concluded from the results of a immunoprecipitation assay (FIG. 2C) of the cell lysates from NIH3T3 expressing wild-type EGFR (wt EGFR) and S492R EGFR after being immunoted with 10 μg/ml cetuximab and panitumumab, wherein non-specific IgG was used as negative control. As shown in FIG. 2C, the Western blot analysis of total EGFR confirmed that cetuximab was not able to bind to and precipitate S492R EGFR mutant. The input (I) and supernatant (SN) fractions of the precipitates were used as controls to confirm the presence of EGFR in the cell lysates.

Finally, the above results were also confirmed by flow cytometry. FIG. 2D shows that while cetuximab and panitumumab were able to interact with 60% of cells expressing wild-type EGFR (wt EGFR), only panitumumab was able to bind to cells expressing the S492R EGFR mutation. Trypsinized NIH3T3 cells overexpressing wild-type EGFR and S492R EGFR mutant were incubated with 1 μg/ml of cetuximab or panitumumab as primary antibodies. The binding was analyzed by flow cytometry using a secondary antibody conjugated with phicoeritrin directed against human IgG. NIH3T3 cells expressing the empty vector (E) were used as a negative control. The histograms show the percentage of cells detected by both antibodies.

Flow citometry was performed as follows:

For cell cycle distribution analysis, cells were grown and treated with cetuximab for 24 h, 48 h and 72 h. After treatment, cells were harvested by trypsinization, washed twice with cold PBS and fixed with 70% ethanol overnight. Ethanol was removed by washing the cells twice with cold PBS. Cells were stained for DNA with PBS containing 50 μg/ml propidium iodide and 100 μg/ml of RNAse at least during 48 h at 4° C. protected from light. Cell cycle distribution was measured using FACScalibur flow cytometer (Beckton Dickinson). To measure cetuximab and panitumumab binding to EGFR, cells were harvested by trypsinization and washed twice with PBS. Cells were incubated with Fc blocking reagent (MACS®) for 15 minutes on ice to block unspecific Fc binding of immonuglobulins. Cells were washed and incubated with the monoclonal antibodies to detect EGFR binding for 30 minutes on ice. A goat anti-human IgGγ Phicoeritrin conjugated (Invitrogen) was used as a secondary antibody. EGFR binding was analyzed using the FACScan flow Cytometer (Beckton Dickinson).

Example 4. Detection of the S492R EGFR Mutation in a Patient with Colorectal Cancer Demonstrating Acquired (or Secondary Treatment) Resistance to Cetuximab To assess the clinical relevance of this mutation as a mechanism of acquired resistance to cetuximab, it was examined whether the S492R EGFR mutation could be found in patients with metastasic colorectal cancer who experienced disease progression following an initial response to cetuximab.

Paired tumor samples from 10 patients before receiving cetuximab therapy and after failure to treatment (post-treatment specimen) were analyzed. All pre-treatment samples were from the primary colon tumor except in one case where the specimen was from a liver lesion, which was a metastasized tissue from a primary mCRC. Post-treatment samples were from liver metastasis obtained by percutaneous biopsy with ultrasound guidance. Most patients had previously received at least one line of chemotherapy for metastasic disease and cetuximab was administered together with irinotecan or oxaliplatin in all cases.

The mutational status of the extracellular domain region of the EGFR protein as well as that of KRAS, BRAF and PIK3CA were assessed by DNA sequence analysis (as detailed above). EGFR gene copy number was also studied by FISH (as detailed in Example 1)

All pre-treatment biopsies were wild-type for EGFR, KRAS, BRAF and PIK3CA. The post-cetuximab treated tumor samples did not harbour any known KRAS, BRAF or PIK3CA mutations; however, the S492R mutation was identified in two patients. Notably, the observed mutation in one patient was associated with nucleotide substitution A→C change at nucleotide 1720 of SEQ ID NO: 7, which also results in a serine to arginine substitution at amino acid 492 of the EGFR protein (SEQ ID NO: 8). Sequencing of normal cells from the patient showed only the wild-type sequence, indicating that the S492R mutation was a somatic mutation. The observed mutation in the other patient was the same as in the in vitro studies.

One of the two patients carrying the S492R mutation was treated with cetuximab (400 $mg/m^2$ initial dose followed by 250 $mg/m^2$/week thereafter) plus oxaliplatin 85 $mg/m^2$ on day 1, plus leucovorin 200 $mg/m^2$ and fluorouracil as a 400 $mg/m^2$ bolus followed by a 600 $mg/m^2$ infusion during 22 hours on days 1 and 2. Three months after onset of treatment, a computed tomographic (CT) scan showed a partial response according to the response evaluation criteria in solid tumors (RECIST) (Eisenhauer et al., "New response evaluation criteria in solid tumours: revised RECIST guideline (version 1.1)", *Eur J Cancer* 2009, Vol. 45(2):228-247). After 10 months of treatment, however, hepatic lesions exhibited frank progression and new liver lesions appeared. Cetuximab treatment was discontinued and a biopsy from pre-existing liver lesion was then obtained for molecular analysis, revealing the S492R EGFR mutation. The patient was then treated with irinotecan-based chemotherapy but did not respond. Therapy with single agent panitumumab 6 mg/Kg every 2 weeks was then initiated, and after two months of treatment, a CT scan showed a reduction in all liver lesions greater than 50%.

REFERENCES CITED IN THE APPLICATION

Mendelsohn J, Baselga J et al., "Epidermal growth factor receptor targeting in cancer". *Semin Oncol* —2006, Vol. 33, pp.: 369-38

Gonçalves et al., "A polymorphism of the EGFR extracellular domain is associated with progression free-survival in metastasic colorectal cancer pateints receiving cetuximab-based treatment", *BMC Cancer* 2008, Vol 8:169.

Eisenhauer et al., "New response evaluation criteria in solid tumours: revised RECIST guideline (version 1.1)", *Eur J Cancer* 2009, Vol. 45(2):228-247.

De Roock et al., "Effects of KRAS, BRAF, NRAS, and PIK3CA mutations on the efficacy of cetuximab plus chemotherapy in chemotherapy-refractory metastasic colorectal cancer: a retrospective consortium analysis", *Lancet Oncol* —2010, Vol. 11, pp.: 753-762

Loupakis et al., "PTEN expression and KRAS mutations on primary tumors and metastases in the prediction of benefit of cetuximab plus irinotecan for patients with metastasic colorectal cancer", *J Clin Oncol* —2009, Vol. 27, pp.: 2622-2629.

Karapetis et al., "K-ras Mutations and Benefit from Cetuximab in Advanced Colorectal Cancer", *The New England Journal of Medicine* —2008, Vol. 359, pp.: 1757-1765.

Montagut et al., "Mitogen-activated protein kinase phosphatase-1 (MKP-1) impairs the response to anti-epidermal growth factor receptor (EGFR) antibody cetuximab in metastasic colorectal cancer patients", *Br. J Cancer* —2010, Vol. 102, pp.: 1137-1144.

Amado et al., "Wild-type KRAS is required for panitumumab efficacy in patients with metastasic colorectal cancer", *J. Clin Oncol* —2008, Vol. 28, pp.: 1626-1634

Pao et al., "Acquired resistance of lung adenocarcinomas to gefitinib or erlotinib is associated with a second mutation in the EGFR kinase domain", *PloS Med* 2005; 2:e73

Lynch T J et al., "Activating mutations in the epidermal growth factor receptor underlying responsiveness of non-small-cell lung cancer to gefitinib", *N Engl J Med*—2004, Vol. 350, pp: 2129-2139.

Paez J G et al., "EGFR mutations in lung cancer: correlation with clinical response to gefitinib therapy", *Science*—2004, Vol. 304, pp.: 1497-500.

Pao W et al., "EGF receptor gene mutations are common in lung cancers from "never smokers" and are associated with sensitivity of tumors to gefitinib and erlotinib", *Proc Natl Acad Sci USA*—2004, Vol. 101, pp.: 13306-13311

The invention claimed is:

1. An in vitro method of predicting the response of a subject therapy regimen comprising cetuximab and/or panitumumab, wherein the method comprises:

i) determining the presence or absence of an arginine at position 492 of the amino acid sequence corresponding to SEQ ID NO: 8 in a sample taken from the subject by one or more of:

genotype methods, and/or protein sequencing methods;

wherein this determining includes amplifying a genomic region comprising SEQ ID NO: 8 of the EGFR coding region with a set of primers including one or more primers consisting of one or both SEQ ID Nos: 3 (gggacctccggtcagaaaa) and 4 (cggtgacttactgcagctgttt);

ii) correlating the presence of the arginine identified in step i) with resistance of the subject to the therapy regimen comprising cetuximab, or correlating the absence of the arginine identified in step i) with response of the subject to the therapy regimen comprising panitumumab.

2. The in vitro method according to claim 1, wherein the subject is affected with cancer.

3. The in vitro method according to claim 2, wherein the cancer is selected from the group consisting of metastasic colorectal cancer and head and neck cancer.

4. An in vitro method of identifying the presence of an arginine in the EGFR gene encoding the amino acid of SEQ ID NO: 10 in a sample taken from a subject, comprising identifying the amino acid at position 492 of SEQ ID NO: 10 as arginine by one or more genotype methods, wherein the one or more genotype methods comprise providing an oligonucleotide that is specific for a codon encoding an arginine at position 492.

5. The in vitro method according to claim 4, wherein the oligonucleotide is a probe oligonucleotide having a sequence of SEQ ID NO: 5.

6. The in vitro method according to claim 4, wherein the one or more genotype methods comprise one or both of PCR or a real time PCR.

* * * * *